(12) United States Patent
Liotta et al.

(10) Patent No.: US 8,378,117 B2
(45) Date of Patent: Feb. 19, 2013

(54) HEXAHYDRO-CYCLOHEPTAPYRAZOLE CANNABINOID MODULATORS

(75) Inventors: Fina Liotta, Westfield, NJ (US); Mingde Xia, Belle Mead, NJ (US); Huajun Lu, Bridgewater, NJ (US); Meng Pan, Neshanic Station, NJ (US); Michael P. Wachter, Bloomsbury, NJ (US); Mark J. Macielag, Branchburg, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 685 days.

(21) Appl. No.: 11/688,552

(22) Filed: Mar. 20, 2007

(65) Prior Publication Data
US 2008/0070968 A1 Mar. 20, 2008

Related U.S. Application Data

(63) Continuation-in-part of application No. 11/522,771, filed on Sep. 18, 2006, now abandoned.

(60) Provisional application No. 60/720,253, filed on Sep. 23, 2005.

(51) Int. Cl.
*C07D 231/54* (2006.01)

(52) U.S. Cl. .................................. 548/360.1

(58) Field of Classification Search ............... 548/360.1
See application file for complete search history.

(56) References Cited

U.S. PATENT DOCUMENTS

| | | | |
|---|---|---|---|
| 2,948,718 | A | 8/1960 | Schindler |
| 4,024,175 | A | 5/1977 | Satzinger et al. |
| 4,087,544 | A | 5/1978 | Satzinger et al. |
| 4,486,354 | A | 12/1984 | Baxter et al. |
| 4,513,006 | A | 4/1985 | Maryanoff |
| 4,699,927 | A | 10/1987 | Deboeck |
| 5,164,381 | A | 11/1992 | Wachter et al. |
| 5,242,942 | A | 9/1993 | Costanzo et al. |
| 5,384,327 | A | 1/1995 | Costanzo et al. |
| 6,083,969 | A | 7/2000 | Ferro et al. |
| 2004/0138315 | A1 | 7/2004 | Travis |
| 2005/0101592 | A1 | 5/2005 | Carpino et al. |
| 2005/0131000 | A1 | 6/2005 | Newcombe et al. |
| 2005/0137197 | A1 | 6/2005 | Lange et al. |
| 2008/0249154 | A1 | 10/2008 | Ohmoto et al. |

FOREIGN PATENT DOCUMENTS

| | | |
|---|---|---|
| WO | WO 01/32629 A1 | 5/2001 |
| WO | WO 01/32663 A2 | 5/2001 |
| WO | WO 2005/095353 A1 | 10/2005 |
| WO | WO 2006/030124 | 6/2006 |
| WO | WO 2007/038036 A1 | 4/2007 |

OTHER PUBLICATIONS

Isomers [online], [retrieved on Mar. 11, 2007]. Retrieved from the Internet, URL; http ://chemed.chem.purdue.edu/genchem/topicreview/bp/ I organic/isomers.html>.*
Prodrug [online], [retrieved on Mar. 11, 2007]. Retrieved from the Internet, URL; http:llen.wikipedia.orglwikilProdrug>.*
Barth, et al. Document No. 144:312083 (2006), retrieved from CAPLUS.*
Cancer and Metastasis Reviews (1998), 17(1), 91-106.*
Science (1999), vol. 286, 531-537.*
Cancer [online], [retrieved on Jun. 7, 2007]. Retrieved from the internet, URL http://www.nlm.nih.gov/medlineplus/cancer.html>.*
Cancer [online], [retrieved on Jun. 7, 2007]. Retrieved from the internet, URL; http://en.wikipedia.orglwikilCancer.*
IUPAC Recommendations for Fundamental Stereochemistry (Section E), *Pure Appl. Chem.*, 1976, 45:13-30.
Rinaldi-Carmona, M., Calandra, B., Shire, D., Bouaboula, M., Oustric, D., Barth, F., Casellas, P., Ferrara, P. and Le Fur, G. (1996) *J. Pharmacol. Exp. Ther.*, 278: 871-878.
Munro, S., Thomas, K.L. and Abu-Shaar, M. (1993) *Nature*, 365: 61-65.
Kimball E.S., Palmer J.M., D'Andrea M.R., Hornby P.J. and Wade P.R., Acute colitis induction by oil of mustard results in later development of an IBS-like accelerated upper GI transit in mice, *Am. J. Physiol. Gastrointest. Liver Physiol.*, 2005, 288: G1266-1273.
Blumberg R.S., Saubermann L.J. and Strober W., Animal models of mucosal inflammation and their relation to human inflammatory bowel disease, *Current Opinion in Immunology*, 1999, vol. 11: 648-656.
Egger B., Bajaj-Elliott M., MacDonald T.T., Inglin R., Eysselein, V.E. and Buchler M.W., Characterization of acute murine dextran sodium sulphate colitis: Cytokine profile and dose dependency, *Digestion*, 2000, vol. 62: 240-248.
Stevceva L., Pavli P., Husband A.J. and Doe, W.F., The inflammatory infiltrate in the acute stage of the dextran sulphate sodium induced colitis: B cell response differs depending on the percentage of DSS used to induce it, *BMC Clinical Pathology*, 2001, vol. 1: 3-13.
Diaz-Granados, Howe K., Lu J. and McKay D.M., Dextran sulfate sodium-induced colonic histopathology, but not altered epithelial ion transport, is reduced by inhibition of phosphodiesterase activity, *Amer. J. Pathology*, 2000, vol. 156: 2169-2177.
Holte, K. and H. Kehlet (2000). "Postoperative ileus: a preventable event." *Br J Surg* 87(11): 1480-93.
Livingston, E. H. and E. P. Passaro (1990) "Postoperative ileus." *Digestive Diseases and Sciences* 35(1): 121-132.
Bauer, A. J., N. T. Schwarz, et al. (2002) "Ileus in critical illness: mechanisms and management." *Curr Opin Crit Care* 8(2): 152-7.

(Continued)

*Primary Examiner* — Shawquia Young
(74) *Attorney, Agent, or Firm* — Thomas J. Dodd

(57) ABSTRACT

This invention is directed to a hexahydro-cycloheptapyrazole cannabinoid modulator compound of formula (I):

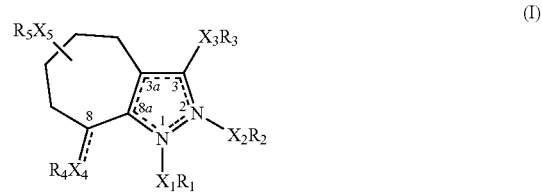

and a method for use in treating, ameliorating or preventing a cannabinoid receptor mediated syndrome, disorder or disease.

1 Claim, No Drawings

OTHER PUBLICATIONS

Mikkelsen, H. B. (1995) "Macrophages in the external muscle layers of mammalian intestines." *Histology and Histopathology* 10: 719-736.

Kalff, J. C., W. H. Schraut, et al. (1998) "Surgical manipulation of the gut elicits an intestinal muscularis inflammatory response resulting in paralytic ileus." *Annals of Surgery* 228: 652-663.

Kalff, Schraut, et al. (1998); Kalff, J. C., N. T. Schwarz, et al. (1998) "Leukocytes of the intestinal muscularis: their phenotype and isolation." *J Leukoc Biol* 63(6): 683-91.

Josephs, M. D., G. Cheng, et al. (1999) "Products of cyclooxygenase-2 catalysis regulate postoperative bowel motility." *J Surg Res* 86(1): 50-4.

Kalff, J. C., T. M. Carlos, et al. (1999) "Surgically induced leukocytic infiltrates within the rat intestinal muscularis mediate postoperative ileus." *Gastroenterology* 117: 378-387.

Kalff, J. C., W. H. Schraut, et al. (2000) "Role of inducible nitric oxide synthase in postoperative intestinal smooth muscle dysfunction in rodents." *Gastroenterology* 118(2): 316-27.

Kalff, J. C., N. T. Schwarz, et al. (1997) "Phagocyte activation and infiltration of the intestinal muscularis with impairment of small bowel motility after surgical manipulation." *Langenbecks Archiv für Chirurgie* Suppl.: 425-428.

Wehner, S., N. T. Schwarz, et al. (2005) "Induction of IL-6 within the rodent intestinal muscularis after intestinal surgical stress." *Surgery* 137(4): 436-46.

Kalff, J. C., B. M. Buchholz, et al. (1999) "Biphasic response to gut manipulation and temporal correlation of cellular infiltrates and muscle dysfunction in rat." *Surgery* 126(3): 498-509.

von Ritter, C., R. Be, et al. (1989) "Neutrophilic proteases: mediators of formyl-methionyl-leucyl-phenylalanine-induced ileitis in rats." *Gastroenterology* 97(3): 605-9.

Bielefeldt, K. and J. L. Conklin (1997) "Intestinal motility during hypoxia and reoxygenation in vitro." *Dig Dis Sci* 42(5): 878-84.

International Search Report dated Nov. 10, 2008 for Application No. PCT/US2008/56011.

International Search Report dated Feb. 6, 2007 for Application No. PCT/US2006/036158.

Barth, et al., Document No. 144:312038 retrieved from CAPLUS.

Isomers: (online) retrieved Nov. 3, 2007, Internet URL: http://chemed.chem.purdue.edu/genchem/topicreview/bp/1organic/isomers.html.

Prudrug, (online) retrieved Mar. 11, 2007, from the Internet:URL: http/llen.wikipedia.orglwikiiProdrug.

* cited by examiner

HEXAHYDRO-CYCLOHEPTAPYRAZOLE CANNABINOID MODULATORS

CROSS REFERENCE TO RELATED APPLICATIONS

This present application is a continuation-in-part application claiming benefit of U.S. Provisional Patent Application Ser. No. 60/720,253, filed Sep. 23, 2005, and U.S. patent application Ser. No. 11/522,771, filed Sep. 18, 2006, now abandoned which are incorporated herein by reference in their entirety and for all purposes.

FIELD OF THE INVENTION

This invention is directed to hexahydro-cycloheptapyrazole cannabinoid (CB) modulator compounds and a method for use in treating, ameliorating or preventing a cannabinoid receptor mediated syndrome, disorder or disease.

BACKGROUND OF THE INVENTION

Before the discovery of the cannabinoid CB1 and CB2 receptors, the term cannabinoid was used to describe the biologically active components of *cannabis sativa*, the most abundant of which are delta-9-tetrahydrocannabinol (THC) and cannabidiol.

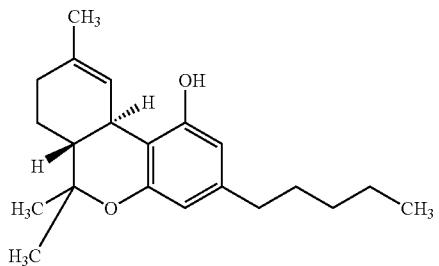

THC

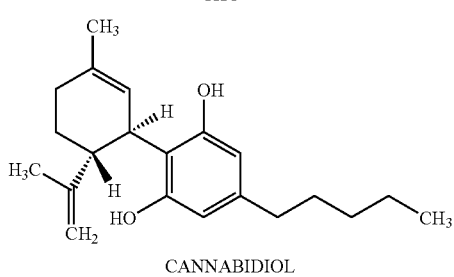

CANNABIDIOL

THC is a moderately potent partial agonist of the CB1 and CB2 receptors and is considered the "classical cannabinoid," a term now used to refer to other analogues and derivatives that are structurally related to the tricyclic dibenzopyran THC core. The term "nonclassical cannabinoid" refers to cannabinoid agonists structurally related to cannabidiol.

Pharmacological investigations have concentrated on selective CB receptor modulators of the pyrazole structural class, which include SR 141716A (the monohydrochloride salt of SR 141716) and SR 144528.

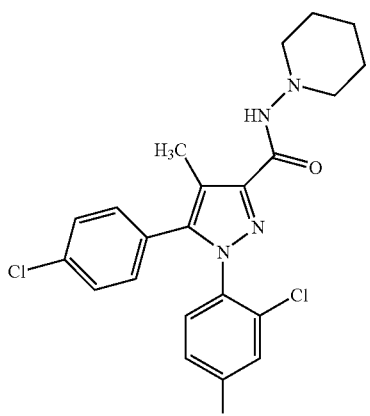

SR 141716

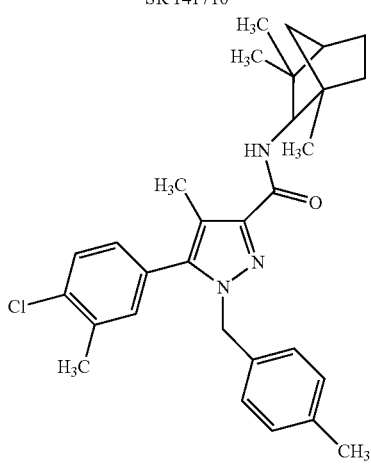

SR 144528

Pyrazole cannabinoid modulators are one among the many different structural classes which have aided the development of CB pharmacology, have helped to determine the biological effects mediated by the cannabinoid receptors, will lead to further refinement of current compounds and will be a source of new chemical classes in the future.

Certain compounds (including SR 141716, SR 144528 and the like) that were originally classified as selective antagonists are now considered to act as "inverse agonists" rather than pure antagonists. Inverse agonists have the ability to decrease the constitutive level of receptor activation in the absence of an agonist instead of only blocking the activation induced by agonist binding at the receptor. The constitutive activity of CB receptors has important implications since there is a level of continuous signaling by both CB1 and CB2 even in the absence of an agonist. For example, SR 141716A increases CB1 protein levels and sensitizes cells toward agonist action, thus indicating that inverse agonists may be another class of ligands used to modulate the endocannabinoid system and the downstream signaling pathways activated by CB receptors.

PCT Application WO2006/030124 describes pyrazole derivatives as CB1 or CB2 receptor agonists.

Advances in the synthesis of CB and cannabimimetic ligands have furthered the development of receptor pharmacology and provided evidence for the existence of additional cannabinoid receptor sub-types. However, there remains an ongoing need for the identification and development of CB1

DETAILED DESCRIPTION OF THE INVENTION

This invention is directed to a compound of formula (I):

$$\text{(I)}$$

or a salt, isomer, prodrug, metabolite or polymorph thereof wherein the dashed lines between positions 2-3 and positions 3a-8a in formula (I) represent locations for each of two double bonds present when $X_1R_1$ is present;

the dashed lines between positions 3-3a and positions 8a-1 in formula (I) represent locations for each of two double bonds present when $X_2R_2$ is present;

the dashed line between position 8 and $X_4R_4$ in formula (I) represents the location for a double bond;

$X_1$ is absent or lower alkylene;

$X_2$ is absent or lower alkylene;

wherein only one of $X_1R_1$ and $X_2R_2$ are present;

$X_3$ is absent, lower alkylene, lower alkylidene or —NH—;

when the dashed line between position 8 and $X_4R_4$ is absent, $X_4$ is absent, or is lower alkylene;

when the dashed line between position 8 and $X_4R_4$ is present, $X_4$ is absent;

$X_5$ is absent or lower alkylene;

$R_1$ is selected from hydrogen, alkyl (optionally substituted at one or more positions by halogen, hydroxy or lower alkoxy), lower alkyl-sulfonyl, aryl, $C_3$-$C_{12}$ cycloalkyl or heterocyclyl, wherein aryl, $C_3$-$C_{12}$ cycloalkyl or heterocyclyl are each optionally substituted at one or more positions by halogen, aminosulfonyl, lower alkyl-aminosulfonyl, alkyl (optionally substituted at one or more positions by halogen, hydroxy or lower alkoxy), hydroxy or lower alkoxy (optionally substituted at one or more positions by halogen or hydroxy);

$R_2$ is selected from hydrogen, alkyl (optionally substituted at one or more positions by halogen, hydroxy or lower alkoxy), lower alkyl-sulfonyl, aryl, $C_3$-$C_{12}$ cycloalkyl or heterocyclyl, wherein aryl, $C_3$-$C_{12}$ cycloalkyl or heterocyclyl are each optionally substituted at one or more positions by halogen, aminosulfonyl, lower alkyl-aminosulfonyl, alkyl (optionally substituted at one or more positions by halogen, hydroxy or lower alkoxy), hydroxy or lower alkoxy (optionally substituted at one or more positions by halogen or hydroxy);

$R_3$ is —C(O)—$Z_1(R_6)$, —$SO_2$—$NR_7$—$Z_2(R_8)$ or —C(O)—$NR_9$—$Z_3(R_{10})$:

when the dashed line between position 8 and $X_4R_4$ is absent, $X_4$ is absent or lower alkylene and $R_4$ is hydroxy, lower alkoxy, halogen, aryl, $C_3$-$C_{12}$ cycloalkyl or heterocyclyl, wherein aryl, $C_3$-$C_{12}$ cycloalkyl or heterocyclyl are each optionally substituted at one or more positions by hydroxy, oxo, lower alkyl (optionally substituted at one or more positions by halogen, hydroxy or lower alkoxy), lower alkoxy (optionally substituted at one or more positions by halogen or hydroxy) or halogen;

when the dashed line between position 8 and $X_4R_4$ is present, $X_4$ is absent and $R_4$ is CH-aryl or CH-heterocyclyl, wherein aryl or heterocyclyl are each optionally substituted at one or more positions by hydroxy, oxo, lower alkyl (optionally substituted at one or more positions by halogen, hydroxy or lower alkoxy), lower alkoxy (optionally substituted at one or more positions by halogen or hydroxy) or halogen;

$R_5$ is hydrogen, hydroxy, oxo, halogen, amino, lower alkyl-amino, alkyl (optionally substituted at one or more positions by halogen, hydroxy or lower alkoxy), lower alkoxy (optionally substituted at one or more positions by halogen or hydroxy), carboxy, carbonylalkoxy, carbamoyl, carbamoylalkyl, aryl, aryloxy, arylalkoxy or heterocyclyl;

$R_6$ is aryl, $C_3$-$C_{12}$ cycloalkyl or heterocyclyl each optionally substituted by one or more hydroxy, oxo, halogen, amino, lower alkyl-amino, alkyl (optionally substituted at one or more positions by halogen, hydroxy or lower alkoxy), lower alkoxy (optionally substituted at one or more positions by halogen or hydroxy), carboxy, carbonylalkoxy, carbamoyl, carbamoylalkyl, aryl, aryloxy, arylalkoxy or heterocyclyl;

$R_7$ is hydrogen or lower alkyl;

$R_8$ is hydrogen, aryl, $C_3$-$C_{12}$ cycloalkyl or heterocyclyl, wherein aryl, $C_3$-$C_{12}$ cycloalkyl or heterocyclyl are each optionally substituted by one or more hydroxy, oxo, halogen, amino, lower alkyl-amino, alkyl (optionally substituted at one or more positions by halogen, hydroxy or lower alkoxy), lower alkoxy (optionally substituted at one or more positions by halogen or hydroxy), carboxy, carbonylalkoxy, carbamoyl, carbamoylalkyl, aryl, aryloxy, arylalkoxy or heterocyclyl;

$R_9$ is hydrogen or lower alkyl;

$R_{10}$ is hydrogen, aryl, $C_3$-$C_{12}$ cycloalkyl or heterocyclyl, wherein aryl, $C_3$-$C_{12}$ cycloalkyl or heterocyclyl are each optionally substituted by one or more hydroxy, oxo, halogen, amino, lower alkyl-amino, alkyl (optionally substituted at one or more positions by halogen, hydroxy or lower alkoxy), lower alkoxy (optionally substituted at one or more positions by halogen or hydroxy), carboxy, carbonylalkoxy, carbamoyl, carbamoylalkyl, aminosulfonyl, lower alkyl-aminosulfonyl, aryl, aryloxy, arylalkoxy or heterocyclyl;

$Z_1$ and $Z_2$ are each absent or alkyl; and, $Z_3$ is absent, —NH—, —$SO_2$— or alkyl (wherein alkyl is optionally substituted at one or more positions by halogen, hydroxy, lower alkyl, lower alkoxy, carboxy or carbonylalkoxy).

An example of the present invention is a compound of formula (I) or a salt, isomer, prodrug, metabolite or polymorph thereof wherein $X_1$ is absent and $R_1$ is selected from hydrogen, alkyl, lower alkyl-sulfonyl, aryl, $C_3$-$C_{12}$ cycloalkyl or heterocyclyl, wherein aryl or heterocyclyl are each optionally substituted at one or more positions by halogen, aminosulfonyl or alkyl (optionally substituted at one or more positions by halogen).

An example of the present invention is a compound of formula (I) or a salt, isomer, prodrug, metabolite or polymorph thereof wherein $R_3$ is —C(O)—$Z_1(R_6)$; $X_3$ is absent or lower alkylidene; $Z_1$ is absent or alkyl; and, $R_6$ is heterocyclyl optionally substituted by one or more hydroxy, halogen, amino, lower alkyl-amino, alkyl (optionally substituted at one or more positions by halogen, hydroxy or lower alkoxy), lower alkoxy (optionally substituted at one or more positions by halogen or hydroxy), carboxy, carbonylalkoxy, carbamoyl, carbamoylalkyl, aryl, aryloxy, arylalkoxy or heterocyclyl.

An example of the present invention is a compound of formula (I) or a salt, isomer, prodrug, metabolite or polymorph thereof wherein $R_3$ is —C(O)—$R_6$; $X_3$ is absent; and, $R_6$ is heterocyclyl optionally substituted by one or more aryl or heterocyclyl.

An example of the present invention is a compound of formula (I) or a salt, isomer, prodrug, metabolite or polymorph thereof wherein $R_3$ is —$SO_2$—$NR_7$—$Z_2(R_8)$; $X_3$ is absent or lower alkylidene; $R_7$ is hydrogen or lower alkyl; $Z_2$ is absent or alkyl; and, $R_8$ is aryl, $C_3$-$C_{12}$ cycloalkyl or heterocyclyl.

An example of the present invention is a compound of formula (I) or a salt, isomer, prodrug, metabolite or polymorph thereof wherein $R_3$ is —$SO_2$—NH—$Z_2(R_8)$; $X_3$ is absent or lower alkylidene; $Z_2$ is absent or alkyl; and, $R_8$ is aryl, $C_3$-$C_{12}$ cycloalkyl or heterocyclyl.

An example of the present invention is a compound of formula (I) or a salt, isomer, prodrug, metabolite or polymorph thereof wherein $R_3$ is —C(O)—$NR_9$—$Z_3(R_{10})$; $X_3$ is absent or lower alkylidene; $R_9$ is hydrogen or lower alkyl; $Z_3$ is absent, —$SO_2$— or alkyl (wherein alkyl is optionally substituted at one or more positions by halogen, hydroxy or carbonylalkoxy); and, $R_{10}$ is hydrogen, aryl, $C_3$-$C_{12}$ cycloalkyl or heterocyclyl, wherein aryl, $C_3$-$C_{12}$ cycloalkyl or heterocyclyl are each optionally substituted by one or more hydroxy, halogen, alkyl (optionally substituted at one or more positions by halogen), alkoxy, carboxy, carbonylalkoxy, carbamoylalkyl or aminosulfonyl.

An example of the present invention is a compound of formula (I) or a salt, isomer, prodrug, metabolite or polymorph thereof wherein $R_3$ is —C(O)—NH—$Z_3(R_{10})$; $X_3$ is absent or lower alkylidene; $Z_3$ is absent, —$SO_2$— or alkyl (wherein alkyl is optionally substituted at one or more positions by halogen, hydroxy or carbonylalkoxy); and, $R_{10}$ is hydrogen, aryl, $C_3$-$C_{12}$ cycloalkyl or heterocyclyl, wherein aryl, $C_3$-$C_{12}$ cycloalkyl or heterocyclyl are each optionally substituted by one or more hydroxy, halogen, alkyl (optionally substituted at one or more positions by halogen), alkoxy, carboxy, carbonylalkoxy, carbamoylalkyl or aminosulfonyl.

An example of the present invention is a compound of formula (I) or a salt, isomer, prodrug, metabolite or polymorph thereof wherein $R_3$ is —C(O)—NH—$Z_3(R_{10})$; $X_3$ is absent or lower alkylidene; $Z_3$ is absent, —$SO_2$— or alkyl (wherein alkyl is optionally substituted at one or more positions by halogen, hydroxy or carbonylalkoxy); and, $R_{10}$ is aryl optionally substituted by one or more hydroxy, halogen, alkyl (optionally substituted at one or more positions by halogen), alkoxy or aminosulfonyl.

An example of the present invention is a compound of formula (I) or a salt, isomer, prodrug, metabolite or polymorph thereof wherein $R_3$ is —C(O)—NH—$Z_3(R_{10})$; $X_3$ is absent or lower alkylidene; $Z_3$ is absent, —$SO_2$— or alkyl (wherein alkyl is optionally substituted at one or more positions by halogen, hydroxy or carbonylalkoxy); and, $R_{10}$ is hydrogen or $C_3$-$C_{12}$ cycloalkyl, wherein $C_3$-$C_{12}$ cycloalkyl is optionally substituted by one or more hydroxy, alkyl, alkoxy, carboxy, carbonylalkoxy or carbamoylalkyl.

An example of the present invention is a compound of formula (I) or a salt, isomer, prodrug, metabolite or polymorph thereof wherein $R_3$ is —C(O)—NH—$Z_3(R_{10})$; $X_3$ is absent or lower alkylidene; $Z_3$ is absent, —$SO_2$— or alkyl (wherein alkyl is optionally substituted at one or more positions by halogen, hydroxy or carbonylalkoxy); and, $R_{10}$ is hydrogen or heterocyclyl, wherein heterocyclyl is optionally substituted by one or more carbonylalkoxy.

An example of the present invention is a compound of formula (I) or a salt, isomer, prodrug, metabolite or polymorph thereof wherein the dashed line between position 8 and $X_4R_4$ is absent, $X_4$ is absent or lower alkylene and $R_4$ is aryl optionally substituted at one or more positions by lower alkyl or halogen.

An example of the present invention is a compound of formula (I) or a salt, isomer, prodrug, metabolite or polymorph thereof wherein the dashed line between position 8 and $X_4R_4$ is present, $X_4$ is absent and $R_4$ is CH-aryl or CH-heterocyclyl, wherein aryl or heterocyclyl are each optionally substituted at one or more positions by lower alkoxy or halogen.

An example of the present invention is a compound of formula (I) or a salt, isomer, prodrug, metabolite or polymorph thereof wherein $X_5$ is absent and $R_5$ is hydrogen.

An example of the present invention is a compound of formula (Ia)

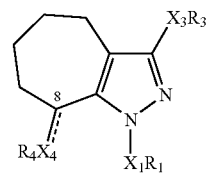

(I)

or a salt, isomer, prodrug, metabolite or polymorph thereof wherein $X_1$ is absent or lower alkylene; $X_3$ is absent or lower alkylidene; $X_4$ is absent or is lower alkylene when the dashed line between position 8 and $X_4R_4$ is absent; $X_4$ is absent when the dashed line between position 8 and $X_4R_4$ is present; $R_1$ is selected from hydrogen, alkyl, lower alkyl-sulfonyl, aryl, $C_3$-$C_{12}$ cycloalkyl or heterocyclyl, wherein aryl or heterocyclyl are each optionally substituted at one or more positions by halogen, aminosulfonyl or alkyl (optionally substituted at one or more positions by halogen); $R_3$ is —C(O)—($R_6$), —$SO_2$—NH—$Z_2(R_8)$ or —C(O)—NH—$Z_3(R_{10})$; when the dashed line between position 8 and $X_4R_4$ is absent, $R_4$ is aryl, wherein aryl is optionally substituted at one or more positions by lower alkyl or halogen; when the dashed line between position 8 and $X_4R_4$ is present, $R_4$ is CH-aryl or CH-heterocyclyl, wherein aryl or heterocyclyl are each optionally substituted at one or more positions by lower alkoxy or halogen; $R_6$ is heterocyclyl optionally substituted by one or more aryl or heterocyclyl; $Z_2$ is absent or alkyl; $R_8$ is aryl, $C_3$-$C_{12}$ cycloalkyl or heterocyclyl; $Z_3$ is absent, —$SO_2$— or alkyl (wherein alkyl is optionally substituted at one or more positions by halogen, hydroxy or carbonylalkoxy); and, $R_{10}$ is hydrogen, aryl, $C_3$-$C_{12}$ cycloalkyl or heterocyclyl, wherein aryl, $C_3$-$C_{12}$ cycloalkyl or heterocyclyl are each optionally substituted by one or more hydroxy, halogen, alkyl (optionally substituted at one or more positions by halogen), alkoxy, carboxy, carbonylalkoxy, carbamoylalkyl or aminosulfonyl.

An example of the present invention is a compound of formula (Ia) or a salt, isomer, prodrug, metabolite or polymorph thereof wherein $X_1$ is absent or lower alkylene; $X_3$ is absent or lower alkylidene; $X_4$ is absent or is lower alkylene when the dashed line between position 8 and $X_4R_4$ is absent; $X_4$ is absent when the dashed line between position 8 and $X_4R_4$ is present; $R_1$ is selected from hydrogen or alkyl; $R_3$ is —$SO_2$—NH—$Z_2(R_8)$ or —C(O)—NH—$Z_3(R_{10})$; when the dashed line between position 8 and $X_4R_4$ is absent, $R_4$ is aryl, wherein aryl is optionally substituted at one or more positions by lower alkyl or halogen; when the dashed line between position 8 and $X_4R_4$ is present, $R_4$ is CH-aryl or CH-heterocyclyl, wherein aryl or heterocyclyl are each optionally substituted at one or more positions by lower alkoxy or halogen; $Z_2$ is absent or alkyl; $R_8$ is aryl or heterocyclyl; $Z_3$ is absent or alkyl (wherein alkyl is optionally substituted at one or more positions by halogen, hydroxy or carbonylalkoxy); and, $R_{10}$ is aryl or heterocyclyl, wherein aryl or heterocyclyl are each optionally substituted by one or more hydroxy, halogen, alkyl (optionally substituted at one or more positions by halogen), alkoxy or carbonylalkoxy.

An example of the present invention is a compound of formula (Ia) or a salt, isomer, prodrug, metabolite or polymorph thereof wherein $X_1R_1$, $X_3R_3$ and $X_4R_4$ are dependently selected from

| Cpd | $X_1R_1$ | $X_3R_3$ | $X_4R_4$ |
|---|---|---|---|
| 1 | 4-F-benzyl | C(O)NH-1,3,3-$(CH_3)_3$-bicyclo[2.2.1]hept-2-yl | 4-$CH_3$-benzyl |
| 2 | cyclohexyl | C(O)NH-(2S)-1,3,3-$(CH_3)_3$-bicyclo[2.2.1]hept-2-yl | 4-Cl-benzyl |
| 3 | 2,4-$Cl_2$-phenyl | (E)-$(CH)_2SO_2NH$—CH(phenyl)-(S)-$CH_3$ | 3-Cl-benzyl |
| 4 | cyclohexyl | C(O)NH-(2S)-1,3,3-$(CH_3)_3$-bicyclo[2.2.1]hept-2-yl | 3-Cl-benzyl |
| 5 | cyclohexyl | C(O)NH—CH(phenyl)-(S)-$CH_3$ | 4-Cl-benzyl |
| 6 | cyclohexyl | C(O)NH—CH(phenyl)-(R)-$CH_3$ | 4-Cl-benzyl |
| 7 | cyclohexyl | C(O)NH—CH(phenyl)-(S)-$CH_3$ | 3-Cl-benzyl |
| 8 | cyclohexyl | C(O)NH—CH(phenyl)-(R)-$CH_3$ | 3-Cl-benzyl |
| 9 | cyclohexyl | C(O)NH-hexahydro-2,5-methano-pentalen-3a-yl | 3-Cl-benzyl |
| 10 | cyclohexyl | C(O)NH—CH(adamantan-1-yl)-$CH_3$ | 3-Cl-benzyl |
| 11 | cyclohexyl | C(O)NH-(2S)-1,3,3-$(CH_3)_3$-bicyclo[2.2.1]hept-2-yl | 2-Cl-benzyl |
| 12 | cyclohexyl | C(O)NH-adamantan-2-yl | 3-Cl-benzyl |
| 13 | cyclohexyl | C(O)NH-adamantan-2-yl | 2-Cl-benzyl |
| 14 | 2,4-$Cl_2$-phenyl | C(O)NH-(2S)-1,3,3-$(CH_3)_3$-bicyclo[2.2.1]hept-2-yl | 4-Cl-benzyl |
| 15 | 2,4-$Cl_2$-phenyl | C(O)NH-(2S)-1,3,3-$(CH_3)_3$-bicyclo[2.2.1]hept-2-yl | 3-Cl-benzyl |
| 16 | cyclohexyl | C(O)NH-adamantan-2-yl | 4-Cl-benzyl |
| 17 | 2,4-$Cl_2$-phenyl | C(O)NH-adamantan-2-yl | 3-Cl-benzyl |
| 18 | 2,4-$Cl_2$-phenyl | C(O)NH-adamantan-2-yl | 4-Cl-benzyl |
| 19 | cyclohexyl | C(O)NH-adamantan-1-yl | 3-Cl-benzyl |
| 20 | cyclohexyl | C(O)NH-adamantan-1-yl | 4-Cl-benzyl |
| 21 | cyclohexyl | C(O)NH-adamantan-1-yl | 2-Cl-benzyl |
| 22 | 2,4-$Cl_2$-phenyl | C(O)NH-adamantan-1-yl | 3-Cl-benzyl |
| 23 | cyclohexyl | C(O)NH-cyclobutyl | 2-Cl-benzyl |
| 24 | 2,4-$Cl_2$-phenyl | C(O)NH-cyclobutyl | 3-Cl-benzyl |
| 25 | 2,4-$Cl_2$-phenyl | C(O)NH-cyclobutyl | 4-Cl-benzyl |
| 26 | 2,4-$Cl_2$-phenyl | C(O)NH-4-$CF_3$-benzyl | 4-Cl-benzyl |
| 27 | 2,4-$Cl_2$-phenyl | C(O)NH-piperidin-1-yl | 4-Cl-benzyl |
| 28 | 2,4-$Cl_2$-phenyl | C(O)NH-piperidin-1-yl | 3-Cl-benzyl |
| 29 | 4-Cl-benzyl | C(O)NH-cyclobutyl | 3-Cl-benzyl |
| 30 | 4-Cl-benzyl | C(O)NH-cyclobutyl | 4-Cl-benzyl |
| 31 | cyclohexyl | C(O)NH-cyclopropyl | 2-Cl-benzyl |
| 32 | cyclohexyl | C(O)NH-cyclopropyl | 3-Cl-benzyl |
| 33 | cyclohexyl | C(O)NH-cyclopropyl | 4-Cl-benzyl |
| 34 | 4-Cl-benzyl | C(O)NH-cyclopropyl | 4-Cl-benzyl |
| 35 | 4-Cl-benzyl | C(O)NH-cyclopropyl | 3-Cl-benzyl |
| 36 | cyclohexyl | C(O)NH-cyclobutyl | 3-Cl-benzyl |
| 37 | cyclohexyl | C(O)NH-cyclobutyl | 4-Cl-benzyl |
| 38 | 2,4-$Cl_2$-phenyl | C(O)NH-cyclopropyl | 4-Cl-benzyl |
| 39 | $CH_3$ | C(O)NH-cyclobutyl | 2-Cl-benzyl |
| 40 | $CH_3$ | C(O)NH-(2S)-1,3,3-$(CH_3)_3$-bicyclo[2.2.1]hept-2-yl | 2-Cl-benzyl |
| 41 | 2,4-$Cl_2$-phenyl | C(O)NH-cyclobutyl | 3-F-benzyl |
| 42 | 2,4-$Cl_2$-phenyl | C(O)NH-(2S)-1,3,3-$(CH_3)_3$-bicyclo[2.2.1]hept-2-yl | 3-F-benzyl |
| 43 | cyclohexyl | C(O)NH-cyclobutyl | 3-F-benzyl |
| 44 | cyclohexyl | C(O)NH-(2S)-1,3,3-$(CH_3)_3$-bicyclo[2.2.1]hept-2-yl | 3-F-benzyl |
| 45 | cyclohexyl | C(O)NH—CH(phenyl)-(S)-$CH_3$ | 3-F-benzyl |
| 46 | cyclohexyl | C(O)NH-1-$CO_2C(CH_3)_3$-piperidin-4-yl | 3-F-benzyl |
| 47 | benzyl | C(O)NH-(2S)-1,3,3-$(CH_3)_3$-bicyclo[2.2.1]hept-2-yl | phenyl |
| 48 | benzyl | C(O)NH—CH(phenyl)-(S)-$CH_3$ | phenyl |
| 49 | cyclohexyl | C(O)NH-cyclopropyl | 3-F-benzyl |
| 50 | cyclohexyl | C(O)NH-piperidin-1-yl | 3-F-benzyl |
| 51 | cyclohexyl | C(O)NH-cyclohexyl | 3-F-benzyl |
| 52 | cyclohexyl | C(O)NH-cyclopentyl | 3-F-benzyl |
| 53 | cyclohexyl | C(O)NH-benzyl | 3-F-benzyl |
| 54 | cyclohexyl | C(O)-4-phenyl-piperazin-1-yl | 3-F-benzyl |
| 55 | cyclohexyl | C(O)NH—CH(phenyl)-(R)-$CH_2OH$ | 3-F-benzyl |
| 56 | cyclohexyl | C(O)NH-cyclopropyl | 4-F-benzyl |

-continued

| Cpd | $X_1R_1$ | $X_3R_3$ | $X_4R_4$ |
|---|---|---|---|
| 57 | cyclohexyl | C(O)NH-cyclobutyl | 4-F-benzyl |
| 58 | cyclohexyl | C(O)NH-(2S)-1,3,3-$(CH_3)_3$-bicyclo[2.2.1]hept-2-yl | 4-F-benzyl |
| 59 | cyclohexyl | C(O)NH-cyclopentyl | 4-F-benzyl |
| 60 | cyclohexyl | C(O)-4-phenyl-piperazin-1-yl | 4-F-benzyl |
| 61 | cyclohexyl | C(O)NH-benzyl | 4-F-benzyl |
| 62 | cyclohexyl | C(O)NH-piperidin-1-yl | 4-F-benzyl |
| 63 | cyclohexyl | C(O)NH—(S—CH)(4-F-benzyl)-$CO_2CH_3$ | 4-F-benzyl |
| 64 | cyclohexyl | C(O)NH—CH(phenyl)-(S)-$CH_3$ | 4-F-benzyl |
| 65 | cyclohexyl | C(O)NH-4-$CF_3$-benzyl | 4-F-benzyl |
| 66 | cyclohexyl | C(O)NH—CH(phenyl)-(R)-$CH_2OH$ | (R*)-4-F-benzyl |
| 67 | cyclohexyl | C(O)NH—CH(phenyl)-(R)-$CH_2OH$ | (S*)-4-F-benzyl |
| 68 | benzyl | C(O)NH-piperidin-1-yl | phenyl |
| 69 | benzyl | C(O)NH-3-$CF_3$-benzyl | phenyl |
| 70 | 2,4-$Cl_2$-phenyl | C(O)NH-cyclobutyl | 4-F-benzyl |
| 71 | 2,4-$Cl_2$-phenyl | C(O)NH-(2S)-1,3,3-$(CH_3)_3$-bicyclo[2.2.1]hept-2-yl | 4-F-benzyl |
| 72 | 2,4-$Cl_2$-phenyl | C(O)NH—(S—CH)(4-F-benzyl)-$CO_2CH_3$ | 4-F-benzyl |
| 73 | cyclohexyl | C(O)NH—(S—CH)(4-F-benzyl)-$CO_2CH_3$ | 3-F-benzyl |
| 74 | cyclohexyl | C(O)NH-(2S,3R)-2-$CO_2CH_2CH_3$-bicyclo[2.2.1]hept-5-en-3-yl | 3-F-benzyl |
| 75 | cyclohexyl | (E)-$(CH)_2SO_2NH$—CH(phenyl)-(S)-$CH_3$ | 3-F-benzyl |
| 76 | 2,4-$Cl_2$-phenyl | C(O)NH—CH(phenyl)-(S)-$CH_3$ | 4-Cl-benzyl |
| 77 | 2,4-$Cl_2$-phenyl | C(O)NH—CH[(R)-4-F-benzyl]-$CO_2CH_3$ | (R*)-3-F-benzyl |
| 78 | 2,4-$Cl_2$-phenyl | C(O)NH—CH[(R)-4-F-benzyl]-$CO_2CH_3$ | (S*)-3-F-benzyl |
| 79 | 2,4-$Cl_2$-phenyl | C(O)NH-(2S,3R)-2-$CO_2CH_2CH_3$-bicyclo[2.2.1]hept-5-en-3-yl | 3-F-benzyl |
| 80 | 2,4-$Cl_2$-phenyl | C(O)NH—(R—CH)(4-OH-benzyl)-$CO_2CH_3$ | 3-F-benzyl |
| 81 | 2,4-$Cl_2$-phenyl | C(O)NH—(R—CH)(4-OH-benzyl)-$CO_2CH_3$ | 4-F-benzyl |
| 82 | cyclohexyl | C(O)NH—(R—CH)(4-OH-benzyl)-$CO_2CH_3$ | 3-F-benzyl |
| 83 | cyclohexyl | C(O)NH—(R—CH)(4-OH-benzyl)-$CO_2CH_3$ | 4-F-benzyl |
| 84 | 2,4-$Cl_2$-phenyl | C(O)NH-piperidin-1-yl | 3-F-benzyl |
| 85 | 2,4-$Cl_2$-phenyl | C(O)NH-piperidin-1-yl | 4-F-benzyl |
| 86 | benzyl | C(O)NH—$CH_2CF_3$ | phenyl |
| 87 | benzyl | C(O)NH—CH(4-F-benzyl)-(R)-$CO_2CH_3$ | phenyl |
| 88 | cyclohexyl | C(O)NH-(2S,3R)-2-$CO_2CH_2CH_3$-bicyclo[2.2.1]hept-5-en-3-yl | 4-F-benzyl |
| 89 | cyclohexyl | C(O)NH-morpholin-4-yl | 4-F-benzyl |
| 90 | cyclohexyl | C(O)NH-morpholin-4-yl | 3-F-benzyl |
| 91 | 2,4-$Cl_2$-phenyl | C(O)NH-morpholin-4-yl | 3-F-benzyl |
| 92 | 2,4-$F_2$-phenyl | C(O)NH-(2S)-1,3,3-$(CH_3)_3$-bicyclo[2.2.1]hept-2-yl | 3-F-benzyl |
| 93 | 2,4-$F_2$-phenyl | (E)-$(CH)_2SO_2NH$—CH(phenyl)-(S)-$CH_3$ | 3-F-benzyl |
| 94 | 2,4-$F_2$-phenyl | (E)-$(CH)_2SO_2NH$—CH(cyclohexyl)-(S)-$CH_3$ | 3-F-benzyl |
| 95 | 2,4-$F_2$-phenyl | C(O)NH—CH[(R)-4-OH-benzyl]-$CO_2CH_3$ | 3-F-benzyl |
| 96 | H | (E)-$(CH)_2SO_2NH$—CH(phenyl)-(S)-$CH_3$ | 3-F-benzyl |
| 97 | 2,4-$F_2$-phenyl | C(O)NH-(2S)-1,3,3-$(CH_3)_3$-bicyclo[2.2.1]hept-2-yl | 4-F-benzyl |
| 98 | 2,4-$F_2$-phenyl | C(O)NH—CH[(R)-4-OH-benzyl]-$CO_2CH_3$ | 4-F-benzyl |
| 99 | 2,4-$F_2$-phenyl | C(O)NH-(2S,3R)-2-$CO_2CH_2CH_3$-bicyclo[2.2.1]hept-5-en-3-yl | 3-F-benzyl |
| 100 | 2,4-$F_2$-phenyl | C(O)NH-(1R,2S)-2-OH-indan-1-yl | 3-F-benzyl |
| 101 | $CH_3$ | (E)-$(CH)_2SO_2NH$—CH(phenyl)-(S)-$CH_3$ | 4-F-benzyl |
| 102 | 2,4-$Cl_2$-phenyl | C(O)NH—CH[(R)-4-OH-benzyl]-$CO_2CH_3$ | 3-Cl-benzyl |
| 103 | 2,4-$Cl_2$-phenyl | C(O)NH—CH[(R)-4-F-benzyl]-$CO_2CH_3$ | 3-Cl-benzyl |
| 104 | $CH_3$ | (E)-$(CH)_2SO_2NH$—CH(phenyl)-(S)-$CH_3$ | 3-F-benzyl |
| 105 | cyclohexyl | C(O)NH-(2R,3S)-2-$CO_2CH_2CH_3$-bicyclo[2.2.1]hept-3-yl | 3-F-benzyl |
| 106 | cyclohexyl | C(O)NH-(2R,3S)-2-$CO_2CH_2CH_3$-bicyclo[2.2.1]hept-3-yl | 4-F-benzyl |
| 107 | 2,4-$F_2$-phenyl | (E)-$(CH)_2SO_2NH$—CH(phenyl)-(S)-$CH_3$ | 4-F-benzyl |
| 108 | H | (E)-$(CH)_2SO_2NH$—CH(phenyl)-(S)-$CH_3$ | 4-F-benzyl |
| 109 | 2,4-$Cl_2$-phenyl | C(O)NH-(2R,3S)-2-$CO_2CH_2CH_3$-bicyclo[2.2.1]hept-3-yl | 3-Cl-benzyl |

-continued

| Cpd | X₁R₁ | X₃R₃ | X₄R₄ |
|---|---|---|---|
| 110 | 2,4-F₂-phenyl | C(O)NH-(2R,3S)-2-CO₂CH₂CH₃-bicyclo[2.2.1]hept-3-yl | 4-F-benzyl |
| 111 | 2,4-F₂-phenyl | C(O)NH-(2R,3S)-2-CO₂CH₂CH₃-bicyclo[2.2.1]hept-3-yl | 3-F-benzyl |
| 112 | 2,4-Cl₂-phenyl | C(O)NH-(1R,2S)-2-OH-indan-1-yl | (R*)-3-Cl-benzyl |
| 113 | 2,4-Cl₂-phenyl | C(O)NH-(1R,2S)-2-OH-indan-1-yl | (S*)-3-Cl-benzyl |
| 114 | cyclohexyl | C(O)NH-(1R,2S)-2-OH-indan-1-yl | (R*)-3-F-benzyl |
| 115 | cyclohexyl | C(O)NH-(1R,2S)-2-OH-indan-1-yl | (S*)-3-F-benzyl |
| 116 | 2,4-F₂-phenyl | C(O)NH-morpholin-4-yl | 3-F-benzyl |
| 117 | 2,4-Cl₂-phenyl | C(O)NH-morpholin-4-yl | 3-Cl-benzyl |
| 118 | 2,4-F₂-phenyl | C(O)-morpholin-4-yl | 3-F-benzyl |
| 119 | 2,4-F₂-phenyl | C(O)NH-(1R,2S)-2-OH-indan-1-yl | 4-F-benzyl |
| 120 | cyclohexyl | C(O)NH-(1R,2S)-2-OH-indan-1-yl | (R*)-4-F-benzyl |
| 121 | cyclohexyl | C(O)NH-(1R,2S)-2-OH-indan-1-yl | (S*)-4-F-benzyl |
| 122 | 2,4-F₂-phenyl | (E)-(CH)₂SO₂NH-piperidin-1-yl | 4-F-benzyl |
| 123 | 2,4-F₂-phenyl | (E)-(CH)₂SO₂NH-piperidin-1-yl | 3-F-benzyl |
| 124 | CH₃ | (E)-(CH)₂SO₂NH-piperidin-1-yl | 3-F-benzyl |
| 125 | CH₃ | (E)-(CH)₂SO₂NH-morpholin-4-yl | 3-F-benzyl |
| 126 | CH₃ | (E)-(CH)₂SO₂NH-morpholin-4-yl | 4-F-benzyl |
| 127 | 2,4-F₂-phenyl | (E)-(CH)₂SO₂NH-morpholin-4-yl | 4-F-benzyl |
| 128 | CH₃ | (E)-(CH)₂SO₂NH-piperidin-1-yl | 4-F-benzyl |
| 129 | H | C(O)NH-benzyl | 4-F-benzyl |
| 130 | SO₂CH₃ | C(O)NH-benzyl | 4-F-benzyl |
| 131 | 2,4-Cl₂-phenyl | C(O)NH—(R—CH)(phenyl)-CH₃ | (E)-4-Cl-benzylidene |
| 132 | 2,4-Cl₂-phenyl | C(O)NH—(R—CH)(cyclohexyl)-CH₃ | (E)-4-Cl-benzylidene |
| 133 | 2,4-Cl₂-phenyl | C(O)NH-piperidin-1-yl | (E)-4-Cl-benzylidene |
| 134 | 2,4-Cl₂-phenyl | C(O)NH-morpholin-4-yl | (E)-4-Cl-benzylidene |
| 135 | 2,4-Cl₂-phenyl | C(O)NH—CH₂-4-SO₂NH₂-phenyl | (E)-4-Cl-benzylidene |
| 136 | 2,4-Cl₂-phenyl | C(O)NH—SO₂-phenyl | (E)-4-Cl-benzylidene |
| 137 | 2,4-Cl₂-phenyl | C(O)NH—CH(4-Cl-phenyl)-CH₃ | (E)-4-Cl-benzylidene |
| 138 | 2,4-Cl₂-phenyl | C(O)NH—(S—CH)(cyclohexyl)-CH₃ | (E)-4-Cl-benzylidene |
| 139 | 2,4-Cl₂-phenyl | C(O)NH—(S—CH)(phenyl)-CH₃ | (E)-4-Cl-benzylidene |
| 140 | H | C(O)NH—(R—CH)(cyclohexyl)-CH₃ | (E)-4-Cl-benzylidene |
| 141 | H | C(O)NH—(S—CH)(phenyl)-CH₃ | (E)-4-Cl-benzylidene |
| 142 | H | C(O)NH—(R—CH)(phenyl)-CH₃ | (E)-4-Cl-benzylidene |
| 143 | H | C(O)NH—(S—CH)(cyclohexyl)-CH₃ | (E)-4-Cl-benzylidene |
| 144 | H | C(O)NH-piperidin-1-yl | (E)-4-Cl-benzylidene |
| 145 | H | C(O)NH-morpholin-4-yl | (E)-4-Cl-benzylidene |
| 146 | 2,4-Cl₂-phenyl | C(O)NH—(R—CH)(phenyl)-CH₃ | (E)-4-F-benzylidene |
| 147 | 2,4-Cl₂-phenyl | C(O)NH—(R—CH)(cyclohexyl)-CH₃ | (E)-4-F-benzylidene |
| 148 | 2,4-Cl₂-phenyl | C(O)NH—(S—CH)(cyclohexyl)-CH₃ | (E)-4-F-benzylidene |
| 149 | 2,4-Cl₂-phenyl | C(O)NH—(S—CH)(phenyl)-CH₃ | (E)-4-F-benzylidene |
| 150 | 2,4-Cl₂-phenyl | C(O)NH-piperidin-1-yl | (E)-4-F-benzylidene |
| 151 | 2,4-Cl₂-phenyl | C(O)NH-morpholin-4-yl | (E)-4-F-benzylidene |
| 152 | 2,4-Cl₂-phenyl | C(O)NH-pyridin-2-yl | (E)-4-Cl-benzylidene |
| 153 | 2,4-Cl₂-phenyl | C(O)NH-pyridin-4-yl | (E)-4-Cl-benzylidene |
| 154 | 2,4-Cl₂-phenyl | C(O)NH-4-SO₂NH₂-phenyl | (E)-4-Cl-benzylidene |
| 155 | 2,4-Cl₂-phenyl | C(O)NH—CH₂-pyridin-2-yl | (E)-4-Cl-benzylidene |
| 156 | 2,4-Cl₂-phenyl | C(O)NH—CH₂-pyridin-4-yl | (E)-4-Cl-benzylidene |
| 157 | 2,4-Cl₂-phenyl | C(O)NH—(CH₂)₂-pyridin-2-yl | (E)-4-Cl-benzylidene |
| 158 | 2,4-Cl₂-phenyl | C(O)NH—CH(S—CH₂OH)—CH(CH₃)₂ | (R*)3-Cl-benzyl |
| 159 | 2,4-Cl₂-phenyl | C(O)NH—CH(S—CH₂OH)—CH(CH₃)₂ | (S*)-3-Cl-benzyl |
| 160 | H | (E)-(CH)₂SO₂NH—CH(phenyl)-(S)-CH₃ | 3-Cl-benzyl |
| 161 | 2,4-Cl₂-phenyl | C(O)NH—CH(S-phenyl)-CH₂OH | (R*)3-Cl-benzyl |
| 162 | 2,4-Cl₂-phenyl | C(O)NH—CH(S-phenyl)-CH₂OH | (S*)-3-Cl-benzyl |
| 163 | 2,4-Cl₂-phenyl | C(O)NH—CH(R-benzyl)-CH₂OH | 3-Cl-benzyl |
| 164 | H | C(O)NH—CH(S-phenyl)-CH₂OH | 3-Cl-benzyl |
| 165 | H | C(O)NH—CH(R-phenyl)-CH₂OH | 3-Cl-benzyl |
| 166 | H | C(O)NH—CH(S-benzyl)-CH₂OH | 3-Cl-benzyl |
| 167 | H | C(O)NH—CH(R-benzyl)-CH₂OH | 3-Cl-benzyl |
| 168 | 2,4-F₂-phenyl | C(O)NH—CH(S-phenyl)-CH₂OH | 3-F-benzyl |
| 169 | 2,4-F₂-phenyl | C(O)NH—CH(S-phenyl)-CH₂Cl | 3-F-benzyl |
| 170 | pyridin-4-yl | C(O)NH—(R—CH)(phenyl)-CH₃ | (E)-4-Cl-benzylidene |
| 171 | pyridin-4-yl | C(O)NH—(S—CH)(phenyl)-CH₃ | (E)-4-Cl-benzylidene |
| 172 | 2,4-F₂-phenyl | C(O)NH—CH(S-phenyl)-CH₂Cl | 4-F-benzyl |
| 173 | 2,4-F₂-phenyl | C(O)NH—CH(phenyl)-(R)-CH₃ | 3-F-benzyl |
| 174 | cyclohexyl | C(O)NH—CH(phenyl)-(R)-CH₃ | 3-F-benzyl |
| 175 | 4-CF₃-pyrimidin-2-yl | C(O)NH—CH(phenyl)-(R)-CH₃ | 3-Cl-benzyl |
| 176 | 4-CF₃-pyrimidin-2-yl | C(O)NH—CH(phenyl)-(R)-CH₂OH | 3-Cl-benzyl |
| 177 | 7-Cl-quinolin-4-yl | C(O)NH—CH(phenyl)-(R)-CH₃ | 3-Cl-benzyl |
| 178 | 4-CF₃-pyrimidin-2-yl | C(O)NH—CH(phenyl)-(R)-CH₂Cl | 3-Cl-benzyl |
| 179 | 4-CF₃-pyrimidin-2-yl | C(O)NH—CH(phenyl)-(S)-CH₂Cl | 3-Cl-benzyl |
| 180 | pyridin-4-yl | C(O)NH—(R—CH)(cyclohexyl)-CH₃ | (E)-4-Cl-benzylidene |

-continued

| Cpd | X₁R₁ | X₃R₃ | X₄R₄ |
|---|---|---|---|
| 181 | pyridin-4-yl | C(O)NH—(S—CH)(cyclohexyl)-CH₃ | (E)-4-Cl-benzylidene |
| 182 | pyridin-4-yl | C(O)NH-piperidin-1-yl | (E)-4-Cl-benzylidene |
| 183 | pyridin-4-yl | C(O)NH-morpholin-4-yl | (E)-4-Cl-benzylidene |
| 184 | 4-SO₂NH₂-phenyl | C(O)NH—(R—CH)(phenyl)-CH₃ | (E)-4-Cl-benzylidene |
| 185 | 4-SO₂NH₂-phenyl | C(O)NH—(R—CH)(cyclohexyl)-CH₃ | (E)-4-Cl-benzylidene |
| 186 | 4-CF₃-pyrimidin-2-yl | C(O)NH—CH(R-benzyl)-CH₂OH | 3-Cl-benzyl |
| 187 | 4-CF₃-pyrimidin-2-yl | C(O)NH—CH(R-benzyl)-CH₂Cl | 3-Cl-benzyl |
| 188 | 2,4-Cl₂-phenyl | C(O)-2-pyridin-2-yl-pyrrolidin-1-yl | (E)-4-F-benzylidene |
| 189 | 2-Cl-phenyl | C(O)NH—(R—CH)(cyclohexyl)-CH₃ | (E)-4-Cl-benzylidene |
| 190 | 2-Cl-phenyl | C(O)NH—(R—CH)(phenyl)-CH₃ | (E)-4-Cl-benzylidene |
| 191 | 2-Cl-phenyl | C(O)NH—(S—CH)(phenyl)-CH₃ | (E)-4-Cl-benzylidene |
| 192 | 2-Cl-phenyl | C(O)NH—(S—CH)(cyclohexyl)-CH₃ | (E)-4-Cl-benzylidene |
| 193 | 2-Cl-phenyl | C(O)NH-piperidin-1-yl | (E)-4-Cl-benzylidene |
| 194 | 2-Cl-phenyl | C(O)NH-morpholin-4-yl | (E)-4-Cl-benzylidene |
| 195 | 2,5-Cl₂-phenyl | C(O)NH—(R—CH)(phenyl)-CH₃ | (E)-4-Cl-benzylidene |
| 196 | 2,5-Cl₂-phenyl | C(O)NH—(R—CH)(cyclohexyl)-CH₃ | (E)-4-Cl-benzylidene |
| 197 | 2,5-Cl₂-phenyl | C(O)NH—(S—CH)(cyclohexyl)-CH₃ | (E)-4-Cl-benzylidene |
| 198 | 2,5-Cl₂-phenyl | C(O)NH—(S—CH)(phenyl)-CH₃ | (E)-4-Cl-benzylidene |
| 199 | 2,5-Cl₂-phenyl | C(O)NH-piperidin-1-yl | (E)-4-Cl-benzylidene |
| 200 | 2,5-Cl₂-phenyl | C(O)NH-morpholin-4-yl | (E)-4-Cl-benzylidene |
| 201 | 2,5-Cl₂-phenyl | C(O)-morpholin-4-yl | (E)-4-Cl-benzylidene |
| 202 | 2,4-Cl₂-phenyl | C(O)NH—(R—CH)(phenyl)-CH₂CH₃ | (E)-4-F-benzylidene |
| 203 | 2,4-Cl₂-phenyl | C(O)NH—(R—CH)(phenyl)-(S)-CH₂OH | (E)-4-F-benzylidene |
| 204 | 2,4-Cl₂-phenyl | C(O)NH—(S—CH)(phenyl)-CH₂OH | (E)-4-F-benzylidene |
| 205 | 2,4-Cl₂-phenyl | C(O)NH—C[(phenyl)(CH₃)₂] | (E)-4-F-benzylidene |
| 206 | 2,4-Cl₂-phenyl | C(O)-2-pyridin-2-yl-piperidin-1-yl | (E)-4-F-benzylidene |
| 207 | 2,4-Cl₂-phenyl | C(O)NH-(1R)-indan-1-yl | (E)-4-F-benzylidene |
| 208 | 2,4-Cl₂-phenyl | C(O)NH-(1S,2R)-2-OH-indan-1-yl | (E)-4-F-benzylidene |
| 209 | 2,4-Cl₂-phenyl | C(O)NH-1,2,3,4-tetrahydro-naphthalen-1-yl | (E)-4-F-benzylidene |
| 210 | 2,4-Cl₂-phenyl | C(O)NH—CH₂-pyridin-2-yl | (E)-4-OCH₃-benzylidene |
| 211 | 2,4-Cl₂-phenyl | C(O)NH—C[(phenyl)(CH₃)₂] | (E)-4-OCH₃-benzylidene |
| 212 | 2,4-Cl₂-phenyl | C(O)NH—(R—CH)(phenyl)-CH₃ | (E)-4-OCH₃-benzylidene |
| 213 | 2,4-Cl₂-phenyl | C(O)NH—(S—CH)(phenyl)-CH₃ | (E)-4-OCH₃-benzylidene |
| 214 | 2,4-Cl₂-phenyl | C(O)NH—(R—CH)(cyclohexyl)-CH₃ | (E)-4-OCH₃-benzylidene |
| 215 | 2,4-Cl₂-phenyl | C(O)NH—(S—CH)(phenyl)-CH₂OH | (E)-4-OCH₃-benzylidene |
| 216 | 2,4-Cl₂-phenyl | C(O)NH-(1R)-indan-1-yl | (E)-4-OCH₃-benzylidene |
| 217 | 2,4-Cl₂-phenyl | C(O)NH-piperidin-1-yl | (E)-4-OCH₃-benzylidene |
| 218 | 4-F-phenyl | C(O)NH-(2S,3R)-2-CO₂CH₂CH₃-bicyclo[2.2.1]hept-3-yl | 4-CH₃-benzyl |
| 219 | cyclohexyl | C(O)NH—CH(phenyl)-(R)-CH₂OH | (E)-4-F-benzylidene |
| 220 | 4-CF₃-pyrimidin-2-yl | C(O)NH—CH(phenyl)-(S)-CH₂OH | (E)-4-F-benzylidene |
| 221 | 2,4-Cl₂-phenyl | C(O)NH-(1R,2R)-2-OH-cyclopentyl | (E)-4-OCH₃-benzylidene |
| 222 | 2,4-Cl₂-phenyl | C(O)NH—CH(pyridin-2-yl)-CH₃ | (E)-4-OCH₃-benzylidene |
| 223 | H | C(O)-piperidin-1-yl | (E)-4-Cl-benzylidene |
| 224 | 2,4-Cl₂-phenyl | C(O)NH—CH(pyridin-2-yl)-CH₃ | (E)-4-F-benzylidene |
| 225 | 2,4-Cl₂-phenyl | C(O)NH—(R—CH)(pyridin-2-yl)-CH₃ | (E)-4-F-benzylidene |
| 226 | 2,4-Cl₂-phenyl | C(O)NH-hexahydro-cyclopenta[c]pyrrol-2-yl | (E)-4-OCH₃-benzylidene |
| 227 | 2,4-Cl₂-phenyl | C(O)NH—(R—CH)(pyridin-2-yl)-CH₃ | (E)-4-OCH₃-benzylidene |
| 228 | H | C(O)NH—CH(phenyl)-(R)-CH₂OH | (S*)-3-Cl-benzyl |
| 229 | H | C(O)NH—CH(phenyl)-(R)-CH₂OH | (R*)-3-Cl-benzyl |
| 230 | H | C(O)NH—CH(phenyl)-(S)-CH₂OH | (R*)-3-Cl-benzyl |
| 231 | H | C(O)NH—CH(phenyl)-(S)-CH₂OH | (S*)-3-Cl-benzyl |
| 232 | H | (E)-(CH₂)SO₂NH—CH(phenyl)-(S)-CH₃ | (R*)-3-F-benzyl |
| 233 | H | (E)-(CH₂)SO₂NH—CH(phenyl)-(S)-CH₃ | (S*)-3-F-benzyl |
| 234 | H | C(O)NH—CH—(R)-phenyl)-CH₂OH | (E)-4-Cl-benzylidene |
| 235 | H | (E)-(CH₂)SO₂NH—CH(phenyl)-(R)-CH₃ | 3-F-benzyl |
| 236 | H | (E)-(CH₂)SO₂NH—CH(phenyl)-(R)-CH₃ | (E)-4-Cl-benzylidene |
| 237 | H | (E)-(CH₂)SO₂NH—CH(phenyl)-(S)-CH₃ | (E)-4-Cl-benzylidene |
| 238 | H | C(O)NH—(S—CH)(4-F-benzyl)-CO₂CH₃ | (E)-4-Cl-benzylidene |
| 239 | H | C(O)NH—CH-(R)-phenyl)-CH₂OH | (E)-3-Cl-benzylidene |
| 240 | H | C(O)NH—(S—CH)(4-F-benzyl)-CO₂CH₃ | (E)-3-Cl-benzylidene |
| 241 | CH₃ | C(O)NH—(S—CH)(4-F-benzyl)-CO₂CH₃ | (E)-3-F-benzylidene |
| 242 | CH₃ | C(O)NH—CH-(R)-phenyl)-CH₂OH | (E)-3-F-benzylidene |
| 243 | CH₃ | C(O)-imidazol-1-yl | (E)-3-F-benzylidene |

-continued

| Cpd | X₁R₁ | X₃R₃ | X₄R₄ |
|---|---|---|---|
| 244 | CH₃ | C(O)NH—CH-[(S)-4-OH-benzyl]-CH₂OH | (E)-3-F-benzylidene |
| 245 | H | C(O)NH—(R—CH)(4-F-benzyl)-CO₂CH₃ | (E)-3-Cl-benzylidene |
| 246 | H | C(O)NH—CH-[(S)-4-OH-benzyl]-CH₂OH | (E)-3-Cl-benzylidene |
| 247 | H | C(O)NH—(R—CH)(4-F-benzyl)-CO₂CH₃ | (E)-4-Cl-benzylidene |
| 248 | CH₃ | C(O)NH—(R—CH)(4-F-benzyl)-CO₂CH₃ | (E)-3-F-benzylidene |
| 249 | CH₃ | C(O)NH—CH-[(R)-phenyl]-(CH₂)₂OH | (E)-3-F-benzylidene |
| 250 | H | C(O)NH—CH-[(R)-phenyl]-(CH₂)₂OH | (E)-3-Cl-benzylidene |
| 251 | H | C(O)NH—CH-[(S)-phenyl]-CH₂OCH₃ | (R*)-3-Cl-benzyl |
| 252 | H | C(O)NH—CH-[(S)-phenyl]-CH₂OCH₃ | (S*)-3-Cl-benzyl |
| 253 | H | C(O)NH—CH-[(R)-phenyl]-CH₂OCH₃ | (S*)-3-Cl-benzyl |
| 254 | H | C(O)NH—CH-[(R)-phenyl]-CH₂OCH₃ | (R*)-3-Cl-benzyl |
| 255 | H | (E)-(CH)₂SO₂NH-piperidin-1-yl | 3-Cl-benzyl |
| 256 | H | C(O)NH—CH(S-phenyl)-CH₃ | 3-Cl-benzyl |
| 257 | H | C(O)NH—CH(R-phenyl)-CH₃ | 3-Cl-benzyl |

Compounds of Formula (I) and pharmaceutically acceptable forms thereof include those selected from:

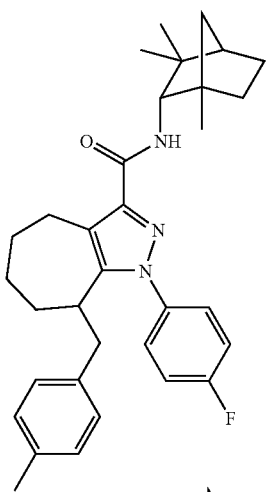

Cpd 1

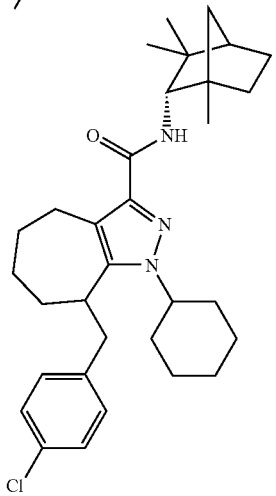

Cpd 2

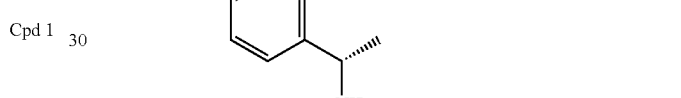

-continued

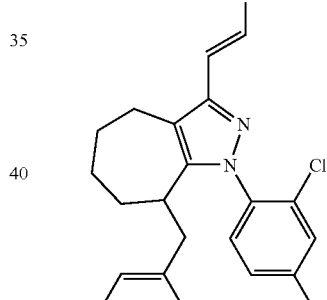

Cpd 3

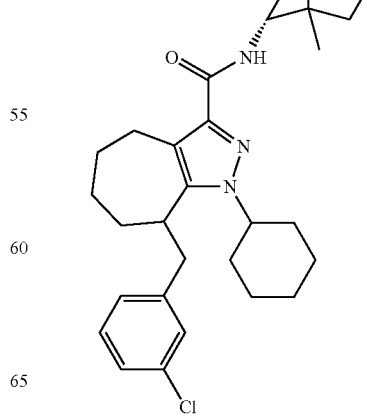

Cpd 4

Cpd 5
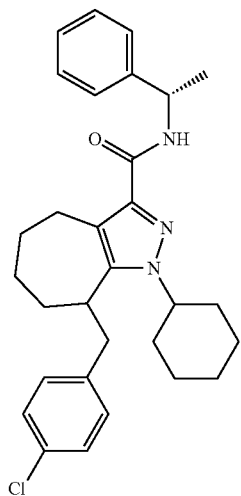
Cpd 6
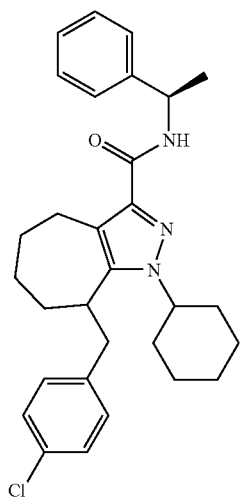
Cpd 7
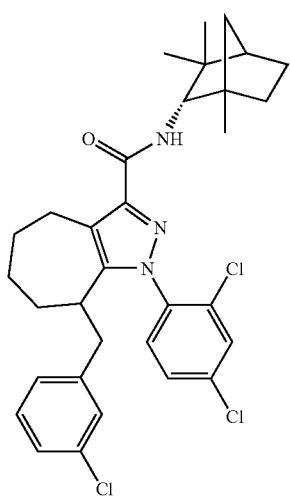
Cpd 8
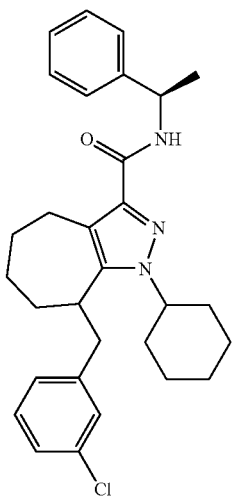
Cpd 9
Cpd 10

Cpd 11
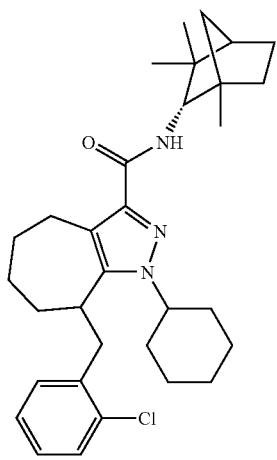
Cpd 14
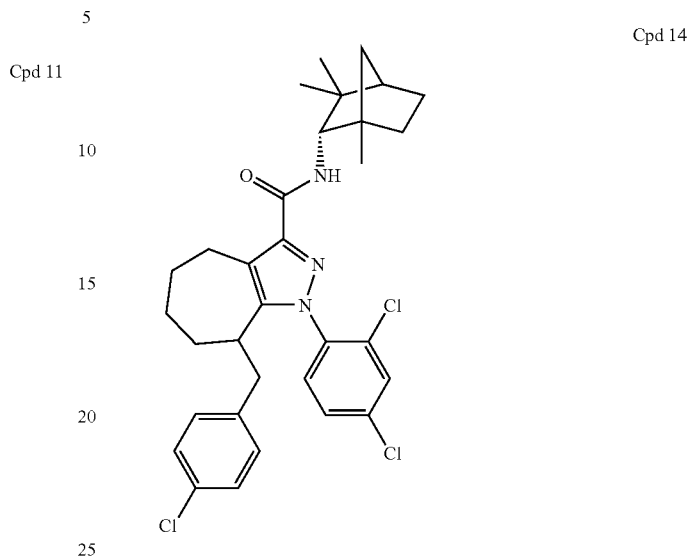
Cpd 12
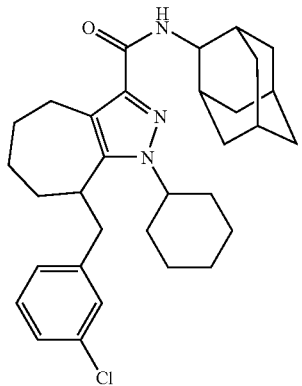
Cpd 15
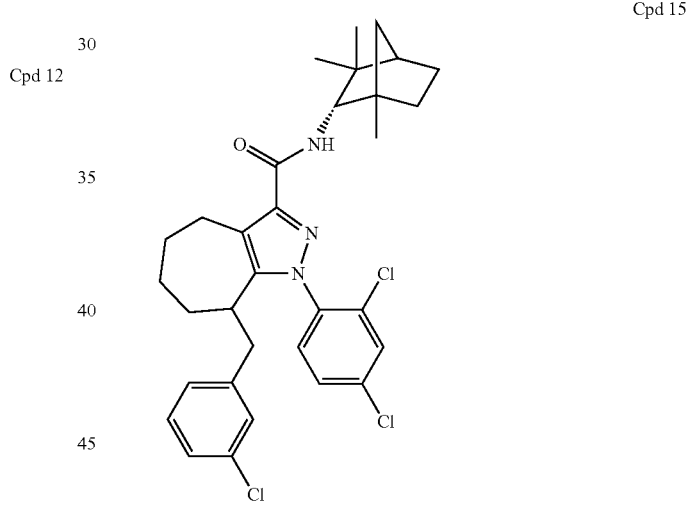
Cpd 13
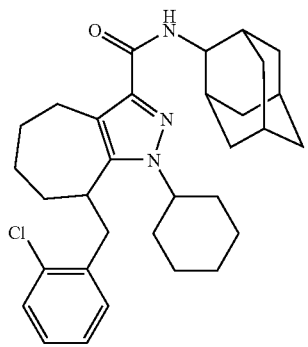
Cpd 16
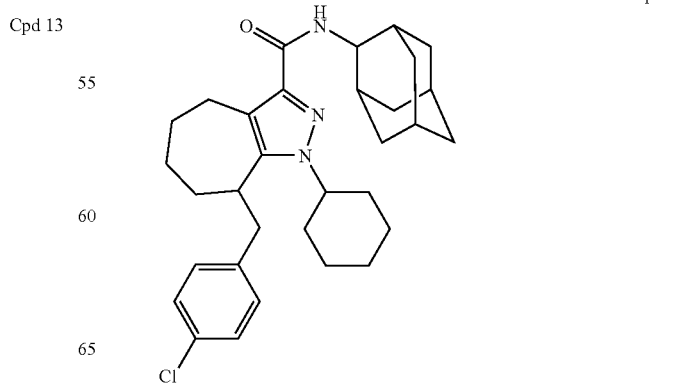

Cpd 17
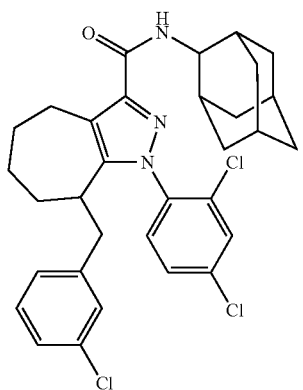
Cpd 18
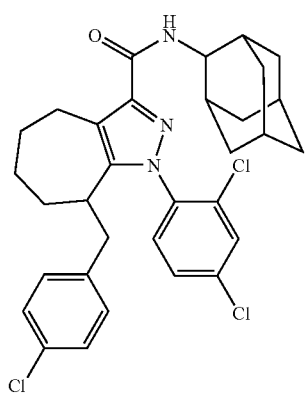
Cpd 19
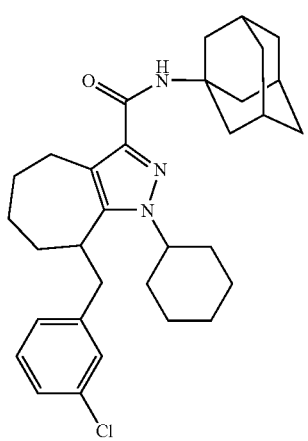
Cpd 20
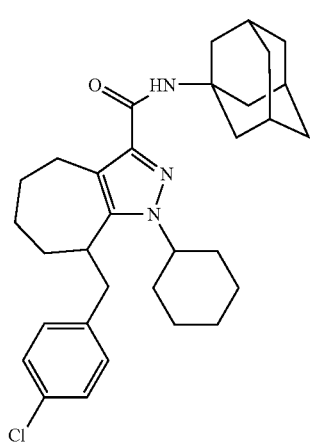
Cpd 21
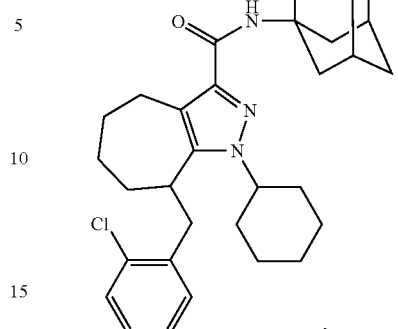
Cpd 22
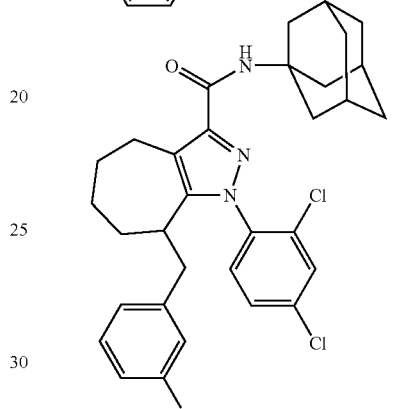
Cpd 23
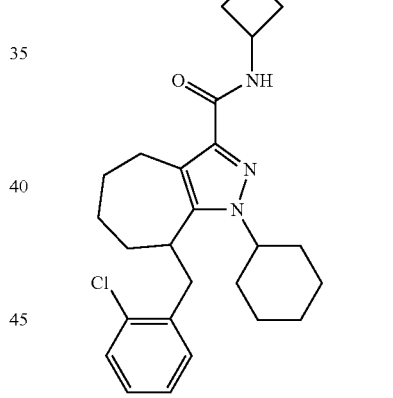
Cpd 24
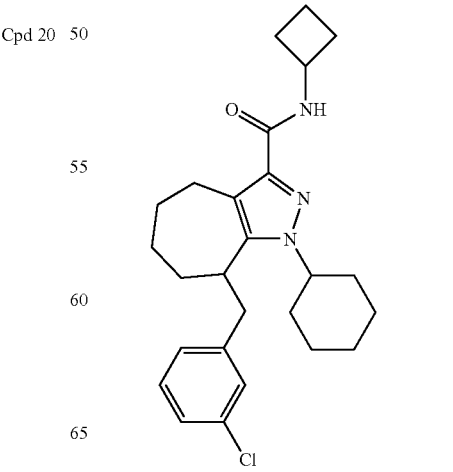

Cpd 25
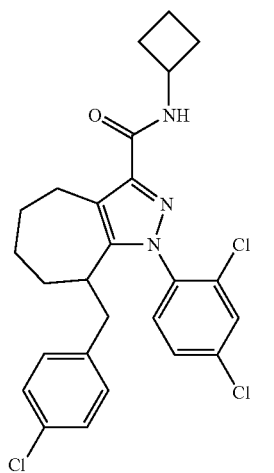
Cpd 28
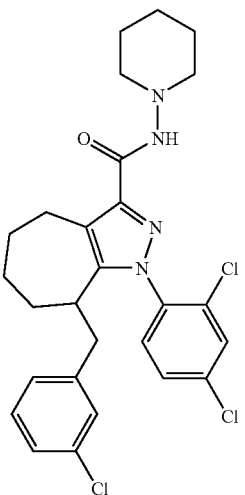
Cpd 26
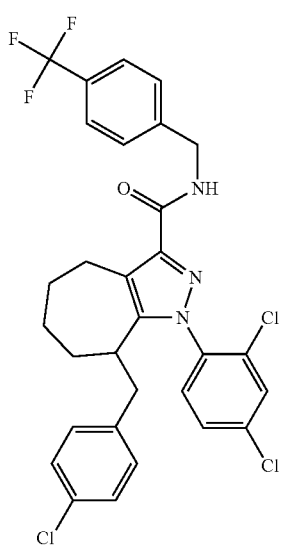
Cpd 29
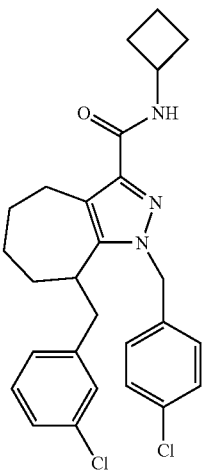
Cpd 27
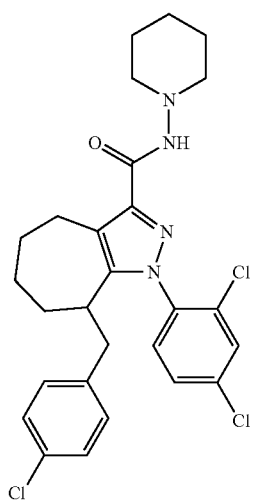
Cpd 30
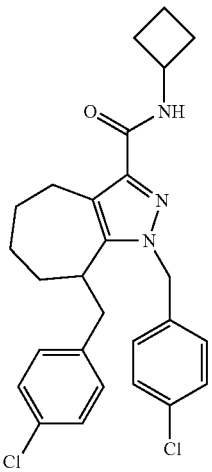

Cpd 31
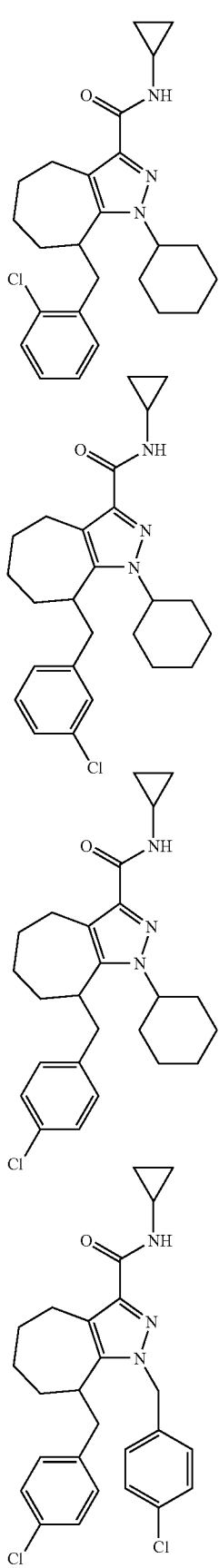
Cpd 32
Cpd 33
Cpd 34
Cpd 35
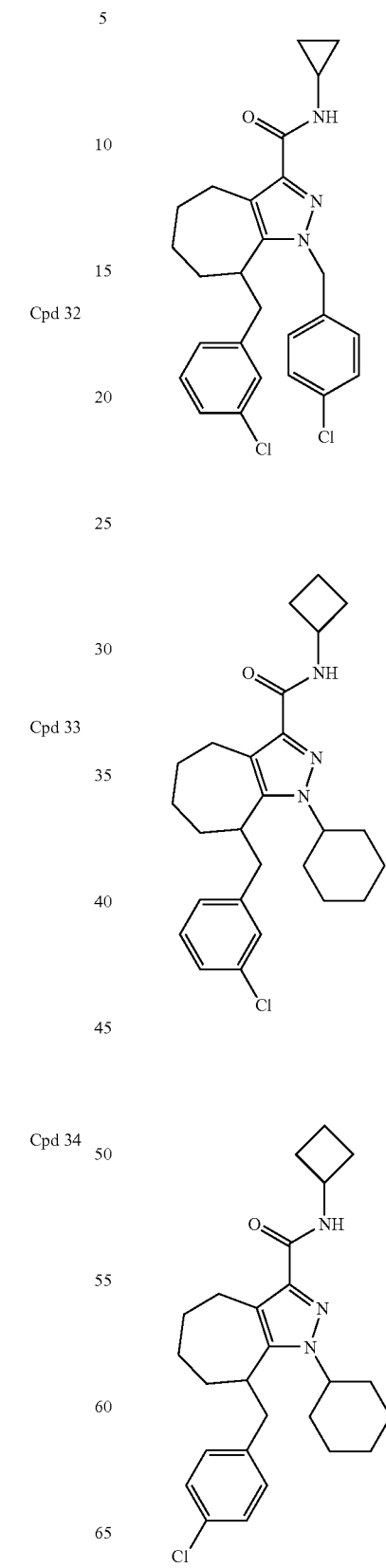
Cpd 36
Cpd 37

Cpd 38 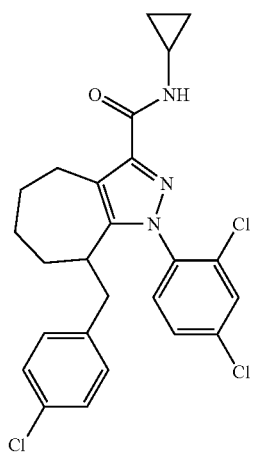
Cpd 39 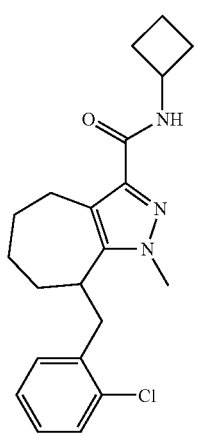
Cpd 40 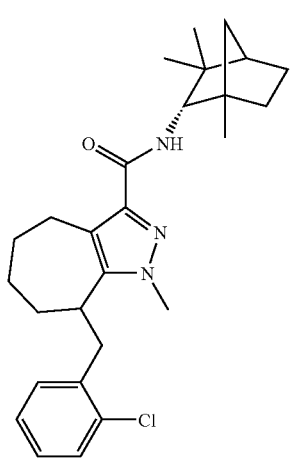
Cpd 41 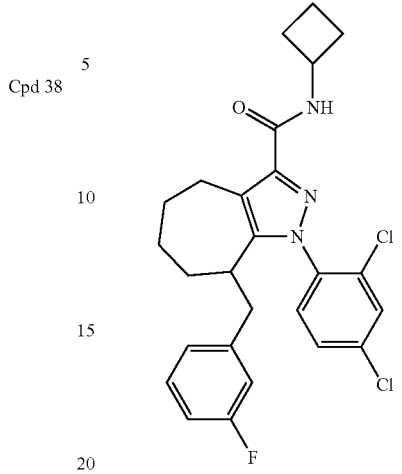
Cpd 42 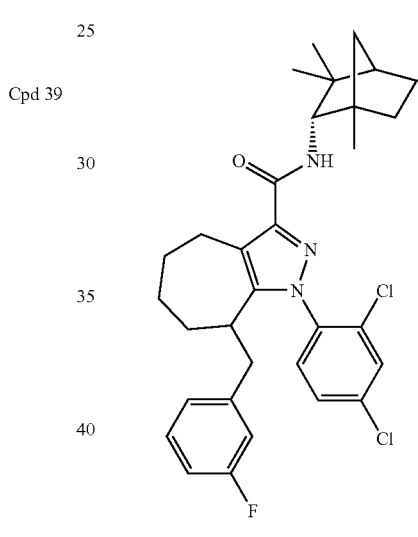
Cpd 43 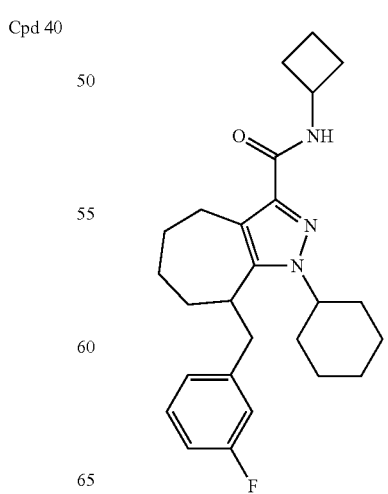

Cpd 44
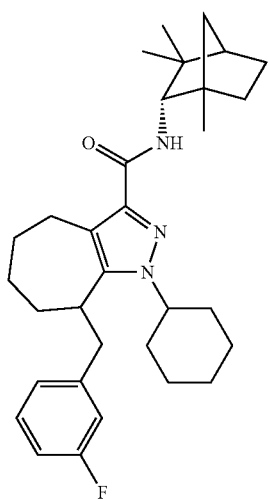
Cpd 47
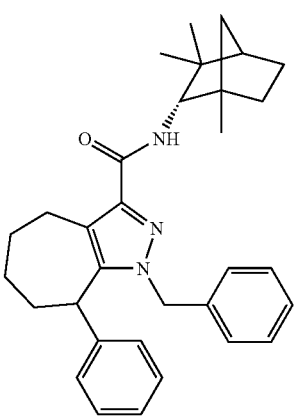
Cpd 45
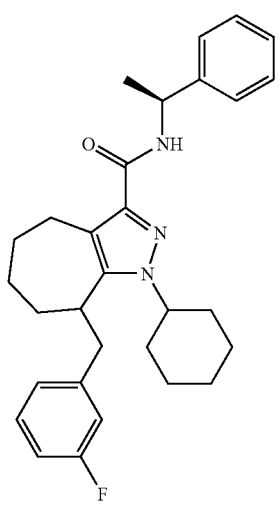
Cpd 48
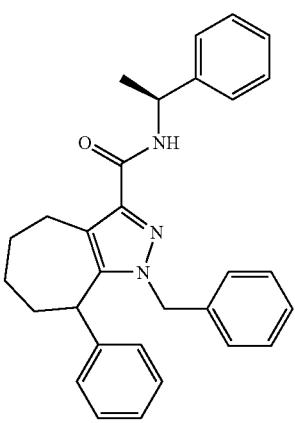
Cpd 46
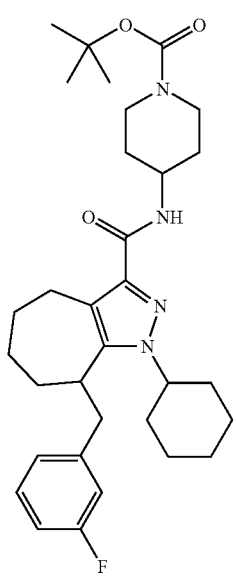
Cpd 49
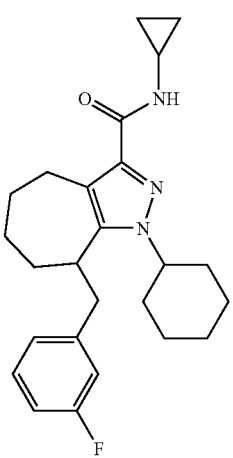

Cpd 50 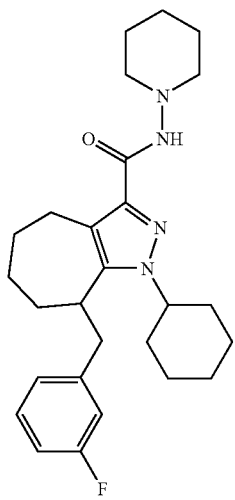
Cpd 51
Cpd 52
Cpd 53 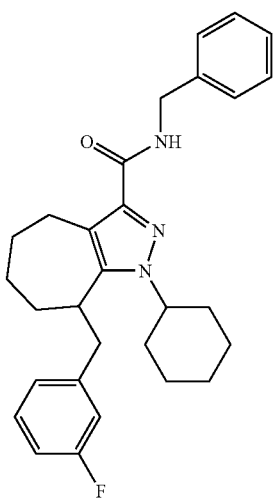
Cpd 54 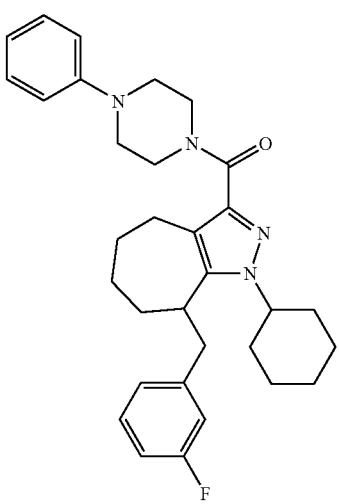
Cpd 55 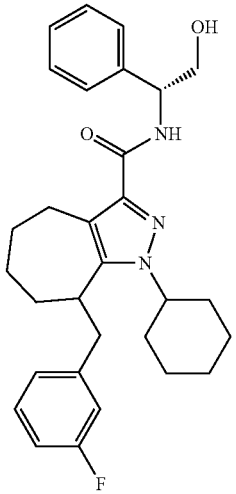

Cpd 56
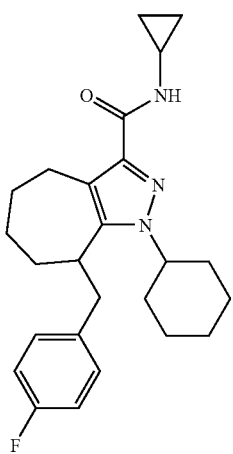
Cpd 59
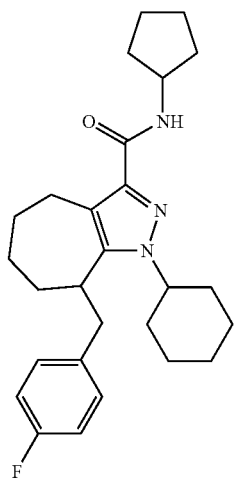
Cpd 57
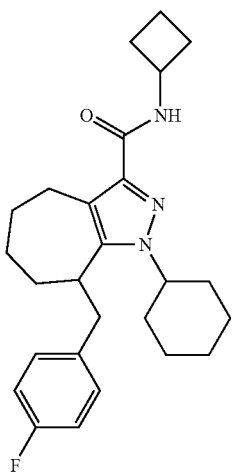
Cpd 60
Cpd 58
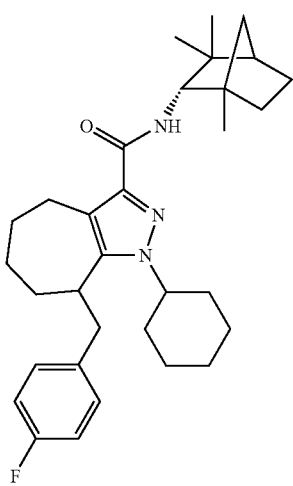
Cpd 61
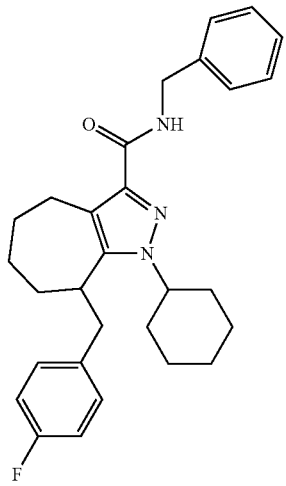

Cpd 62
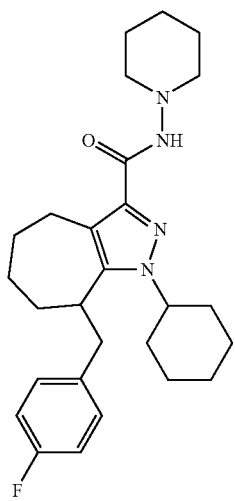
Cpd 63
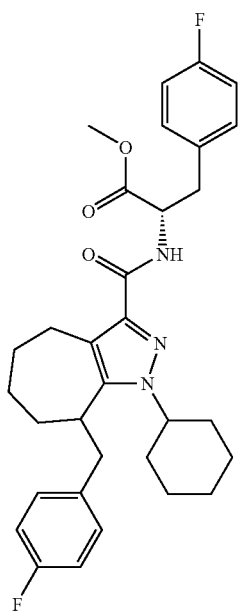
Cpd 64
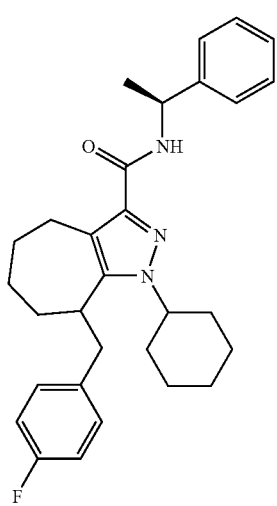
Cpd 65
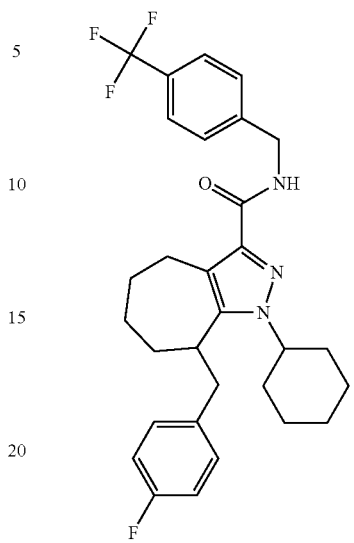
Cpd 66
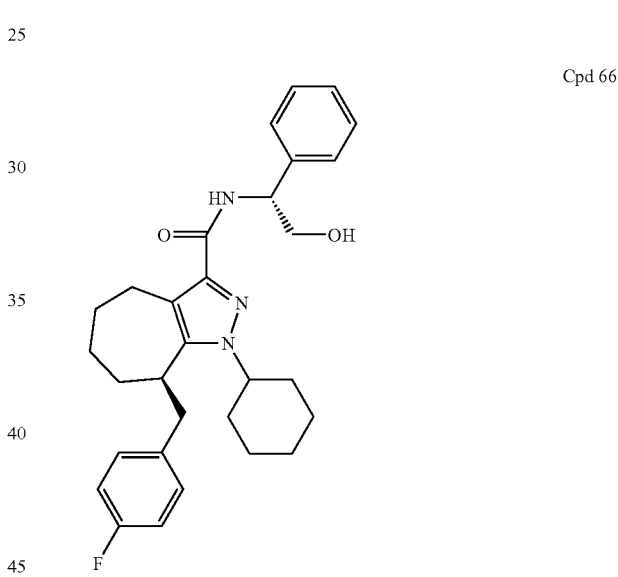
Cpd 67
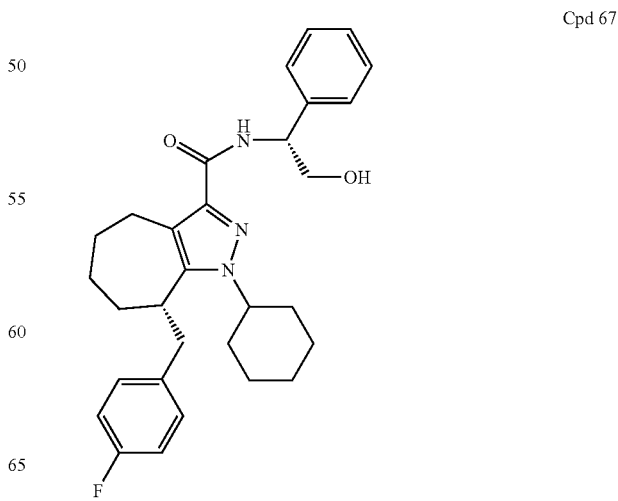

-continued
Cpd 68
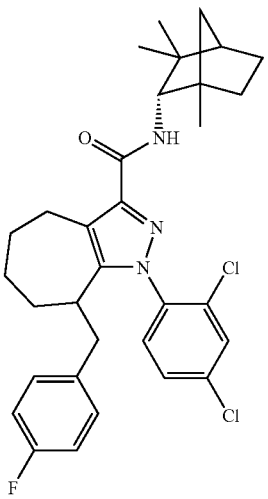
Cpd 69
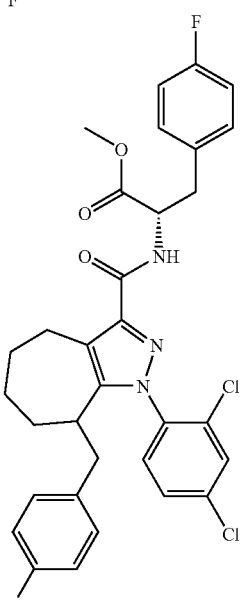
Cpd 70
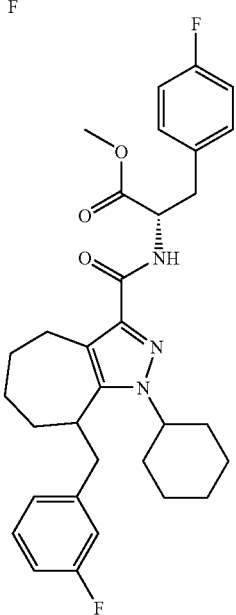
Cpd 71
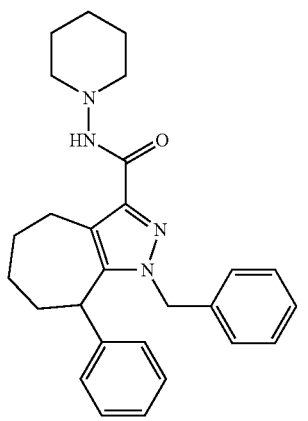
Cpd 72
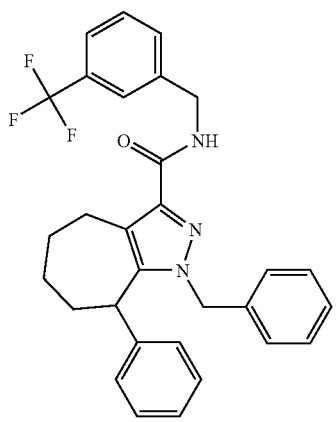
Cpd 73
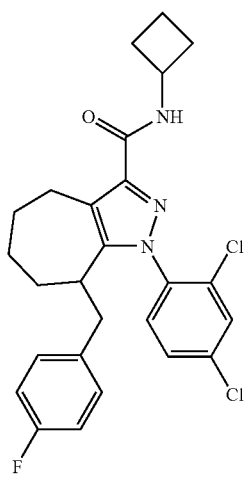

Cpd 74
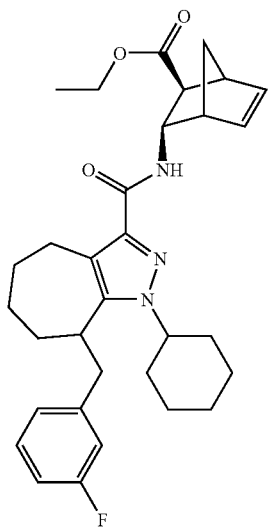
Cpd 75
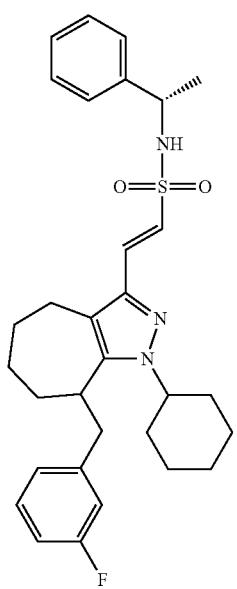
Cpd 76
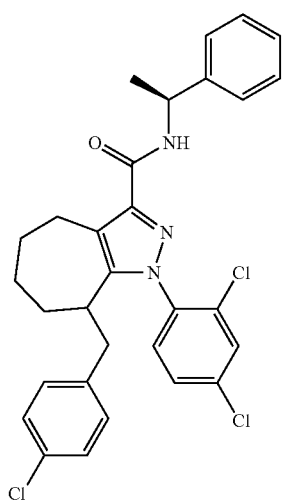
Cpd 77
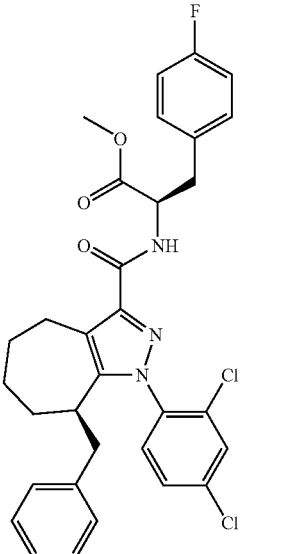
Cpd 78
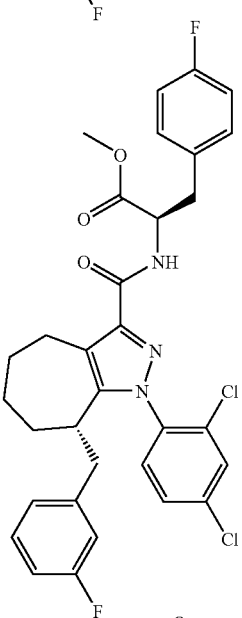
Cpd 79
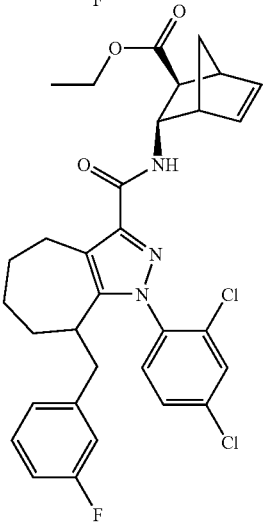

Cpd 80
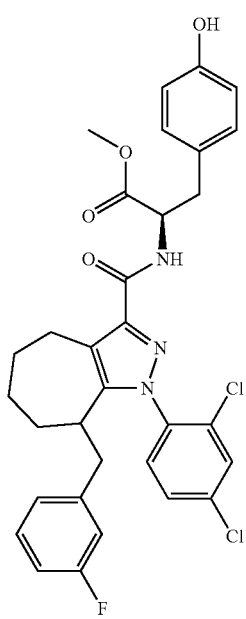
Cpd 82
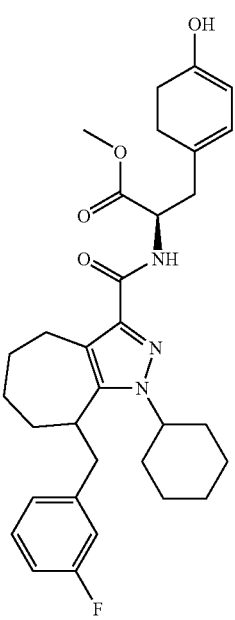
Cpd 81
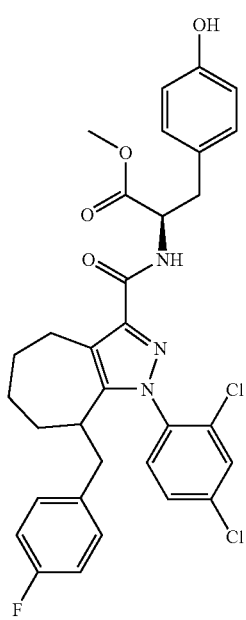
Cpd 83
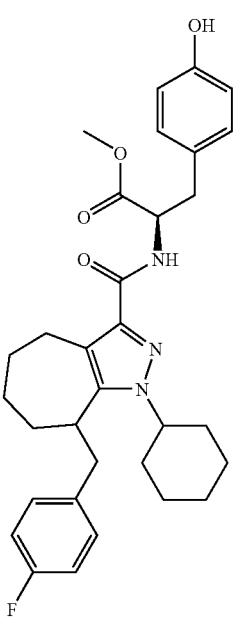

Cpd 84
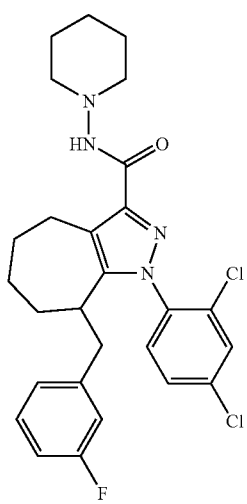
Cpd 87
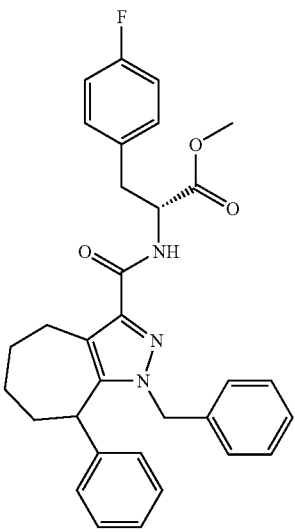
Cpd 85
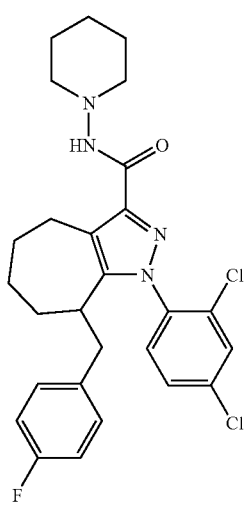
Cpd 88
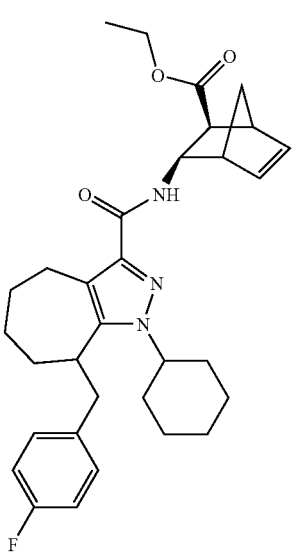
Cpd 86
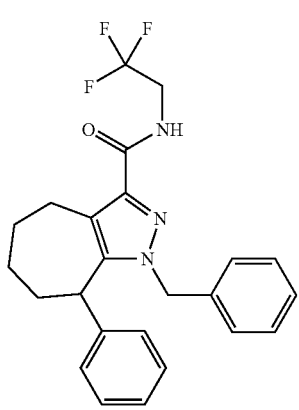
Cpd 89
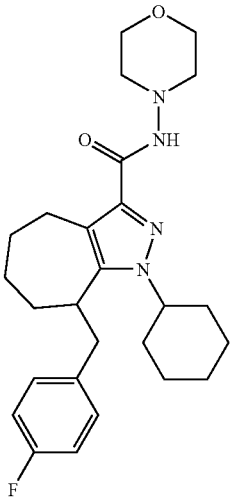

Cpd 90
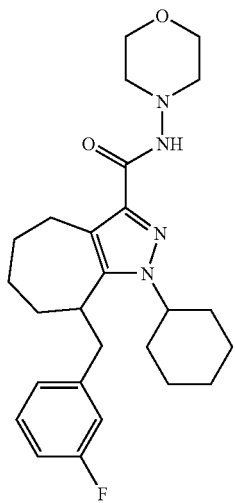
Cpd 91
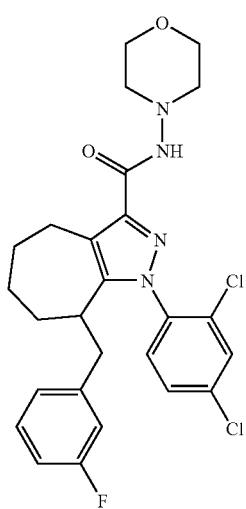
Cpd 92
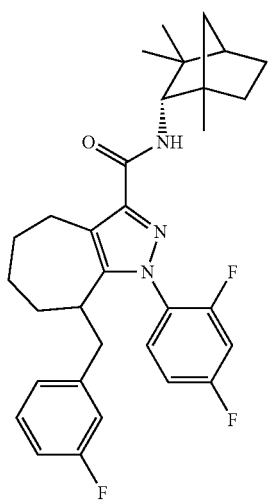
Cpd 93
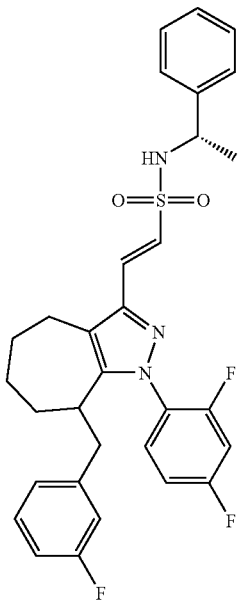
Cpd 94
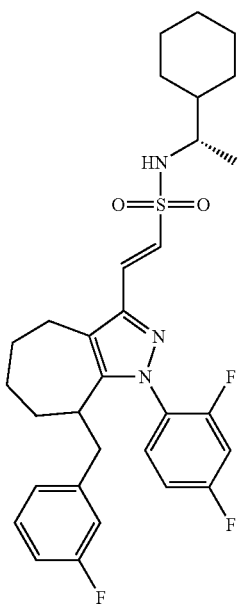

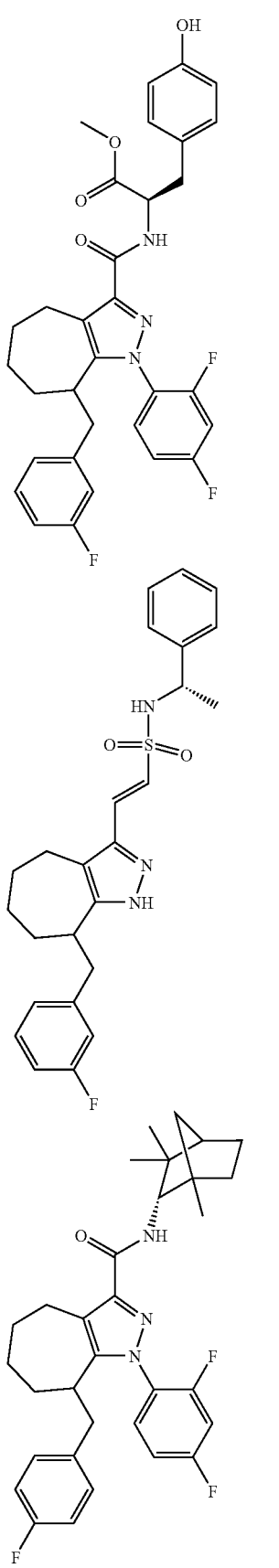
Cpd 95
Cpd 96
Cpd 97
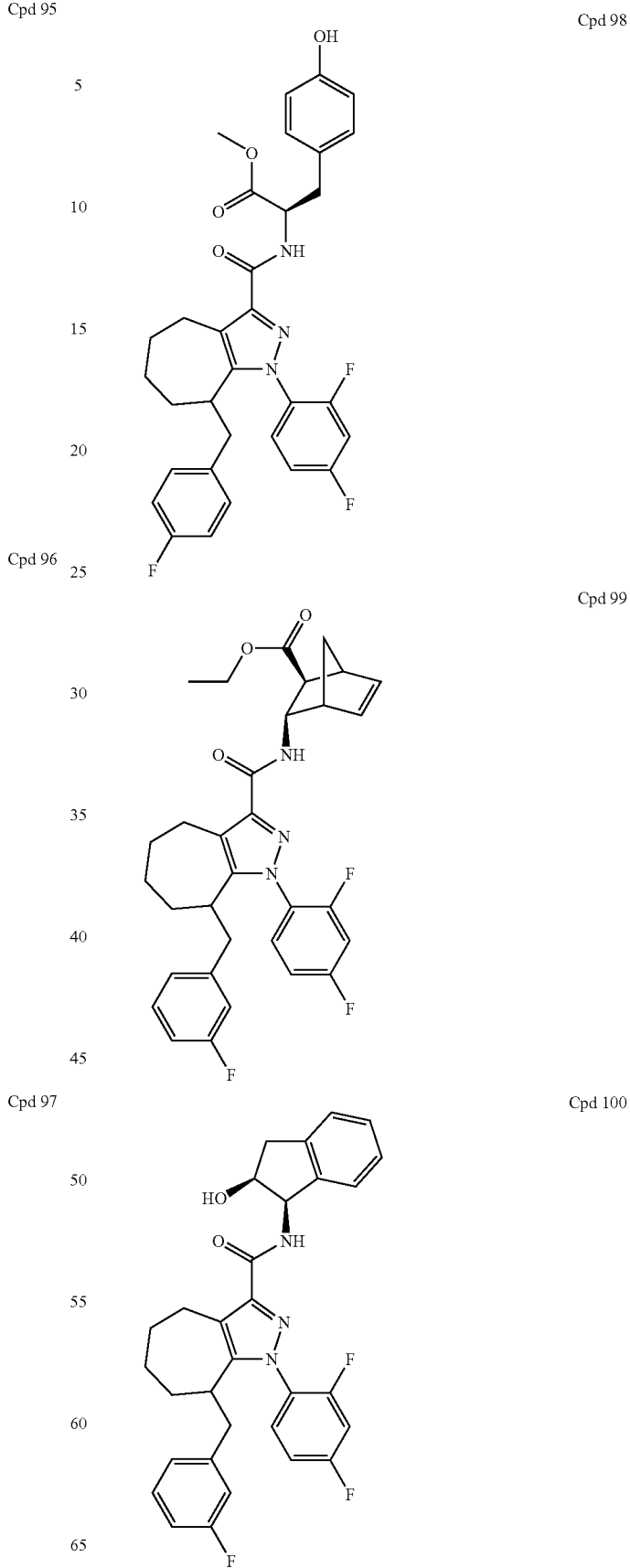
Cpd 98
Cpd 99
Cpd 100

Cpd 101
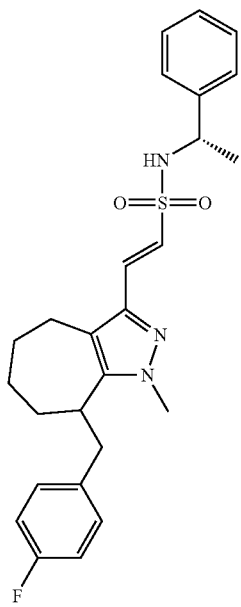
Cpd 103
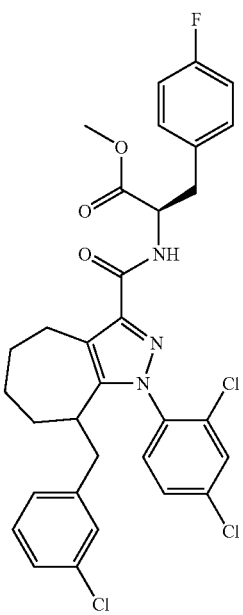
Cpd 102
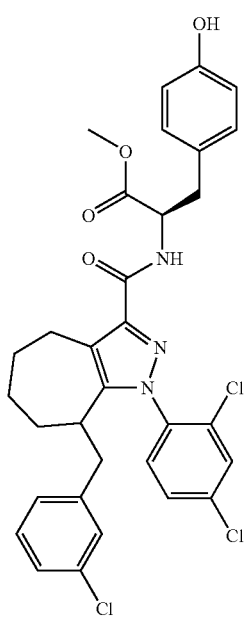
Cpd 104
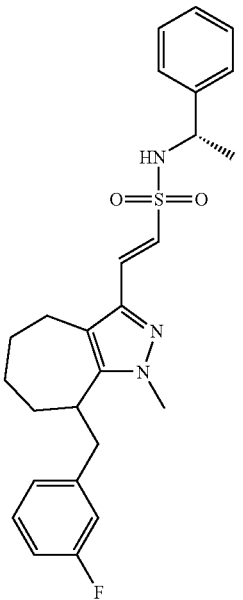

Cpd 105
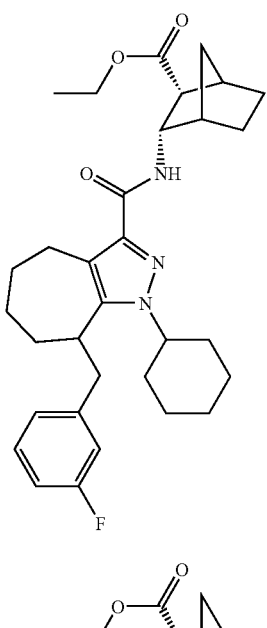
Cpd 106
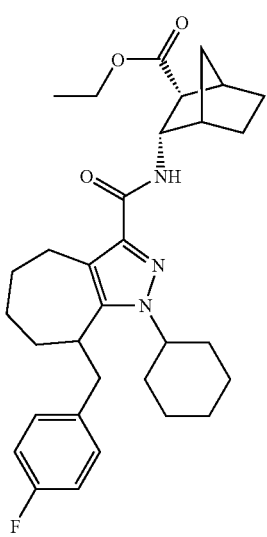
Cpd 107
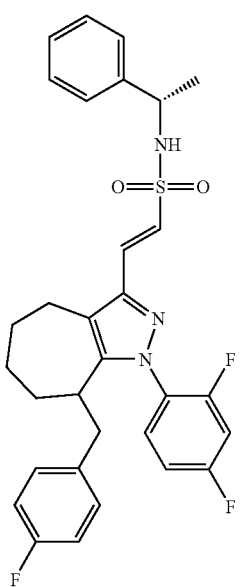
Cpd 108
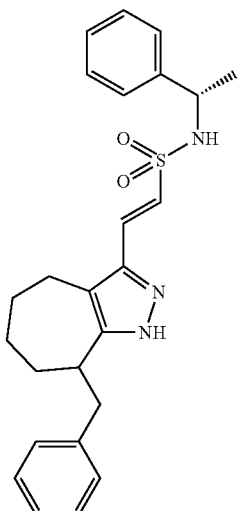
Cpd 109
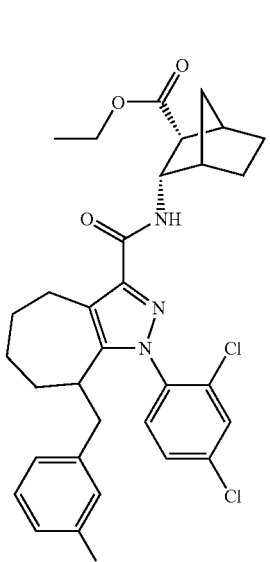
Cpd 110
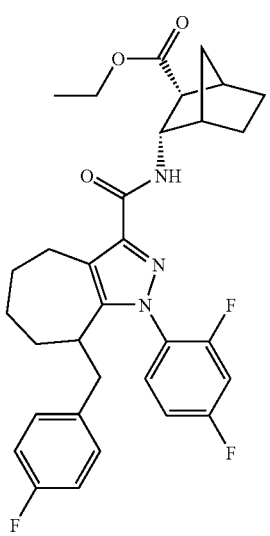

Cpd 111
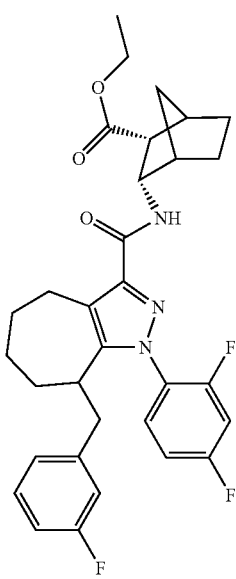
Cpd 112
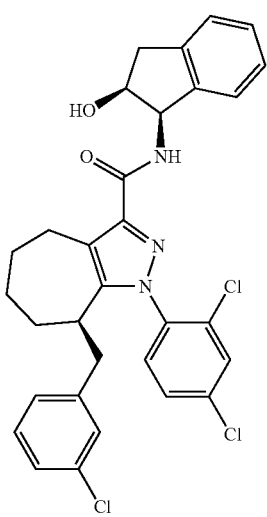
Cpd 113
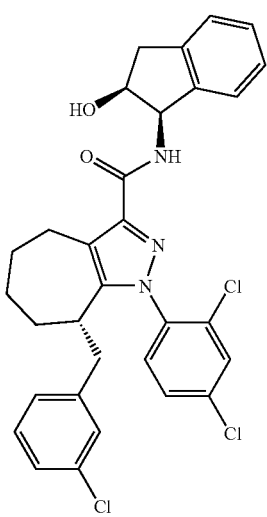
Cpd 114
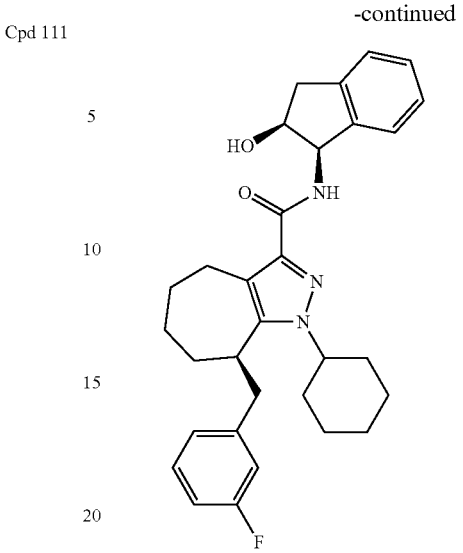
Cpd 115
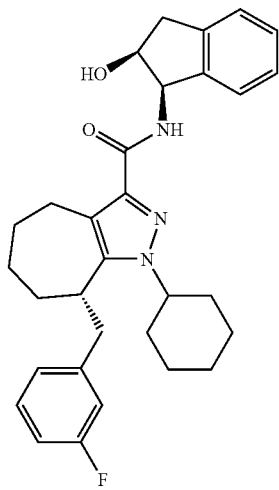
Cpd 116
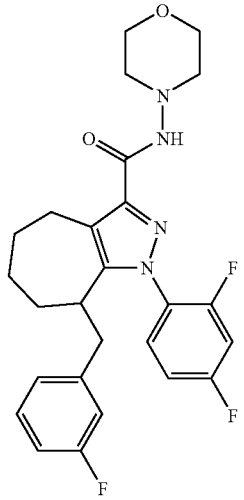

Cpd 117 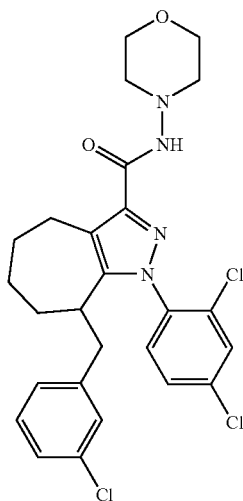
Cpd 118 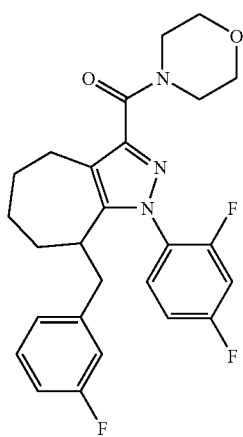
Cpd 119 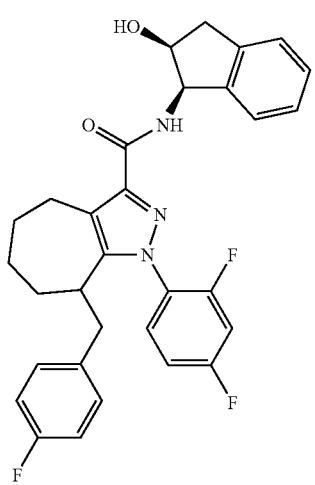
Cpd 120 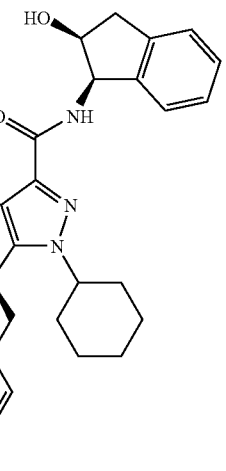
Cpd 121 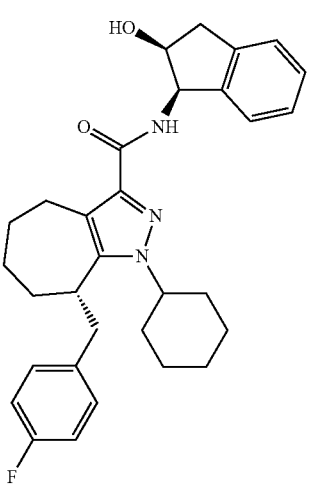
Cpd 122 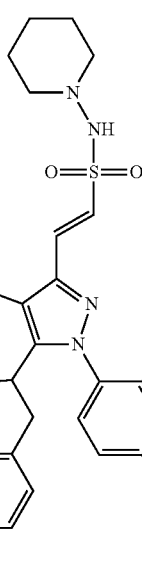

Cpd 123
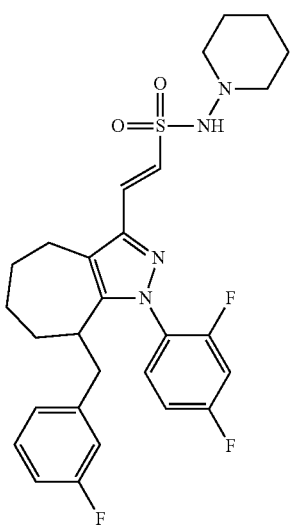
Cpd 124
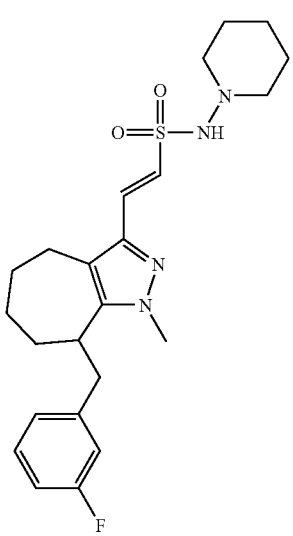
Cpd 125
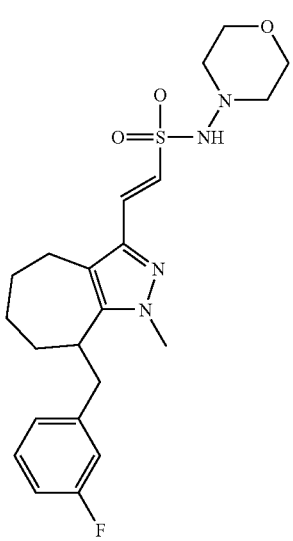
Cpd 126
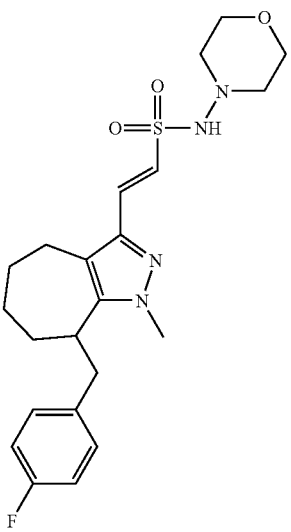
Cpd 127
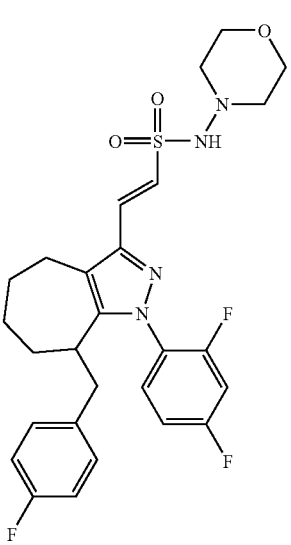
Cpd 128
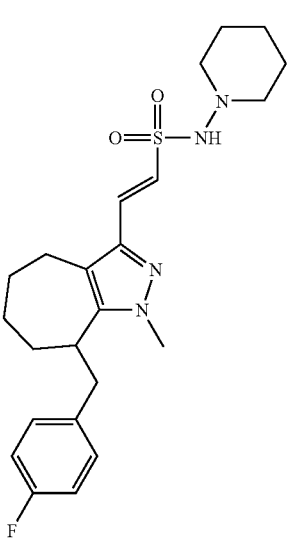

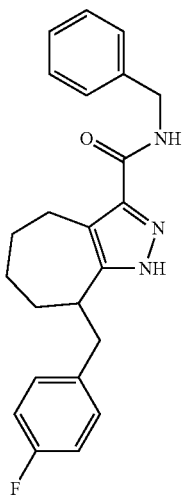
Cpd 129
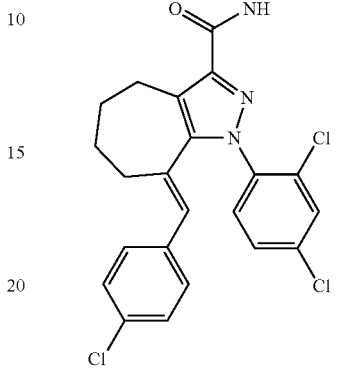
Cpd 130
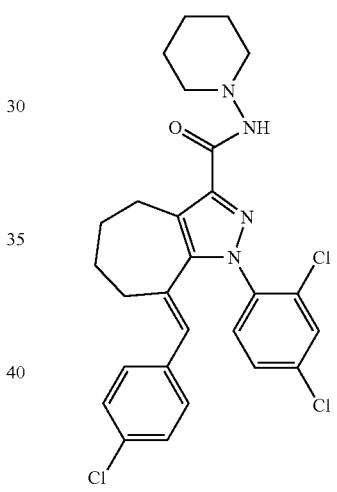
Cpd 131
Cpd 132
Cpd 133
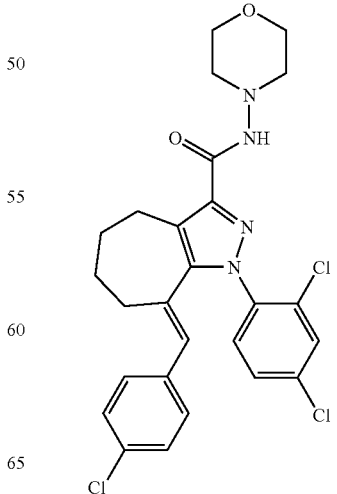
Cpd 134

Cpd 135
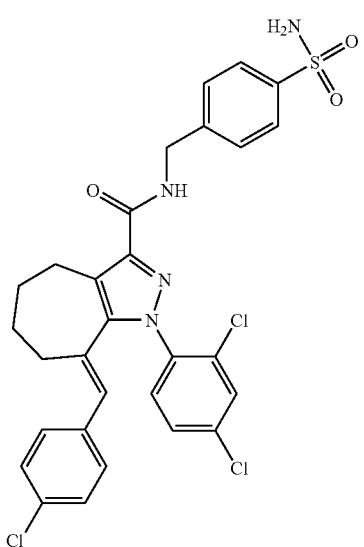
Cpd 136
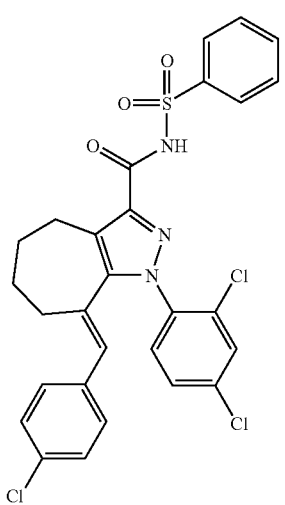
Cpd 137
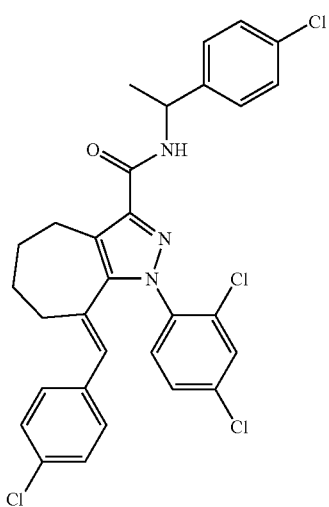
Cpd 138
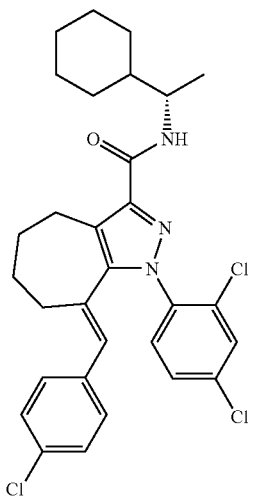
Cpd 139
Cpd 140
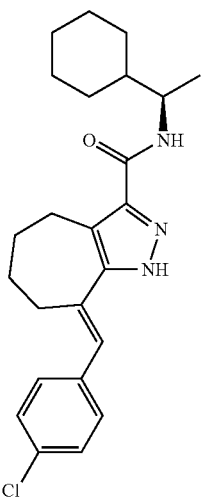

Cpd 141 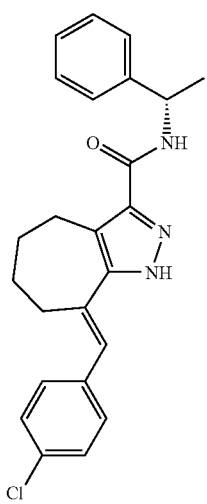 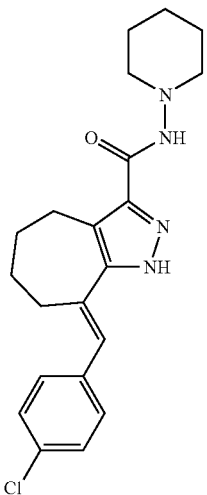 Cpd 144
Cpd 142 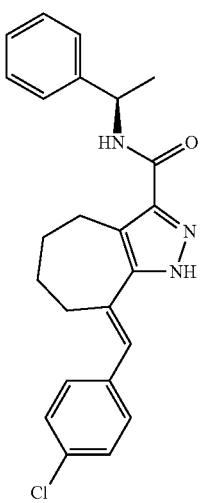 Cpd 145
Cpd 143 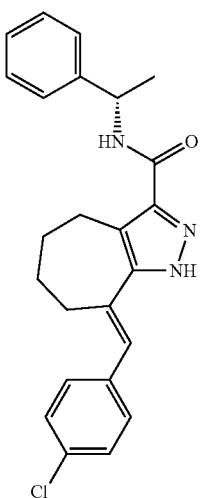 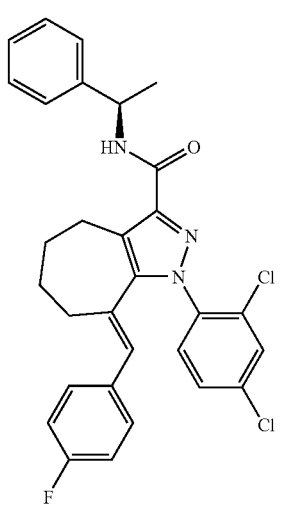 Cpd 146

Cpd 147
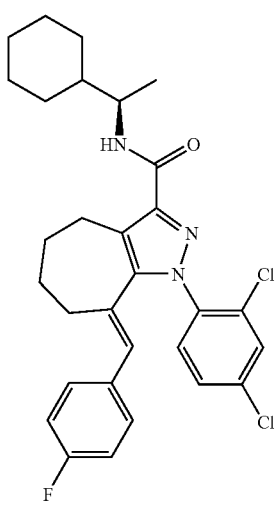
Cpd 148
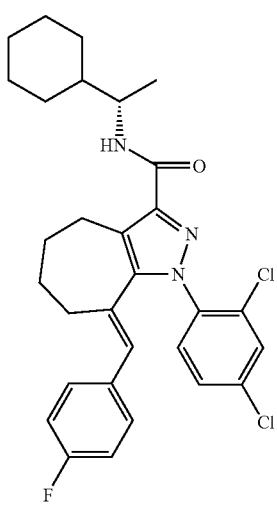
Cpd 149
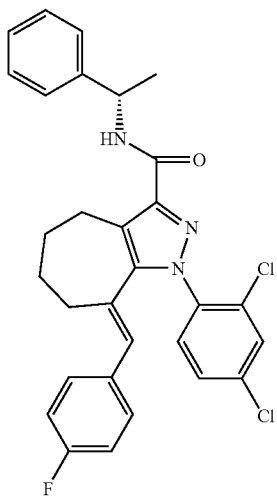
Cpd 150
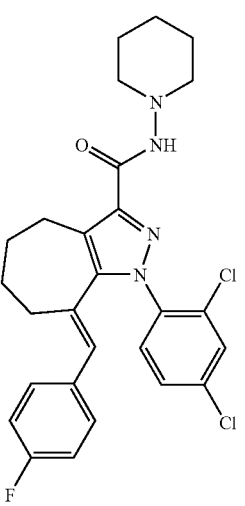
Cpd 151
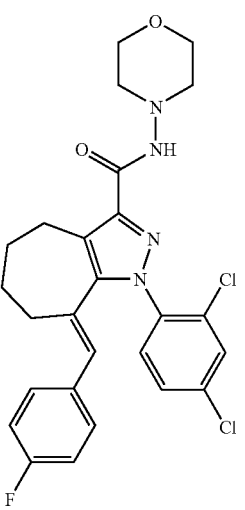
Cpd 152
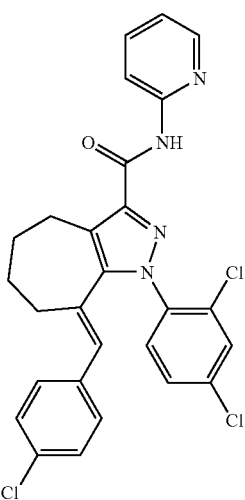

Cpd 153
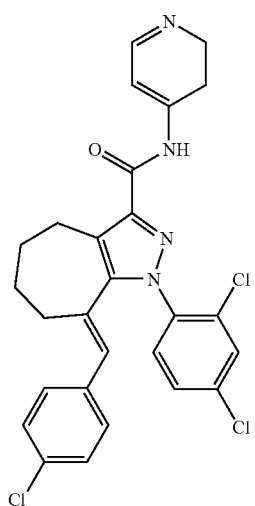
Cpd 154
Cpd 155
Cpd 156
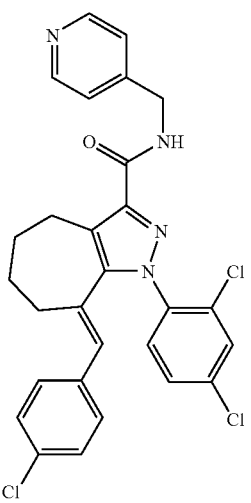
Cpd 157
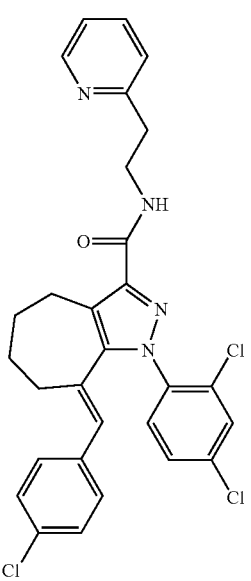
Cpd 158
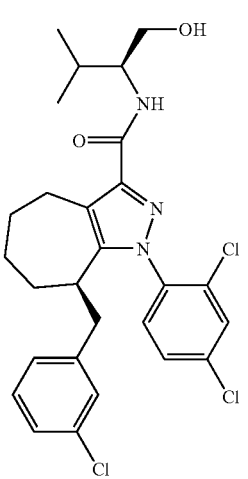

Cpd 159 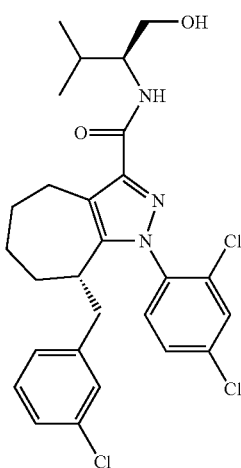
Cpd 162 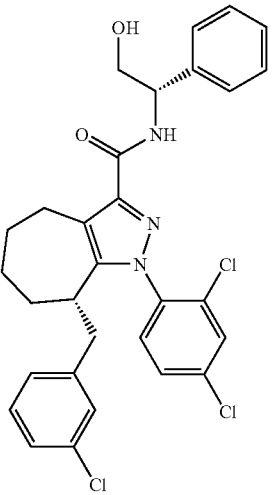
Cpd 160
Cpd 163 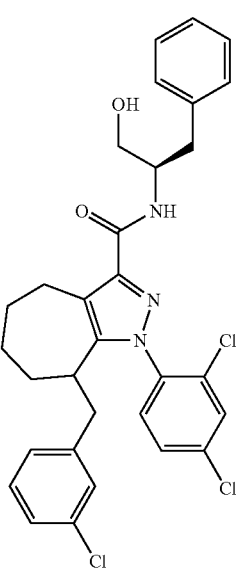
Cpd 161
Cpd 164 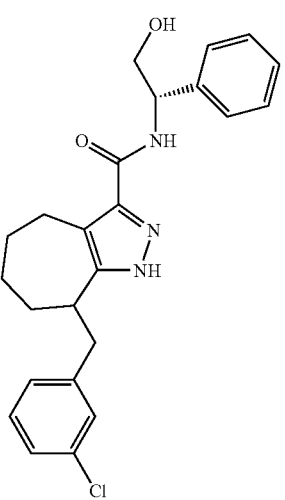

Cpd 165
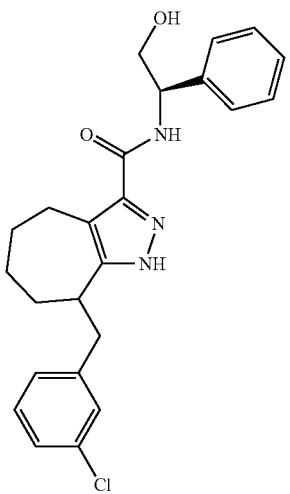
Cpd 168
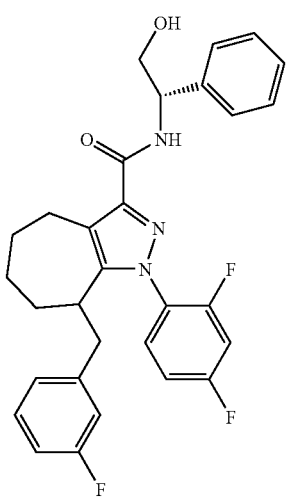
Cpd 166
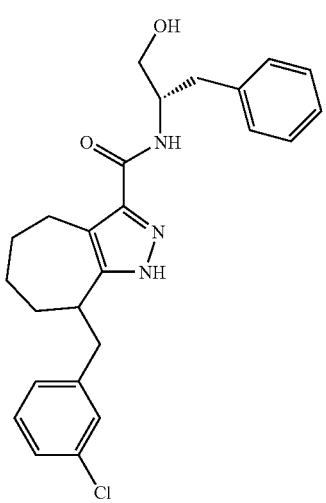
Cpd 169
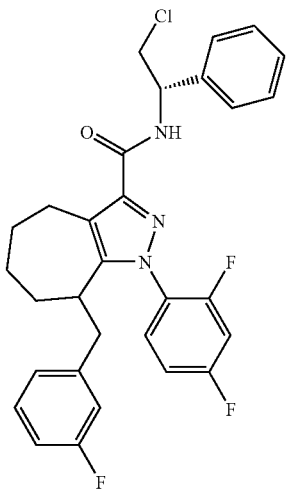
Cpd 167
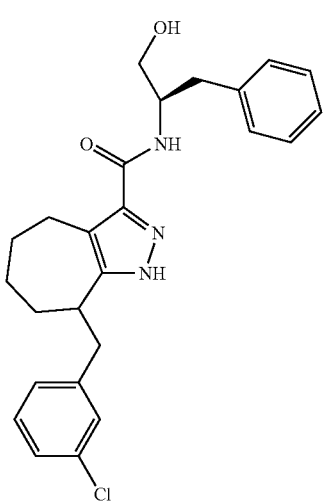
Cpd 170
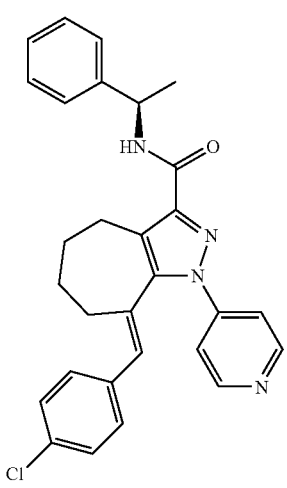

Cpd 171

Cpd 172

Cpd 173

Cpd 174

Cpd 175

Cpd 176

-continued
Cpd 177
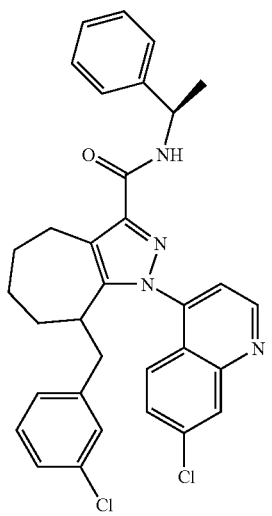
Cpd 178
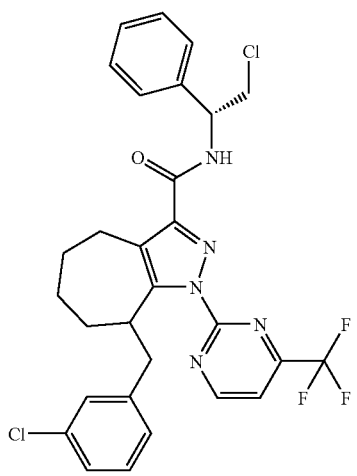
Cpd 179
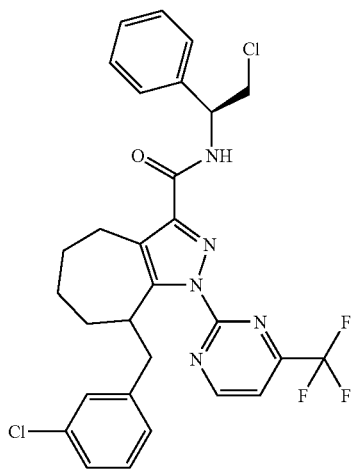
-continued
Cpd 180
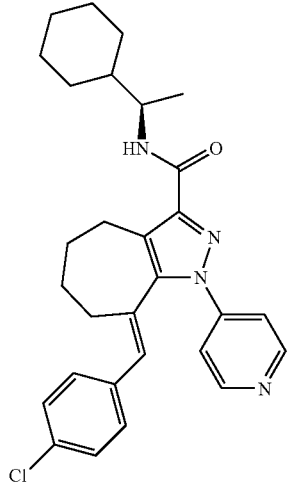
Cpd 181
Cpd 182
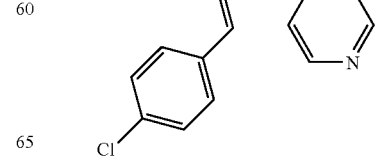

Cpd 183
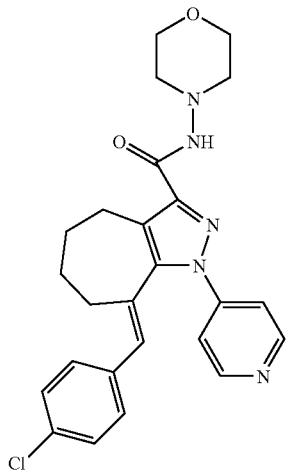
Cpd 186
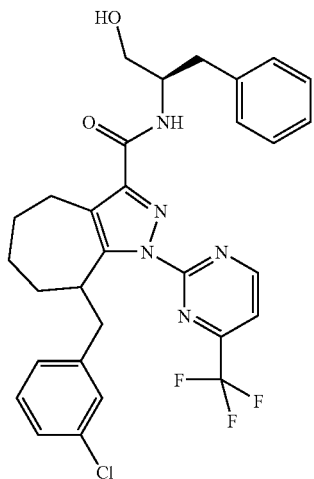
Cpd 184
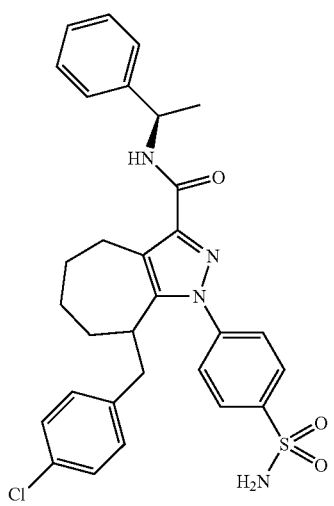
Cpd 187
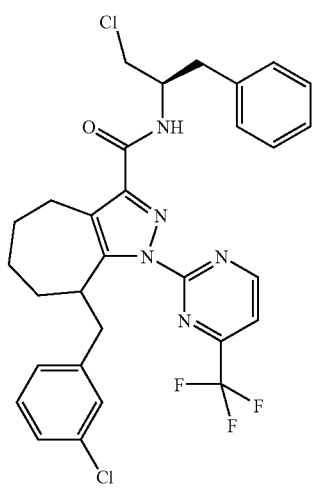
Cpd 185
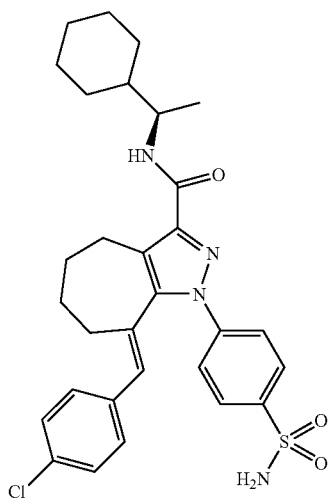
Cpd 188
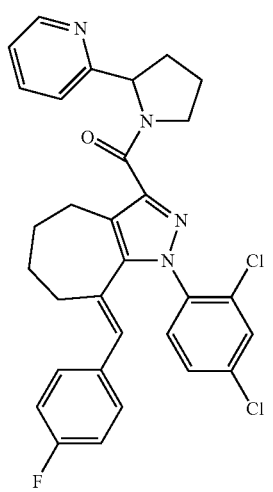

Cpd 189
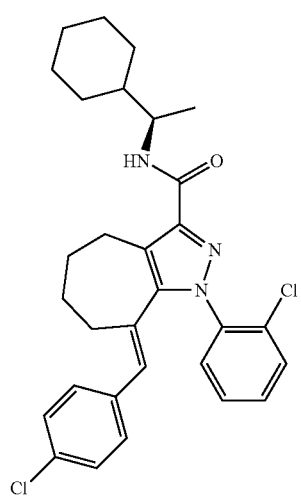
Cpd 192
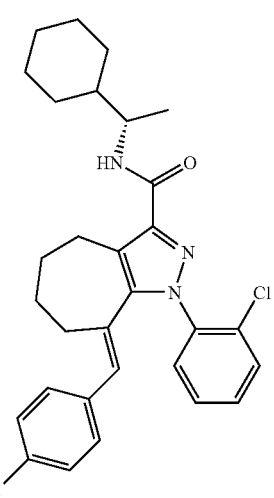
Cpd 190
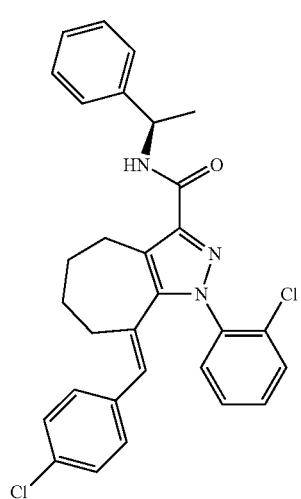
Cpd 193
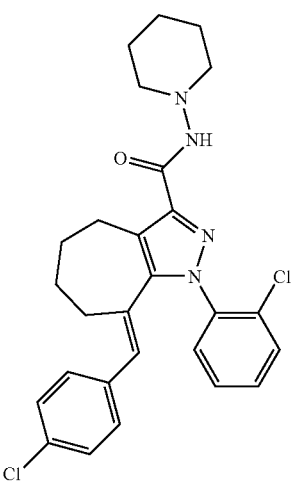
Cpd 191
Cpd 194
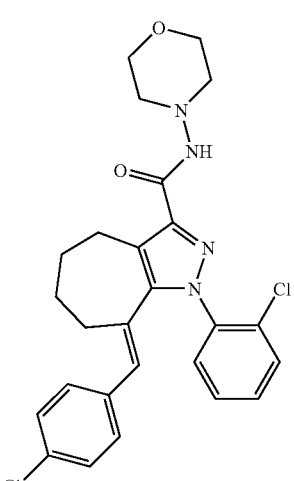

Cpd 195
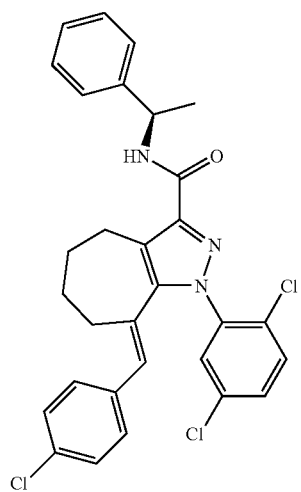
Cpd 198
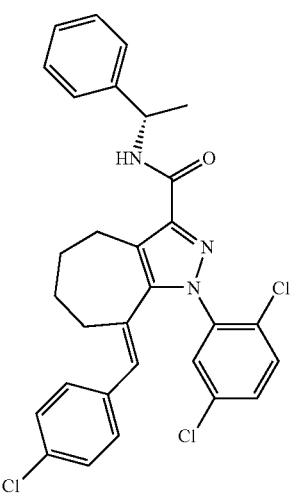
Cpd 196
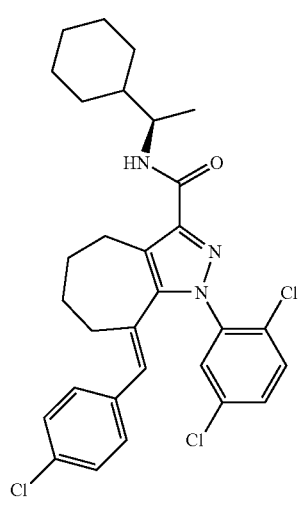
Cpd 199
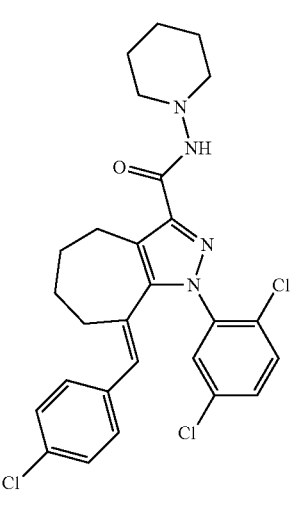
Cpd 197
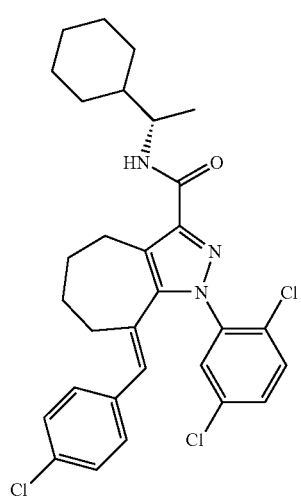
Cpd 200
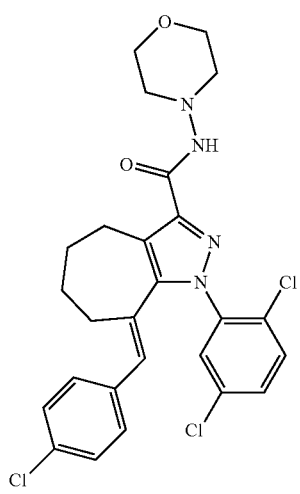

Cpd 201
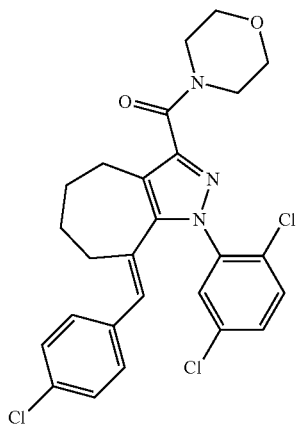
Cpd 204
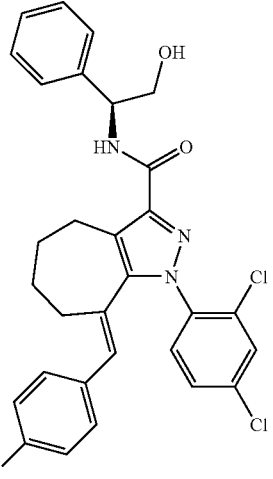
Cpd 202
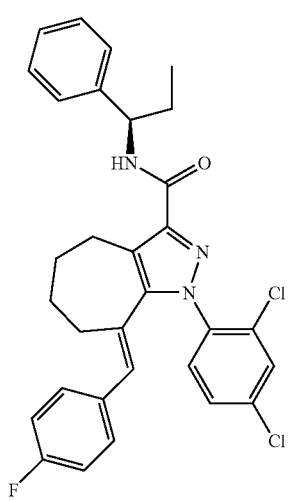
Cpd 205
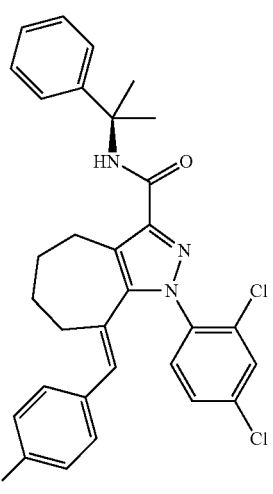
Cpd 203
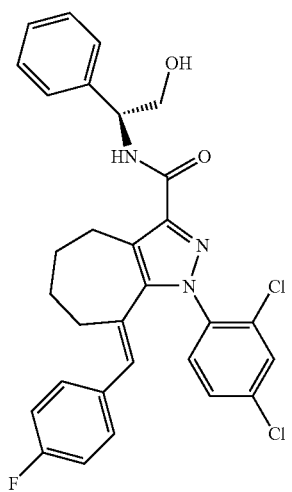
Cpd 206
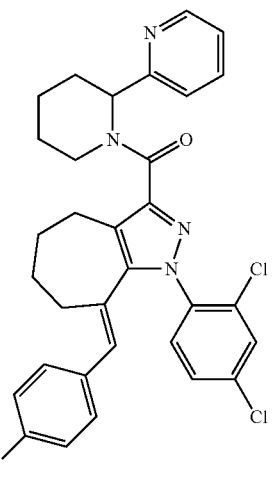

Cpd 207 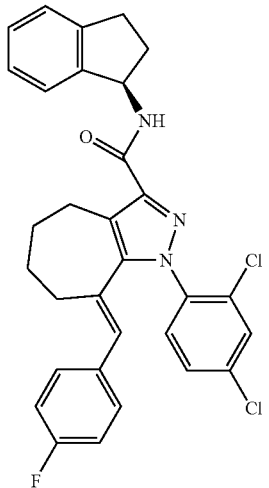
Cpd 208 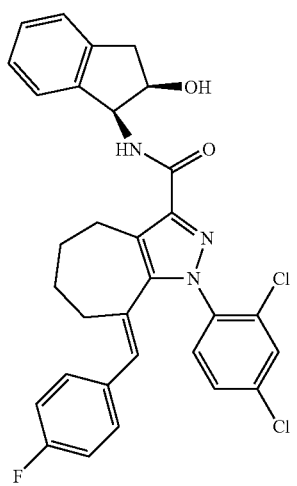
Cpd 209 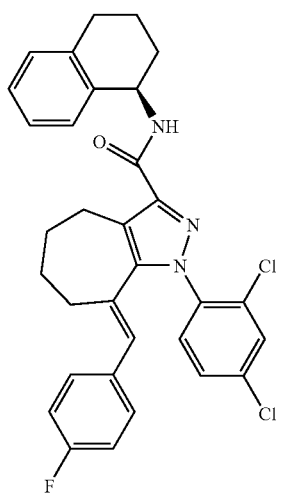
Cpd 210 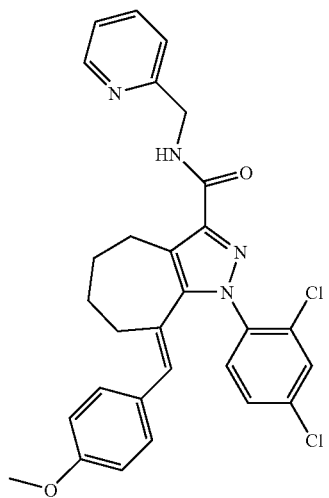
Cpd 211 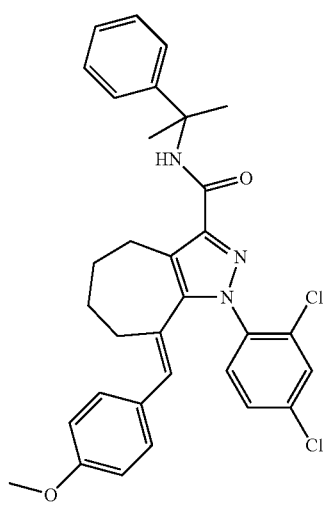
Cpd 212 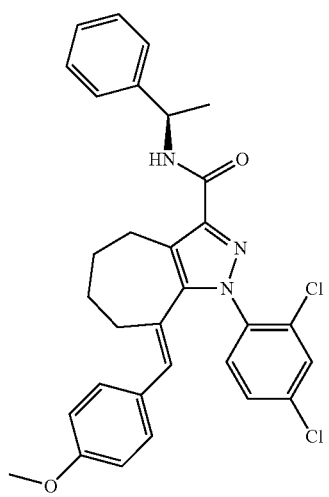

Cpd 213
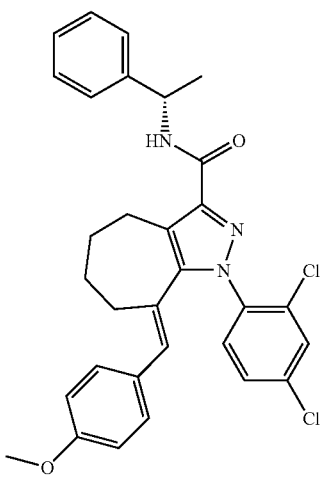
Cpd 216
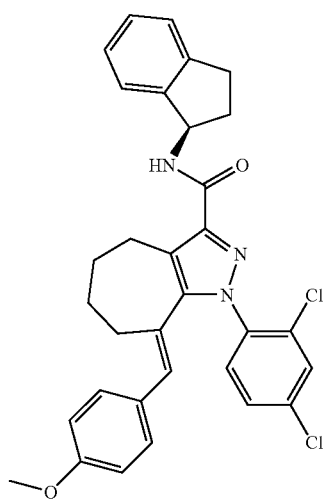
Cpd 214
Cpd 217
Cpd 215
Cpd 218

-continued
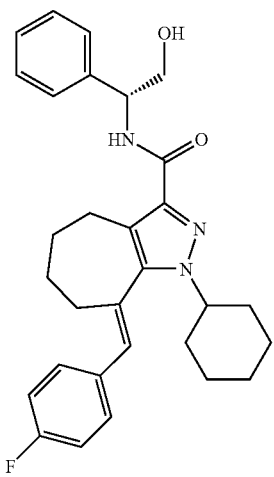
Cpd 219
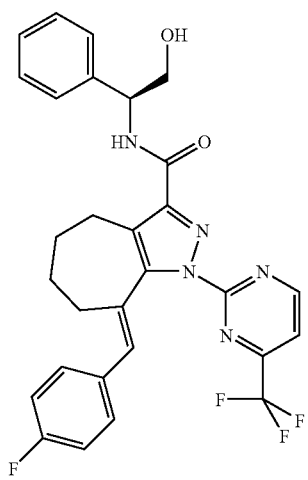
Cpd 220
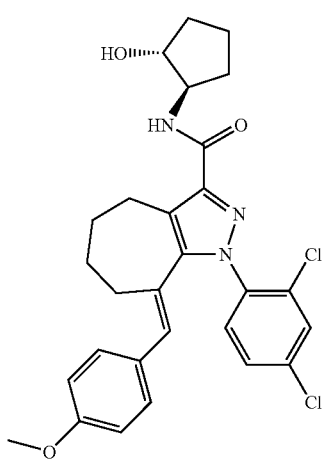
Cpd 221
-continued
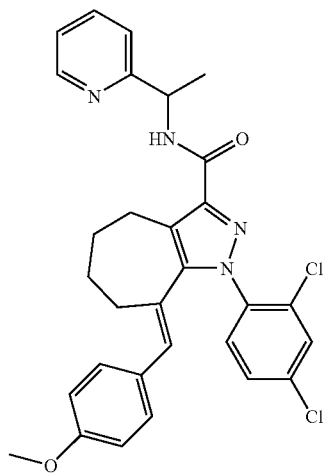
Cpd 222
Cpd 223
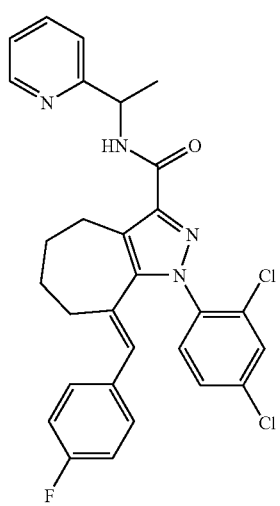
Cpd 224

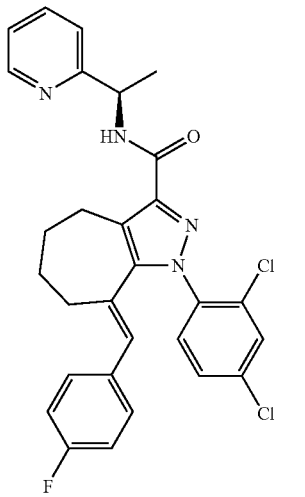
Cpd 225
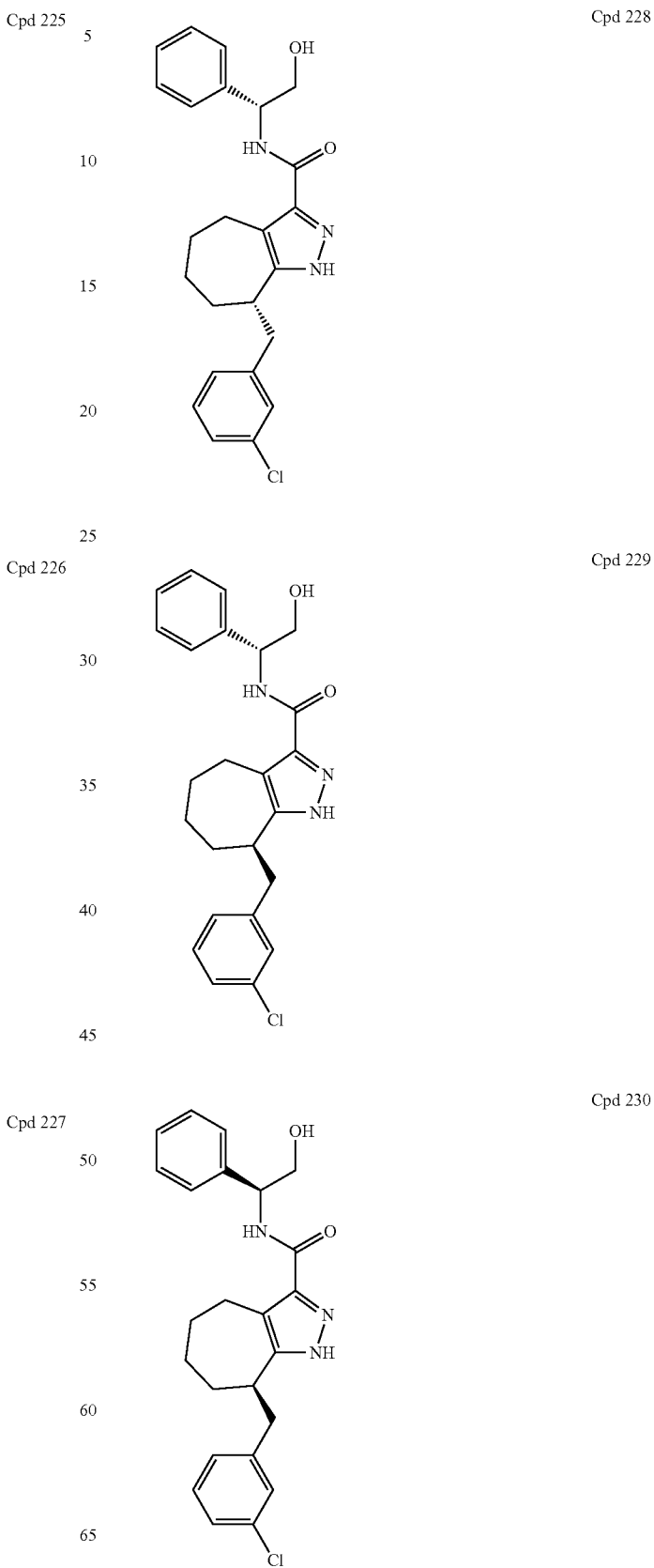
Cpd 228
Cpd 226
Cpd 229
Cpd 227
Cpd 230

-continued
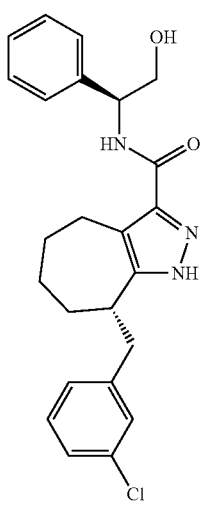
Cpd 231
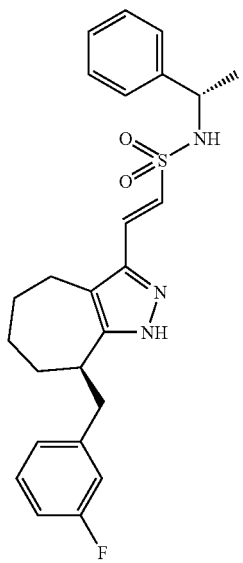
Cpd 232
Cpd 233
-continued
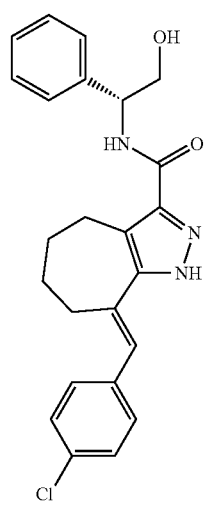
Cpd 234
Cpd 235
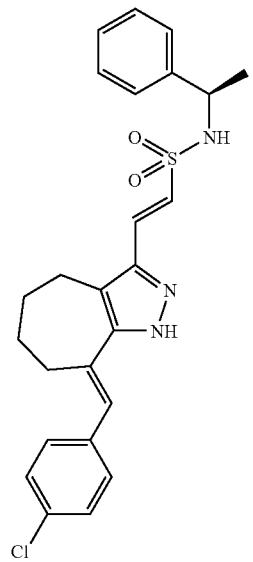
Cpd 236

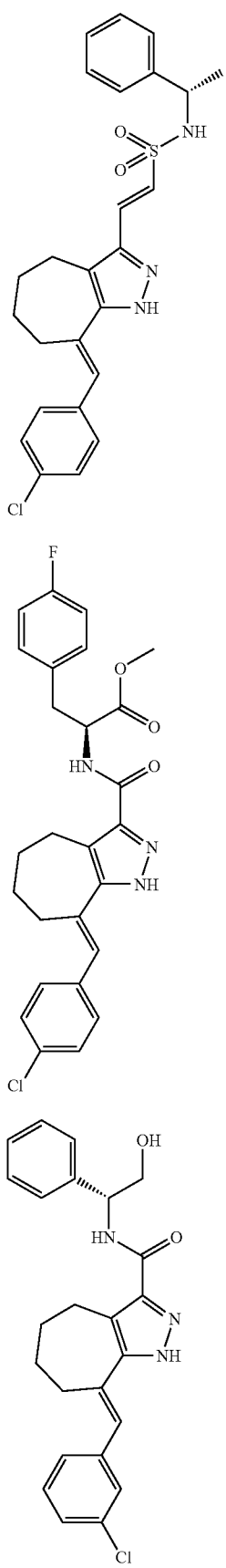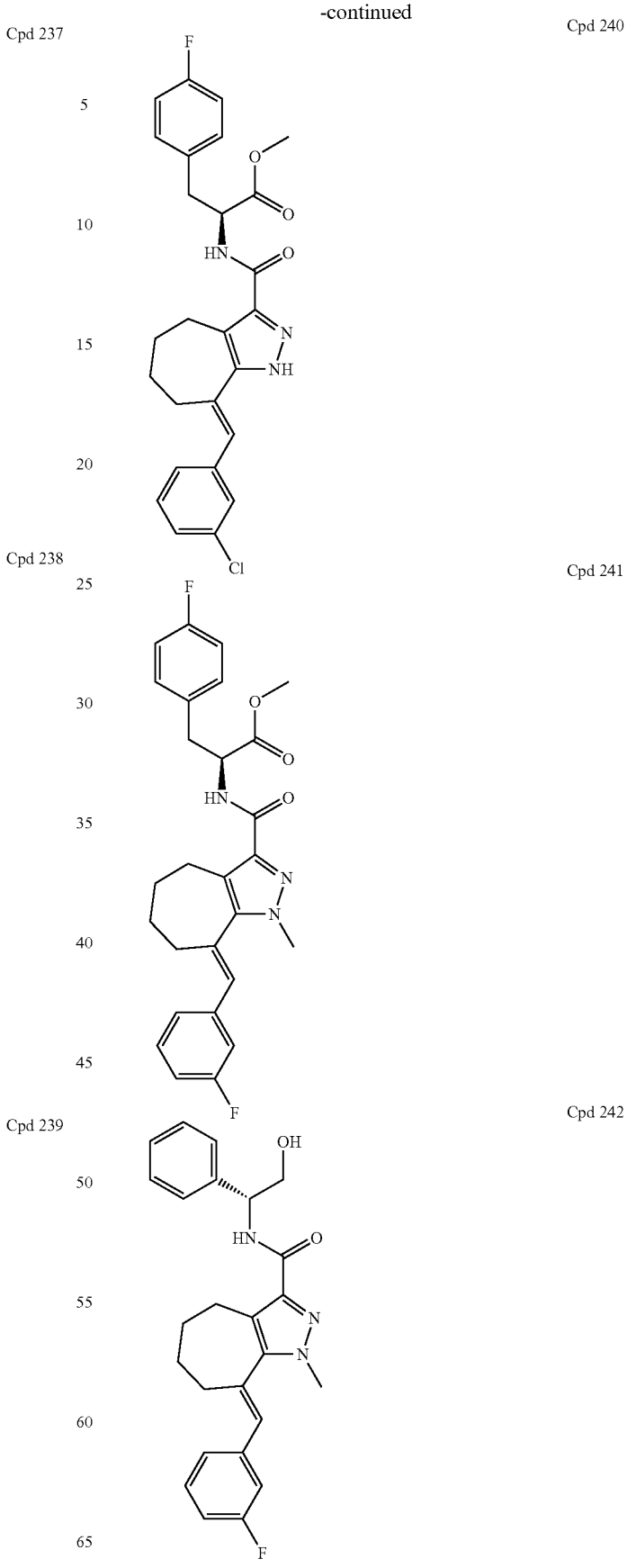

Cpd 243
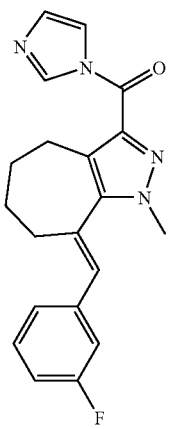
Cpd 244
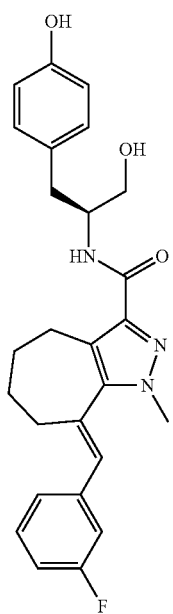
Cpd 245
Cpd 246
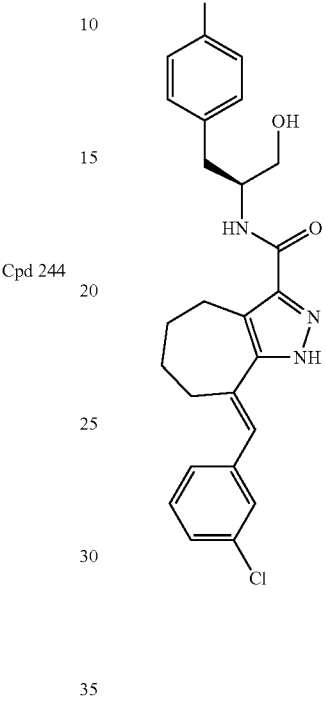
Cpd 247
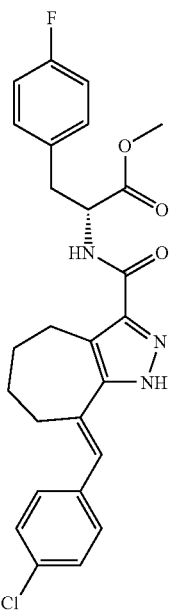

-continued
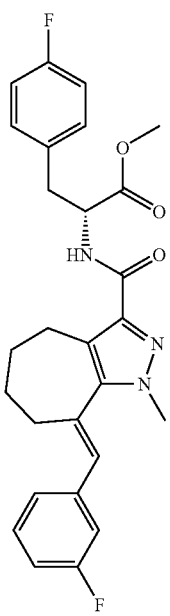
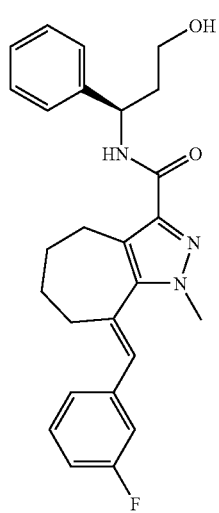
Cpd 249
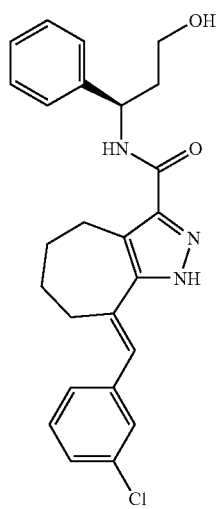
Cpd 250
-continued
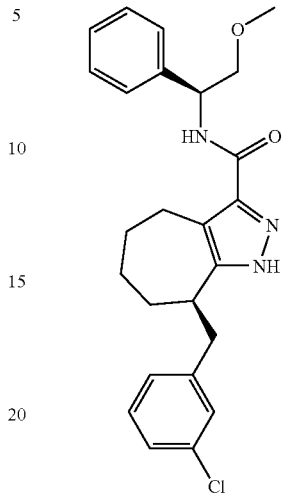
Cpd 248
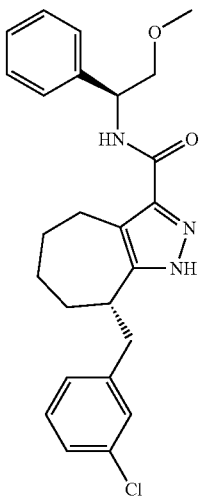
Cpd 251
Cpd 252
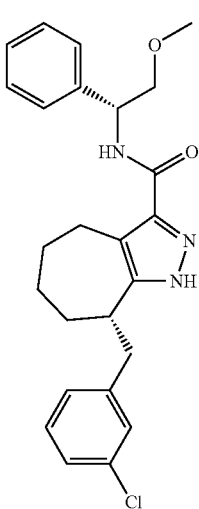
Cpd 253

-continued

Cpd 254

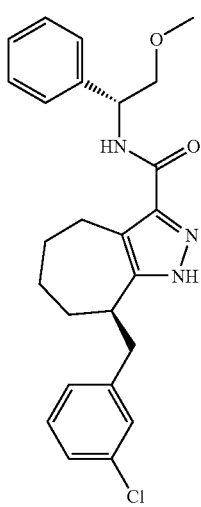

Cpd 255

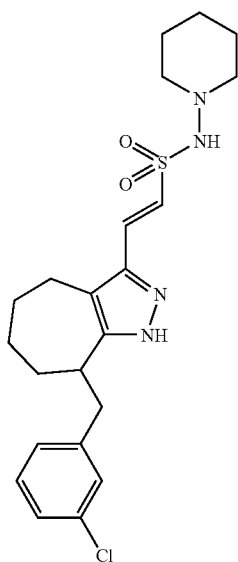

Cpd 257

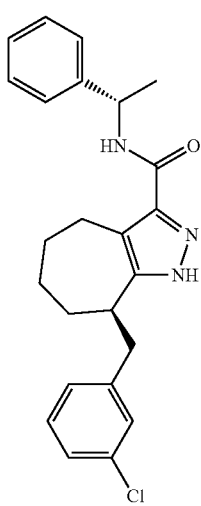

-continued

Cpd 258

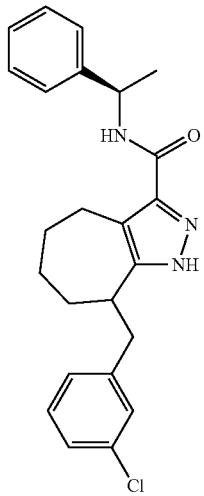

DEFINITIONS

As used herein, the following terms have the following meanings:

The term "alkyl" means a saturated branched or straight chain monovalent hydrocarbon radical of up to 10 carbon atoms. Alkyl typically includes, but is not limited to, methyl, ethyl, propyl, isopropyl, n-butyl, t-butyl, pentyl, hexyl, heptyl and the like.

The term "lower alkyl" means an alkyl radical of up to 4 carbon atoms. The point of attachment may be on any alkyl or lower alkyl carbon atom and, when further substituted, substituent variables may be placed on any carbon atom.

The term "alkylene" means a saturated branched or straight chain monovalent hydrocarbon linking group of up to 10 carbon atoms, whereby the linking group is derived by the removal of one hydrogen atom each from two carbon atoms. Alkylene typically includes, but is not limited to, methylene, ethylene, propylene, isopropylene, n-butylene, t-butylene, pentylene, hexylene, heptylene and the like. The term "lower alkylene" means an alkylene linking group of up to 4 carbon atoms. The point of attachment may be on any alkylene or lower alkylene carbon atom and, when further substituted, substituent variables may be placed on any carbon atom.

The term "alkylidene" means an alkylene linking group of from 1 to 10 carbon atoms having at least one double bond formed between two adjacent carbon atoms, wherein the double bond is derived by the removal of one hydrogen atom each from the two carbon atoms. Atoms may be oriented about the double bond in either the cis (E) or trans (Z) conformation. Alkylidene typically includes, but is not limited to, methylidene, vinylidene, propylidene, iso-propylidene, methallylene, allylidene (2-propenylidene), crotylene (2-butenylene), prenylene (3-methyl-2-butenylene) and the like. The term "lower alkylidene" means a radical or linking group of from 1 to 4 carbon atoms. The point of attachment may be on any alkylidene or lower alkylidene carbon atom and, when further substituted, substituent variables may be placed on any carbon atom.

The term "alkoxy" means an alkyl, alkylene or alkylidene radical of up to 10 carbon atoms attached via an oxygen atom, whereby the point of attachment is formed by the removal of the hydrogen atom from a hydroxide substituent on a parent radical.

The term "lower alkoxy" means an alkyl, alkylene or alkylidene radical of up to 4 carbon atoms. Lower alkoxy typically includes, but is not limited to, methoxy, ethoxy, propoxy, butoxy and the like. When further substituted, substituent variables may be placed on any alkoxy carbon atom.

The term "cycloalkyl" means a saturated or partially unsaturated monocyclic, polycyclic or bridged hydrocarbon ring system radical or linking group. A ring of 3 to 20 carbon atoms may be designated by $C_{3-20}$ cycloalkyl; a ring of 3 to 12 carbon atoms may be designated by $C_{3-12}$ cycloalkyl, a ring of 3 to 8 carbon atoms may be designated by $C_{3-8}$ cycloalkyl and the like.

Cycloalkyl typically includes, but is not limited to, cyclopropyl, cyclobutyl, cyclopentyl, cyclohexyl, cyclohexenyl, cycloheptyl, cyclooctyl, indanyl, indenyl, 1,2,3,4-tetrahydro-naphthalenyl, 5,6,7,8-tetrahydro-naphthalenyl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantanyl, octahydro-4,7-methano-1H-indenyl, octahydro-2,5-methano-pentalenyl (also referred to as hexahydro-2,5-methano-pentalenyl) and the like. When further substituted, substituent variables may be placed on any ring carbon atom.

The term "heterocyclyl" means a saturated, partially unsaturated or unsaturated monocyclic, polycyclic or bridged hydrocarbon ring system radical or linking group, wherein at least one ring carbon atom has been replaced with one or more heteroatoms independently selected from N, O or S. A heterocyclyl ring system further includes a ring system having up to 4 nitrogen atom ring members or a ring system having from 0 to 3 nitrogen atom ring members and 1 oxygen or sulfur atom ring member. When allowed by available valences, up to two adjacent ring members may be a heteroatom, wherein one heteroatom is nitrogen and the other is selected from N, O or S. A heterocyclyl radical is derived by the removal of one hydrogen atom from a single carbon or nitrogen ring atom. A heterocyclyl linking group is derived by the removal of two hydrogen atoms each from either carbon or nitrogen ring atoms.

Heterocyclyl typically includes, but is not limited to, furyl, thienyl, 2H-pyrrole, 2-pyrrolinyl, 3-pyrrolinyl, pyrrolidinyl, pyrrolyl, 1,3-dioxolanyl, oxazolyl, thiazolyl, imidazolyl, 2-imidazolinyl (also referred to as 4,5-dihydro-1H-imidazolyl), imidazolidinyl, 2-pyrazolinyl, pyrazolidinyl, pyrazolyl, isoxazolyl, isothiazolyl, oxadiazolyl, triazolyl, thiadiazolyl, tetrazolyl, 2H-pyran, 4H-pyran, pyridinyl, piperidinyl, 1,4-dioxanyl, morpholinyl, 1,4-dithianyl, thiomorpholinyl, pyridazinyl, pyrimidinyl, pyrazinyl, piperazinyl, azepanyl, indolizinyl, indolyl, isoindolyl, 3H-indolyl, indolinyl, benzo[b]furyl, benzo[b]thienyl, 1H-indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl, quinuclidinyl, hexahydro-1,4-diazepinyl, 1,3-benzodioxolyl (also known as 1,3-methylenedioxyphenyl), 2,3-dihydro-1,4-benzodioxinyl (also known as 1,4-ethylenedioxyphenyl), benzo-dihydro-furyl, benzo-tetrahydro-pyranyl, benzo-dihydro-thienyl, 5,6,7,8-tetrahydro-4H-cyclohepta(b)thienyl, 5,6,7-trihydro-4H-cyclohexa(b)thienyl, 5,6-dihydro-4H-cyclopenta(b)thienyl, hexahydro-cyclopenta[c]pyrrolyl, 2-aza-bicyclo[2.2.1]heptyl, 1-aza-bicyclo[2.2.2]octyl, 8-aza-bicyclo[3.2.1]octyl, 7-oxa-bicyclo[2.2.1]heptyl and the like.

The term "aryl" means an unsaturated, conjugated π electron monocyclic or polycyclic hydrocarbon ring system radical or linking group of 6, 9, 10 or 14 carbon atoms. An aryl radical is derived by the removal of one hydrogen atom from a single carbon ring atom. An arylene linking group is derived by the removal of two hydrogen atoms each of two carbon ring atoms. Aryl typically includes, but is not limited to, phenyl, naphthalenyl, azulenyl, anthracenyl and the like.

The term "alkylsulfonylamino" means a linking group of the formula -alkyl-$SO_2NH$—.

The term "alkylcarbamoyl" means a linking group of formula -alkyl-C(O)NH—.

The term "amino" means a radical of the formula —$NH_2$ or a linking group of the formula —NH—.

The term "aminosulfonyl" means a radical of the formula —$SO_2NH_2$.

The term "arylalkoxy" means a radical of the formula —O-alkyl-aryl.

The term "aryloxy" means a radical of the formula —O-aryl.

The term "carbamoyl" means a radical of the formula —C(O)$NH_2$.

The term "carbamoylalkyl" means a radical of the formula —C(O)NH-alkyl or —C(O)N(alkyl)$_2$.

The term "carbonylalkoxy" means a radical of the formula —C(O)O-alkyl.

The term "carboxy" means a radical of the formula —COOH or —$CO_2H$.

The term "halo" or "halogen" means fluoro, chloro, bromo or iodo.

The term "lower alkyl-amino" means a radical of the formula —NH-alkyl or —N(alkyl)$_2$.

The term "lower alkyl-aminosulfonyl" means a radical of the formula —$SO_2$NH-alkyl or —$SO_2$N(alkyl)$_2$.

The term "lower alkyl-sulfonyl" means a radical of the formula —$SO_2$-alkyl or —C(O)N(alkyl)$_2$.

The term "substituted" means one or more hydrogen atoms on a core molecule have been replaced with one or more radicals or linking groups, wherein the linking group, by definition is also further substituted. The ability of a particular radical or linking group to replace a hydrogen atom is optimally expected by one skilled to art to result in a chemically stable core molecule.

The term "dependently selected" means one or more substituent variables are present in a specified combination (e.g. groups of substituents commonly appearing in a tabular list).

The substituent nomenclature used in the disclosure of the present invention was derived using nomenclature rules well known to those skilled in the art (e.g., IUPAC).

Pharmaceutical Forms

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The present invention includes within its scope prodrugs and metabolites of the compounds of this invention. In general, such prodrugs and metabolites will be functional derivatives of the compounds that are readily convertible in vivo into an active compound.

Thus, in the methods of treatment of the present invention, the term "administering" shall encompass the means for treating, ameliorating or preventing a syndrome, disorder or disease described herein with a compound specifically disclosed or a compound, or prodrug or metabolite thereof, which would obviously be included within the scope of the invention albeit not specifically disclosed for certain of the instant compounds.

The term "prodrug" means a pharmaceutically acceptable form of a functional derivative of a compound of the invention (or a salt thereof), wherein the prodrug may be: 1) a relatively active precursor which converts in vivo to an active prodrug component; 2) a relatively inactive precursor which converts in vivo to an active prodrug component; or 3) a relatively less active component of the compound that contributes to therapeutic biological activity after becoming available in vivo (i.e., as a metabolite). Conventional procedures for the selection and preparation of suitable prodrug derivatives are described in, for example, "Design of Prodrugs", ed. H. Bundgaard, Elsevier, 1985.

The term "metabolite" means a pharmaceutically acceptable form of a metabolic derivative of a compound of the invention (or a salt thereof), wherein the derivative is a relatively less active component of the compound that contributes to therapeutic biological activity after becoming available in vivo.

The present invention contemplates compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" refers to isomers of identical constitution that differ in the arrangement of their atoms in space. Enantiomers and diastereomers are stereoisomers wherein an asymmetrically substituted carbon atom acts as a chiral center. The term "chiral" refers to a molecule that is not superposable on its mirror image, implying the absence of an axis and a plane or center of symmetry. The term "enantiomer" refers to one of a pair of molecular species that are mirror images of each other and are not superposable. The term "diastereomer" refers to stereoisomers that are not related as mirror images. The symbols "R" and "S" represent the configuration of substituents around a chiral carbon atom(s). The symbols "R*" and "S*" denote the relative configurations of substituents around a chiral carbon atom(s).

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) or "chair" configuration, the substituents are on opposite sides in relationship to the carbon-carbon double bond; in the "Z" (same sided) or "boat" configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans". Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "S*," "R*," "E," "Z," "cis," "trans," "exo" and "endo" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Furthermore, compounds of the present invention may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Therapeutic Use

CB1 and CB2 cannabinoid receptors belong to the G-protein-coupled receptor (GCPR) family, a receptor super-family with a distinctive pattern of seven transmembrane domains, which inhibits N-type calcium channels and/or adenylate cyclase to inhibit Q-type calcium channels.

CB1 receptors are present in the CNS, predominately expressed in brain regions associated with memory and movement such as the hippocampus (memory storage), cerebellum (coordination of motor function, posture and balance), basal ganglia (movement control), hypothalamus (thermal regulation, neuroendocrine release, appetite), spinal cord (nociception), cerebral cortex (emesis) and periphery regions such as lymphoid organs (cell mediated and innate immunity), vascular smooth muscle cells (blood pressure), gastrointestinal tract (innate antiinflammatory in the tract and in the esophagus, duodenum, jejunum, ileum and colon, controlling esophageal and gastrointestinal motility), lung smooth muscle cells (bronchodilation), eye ciliary body (intraocular pressure).

CB2 receptors appear to be primarily expressed peripherally in lymphoid tissue (cell mediated and innate immunity), peripheral nerve terminals (peripheral nervous system), spleen immune cells (immune system modulation) and retina (intraocular pressure). CB2 mRNA is found in the CNS in cerebellar granule cells (coordinating motor function).

Pharmacological and physiological evidence also suggests that there may be other cannabinoid receptor subtypes that have yet to be cloned and characterized.

Where activation or inhibition of a CB receptor appears to mediate various syndromes, disorders or diseases, potential areas of clinical application include, but are not limited to, controlling appetite, regulating metabolism, diabetes, reducing glaucoma-associated intraocular pressure, treating social and mood disorders, treating seizure-related disorders, treating substance abuse disorders, enhancing learning, cognition and memory, controlling organ contraction and muscle spasm, treating bowel disorders, treating respiratory disorders, treating locomotor activity or movement disorders, treating immune and inflammation disorders, regulating cell growth, use in pain management, use as a neuroprotective agent and the like.

Thus, cannabinoid receptor modulators, including the compounds of the formula (I) or (Ia) of the present invention, are useful for treating, ameliorating or preventing a cannabinoid receptor mediated syndrome, disorder or disease including, but not limited to, controlling appetite, regulating metabolism, diabetes, glaucoma-associated intraocular pressure, pain, social and mood disorders, seizure-related disorders, substance abuse disorders, learning, cognition and/or memory disorders, bowel disorders, respiratory disorders, locomotor activity disorders, movement disorders, immune disorders or inflammation disorders, controlling organ contraction and muscle spasm, enhancing learning, cognition and/or memory, regulating cell growth, providing neuroprotection and the like.

The present invention is directed to a method for treating, ameliorating or preventing a cannabinoid receptor mediated syndrome, disorder or disease in a subject in need thereof comprising the step of administering to the subject an effective amount of a compound of formula (I).

The present invention is directed to a method for treating, ameliorating or preventing a cannabinoid receptor mediated syndrome, disorder or disease in a subject in need thereof comprising the step of administering to the subject an effective amount of a compound of formulae (Ia) or prodrug, metabolite, or composition thereof.

The present invention is directed to a method for treating, ameliorating or preventing a cannabinoid receptor mediated syndrome, disorder or disease in a subject in need thereof comprising the step of administering to the subject a combination product and/or therapy comprising an effective amount of a compound of formula (I) and a therapeutic agent.

The present invention is directed to a method for treating, ameliorating or preventing a cannabinoid receptor mediated syndrome, disorder or disease in a subject in need thereof comprising the step of administering to the subject a combination product and/or therapy comprising an effective amount of a compound of formulae (Ia) and a therapeutic agent.

Therapeutic agents contemplated for use in a combination product and/or therapies of the present invention include an anticonvulsant or a contraceptive agent. The anticonvulsant agents include, and are not limited to, topiramate, analogs of topiramate, carbamazepine, valproic acid, lamotrigine, gabapentin, phenytoin and the like and mixtures or pharmaceutically acceptable salts thereof. The contraceptive agents include, and are not limited to, such as progestin-only contraceptives and contraceptives that include both a progestin component and an estrogen component. The invention further includes a pharmaceutical composition wherein the contraceptive is an oral contraceptive, and wherein the contraceptive optionally includes a folic acid component.

The invention also includes a method of contraception in a subject comprising the step of administering to the subject a composition, wherein the composition comprises a contraceptive and a CB1 receptor inverse-agonist or antagonist compound of formulae (I) or (Ia), wherein the composition reduces the urge to smoke in the subject and/or assists the subject in losing weight.

The present invention includes cannabinoid receptor modulators useful for treating, ameliorating or preventing a CB receptor mediated syndrome, disorder or disease. The usefulness of a compound of the present invention or composition thereof as a CB modulator can be determined according to the methods disclosed herein. The scope of such use includes treating, ameliorating or preventing a plurality of CB receptor mediated syndromes, disorders or diseases.

The present invention is also directed to a method for treating, ameliorating or preventing a CB receptor mediated syndrome, disorder or disease in a subject in need thereof wherein the syndrome, disorder or disease is related to appetite, metabolism, diabetes, glaucoma-associated intraocular pressure, social and mood disorders, seizures, substance abuse, learning, cognition or memory, organ contraction or muscle spasm, bowel disorders, respiratory disorders, locomotor activity or movement disorders, immune and inflammation disorders, unregulated cell growth, pain management, neuroprotection and the like.

A compound of formulae (I) or (Ia) for use as a CB receptor modulator includes a compound having a mean inhibition constant ($IC_{50}$) for CB receptor binding activity of between about 50 µM to about 0.01 nM; between about 25 µM to about 0.01 nM; between about 15 µM to about 0.01 nM; between about 10 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB1 agonist $IC_{50}$ for CB1 agonist binding activity of between about 50 µM to about 0.01 nM; between about 25 µM to about 0.01 nM; between about 15 µM to about 0.01 nM; between about 10 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB1 antagonist $IC_{50}$ for CB1 antagonist binding activity of between about 50 µM to about 0.01 nM; between about 25 µM to about 0.01 nM; between about 15 µM to about 0.01 nM; between about 10 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB1 inverse-agonist $IC_{50}$ for CB1 inverse-agonist binding activity of between about 50 µM to about 0.01 nM; between about 25 µM to about 0.01 nM; between about 15 µM to about 0.01 nM; between about 10 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB2 agonist $IC_{50}$ for CB2 agonist binding activity of between about 50 µM to about 0.01 nM; between about 25 µM to about 0.01 nM; between about 15 µM to about 0.01 nM; between about 10 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB2 antagonist $IC_{50}$ for CB2 antagonist binding activity of between about 50 µM to about 0.01 nM; between about 25 µM to about 0.01 nM; between about 15 µM to about 0.01 nM; between about 10 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB2 inverse-agonist $IC_{50}$ for CB2 inverse-agonist binding activity of between about 50 µM to about 0.01 nM; between about 25 µM to about 0.01 nM; between about 15 µM to about 0.01 nM; between about 10 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

The term "cannabinoid receptor" refers to any one of the known or heretofore unknown subtypes of the class of cannabinoid receptors that may be bound by a cannabinoid modulator compound of the present invention; in particular, a cannabinoid receptor selected from the group consisting of a CB1 receptor and a CB2 receptor. The term "modulator" further refers to the use of a compound of the invention as a CB receptor agonist, antagonist or inverse-agonist.

The present invention includes a method for treating, ameliorating or preventing a CB receptor mediated syndrome, disorder or disease in a subject in need thereof comprising the step of administering to the subject an effective amount of a compound of the present invention or composition thereof, wherein the cannabinoid receptor is a CB1 or CB2 receptor; and, the compound is an agonist, antagonist or inverse-agonist of the receptor.

The present invention includes a method for treating, ameliorating or preventing a CB receptor mediated syndrome, disorder or disease in a subject in need thereof comprising the step of administering to the subject an effective amount of a compound of the present invention in a combination product and/or therapy with a therapeutic agent such as an anticonvulsant or contraceptive agent or composition thereof, wherein the cannabinoid receptor is a CB1 or CB2 receptor; and, the compound is an agonist, antagonist or inverse-agonist of the receptor.

It should be understood that contraceptive agents suitable for use in a combination product and/or therapy are not limited to oral contraceptives, but also include other commonly available contraceptives such as those that are administered transdermally, by injection or via implant.

Except as further specified, "combination product and/or therapy" means a pharmaceutical composition comprising a compound of formulae (I) or (Ia) in combination with one or more therapeutic agents. The dosages of the compound of formula (I) or (Ia) and the one or more therapeutic agents are adjusted when combined to achieve an effective amount.

The term "subject" as used herein, refers to a patient, which may be an animal, preferably a mammal, most preferably a human, which has been the object of treatment, observation or experiment and is at risk of (or susceptible to) developing a CB receptor mediated syndrome, disorder or disease.

The term "administering" is to be interpreted in accordance with the methods of the present invention. Such methods include therapeutically or prophylactically administering an effective amount of a composition or medicament of the present invention at different times during the course of a therapy or concurrently as a product in a combination form.

Prophylactic administration can occur prior to the manifestation of symptoms characteristic of a CB receptor mediated syndrome, disorder or disease such that the syndrome, disorder or disease is treated, ameliorated, prevented or otherwise delayed in its progression. The methods of the present invention are further to be understood as embracing all therapeutic or prophylactic treatment regimens used by those skilled in the art.

The term "effective amount" refers to that amount of active compound or pharmaceutical agent that elicits the biological or medicinal response in a tissue system, animal or human, that is being sought by a researcher, veterinarian, medical doctor, or other clinician, which includes alleviation of the symptoms of the syndrome, disorder or disease being treated. The effective amount of a compound of the invention is from about 0.001 mg/kg/day to about 300 mg/kg/day.

Wherein the present invention is directed to the administration of a combination of a compound of formula (I) and an anticonvulsant or contraceptive agent, the term "effective amount" means that amount of the combination of agents taken together so that the combined effect elicits the desired biological or medicinal response.

As those skilled in the art will appreciate, the effective amounts of the components comprising the combination product may be independently optimized and combined to achieve a synergistic result whereby the pathology is reduced more than it would be if the components of the combination product were used alone.

For example, the effective amount of a combination product and/or therapy comprising administration of a compound of formula (I) and topiramate would be the amount of the compound of formula (I) and the amount of topiramate that when taken together or sequentially have a combined effect that is effective. Further, it will be recognized by one skilled in the art that in the case of combination product and/or therapy with an effective amount, as in the example above, the amount of the compound of formula (I) and/or the amount of the anticonvulsant (e.g., topiramate) individually may or may not be effective.

Wherein the present invention is directed to the administration of a combination product and/or therapy, the instant compound and the anticonvulsant or contraceptive agent may be co-administered by any suitable means, simultaneously, sequentially or in a single pharmaceutical composition. Where the instant compound(s) and the anticonvulsant or contraceptive agent components are administered separately, the number of dosages of each compound(s) given per day, may not necessarily be the same, e.g. where one compound may have a greater duration of activity, and will therefore, be administered less frequently.

The compound(s) of formula (I) and the anticonvulsant(s) or contraceptive agent(s) may be administered via the same or different routes of administration. The compound(s) of formula (I) and the anticonvulsant(s) or contraceptive agent(s) may be administered via the same or different routes of administration.

Suitable examples of methods of administration are orally, intravenous (iv), intramuscular (im), and subcutaneous (sc). Compounds may also be administrated directly to the nervous system including, but not limited to the intracerebral, intraventricular, intracerebroventricular, intrathecal, intracisternal, intraspinal and/or peri-spinal routes of administration by delivery via intracranial or intravertebral needles and/or catheters with or without pump devices.

The compound(s) of formula (I) and the anticonvulsant(s) or contraceptive agent(s) may be administered according to simultaneous or alternating regimens, at the same or different times during the course of the therapy, concurrently in divided or single forms.

Optimal dosages to be administered may be readily determined by those skilled in the art, and will vary with the particular compound used, the mode of administration, the strength of the preparation and the advancement of the disease condition. In addition, factors associated with the particular patient being treated, including patient's sex, age, weight, diet, time of administration and concomitant diseases, will result in the need to adjust dosages.

The term "CB receptor mediated syndrome, disorder, or disease" refers to syndromes, disorders or diseases associated with a biological response mediated by a CB receptor such that there is discomfort or decreased life expectancy to the organism.

CB receptor mediated syndromes, disorders or diseases can occur in both animals and humans and include appetite, metabolism, diabetes, obesity, glaucoma-associated intraocular pressure, social, mood, seizure, substance abuse, learning, cognition, memory, organ contraction, muscle spasm, bowel, respiratory, locomotor activity, movement, immune, inflammation, cell growth, pain or neurodegenerative related syndromes, disorders or diseases.

Appetite related syndromes, disorders or diseases include obesity, overweight condition, anorexia, bulimia, cachexia, dysregulated appetite and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

Metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

Diabetes related syndromes, disorders or diseases include glucose dysregulation, insulin resistance, glucose intolerance, hyperinsulinemia, dyslipidemia, hypertension, obesity and the like.

Type II diabetes mellitus (non-insulin-dependent diabetes mellitus) is a metabolic disorder (i.e., a metabolism related syndrome, disorder or disease) in which glucose dysregulation and insulin resistance results in chronic, long-term medical complications for both adolescents and adults affecting the eyes, kidneys, nerves and blood vessels and can lead to blindness, end-stage renal disease, myocardial infarction or limb amputation and the like. Glucose dysregulation includes the inability to make sufficient insulin (abnormal insulin secretion) and the inability to effectively use insulin (resistance to insulin action in target organs and tissues). Individuals suffering from Type II diabetes mellitus have a relative insulin deficiency. That is, in such individuals, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension. These micro- and macro-vascular complications can lead to blindness, end-stage renal disease, limb amputation and myocardial infarction.

Insulin Resistance Syndrome (IRS) (also referred to as Syndrome X, Metabolic Syndrome or Metabolic Syndrome X) is a disorder that presents risk factors for the development of Type II diabetes and cardiovascular disease including glucose intolerance, hyperinsulinemia, insulin resistance, dyslipidemia (e.g. high triglycerides, low HDL-cholesterol and the like), hypertension and obesity.

Social or mood related syndromes, disorders or diseases include depression, anxiety, psychosis, social affective disorders or cognitive disorders and the like.

Substance abuse related syndromes, disorders or diseases include drug abuse, drug withdrawal, alcohol abuse, alcohol withdrawal, nicotine withdrawal, cocaine abuse, cocaine withdrawal, heroin abuse, heroin withdrawal and the like.

Learning, cognition or memory related syndromes, disorders or diseases include memory loss or impairment as a result of age, disease, side effects of medications (adverse events) and the like.

Muscle spasm syndromes, disorders or diseases include multiple sclerosis, cerebral palsy and the like.

Locomotor activity and movement syndromes, disorders or diseases include stroke, Parkinson's disease, multiple sclerosis, epilepsy and the like.

Bowel related syndromes, disorders or diseases include bowel dysmotility associated disorders (either accompanied by pain, diarrhea or constipation or without), irritable bowel syndrome (and other forms of bowel dysmotility and the like), inflammatory bowel diseases (such as ulcerative colitis, Crohn's disease and the like) and celiac disease.

An example of the invention includes bowel related syndromes, disorders, or diseases associated with inflammation, with or without pain, such as inflammatory bowel disease, disordered bowel motility associated with inflammation arising from surgery, traumatic injury or any sequelae resulting from traumatic injury, intraperitoneal inflammation, basal pneumonia, myocardial infarction, metabolic disturbances or any combination thereof.

An example of the invention bowel related syndromes, disorders, or diseases associated with inflammation, with or without pain, include inflammatory bowel diseases such as ulcerative colitis, Crohn's disease or celiac disease. Disordered bowel motility associated with inflammation arising from surgery includes abdominal surgery, transplantation surgery, bowel resection, orthopedic surgery, cardiovascular surgery or gynecological surgery. Traumatic injury includes falls, car accident or personal assault. Sequelae resulting from traumatic injury includes limb fractures, rib fractures, fractures of the spine, thoracic lesions, ischemia or retroperitoneal hecatomb. Intraperitoneal inflammation includes intraabdominal sepsis, acute appendicitis, cholecystitis, pancreatitis or ureteric colic.

Respiratory related syndromes, disorders or diseases include chronic pulmonary obstructive disorder, emphysema, asthma, bronchitis and the like.

Immune or inflammation related syndromes, disorders or diseases include allergy, rheumatoid arthritis, dermatitis, autoimmune disease, immunodeficiency, chronic neuropathic pain and the like.

Cell growth related syndromes, disorders or diseases include dysregulated mammalian cell proliferation, breast cancer cell proliferation, prostrate cancer cell proliferation and the like.

Pain related syndromes, disorders or diseases include central and peripheral pathway mediated pain, bone and joint pain, migraine headache associated pain, cancer pain, menstrual cramps, labor pain and the like.

Neurodegenerative related syndromes, disorders or diseases include Parkinson's Disease, multiple sclerosis, epilepsy, ischemia or secondary biochemical injury collateral to traumatic head or brain injury, brain inflammation, eye injury or stroke and the like.

The present invention includes a method for treating, ameliorating or preventing a cannabinoid receptor agonist mediated syndrome, disorder or disease in a subject in need thereof comprising the step of administering to the subject an effective amount of a cannabinoid agonist compound of the present invention or composition thereof.

The present invention includes a method for treating, ameliorating or preventing a cannabinoid receptor agonist mediated syndrome, disorder or disease in a subject in need thereof comprising the step of administering to the subject an effective amount of a cannabinoid agonist compound of the present invention in a combination product and/or therapy with an anticonvulsant or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention in a combination product and/or therapy with an anticonvulsant or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention in a combination product and/or therapy with one or more contraceptives or composition thereof.

The present invention includes a method for treating, ameliorating or preventing a cannabinoid receptor antagonist mediated syndrome, disorder or disease in a subject in need thereof comprising the step of administering to the subject an effective amount of a cannabinoid antagonist compound of the present invention or composition thereof.

The present invention includes a method for treating, ameliorating or preventing a cannabinoid receptor antagonist mediated syndrome, disorder or disease in a subject in need thereof comprising the step of administering to the subject an effective amount of a cannabinoid antagonist compound of the present invention in a combination product and/or therapy with an anticonvulsant or composition thereof.

The present invention includes a method for treating, ameliorating or preventing a cannabinoid receptor antagonist mediated syndrome, disorder or disease in a subject in need thereof comprising the step of administering to the subject a therapeutically or prophylactically effective amount of a cannabinoid antagonist compound of the present invention in a combination product and/or therapy with one or more contraceptives or composition thereof.

The present invention includes a method for treating, ameliorating or preventing a CB1 receptor agonist mediated syndrome, disorder or disease in a subject in need thereof comprising the step of administering to the subject an effective amount of a CB1 agonist compound of the present invention or composition thereof.

The present invention includes a method for treating, ameliorating or preventing a CB1 receptor agonist mediated syndrome, disorder or disease in a subject in need thereof comprising the step of administering to the subject an effective amount of a CB1 agonist compound of the present invention in a combination product and/or therapy with an anticonvulsant or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention in a combination product and/or therapy with an anticonvulsant or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention in a combination product and/or therapy with one or more contraceptives or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention in a combination product and/or therapy with an anticonvulsant or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention in a combination product and/or therapy with one or more contraceptives or composition thereof.

Appetite related syndromes, disorders or diseases include obesity, overweight condition, anorexia, bulimia, cachexia, dysregulated appetite and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

Metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention or composition thereof.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention in a combination product and/or therapy with an anticonvulsant or composition thereof.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention in a combination product and/or therapy with one or more contraceptives or composition thereof.

The present invention includes a method for treating, ameliorating or preventing a CB2 receptor agonist mediated syndrome, disorder or disease in a subject in need thereof comprising the step of administering to the subject an effective amount of a CB2 agonist compound of the present invention or composition thereof.

The present invention includes a method for treating, ameliorating or preventing a CB2 receptor agonist mediated syndrome, disorder or disease in a subject in need thereof comprising the step of administering to the subject an effective amount of a CB2 agonist compound of the present invention in a combination product and/or therapy with an anticonvulsant or composition thereof.

The present invention includes include a method for treating, ameliorating or preventing a CB2 receptor inverse-agonist mediated syndrome, disorder or disease in a subject in need thereof comprising the step of administering to the subject an effective amount of a CB2 inverse-agonist compound of the present invention or composition thereof.

The present invention includes a method for treating, ameliorating or preventing a CB2 receptor inverse-agonist mediated syndrome, disorder or disease in a subject in need thereof comprising the step of administering to the subject an effective amount of a CB2 inverse-agonist compound of the present invention in a combination product and/or therapy with an anticonvulsant or composition thereof.

The present invention includes a method for treating, ameliorating or preventing a CB2 receptor antagonist mediated syndrome, disorder or disease in a subject in need thereof comprising the step of administering to the subject an effective amount of a CB2 antagonist compound of the present invention or composition thereof.

The present invention includes a method for treating, ameliorating or preventing a CB2 receptor antagonist mediated syndrome, disorder or disease in a subject in need thereof comprising the step of administering to the subject an effective amount of a CB2 antagonist compound of the present invention in a combination product and/or therapy with an anticonvulsant or composition thereof.

The present invention includes a method for treating, ameliorating or preventing a metabolism related syndrome, disorder or disease, an appetite related syndrome, disorder or disease, a diabetes related syndrome, disorder or disease, an obesity related syndrome, disorder or disease or a learning, cognition or memory related syndrome, disorder or disease in a subject in need thereof comprising the step of administering to the subject an effective amount of a compound of the present invention or composition thereof.

The present invention includes a method for treating, ameliorating or preventing a metabolism related syndrome, disorder or disease, an appetite related syndrome, disorder or disease, a diabetes related syndrome, disorder or disease, an obesity related syndrome, disorder or disease or a learning, cognition or memory related syndrome, disorder or disease in a subject in need thereof comprising the step of administering to the subject an effective amount of a compound of the present invention in a combination product and/or therapy with an anticonvulsant or composition thereof.

The present invention includes a pharmaceutical composition or medicament comprising an admixture of a compound of the present invention and an optional pharmaceutically acceptable carrier.

The present invention includes a pharmaceutical composition or medicament comprising an admixture of two or more compounds of the present invention and an optional pharmaceutically acceptable carrier.

The present invention also includes a pharmaceutical composition or medicament comprising an admixture of a compound of formula (I), an anticonvulsant and an optional pharmaceutically acceptable carrier.

Such pharmaceutical compositions are particularly useful for treating a subject suffering from a metabolism related syndrome, disorder or disease, an appetite related syndrome, disorder or disease, a diabetes related syndrome, disorder or disease, an obesity related syndrome, disorder or disease, or a learning, cognition or memory related syndrome, disorder or disease.

Anticonvulsants useful in the methods and compositions of the present invention in combination with a compound of formula (I) or (Ia) include, but are not limited to, topiramate, analogs of topiramate, carbamazepine, valproic acid, lamotrigine, gabapentin, phenytoin and the like and mixtures or pharmaceutically acceptable salts thereof.

Topiramate, 2,3:4,5-bis-O-(1-methylethylidene)-β-D-fructopyranose sulfamate, is currently marketed for the treatment of seizures in patients with simple and complex partial epilepsy and seizures in patients with primary or secondary generalized seizures in the United States, Europe and most other markets throughout the world. Topiramate is currently available for oral administration in round tablets containing 25 mg, 100 mg or 200 mg of active agent, and as 15 mg and 25 mg sprinkle capsules for oral administration as whole capsules or opened and sprinkled onto soft food. U.S. Pat. No. 4,513,006, incorporated herein by reference, discloses topiramate and analogs of topiramate, their manufacture and use for treating epilepsy. Additionally, topiramate may also be made by the process disclosed in U.S. Pat. Nos. 5,242,942 and 5,384,327, which are incorporated by reference herein. The term "analogs of topiramate", as used herein, refers to the sulfamate compounds of formula (I), which are disclosed in U.S. Pat. No. 4,513,006 (see, e.g., column 1, lines 36-65 of U.S. Pat. No. 4,513,006).

For use in the methods of the present invention in combination with a compound of the formula (I) or (Ia), topiramate (or an analog of topiramate) can be administered in the range of about 10 to about 1000 mg daily, preferably in the range of about 10 to about 650 mg daily, more preferably in the range of about 15 to about 325 mg once or twice daily.

Carbamazepine, 5H-dibenz[b,f]azepine-5-carboxamide, is an anticonvulsant and specific analgesic for trigeminal neuralgia, available for oral administration as chewable tablets of 100 mg, tablets of 200 mg, XR (extended release) tablets of 100, 200, and 400 mg, and as a suspension of 100 mg/5 mL (teaspoon); U.S. Pat. No. 2,948,718, herein incorporated by reference in its entirety, discloses carbamazepine and its methods of use.

For use in the methods of the present invention in combination with a compound of the formula (I) or (Ia), carbamazepine can be administered in the range of about 200 to about 1200 mg/day; preferably, about 400 mg/day.

Valproic acid, 2-propylpentanoic acid or dipropylacetic acid, is an antiepileptic agent commercially available as soft elastic capsules containing 250 mg valproic acid, and as syrup containing the equivalent of 250 mg valproic acid per 5 mL as the sodium salt. Valproic acid and various pharmaceutically acceptable salts are disclosed in U.S. Pat. No. 4,699,927, which is incorporated by reference herein in its entirety.

For use in the methods of the present invention in combination with a compound of the formula (I) or (Ia), valproic acid can be administered in the range of about 250 to about 2500 mg/day; preferably, about 1000 mg/day.

Lamotrigine, 3,5-diamino-6-(2,3-dichlorophenyl)-1,2,4-triazine, is an antiepileptic drug commercially available for oral administration as tablets containing 25 mg, 100 mg, 150 mg, and 200 mg of lamotrigine, and as chewable dispersible tablets containing 2 mg, 5 mg, or 25 mg of lamotrigine. Lamotrigine and its uses are disclosed in U.S. Pat. No. 4,486,354, incorporated by reference herein in its entirety.

For use in the methods of the present invention in combination with a compound of the formula (I) or (Ia), lamotrigine can be administered in the range of about 50 to about 600 mg/day in one to two doses; preferably, about 200 to about 400 mg/day; most preferably, about 200 mg/day.

Gabapentin, 1-(aminomethyl)cyclohexaneacetic acid, is commercially available for the adjunctive treatment of epilepsy and for postherpetic neuralgia in adults as capsules containing 100 mg, 300 mg, and 400 mg of gabapentin, film-coated tablets containing 600 mg and 800 mg of gabapentin, and an oral solution containing 250 mg/5 mL of gabapentin. Gabapentin and its methods of use are described in U.S. Pat. No. 4,024,175 and U.S. Pat. No. 4,087,544, herein incorporated by reference in their entirety.

For use in the methods of the present invention in combination with a compound of the formula (I) or (Ia), gabapentin can be administered in the range of about 300 to about 3600 mg/day in two to three divided doses; preferably, about 300 to about 1800 mg/day; most preferably, about 900 mg/day.

Phenytoin sodium, 5,5-diphenylhydantoin sodium salt, is an anticonvulsant, which is commercially available for oral administration as capsules containing 100 mg, 200 mg or 300 mg of phenytoin sodium.

For use in the methods of the present invention in combination with a compound of the formula (I) or (Ia), phenytoin sodium can be administered in the range of about 100 to about 500 mg/day; preferably, about 300 to about 400 mg/day; most preferably, about 300 mg/day.

The present invention also includes a pharmaceutical composition or medicament comprising an admixture of a compound of formula (I) or (Ia), one or more contraceptives and an optional pharmaceutically acceptable carrier.

Contraceptives suitable for use in a combination product and/or therapy include, for example, ORTHO CYCLEN®, ORTHO TRI-CYCLEN®, ORTHO TRI-CYCLEN LO®, and ORTHO EVRA®, all available from Ortho-McNeil Pharmaceutical, Inc., Raritan, N.J. It should also be understood that contraceptives suitable for use in the invention encompass those contraceptives that include a folic acid component.

Smoking and/or obesity have been identified as risk factors in women taking oral contraceptives. CB1 receptor antagonists and inverse agonists have been found to be useful therapeutic agents for reducing the urge to smoke and for assisting patients with eating disorders to lose weight.

Accordingly, the invention further includes a method of reducing the risk factors associated with smoking and/or obesity for women taking contraceptives by co-administering with a contraceptive at least one of a CB1 receptor antagonist and/or CB1 receptor inverse-agonist compound of formula (I) or (Ia).

The use of such compounds or a pharmaceutical composition or medicament thereof is to reduce the desire to smoke and/or to assist in weight loss for patients taking contraceptives.

Pharmaceutical Compositions

The term "composition" refers to a product comprising the specified ingredients in the specified amounts, as well as any product that results, directly or indirectly, from combinations of the specified ingredients in the specified amounts. The invention further comprises mixing one or more of the compounds of the invention and a pharmaceutically acceptable carrier; and, includes those compositions resulting from such a process. Contemplated processes include both traditional and modern pharmaceutical techniques.

Pharmaceutical compositions of the invention may, alternatively or in addition to a compound of formula (I) or (Ia), comprise a pharmaceutically acceptable salt of a compound of formula (I) or (Ia) or a prodrug or pharmaceutically active metabolite of such a compound or salt in admixture with a pharmaceutically acceptable carrier.

The term "medicament" refers to a product for use in treating, ameliorating or preventing a cannabinoid receptor mediated syndrome, disorder or disease.

"Pharmaceutically acceptable carrier" means molecular entities and compositions that are of sufficient purity and quality for use in the formulation of a composition of the invention and that, when appropriately administered to an animal or a human, do not produce an adverse, allergic, or other untoward reaction.

Since both clinical and veterinary uses are equally included within the scope of the present invention, a pharmaceutically acceptable formulation would include a composition or medicament formulation for either clinical or veterinary use.

The present invention includes a process for making the composition or medicament comprising mixing any of the instant compounds and a pharmaceutically acceptable carrier and include those compositions or medicaments resulting from such a process. Contemplated processes include both conventional and unconventional pharmaceutical techniques. Other examples include a composition or medicament comprising a mixture of at least two of the instant compounds in association with a pharmaceutically acceptable carrier.

The composition or medicament may be administered in a wide variety of dosage unit forms depending on the method of administration; wherein such methods include (without limitation) oral, sublingual, nasal (inhaled or insufflated), transdermal, rectal, vaginal, topical (with or without occlusion), intravenous (bolus or infusion) or for injection (intraperitoneally, subcutaneously, intramuscularly, intratumorally or parenterally) using a suitable dosage form well known to those of ordinary skill in the area of pharmaceutical administration. Accordingly, the term "dosage unit" or "dosage form" is alternatively used to refer to (without limitation) a tablet, pill, capsule, solution, syrup, elixir, emulsion, suspension, suppository, powder, granule or sterile solution, emulsion or suspension (for injection from an ampoule or using a device such as an auto-injector or for use as an aerosol, spray or drop). Furthermore, the composition may be provided in a form suitable for weekly or monthly administration (e.g. as an insoluble salt of the active compound (such as the decanoate salt) adapted to provide a depot preparation for intramuscular injection).

In preparing a dosage form, the principal active ingredient (such as a compound of the present invention or a pharmaceutically acceptable salt, racemate, enantiomer, or diastereomer thereof) is optionally mixed with one or more pharmaceutical carriers (such as a starch, sugar, diluent, granulating agent, lubricant, glidant, binder, disintegrating agent and the like), one or more inert pharmaceutical excipients (such as water, glycols, oils, alcohols, flavoring agents, preservatives, coloring agents, syrup and the like), one or more conventional tableting ingredient (such as corn starch, lactose, sucrose, sorbitol, talc, stearic acid, magnesium stearate, dicalcium phosphate, any of a variety of gums and the like) and a diluent (such as water and the like) to form a homogeneous composition (whereby the active ingredient is dispersed or suspended evenly throughout the mixture) which may be readily subdivided into dosage units containing equal amounts of a compound of the present invention.

Binders include, without limitation, starch, gelatin, natural sugars (such as glucose, beta-lactose and the like), corn sweeteners and natural and synthetic gums (such as acacia, tragacanth, sodium oleate, sodium stearate, magnesium stearate, sodium benzoate, sodium acetate, sodium chloride and the like). Disintegrating agents include, without limitation, starch, methyl cellulose, agar, bentonite, xanthan gum and the like.

Because of the ease of administration, tablets and capsules represent an advantageous oral dosage unit form, wherein solid pharmaceutical carriers are employed. If desired, tablets may be sugar or film coated or enteric-coated by standard techniques. Tablets may also be coated or otherwise compounded to provide a prolonged therapeutic effect. For example, the dosage form may comprise an inner dosage and an outer dosage component, whereby the outer component is in the form of an envelope over the inner component. The two components may further be separated by a layer, which resists disintegration in the stomach (such as an enteric layer) and permits the inner component to pass intact into the duodenum or a layer which delays or sustains release. A variety of enteric and nonenteric layer or coating materials may be used (such as polymeric acids, shellacs, acetyl alcohol, cellulose acetate and the like) or combinations thereof.

The liquid forms in which a compound of the present invention may be incorporated for oral administration include (without limitation), aqueous solutions, suitably flavored syrups, aqueous or oil suspensions (using a suitable synthetic or natural gum dispersing or suspending agent such as tragacanth, acacia, alginate, dextran, sodium carboxymethylcellulose, methylcellulose, polyvinyl-pyrrolidone, gelatin and the like), flavored emulsions (using a suitable edible oil such as cottonseed oil, sesame oil, coconut oil, peanut oil and the like), elixirs and other similar liquid forms with a variety of pharmaceutically acceptable vehicles.

As is also known in the art, the compounds may alternatively be administered parenterally via injection. For parenteral administration, sterile solutions or injectable suspensions may be parenteral vehicles wherein appropriate liquid carriers, suspending agents and the like are employed. Sterile solutions are a preferred parenteral vehicle. Isotonic preparations that generally contain suitable preservatives are employed when intravenous administration is desired. A parenteral formulation may consist of the active ingredient dissolved in or mixed with an appropriate inert liquid carrier. Acceptable liquid carriers comprise aqueous solvents and the like and other optional ingredients for aiding solubility or preservation. Such aqueous solvents include sterile water, Ringer's solution or an isotonic aqueous saline solution. Alternatively, a sterile non-volatile oil may be employed as a solvent agent. Other optional ingredients include vegetable oils (such as peanut oil, cottonseed oil, sesame oil and the like), organic solvents (such as solketal, glycerol, formyl and the like), preservatives, isotonizers, solubilizers, stabilizers, pain-soothing agents and the like. A parenteral formulation is prepared by dissolving or suspending the active ingredient in the liquid carrier whereby the final dosage unit contains from 0.005 to 10% by weight of the active ingredient.

Compounds of the present invention may be administered intranasally using a suitable intranasal vehicle. Compounds of the present invention may be administered topically using a suitable topical transdermal vehicle or a transdermal patch. Administration via a transdermal delivery system requires a continuous rather than intermittent dosage regimen.

Compounds of the present invention may also be administered via a rapid dissolving or a slow release composition, wherein the composition includes a biodegradable rapid dissolving or slow release carrier (such as a polymer carrier and the like) and a compound of the invention. Rapid dissolving or slow release carriers are well known in the art and are used to form complexes that capture therein an active compound(s) and either rapidly or slowly degrade/dissolve in a suitable environment (e.g., aqueous, acidic, basic, etc). Such particles are useful because they degrade/dissolve in body fluids and release the active compound(s) therein. The particle size of a compound of the present invention, carrier or any excipient used in such a composition may be optimally adjusted using techniques known to those of ordinary skill in the art.

The present invention includes a composition of an instant compound or prodrug thereof present in a prophylactically or therapeutically effective amount necessary for symptomatic relief to a subject in need thereof.

A prophylactically or therapeutically effective amount of an instant compound or prodrug thereof may range from about 0.001 mg to about 1 g and may be constituted into any form suitable for the administration method and regimen selected for the subject.

Depending on the subject and disease to be treated, the prophylactically or therapeutically effective amount for a person of average body weight of about 70 kg per day may range from about 0.001 mg/kg to about 300 mg/kg; from about 0.01 mg/kg to about 200 mg/kg; from about 0.05 mg/kg to about 100 mg/kg; or, from about 0.1 mg/kg to about 50 mg/kg.

An optimal prophylactically or therapeutically effective amount and administration method and regimen may be readily determined by those skilled in the art, and will vary depending on factors associated with the particular patient being treated (age, weight, diet and time of administration), the severity of the condition being treated, the compound and dosage unit being employed, the mode of administration and the strength of the preparation.

Dosage unit(s) may be administered to achieve the therapeutically or prophylactically effective amount in a regimen of from about once per day to about 5 times per day. The preferred dosage unit for oral administration is a tablet containing 0.01, 0.05, 0.1, 0.5, 1.0, 2.5, 5.0, 10.0, 15.0, 25.0, 50.0, 100, 150, 200, 250 or 500 mg of the active ingredient.

Representative compounds described herein include compounds selected from:

| Cpd | Name |
|---|---|
| 1 | 1-(4-fluoro-phenyl)-8-(4-methyl-benzyl)-1,4,5,6,7,8-hexahydro-cycloheptapyrazole-3-carboxylic acid (1,3,3-trimethyl-bicyclo[2.2.1]hept-2-yl)-amide, |
| 2 | 8-(4-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide, |
| 3 | (2E)-2-[8-(3-chloro-benzyl)-1-(2,4-dichloro-phenyl)-1,4,5,6,7,8-hexahydro-cycloheptapyrazol-3-yl]-ethenesulfonic acid [(1S)-1-phenyl-ethyl]-amide, |
| 4 | 8-(3-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide, |
| 5 | 8-(4-chloro-benzyl)-1-cyclohexyl-1,4,5,6,7,8-hexahydro-cycloheptapyrazole-3-carboxylic acid [(1S)-1-phenyl-ethyl]-amide, |
| 6 | 8-(4-chloro-benzyl)-1-cyclohexyl-1,4,5,6,7,8-hexahydro-cycloheptapyrazole-3-carboxylic acid [(1R)-1-phenyl-ethyl]-amide, |
| 7 | 8-(3-chloro-benzyl)-1-cyclohexyl-1,4,5,6,7,8-hexahydro-cycloheptapyrazole-3-carboxylic acid [(1S)-1-phenyl-ethyl]-amide, |
| 8 | 8-(3-chloro-benzyl)-1-cyclohexyl-1,4,5,6,7,8-hexahydro-cycloheptapyrazole-3-carboxylic acid [(1R)-1-phenyl-ethyl]-amide, |
| 9 | 8-(3-chloro-benzyl)-1-cyclohexyl-1,4,5,6,7,8-hexahydro-cycloheptapyrazole-3-carboxylic acid (hexahydro-2,5-methano-pentalen-3a-yl)-amide, |
| 10 | 8-(3-chloro-benzyl)-1-cyclohexyl-1,4,5,6,7,8-hexahydro-cycloheptapyrazole-3-carboxylic acid (1-adamantan-1-yl-ethyl)-amide, |
| 11 | 8-(2-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide, |
| 12 | 8-(3-chloro-benzyl)-1-cyclohexyl-1,4,5,6,7,8-hexahydro-cycloheptapyrazole-3-carboxylic acid adamantan-2-ylamide, |
| 13 | 8-(2-chloro-benzyl)-1-cyclohexyl-1,4,5,6,7,8-hexahydro-cycloheptapyrazole-3-carboxylic acid adamantan-2-ylamide, |
| 14 | 8-(4-chloro-benzyl)-1-(2,4-dichloro-phenyl)-1,4,5,6,7,8-hexahydro-cycloheptapyrazole-3-carboxylic acid [(2S)-1,3,3-trimethyl-bicyclo[2.2.1]hept-2-yl]-amide, |
| 15 | 8-(3-chloro-benzyl)-1-(2,4-dichloro-phenyl)-1,4,5,6,7,8-hexahydro-cycloheptapyrazole-3-carboxylic acid [(2S)-1,3,3-trimethyl-bicyclo[2.2.1]hept-2-yl]-amide, |
| 16 | 8-(4-chloro-benzyl)-1-cyclohexyl-1,4,5,6,7,8-hexahydro-cycloheptapyrazole-3-carboxylic acid adamantan-2-ylamide, |
| 17 | 8-(3-chloro-benzyl)-1-(2,4-dichloro-phenyl)-1,4,5,6,7,8-hexahydro-cycloheptapyrazole-3-carboxylic acid adamantan-2-ylamide, |
| 18 | 8-(4-chloro-benzyl)-1-(2,4-dichloro-phenyl)-1,4,5,6,7,8-hexahydro-cycloheptapyrazole-3-carboxylic acid adamantan-2-ylamide, |
| 19 | 8-(3-chloro-benzyl)-1-cyclohexyl-1,4,5,6,7,8-hexahydro-cycloheptapyrazole-3-carboxylic acid adamantan-1-ylamide, |
| 20 | 8-(4-chloro-benzyl)-1-cyclohexyl-1,4,5,6,7,8-hexahydro-cycloheptapyrazole-3-carboxylic acid adamantan-1-ylamide, |
| 21 | 8-(2-chloro-benzyl)-1-cyclohexyl-1,4,5,6,7,8-hexahydro-cycloheptapyrazole-3-carboxylic acid adamantan-1-ylamide, |
| 22 | 8-(3-chloro-benzyl)-1-(2,4-dichloro-phenyl)-1,4,5,6,7,8-hexahydro-cycloheptapyrazole-3-carboxylic acid adamantan-1-ylamide, |
| 23 | 8-(2-chloro-benzyl)-1-cyclohexyl-1,4,5,6,7,8-hexahydro-cycloheptapyrazole-3-carboxylic acid cyclobutylamide, |
| 24 | 8-(3-chloro-benzyl)-1-(2,4-dichloro-phenyl)-1,4,5,6,7,8-hexahydro-cycloheptapyrazole-3-carboxylic acid cyclobutylamide, |

| Cpd | Name |
|---|---|
| 25 | 8-(4-chloro-benzyl)-1-(2,4-dichloro-phenyl)-1,4,5,6,7,8-hexahydro-cycloheptapyrazole-3-carboxylic acid cyclobutylamide, |
| 26 | 8-(4-chloro-benzyl)-1-(2,4-dichloro-phenyl)-1,4,5,6,7,8-hexahydro-cycloheptapyrazole-3-carboxylic acid 4-trifluoromethyl-benzylamide, |
| 27 | 8-(4-chloro-benzyl)-1-(2,4-dichloro-phenyl)-1,4,5,6,7,8-hexahydro-cycloheptapyrazole-3-carboxylic acid piperidin-1-ylamide, |
| 28 | 8-(3-chloro-benzyl)-1-(2,4-dichloro-phenyl)-1,4,5,6,7,8-hexahydro-cycloheptapyrazole-3-carboxylic acid piperidin-1-ylamide, |
| 29 | 1-(4-chloro-benzyl)-8-(3-chloro-benzyl)-1,4,5,6,7,8-hexahydro-cycloheptapyrazole-3-carboxylic acid cyclobutylamide, |
| 30 | 1,8-bis-(4-chloro-benzyl)-1,4,5,6,7,8-hexahydro-cycloheptapyrazole-3-carboxylic acid cyclobutylamide, |
| 31 | 8-(2-chloro-benzyl)-1-cyclohexyl-1,4,5,6,7,8-hexahydro-cycloheptapyrazole-3-carboxylic acid cyclopropylamide, |
| 32 | 8-(3-chloro-benzyl)-1-cyclohexyl-1,4,5,6,7,8-hexahydro-cycloheptapyrazole-3-carboxylic acid cyclopropylamide, |
| 33 | 8-(4-chloro-benzyl)-1-cyclohexyl-1,4,5,6,7,8-hexahydro-cycloheptapyrazole-3-carboxylic acid cyclopropylamide, |
| 34 | 1,8-bis-(4-chloro-benzyl)-1,4,5,6,7,8-hexahydro-cycloheptapyrazole-3-carboxylic acid cyclopropylamide, |
| 35 | 1-(4-chloro-benzyl)-8-(3-chloro-benzyl)-1,4,5,6,7,8-hexahydro-cycloheptapyrazole-3-carboxylic acid cyclopropylamide, |
| 36 | 8-(3-chloro-benzyl)-1-cyclohexyl-1,4,5,6,7,8-hexahydro-cycloheptapyrazole-3-carboxylic acid cyclobutylamide, |
| 37 | 8-(4-chloro-benzyl)-1-cyclohexyl-1,4,5,6,7,8-hexahydro-cycloheptapyrazole-3-carboxylic acid cyclobutylamide, |
| 38 | 8-(4-chloro-benzyl)-1-(2,4-dichloro-phenyl)-1,4,5,6,7,8-hexahydro-cycloheptapyrazole-3-carboxylic acid cyclopropylamide, |
| 39 | 8-(2-chloro-benzyl)-1-methyl-1,4,5,6,7,8-hexahydro-cycloheptapyrazole-3-carboxylic acid cyclobutylamide, |
| 40 | 8-(2-chloro-benzyl)-1-methyl-1,4,5,6,7,8-hexahydro-cycloheptapyrazole-3-carboxylic acid [(2S)-1,3,3-trimethyl-bicyclo[2.2.1]hept-2-yl]-amide, |
| 41 | 1-(2,4-dichloro-phenyl)-8-(3-fluoro-benzyl)-1,4,5,6,7,8-hexahydro-cycloheptapyrazole-3-carboxylic acid cyclobutylamide, |
| 42 | 1-(2,4-dichloro-phenyl)-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 43 | 1-cyclohexyl-8-(3-fluoro-benzyl)-1,4,5,6,7,8-hexahydro-cycloheptapyrazole-3-carboxylic acid cyclobutylamide |
| 44 | 1-cyclohexyl-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 45 | 1-cyclohexyl-8-(3-fluoro-benzyl)-1,4,5,6,7,8-hexahydro-cycloheptapyrazole-3-carboxylic acid [(1S)-1-phenyl-ethyl]-amide, |
| 46 | 4-{[1-cyclohexyl-8-(3-fluoro-benzyl)-1,4,5,6,7,8-hexahydro-cycloheptapyrazole-3-carbonyl]-amino}-piperidine-1-carboxylic acid tert-butyl ester, |
| 47 | 1-benzyl-8-phenyl-1,4,5,6,7,8-hexahydro-cycloheptapyrazole-3-carboxylic acid [(2S)-1,3,3-trimethyl-bicyclo[2.2.1]hept-2-yl]-amide, |
| 48 | 1-benzyl-8-phenyl-1,4,5,6,7,8-hexahydro-cycloheptapyrazole-3-carboxylic acid [(1S)-1-phenyl-ethyl]-amide, |
| 49 | 1-cyclohexyl-8-(3-fluoro-benzyl)-1,4,5,6,7,8-hexahydro-cycloheptapyrazole-3-carboxylic acid cyclopropylamide, |
| 50 | 1-cyclohexyl-8-(3-fluoro-benzyl)-1,4,5,6,7,8-hexahydro-cycloheptapyrazole-3-carboxylic acid piperidin-1-ylamide, |
| 51 | 1-cyclohexyl-8-(3-fluoro-benzyl)-1,4,5,6,7,8-hexahydro-cycloheptapyrazole-3-carboxylic acid cyclohexylamide, |
| 52 | 1-cyclohexyl-8-(3-fluoro-benzyl)-1,4,5,6,7,8-hexahydro-cycloheptapyrazole-3-carboxylic acid cyclopentylamide, |
| 53 | 1-cyclohexyl-8-(3-fluoro-benzyl)-1,4,5,6,7,8-hexahydro-cycloheptapyrazole-3-carboxylic acid benzylamide, |
| 54 | [1-cyclohexyl-8-(3-fluoro-benzyl)-1,4,5,6,7,8-hexahydro-cycloheptapyrazol-3-yl]-(4-phenyl-piperazin-1-yl)-methanone, |
| 55 | 1-cyclohexyl-8-(3-fluoro-benzyl)-1,4,5,6,7,8-hexahydro-cycloheptapyrazole-3-carboxylic acid [(1R)-2-hydroxy-1-phenyl-ethyl]-amide, |
| 56 | 1-cyclohexyl-8-(4-fluoro-benzyl)-1,4,5,6,7,8-hexahydro-cycloheptapyrazole-3-carboxylic acid cyclopropylamide, |
| 57 | 1-cyclohexyl-8-(4-fluoro-benzyl)-1,4,5,6,7,8-hexahydro-cycloheptapyrazole-3-carboxylic acid cyclobutylamide, |
| 58 | 1-cyclohexyl-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 59 | 1-cyclohexyl-8-(4-fluoro-benzyl)-1,4,5,6,7,8-hexahydro-cycloheptapyrazole-3-carboxylic acid cyclopentylamide, |
| 60 | [1-cyclohexyl-8-(4-fluoro-benzyl)-1,4,5,6,7,8-hexahydro-cycloheptapyrazol-3-yl]-(4-phenyl-piperazin-1-yl)-methanone |
| 61 | 1-cyclohexyl-8-(4-fluoro-benzyl)-1,4,5,6,7,8-hexahydro-cycloheptapyrazole-3-carboxylic acid benzylamide, |
| 62 | 1-cyclohexyl-8-(4-fluoro-benzyl)-1,4,5,6,7,8-hexahydro-cycloheptapyrazole-3-carboxylic acid piperidin-1-ylamide, |

| Cpd | Name |
|---|---|
| 63 | (2S)-2-{[1-cyclohexyl-8-(4-fluoro-benzyl)-1,4,5,6,7,8-hexahydro-cycloheptapyrazole-3-carbonyl]-amino}-3-(4-fluoro-phenyl)-propionic acid methyl ester, |
| 64 | 1-cyclohexyl-8-(4-fluoro-benzyl)-1,4,5,6,7,8-hexahydro-cycloheptapyrazole-3-carboxylic acid [(1S)-1-phenyl-ethyl]-amide, |
| 65 | 1-cyclohexyl-8-(4-fluoro-benzyl)-1,4,5,6,7,8-hexahydro-cycloheptapyrazole-3-carboxylic acid 4-trifluoromethyl-benzylamide, |
| 66 | (8R)-1-cyclohexyl-8-(4-fluoro-benzyl)-1,4,5,6,7,8-hexahydro-cycloheptapyrazole-3-carboxylic acid [(1R)-2-hydroxy-1-phenyl-ethyl]-amide, |
| 67 | (8S*)-1-cyclohexyl-8-(4-fluoro-benzyl)-1,4,5,6,7,8-hexahydro-cycloheptapyrazole-3-carboxylic acid [(1R)-2-hydroxy-1-phenyl-ethyl]-amide, |
| 68 | 1-benzyl-8-phenyl-1,4,5,6,7,8-hexahydro-cycloheptapyrazole-3-carboxylic acid piperidin-1-ylamide, |
| 69 | 1-benzyl-8-phenyl-1,4,5,6,7,8-hexahydro-cycloheptapyrazole-3-carboxylic acid 3-trifluoromethyl-benzylamide, |
| 70 | 1-(2,4-dichloro-phenyl)-8-(4-fluoro-benzyl)-1,4,5,6,7,8-hexahydro-cycloheptapyrazole-3-carboxylic acid cyclobutylamide, |
| 71 | 1-(2,4-dichloro-phenyl)-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 72 | (2S)-2-{[1-(2,4-dichloro-phenyl)-8-(4-fluoro-benzyl)-1,4,5,6,7,8-hexahydro-cycloheptapyrazole-3-carbonyl]-amino}-3-(4-fluoro-phenyl)-propionic acid methyl ester, |
| 73 | (2S)-2-{[1-cyclohexyl-8-(3-fluoro-benzyl)-1,4,5,6,7,8-hexahydro-cycloheptapyrazole-3-carbonyl]-amino}-3-(4-fluoro-phenyl)-propionic acid methyl ester, |
| 74 | (2S,3R)-3-{[1-cyclohexyl-8-(3-fluoro-benzyl)-1,4,5,6,7,8-hexahydro-cycloheptapyrazole-3-carbonyl]-amino}-bicyclo[2.2.1]hept-5-ene-2-carboxylic acid ethyl ester, |
| 75 | (2E)-2-[1-cyclohexyl-8-(3-fluoro-benzyl)-1,4,5,6,7,8-hexahydro-cycloheptapyrazol-3-yl]-ethenesulfonic acid [(1S)-1-phenyl-ethyl]-amide, |
| 76 | 8-(4-chloro-benzyl)-1-(2,4-dichloro-phenyl)-1,4,5,6,7,8-hexahydro-cycloheptapyrazole-3-carboxylic acid [(1S)-1-phenyl-ethyl]-amide, |
| 77 | (2R)-2-{[(8R)-1-(2,4-dichloro-phenyl)-8-(3-fluoro-benzyl)-1,4,5,6,7,8-hexahydro-cycloheptapyrazole-3-carbonyl]-amino}-3-(4-fluoro-phenyl)-propionic acid methyl ester, |
| 78 | (2R)-2-{[(8S)-1-(2,4-dichloro-phenyl)-8-(3-fluoro-benzyl)-1,4,5,6,7,8-hexahydro-cycloheptapyrazole-3-carbonyl]-amino}-3-(4-fluoro-phenyl)-propionic acid methyl ester, |
| 79 | (2S,3R)-3-{[1-(2,4-dichloro-phenyl)-8-(3-fluoro-benzyl)-1,4,5,6,7,8-hexahydro-cycloheptapyrazole-3-carbonyl]-amino}-bicyclo[2.2.1]hept-5-ene-2-carboxylic acid ethyl ester, |
| 80 | (2R)-2-{[1-(2,4-dichloro-phenyl)-8-(3-fluoro-benzyl)-1,4,5,6,7,8-hexahydro-cycloheptapyrazole-3-carbonyl]-amino}-3-(4-hydroxy-phenyl)-propionic acid methyl ester, |
| 81 | (2R)-2-{[1-(2,4-dichloro-phenyl)-8-(4-fluoro-benzyl)-1,4,5,6,7,8-hexahydro-cycloheptapyrazole-3-carbonyl]-amino}-3-(4-hydroxy-phenyl)-propionic acid methyl ester, |
| 82 | (2R)-2-{[1-cyclohexyl-8-(3-fluoro-benzyl)-1,4,5,6,7,8-hexahydro-cycloheptapyrazole-3-carbonyl]-amino}-3-(4-hydroxy-phenyl)-propionic acid methyl ester, |
| 83 | (2R)-2-{[1-cyclohexyl-8-(4-fluoro-benzyl)-1,4,5,6,7,8-hexahydro-cycloheptapyrazole-3-carbonyl]-amino}-3-(4-hydroxy-phenyl)-propionic acid methyl ester, |
| 84 | 1-(2,4-dichloro-phenyl)-8-(3-fluoro-benzyl)-1,4,5,6,7,8-hexahydro-cycloheptapyrazole-3-carboxylic acid piperidin-1-ylamide, |
| 85 | 1-(2,4-dichloro-phenyl)-8-(4-fluoro-benzyl)-1,4,5,6,7,8-hexahydro-cycloheptapyrazole-3-carboxylic acid piperidin-1-ylamide, |
| 86 | 1-benzyl-8-phenyl-1,4,5,6,7,8-hexahydro-cycloheptapyrazole-3-carboxylic acid (2,2,2-trifluoro-ethyl)-amide, |
| 87 | (2R)-2-[(1-benzyl-8-phenyl-1,4,5,6,7,8-hexahydro-cycloheptapyrazole-3-carbonyl)-amino]-3-(4-fluoro-phenyl)-propionic acid methyl ester, |
| 88 | (2S,3R)-3-{[1-cyclohexyl-8-(4-fluoro-benzyl)-1,4,5,6,7,8-hexahydro-cycloheptapyrazole-3-carbonyl]-amino}-bicyclo[2.2.1]hept-5-ene-2-carboxylic acid ethyl ester, |
| 89 | 1-cyclohexyl-8-(4-fluoro-benzyl)-1,4,5,6,7,8-hexahydro-cycloheptapyrazole-3-carboxylic acid morpholin-4-ylamide, |
| 90 | 1-cyclohexyl-8-(3-fluoro-benzyl)-1,4,5,6,7,8-hexahydro-cycloheptapyrazole-3-carboxylic acid morpholin-4-ylamide, |
| 91 | 1-(2,4-dichloro-phenyl)-8-(3-fluoro-benzyl)-1,4,5,6,7,8-hexahydro-cycloheptapyrazole-3-carboxylic acid morpholin-4-ylamide, |
| 92 | 1-(2,4-difluoro-phenyl)-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 93 | (2E)-2-[1-(2,4-difluoro-phenyl)-8-(3-fluoro-benzyl)-1,4,5,6,7,8-hexahydro-cycloheptapyrazol-3-yl]-ethenesulfonic acid [(1S)-1-phenyl-ethyl]-amide, |
| 94 | (2E)-2-[1-(2,4-difluoro-phenyl)-8-(3-fluoro-benzyl)-1,4,5,6,7,8-hexahydro-cycloheptapyrazol-3-yl]-ethenesulfonic acid [(1S)-1-cyclohexyl-ethyl]-amide, |

| Cpd | Name |
|---|---|
| 95 | (2R)-2-{[1-(2,4-difluoro-phenyl)-8-(3-fluoro-benzyl)-1,4,5,6,7,8-hexahydro-cycloheptapyrazole-3-carbonyl]-amino}-3-(4-hydroxy-phenyl)-propionic acid methyl ester, |
| 96 | (2E)-2-[8-(3-fluoro-benzyl)-1,4,5,6,7,8-hexahydro-cycloheptapyrazol-3-yl]-ethenesulfonic acid [(1S)-1-phenyl-ethyl]-amide, |
| 97 | 1-(2,4-difluoro-phenyl)-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 98 | (2R)-2-{[1-(2,4-difluoro-phenyl)-8-(4-fluoro-benzyl)-1,4,5,6,7,8-hexahydro-cycloheptapyrazole-3-carbonyl]-amino}-3-(4-hydroxy-phenyl)-propionic acid methyl ester, |
| 99 | (2S,3R)-3-{[1-(2,4-difluoro-phenyl)-8-(3-fluoro-benzyl)-1,4,5,6,7,8-hexahydro-cycloheptapyrazole-3-carbonyl]-amino}-bicyclo[2.2.1]hept-5-ene-2-carboxylic acid ethyl ester, |
| 100 | 1-(2,4-difluoro-phenyl)-8-(3-fluoro-benzyl)-1,4,5,6,7,8-hexahydro-cycloheptapyrazole-3-carboxylic acid [(1R,2S)-2-hydroxy-indan-1-yl]-amide, |
| 101 | (2E)-2-[8-(4-fluoro-benzyl)-1-methyl-1,4,5,6,7,8-hexahydro-cycloheptapyrazol-3-yl]-ethenesulfonic acid [(1S)-1-phenyl-ethyl]-amide, |
| 102 | (2R)-2-{[8-(3-chloro-benzyl)-1-(2,4-dichloro-phenyl)-1,4,5,6,7,8-hexahydro-cycloheptapyrazole-3-carbonyl]-amino}-3-(4-hydroxy-phenyl)-propionic acid methyl ester, |
| 103 | (2R)-2-{[8-(3-chloro-benzyl)-1-(2,4-dichloro-phenyl)-1,4,5,6,7,8-hexahydro-cycloheptapyrazole-3-carbonyl]-amino}-3-(4-fluoro-phenyl)-propionic acid methyl ester, |
| 104 | (2E)-2-[8-(3-fluoro-benzyl)-1-methyl-1,4,5,6,7,8-hexahydro-cycloheptapyrazol-3-yl]-ethenesulfonic acid [(1S)-1-phenyl-ethyl]-amide, |
| 105 | (2R,3S)-3-{[1-cyclohexyl-8-(3-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 106 | (2R,3S)-3-{[1-cyclohexyl-8-(4-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 107 | (2E)-2-[1-(2,4-difluoro-phenyl)-8-(4-fluoro-benzyl)-1,4,5,6,7,8-hexahydro-cycloheptapyrazol-3-yl]-ethenesulfonic acid [(1S)-1-phenyl-ethyl]-amide, |
| 108 | (2E)-2-[8-(4-fluoro-benzyl)-1,4,5,6,7,8-hexahydro-cycloheptapyrazol-3-yl]-ethenesulfonic acid [(1S)-1-phenyl-ethyl]-amide, |
| 109 | (2R,3S)-3-{[8-(3-chloro-benzyl)-1-(2,4-dichloro-phenyl)-1,4,5,6,7,8-hexahydro-cycloheptapyrazole-3-carbonyl]-amino}-bicyclo[2.2.1]heptane-2-carboxylic acid ethyl ester, |
| 110 | (2R,3S)-3-{[1-(2,4-difluoro-phenyl)-8-(4-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 111 | (2R,3S)-3-{[1-(2,4-difluoro-phenyl)-8-(3-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 112 | (8R*)-8-(3-chloro-benzyl)-1-(2,4-dichloro-phenyl)-1,4,5,6,7,8-hexahydro-cycloheptapyrazole-3-carboxylic acid [(1R,2S)-2-hydroxy-indan-1-yl]-amide, |
| 113 | (8S*)-8-(3-chloro-benzyl)-1-(2,4-dichloro-phenyl)-1,4,5,6,7,8-hexahydro-cycloheptapyrazole-3-carboxylic acid [(1R,2S)-2-hydroxy-indan-1-yl]-amide, |
| 114 | (8R*)-1-cyclohexyl-8-(3-fluoro-benzyl)-1,4,5,6,7,8-hexahydro-cycloheptapyrazole-3-carboxylic acid [(1R,2S)-2-hydroxy-indan-1-yl]-amide, |
| 115 | (8S*)-1-cyclohexyl-8-(3-fluoro-benzyl)-1,4,5,6,7,8-hexahydro-cycloheptapyrazole-3-carboxylic acid [(1R,2S)-2-hydroxy-indan-1-yl]-amide, |
| 116 | 1-(2,4-difluoro-phenyl)-8-(3-fluoro-benzyl)-1,4,5,6,7,8-hexahydro-cycloheptapyrazole-3-carboxylic acid morpholin-4-ylamide, |
| 117 | 8-(3-chloro-benzyl)-1-(2,4-dichloro-phenyl)-1,4,5,6,7,8-hexahydro-cycloheptapyrazole-3-carboxylic acid morpholin-4-ylamide, |
| 118 | [1-(2,4-difluoro-phenyl)-8-(3-fluoro-benzyl)-1,4,5,6,7,8-hexahydro-cycloheptapyrazol-3-yl]-morpholin-4-yl-methanone, |
| 119 | 1-(2,4-difluoro-phenyl)-8-(4-fluoro-benzyl)-1,4,5,6,7,8-hexahydro-cycloheptapyrazole-3-carboxylic acid [(1R,2S)-2-hydroxy-indan-1-yl]-amide, |
| 120 | (8R)-1-cyclohexyl-8-(4-fluoro-benzyl)-1,4,5,6,7,8-hexahydro-cycloheptapyrazole-3-carboxylic acid [(1R,2S)-2-hydroxy-indan-1-yl]-amide, |
| 121 | (8S*)-1-cyclohexyl-8-(4-fluoro-benzyl)-1,4,5,6,7,8-hexahydro-cycloheptapyrazole-3-carboxylic acid [(1R,2S)-2-hydroxy-indan-1-yl]-amide, |
| 122 | (2E)-2-[1-(2,4-difluoro-phenyl)-8-(4-fluoro-benzyl)-1,4,5,6,7,8-hexahydro-cycloheptapyrazol-3-yl]-ethenesulfonic acid piperidin-1-ylamide, |
| 123 | (2E)-2-[1-(2,4-difluoro-phenyl)-8-(3-fluoro-benzyl)-1,4,5,6,7,8-hexahydro-cycloheptapyrazol-3-yl]-ethenesulfonic acid piperidin-1-ylamide, |
| 124 | (2E)-2-[8-(3-fluoro-benzyl)-1-methyl-1,4,5,6,7,8-hexahydro-cycloheptapyrazol-3-yl]-ethenesulfonic acid piperidin-1-ylamide, |
| 125 | (2E)-2-[8-(3-fluoro-benzyl)-1-methyl-1,4,5,6,7,8-hexahydro-cycloheptapyrazol-3-yl]-ethenesulfonic acid morpholin-4-ylamide, |
| 126 | (2E)-2-[8-(4-fluoro-benzyl)-1-methyl-1,4,5,6,7,8-hexahydro-cycloheptapyrazol-3-yl]-ethenesulfonic acid morpholin-4-ylamide, |
| 127 | (2E)-2-[1-(2,4-difluoro-phenyl)-8-(4-fluoro-benzyl)-1,4,5,6,7,8-hexahydro-cycloheptapyrazol-3-yl]-ethenesulfonic acid morpholin-4-ylamide, |

-continued

| Cpd | Name |
|---|---|
| 128 | (2E)-2-[8-(4-fluoro-benzyl)-1-methyl-1,4,5,6,7,8-hexahydro-cycloheptapyrazol-3-yl]-ethenesulfonic acid piperidin-1-ylamide, |
| 129 | 8-(4-fluoro-benzyl)-1,4,5,6,7,8-hexahydro-cycloheptapyrazole-3-carboxylic acid benzylamide, |
| 130 | 8-(4-fluoro-benzyl)-1-methanesulfonyl-1,4,5,6,7,8-hexahydro-cycloheptapyrazole-3-carboxylic acid benzylamide, |
| 131 | (8E)-8-(4-chloro-benzylidene)-1-(2,4-dichloro-phenyl)-1,4,5,6,7,8-hexahydro-cycloheptapyrazole-3-carboxylic acid [(1R)-1-phenyl-ethyl]-amide, |
| 132 | (8E)-8-(4-chloro-benzylidene)-1-(2,4-dichloro-phenyl)-1,4,5,6,7,8-hexahydro-cycloheptapyrazole-3-carboxylic acid [(1R)-1-cyclohexyl-ethyl]-amide, |
| 133 | (8E)-8-(4-chloro-benzylidene)-1-(2,4-dichloro-phenyl)-1,4,5,6,7,8-hexahydro-cycloheptapyrazole-3-carboxylic acid piperidin-1-ylamide, |
| 134 | (8E)-8-(4-chloro-benzylidene)-1-(2,4-dichloro-phenyl)-1,4,5,6,7,8-hexahydro-cycloheptapyrazole-3-carboxylic acid morpholin-4-ylamide, |
| 135 | (8E)-8-(4-chloro-benzylidene)-1-(2,4-dichloro-phenyl)-1,4,5,6,7,8-hexahydro-cycloheptapyrazole-3-carboxylic acid 4-sulfamoyl-benzylamide, |
| 136 | (8E)-N-[8-(4-chloro-benzylidene)-1-(2,4-dichloro-phenyl)-1,4,5,6,7,8-hexahydro-cycloheptapyrazole-3-carbonyl]-benzenesulfonamide, |
| 137 | (8E)-8-(4-chloro-benzylidene)-1-(2,4-dichloro-phenyl)-1,4,5,6,7,8-hexahydro-cycloheptapyrazole-3-carboxylic acid [1-(4-chloro-phenyl)-ethyl]-amide, |
| 138 | (8E)-8-(4-chloro-benzylidene)-1-(2,4-dichloro-phenyl)-1,4,5,6,7,8-hexahydro-cycloheptapyrazole-3-carboxylic acid [(1S)-1-cyclohexyl-ethyl]-amide, |
| 139 | (8E)-8-(4-chloro-benzylidene)-1-(2,4-dichloro-phenyl)-1,4,5,6,7,8-hexahydro-cycloheptapyrazole-3-carboxylic acid [(1S)-1-phenyl-ethyl]-amide, |
| 140 | (8E)-8-(4-chloro-benzylidene)-1,4,5,6,7,8-hexahydro-cycloheptapyrazole-3-carboxylic acid [(1R)-1-cyclohexyl-ethyl]-amide, |
| 141 | (8E)-8-(4-chloro-benzylidene)-1,4,5,6,7,8-hexahydro-cycloheptapyrazole-3-carboxylic acid [(1S)-1-phenyl-ethyl]-amide, |
| 142 | (8E)-8-(4-chloro-benzylidene)-1,4,5,6,7,8-hexahydro-cycloheptapyrazole-3-carboxylic acid [(1R)-1-phenyl-ethyl]-amide, |
| 143 | (8E)-8-(4-chloro-benzylidene)-1,4,5,6,7,8-hexahydro-cycloheptapyrazole-3-carboxylic acid [(1S)-1-cyclohexyl-ethyl]-amide, |
| 144 | (8E)-8-(4-chloro-benzylidene)-1,4,5,6,7,8-hexahydro-cycloheptapyrazole-3-carboxylic acid piperidin-1-ylamide, |
| 145 | (8E)-8-(4-chloro-benzylidene)-1,4,5,6,7,8-hexahydro-cycloheptapyrazole-3-carboxylic acid morpholin-4-ylamide, |
| 146 | (8E)-1-(2,4-dichloro-phenyl)-8-(4-fluoro-benzylidene)-1,4,5,6,7,8-hexahydro-cycloheptapyrazole-3-carboxylic acid [(1R)-1-phenyl-ethyl]-amide, |
| 147 | (8E)-1-(2,4-dichloro-phenyl)-8-(4-fluoro-benzylidene)-1,4,5,6,7,8-hexahydro-cycloheptapyrazole-3-carboxylic acid [(1R)-1-cyclohexyl-ethyl]-amide, |
| 148 | (8E)-1-(2,4-dichloro-phenyl)-8-(4-fluoro-benzylidene)-1,4,5,6,7,8-hexahydro-cycloheptapyrazole-3-carboxylic acid [(1S)-1-cyclohexyl-ethyl]-amide, |
| 149 | (8E)-1-(2,4-dichloro-phenyl)-8-(4-fluoro-benzylidene)-1,4,5,6,7,8-hexahydro-cycloheptapyrazole-3-carboxylic acid [(1S)-1-phenyl-ethyl]-amide, |
| 150 | (8E)-1-(2,4-dichloro-phenyl)-8-(4-fluoro-benzylidene)-1,4,5,6,7,8-hexahydro-cycloheptapyrazole-3-carboxylic acid piperidin-1-ylamide, |
| 151 | (8E)-1-(2,4-dichloro-phenyl)-8-(4-fluoro-benzylidene)-1,4,5,6,7,8-hexahydro-cycloheptapyrazole-3-carboxylic acid morpholin-4-ylamide, |
| 152 | (8E)-8-(4-chloro-benzylidene)-1-(2,4-dichloro-phenyl)-1,4,5,6,7,8-hexahydro-cycloheptapyrazole-3-carboxylic acid pyridin-2-ylamide, |
| 153 | (8E)-8-(4-chloro-benzylidene)-1-(2,4-dichloro-phenyl)-1,4,5,6,7,8-hexahydro-cycloheptapyrazole-3-carboxylic acid pyridin-4-ylamide, |
| 154 | (8E)-8-(4-chloro-benzylidene)-1-(2,4-dichloro-phenyl)-1,4,5,6,7,8-hexahydro-cycloheptapyrazole-3-carboxylic acid (4-sulfamoyl-phenyl)-amide, |
| 155 | (8E)-8-(4-chloro-benzylidene)-1-(2,4-dichloro-phenyl)-1,4,5,6,7,8-hexahydro-cycloheptapyrazole-3-carboxylic acid (pyridin-2-ylmethyl)-amide, |
| 156 | (8E)-8-(4-chloro-benzylidene)-1-(2,4-dichloro-phenyl)-1,4,5,6,7,8-hexahydro-cycloheptapyrazole-3-carboxylic acid (pyridin-4-ylmethyl)-amide, |
| 157 | (8E)-8-(4-chloro-benzylidene)-1-(2,4-dichloro-phenyl)-1,4,5,6,7,8-hexahydro-cycloheptapyrazole-3-carboxylic acid (2-pyridin-2-yl-ethyl)-amide, |
| 158 | (8R)-8-(3-chloro-benzyl)-1-(2,4-dichloro-phenyl)-1,4,5,6,7,8-hexahydro-cycloheptapyrazole-3-carboxylic acid [(1S)-1-hydroxymethyl-2-methyl-propyl]-amide |
| 159 | (8S)-8-(3-chloro-benzyl)-1-(2,4-dichloro-phenyl)-1,4,5,6,7,8-hexahydro-cycloheptapyrazole-3-carboxylic acid [(1S)-1-hydroxymethyl-2-methyl-propyl]-amide |
| 160 | (2E)-2-[8-(3-chloro-benzyl)-1,4,5,6,7,8-hexahydro-cycloheptapyrazol-3-yl]-ethenesulfonic acid [(1S)-1-phenyl-ethyl]-amide, |
| 161 | (8R)-8-(3-chloro-benzyl)-1-(2,4-dichloro-phenyl)-1,4,5,6,7,8-hexahydro-cycloheptapyrazole-3-carboxylic acid [(1S)-2-hydroxy-1-phenyl-ethyl]-amide, |
| 162 | (8S)-8-(3-chloro-benzyl)-1-(2,4-dichloro-phenyl)-1,4,5,6,7,8-hexahydro-cycloheptapyrazole-3-carboxylic acid [(1S)-2-hydroxy-1-phenyl-ethyl]-amide, |
| 163 | 8-(3-chloro-benzyl)-1-(2,4-dichloro-phenyl)-1,4,5,6,7,8-hexahydro-cycloheptapyrazole-3-carboxylic acid [(1R)-1-benzyl-2-hydroxy-ethyl]-amide, |
| 164 | 8-(3-chloro-benzyl)-1,4,5,6,7,8-hexahydro-cycloheptapyrazole-3-carboxylic acid [(1S)-2-hydroxy-1-phenyl-ethyl]-amide, |
| 165 | 8-(3-chloro-benzyl)-1,4,5,6,7,8-hexahydro-cycloheptapyrazole-3-carboxylic acid [(1R)-2-hydroxy-1-phenyl-ethyl]-amide, |

| Cpd | Name |
|---|---|
| 166 | 8-(3-chloro-benzyl)-1,4,5,6,7,8-hexahydro-cycloheptapyrazole-3-carboxylic acid [(1S)-1-benzyl-2-hydroxy-ethyl]-amide, |
| 167 | 8-(3-chloro-benzyl)-1,4,5,6,7,8-hexahydro-cycloheptapyrazole-3-carboxylic acid [(1R)-1-benzyl-2-hydroxy-ethyl]-amide, |
| 168 | 1-(2,4-difluoro-phenyl)-8-(3-fluoro-benzyl)-1,4,5,6,7,8-hexahydro-cycloheptapyrazole-3-carboxylic acid [(1S)-2-hydroxy-1-phenyl-ethyl]-amide, |
| 169 | 1-(2,4-difluoro-phenyl)-8-(3-fluoro-benzyl)-1,4,5,6,7,8-hexahydro-cycloheptapyrazole-3-carboxylic acid [(1S)-2-chloro-1-phenyl-ethyl]-amide, |
| 170 | (8E)-8-(4-chloro-benzylidene)-1-pyridin-4-yl-1,4,5,6,7,8-hexahydro-cycloheptapyrazole-3-carboxylic acid [(1R)-1-phenyl-ethyl]-amide, |
| 171 | (8E)-8-(4-chloro-benzylidene)-1-pyridin-4-yl-1,4,5,6,7,8-hexahydro-cycloheptapyrazole-3-carboxylic acid [(1S)-1-phenyl-ethyl]-amide, |
| 172 | 1-(2,4-difluoro-phenyl)-8-(4-fluoro-benzyl)-1,4,5,6,7,8-hexahydro-cycloheptapyrazole-3-carboxylic acid [(1S)-2-chloro-1-phenyl-ethyl]-amide, |
| 173 | 1-(2,4-difluoro-phenyl)-8-(3-fluoro-benzyl)-1,4,5,6,7,8-hexahydro-cycloheptapyrazole-3-carboxylic acid [(1R)-1-phenyl-ethyl]-amide, |
| 174 | 1-cyclohexyl-8-(3-fluoro-benzyl)-1,4,5,6,7,8-hexahydro-cycloheptapyrazole-3-carboxylic acid [(1R)-1-phenyl-ethyl]-amide, |
| 175 | 8-(3-chloro-benzyl)-1-(4-trifluoromethyl-pyrimidin-2-yl)-1,4,5,6,7,8-hexahydro-cycloheptapyrazole-3-carboxylic acid [(1R)-1-phenyl-ethyl]-amide, |
| 176 | 8-(3-chloro-benzyl)-1-(4-trifluoromethyl-pyrimidin-2-yl)-1,4,5,6,7,8-hexahydro-cycloheptapyrazole-3-carboxylic acid [(1R)-2-hydroxy-1-phenyl-ethyl]-amide, |
| 177 | 8-(3-chloro-benzyl)-1-(7-chloro-quinolin-4-yl)-1,4,5,6,7,8-hexahydro-cycloheptapyrazole-3-carboxylic acid [(1R)-1-phenyl-ethyl]-amide, |
| 178 | 8-(3-chloro-benzyl)-1-(4-trifluoromethyl-pyrimidin-2-yl)-1,4,5,6,7,8-hexahydro-cycloheptapyrazole-3-carboxylic acid [(1R)-2-chloro-1-phenyl-ethyl]-amide, |
| 179 | 8-(3-chloro-benzyl)-1-(4-trifluoromethyl-pyrimidin-2-yl)-1,4,5,6,7,8-hexahydro-cycloheptapyrazole-3-carboxylic acid [(1S)-2-chloro-1-phenyl-ethyl]-amide, |
| 180 | (8E)-8-(4-chloro-benzylidene)-1-pyridin-4-yl-1,4,5,6,7,8-hexahydro-cycloheptapyrazole-3-carboxylic acid [(1R)-1-cyclohexyl-ethyl]-amide, |
| 181 | (8E)-8-(4-chloro-benzylidene)-1-pyridin-4-yl-1,4,5,6,7,8-hexahydro-cycloheptapyrazole-3-carboxylic acid [(1S)-1-cyclohexyl-ethyl]-amide, |
| 182 | (8E)-8-(4-chloro-benzylidene)-1-pyridin-4-yl-1,4,5,6,7,8-hexahydro-cycloheptapyrazole-3-carboxylic acid piperidin-1-ylamide, |
| 183 | (8E)-8-(4-chloro-benzylidene)-1-pyridin-4-yl-1,4,5,6,7,8-hexahydro-cycloheptapyrazole-3-carboxylic acid morpholin-4-ylamide, |
| 184 | (8E)-8-(4-chloro-benzylidene)-1-(4-sulfamoyl-phenyl)-1,4,5,6,7,8-hexahydro-cycloheptapyrazole-3-carboxylic acid [(1R)-1-phenyl-ethyl]-amide, |
| 185 | (8E)-8-(4-chloro-benzylidene)-1-(4-sulfamoyl-phenyl)-1,4,5,6,7,8-hexahydro-cycloheptapyrazole-3-carboxylic acid [(1R)-1-cyclohexyl-ethyl]-amide, |
| 186 | 8-(3-chloro-benzyl)-1-(4-trifluoromethyl-pyrimidin-2-yl)-1,4,5,6,7,8-hexahydro-cycloheptapyrazole-3-carboxylic acid [(1R)-1-benzyl-2-hydroxy-ethyl]-amide, |
| 187 | 8-(3-chloro-benzyl)-1-(4-trifluoromethyl-pyrimidin-2-yl)-1,4,5,6,7,8-hexahydro-cycloheptapyrazole-3-carboxylic acid [(1R)-1-benzyl-2-chloro-ethyl]-amide, |
| 188 | (8E)-[1-(2,4-dichloro-phenyl)-8-(4-fluoro-benzylidene)-1,4,5,6,7,8-hexahydro-cycloheptapyrazol-3-yl]-(2-pyridin-2-yl-pyrrolidin-1-yl)-methanone, |
| 189 | (8E)-8-(4-chloro-benzylidene)-1-(2-chloro-phenyl)-1,4,5,6,7,8-hexahydro-cycloheptapyrazole-3-carboxylic acid [(1R)-1-cyclohexyl-ethyl]-amide, |
| 190 | (8E)-8-(4-chloro-benzylidene)-1-(2-chloro-phenyl)-1,4,5,6,7,8-hexahydro-cycloheptapyrazole-3-carboxylic acid [(1R)-1-phenyl-ethyl]-amide, |
| 191 | (8E)-8-(4-chloro-benzylidene)-1-(2-chloro-phenyl)-1,4,5,6,7,8-hexahydro-cycloheptapyrazole-3-carboxylic acid [(1S)-1-phenyl-ethyl]-amide, |
| 192 | (8E)-8-(4-chloro-benzylidene)-1-(2-chloro-phenyl)-1,4,5,6,7,8-hexahydro-cycloheptapyrazole-3-carboxylic acid [(1S)-1-cyclohexyl-ethyl]-amide, |
| 193 | (8E)-8-(4-chloro-benzylidene)-1-(2-chloro-phenyl)-1,4,5,6,7,8-hexahydro-cycloheptapyrazole-3-carboxylic acid piperidin-1-ylamide, |
| 194 | (8E)-8-(4-chloro-benzylidene)-1-(2-chloro-phenyl)-1,4,5,6,7,8-hexahydro-cycloheptapyrazole-3-carboxylic acid morpholin-4-ylamide, |
| 195 | (8E)-8-(4-chloro-benzylidene)-1-(2,5-dichloro-phenyl)-1,4,5,6,7,8-hexahydro-cycloheptapyrazole-3-carboxylic acid [(1R)-1-phenyl-ethyl]-amide, |
| 196 | (8E)-8-(4-chloro-benzylidene)-1-(2,5-dichloro-phenyl)-1,4,5,6,7,8-hexahydro-cycloheptapyrazole-3-carboxylic acid [(1R)-1-cyclohexyl-ethyl]-amide, |
| 197 | (8E)-8-(4-chloro-benzylidene)-1-(2,5-dichloro-phenyl)-1,4,5,6,7,8-hexahydro-cycloheptapyrazole-3-carboxylic acid [(1S)-1-cyclohexyl-ethyl]-amide, |
| 198 | (8E)-8-(4-chloro-benzylidene)-1-(2,5-dichloro-phenyl)-1,4,5,6,7,8-hexahydro-cycloheptapyrazole-3-carboxylic acid [(1S)-1-phenyl-ethyl]-amide, |
| 199 | (8E)-8-(4-chloro-benzylidene)-1-(2,5-dichloro-phenyl)-1,4,5,6,7,8-hexahydro-cycloheptapyrazole-3-carboxylic acid piperidin-1-ylamide, |
| 200 | (8E)-8-(4-chloro-benzylidene)-1-(2,5-dichloro-phenyl)-1,4,5,6,7,8-hexahydro-cycloheptapyrazole-3-carboxylic acid morpholin-4-ylamide, |
| 201 | (8E)-[8-(4-chloro-benzylidene)-1-(2,5-dichloro-phenyl)-1,4,5,6,7,8-hexahydro-cycloheptapyrazol-3-yl]-morpholin-4-yl-methanone, |

| Cpd | Name |
|---|---|
| 202 | (8E)-1-(2,4-dichloro-phenyl)-8-(4-fluoro-benzylidene)-1,4,5,6,7,8-hexahydro-cycloheptapyrazole-3-carboxylic acid [(1R)-1-phenyl-propyl]-amide, |
| 203 | (8E)-1-(2,4-dichloro-phenyl)-8-(4-fluoro-benzylidene)-1,4,5,6,7,8-hexahydro-cycloheptapyrazole-3-carboxylic acid [(1R)-2-hydroxy-1-phenyl-ethyl]-amide, |
| 204 | (8E)-1-(2,4-dichloro-phenyl)-8-(4-fluoro-benzylidene)-1,4,5,6,7,8-hexahydro-cycloheptapyrazole-3-carboxylic acid [(1S)-2-hydroxy-1-phenyl-ethyl]-amide, |
| 205 | (8E)-1-(2,4-dichloro-phenyl)-8-(4-fluoro-benzylidene)-1,4,5,6,7,8-hexahydro-cycloheptapyrazole-3-carboxylic acid (1-methyl-1-phenyl-ethyl)-amide, |
| 206 | (8E)-[1-(2,4-dichloro-phenyl)-8-(4-fluoro-benzylidene)-1,4,5,6,7,8-hexahydro-cycloheptapyrazol-3-yl]-(3,4,5,6-tetrahydro-2H-[2,2']bipyridinyl-1-yl)-methanone, |
| 207 | (8E)-1-(2,4-dichloro-phenyl)-8-(4-fluoro-benzylidene)-1,4,5,6,7,8-hexahydro-cycloheptapyrazole-3-carboxylic acid (1R)-indan-1-ylamide, |
| 208 | (8E)-1-(2,4-dichloro-phenyl)-8-(4-fluoro-benzylidene)-1,4,5,6,7,8-hexahydro-cycloheptapyrazole-3-carboxylic acid [(1S,2R)-2-hydroxy-indan-1-yl]-amide, |
| 209 | (8E)-1-(2,4-dichloro-phenyl)-8-(4-fluoro-benzylidene)-1,4,5,6,7,8-hexahydro-cycloheptapyrazole-3-carboxylic acid (1,2,3,4-tetrahydro-naphthalen-1-yl)-amide, |
| 210 | (8E)-1-(2,4-dichloro-phenyl)-8-(4-methoxy-benzylidene)-1,4,5,6,7,8-hexahydro-cycloheptapyrazole-3-carboxylic acid (pyridin-2-ylmethyl)-amide, |
| 211 | (8E)-1-(2,4-dichloro-phenyl)-8-(4-methoxy-benzylidene)-1,4,5,6,7,8-hexahydro-cycloheptapyrazole-3-carboxylic acid (1-methyl-1-phenyl-ethyl)-amide, |
| 212 | (8E)-1-(2,4-dichloro-phenyl)-8-(4-methoxy-benzylidene)-1,4,5,6,7,8-hexahydro-cycloheptapyrazole-3-carboxylic acid [(1R)-1-phenyl-ethyl]-amide, |
| 213 | (8E)-1-(2,4-dichloro-phenyl)-8-(4-methoxy-benzylidene)-1,4,5,6,7,8-hexahydro-cycloheptapyrazole-3-carboxylic acid [(1S)-1-phenyl-ethyl]-amide, |
| 214 | (8E)-1-(2,4-dichloro-phenyl)-8-(4-methoxy-benzylidene)-1,4,5,6,7,8-hexahydro-cycloheptapyrazole-3-carboxylic acid [(1R)-1-cyclohexyl-ethyl]-amide, |
| 215 | (8E)-1-(2,4-dichloro-phenyl)-8-(4-methoxy-benzylidene)-1,4,5,6,7,8-hexahydro-cycloheptapyrazole-3-carboxylic acid [(1S)-2-hydroxy-1-phenyl-ethyl]-amide, |
| 216 | (8E)-1-(2,4-dichloro-phenyl)-8-(4-methoxy-benzylidene)-1,4,5,6,7,8-hexahydro-cycloheptapyrazole-3-carboxylic acid (1R)-indan-1-ylamide, |
| 217 | (8E)-1-(2,4-dichloro-phenyl)-8-(4-methoxy-benzylidene)-1,4,5,6,7,8-hexahydro-cycloheptapyrazole-3-carboxylic acid piperidin-1-ylamide, |
| 218 | (2S,3R)-3-{[1-(4-fluoro-phenyl)-8-(4-methyl-benzyl)-1,4,5,6,7,8-hexahydro-cycloheptapyrazole-3-carbonyl]-amino}-bicyclo[2.2.1]heptane-2-carboxylic acid ethyl ester, |
| 219 | (8E)-1-cyclohexyl-8-(4-fluoro-benzylidene)-1,4,5,6,7,8-hexahydro-cycloheptapyrazole-3-carboxylic acid [(1R)-2-hydroxy-1-phenyl-ethyl]-amide, |
| 220 | (8E)-8-(4-fluoro-benzylidene)-1-(4-trifluoromethyl-pyrimidin-2-yl)-1,4,5,6,7,8-hexahydro-cycloheptapyrazole-3-carboxylic acid [(1S)-2-hydroxy-1-phenyl-ethyl]-amide, |
| 221 | (8E)-1-(2,4-dichloro-phenyl)-8-(4-methoxy-benzylidene)-1,4,5,6,7,8-hexahydro-cycloheptapyrazole-3-carboxylic acid [(1R,2R)-2-hydroxy-cyclopentyl)-amide, |
| 222 | (8E)-1-(2,4-dichloro-phenyl)-8-(4-methoxy-benzylidene)-1,4,5,6,7,8-hexahydro-cycloheptapyrazole-3-carboxylic acid (1-pyridin-2-yl-ethyl)-amide, |
| 223 | (8E)-[8-(4-chloro-benzylidene)-1,4,5,6,7,8-hexahydro-cycloheptapyrazol-3-yl]-piperidin-1-yl-methanone, |
| 224 | (8E)-1-(2,4-dichloro-phenyl)-8-(4-fluoro-benzylidene)-1,4,5,6,7,8-hexahydro-cycloheptapyrazole-3-carboxylic acid (1-pyridin-2-yl-ethyl)-amide, |
| 225 | (8E)-1-(2,4-dichloro-phenyl)-8-(4-fluoro-benzylidene)-1,4,5,6,7,8-hexahydro-cycloheptapyrazole-3-carboxylic acid [(1R)-1-pyridin-2-yl-ethyl]-amide, |
| 226 | (8E)-1-(2,4-dichloro-phenyl)-8-(4-methoxy-benzylidene)-1,4,5,6,7,8-hexahydro-cycloheptapyrazole-3-carboxylic acid (hexahydro-cyclopenta[c]pyrrol-2-yl)-amide, |
| 227 | (8E)-1-(2,4-dichloro-phenyl)-8-(4-methoxy-benzylidene)-1,4,5,6,7,8-hexahydro-cycloheptapyrazole-3-carboxylic acid [(1R)-1-pyridin-2-yl-ethyl)-amide, |
| 228 | (8S*)-8-(3-chloro-benzyl)-1,4,5,6,7,8-hexahydro-cycloheptapyrazole-3-carboxylic acid [(1R)-2-hydroxy-1-phenyl-ethyl]-amide, |
| 229 | (8R*)-8-(3-chloro-benzyl)-1,4,5,6,7,8-hexahydro-cycloheptapyrazole-3-carboxylic acid [(1R)-2-hydroxy-1-phenyl-ethyl]-amide, |
| 230 | (8R*)-8-(3-chloro-benzyl)-1,4,5,6,7,8-hexahydro-cycloheptapyrazole-3-carboxylic acid [(1S)-2-hydroxy-1-phenyl-ethyl]-amide, |
| 231 | (8S*)-8-(3-chloro-benzyl)-1,4,5,6,7,8-hexahydro-cycloheptapyrazole-3-carboxylic acid [(1S)-2-hydroxy-1-phenyl-ethyl]-amide, |
| 232 | (2E)-2-[(8R*)-8-(3-fluoro-benzyl)-1,4,5,6,7,8-hexahydro-cycloheptapyrazol-3-yl]-ethenesulfonic acid [(1S)-1-phenyl-ethyl]-amide, |
| 233 | (2E)-2-[(8S*)-8-(3-fluoro-benzyl)-1,4,5,6,7,8-hexahydro-cycloheptapyrazol-3-yl]-ethenesulfonic acid [(1S)-1-phenyl-ethyl]-amide, |
| 234 | (8E)-8-(4-chloro-benzylidene)-1,4,5,6,7,8-hexahydro-cycloheptapyrazole-3-carboxylic acid [(1R)-2-hydroxy-1-phenyl-ethyl]-amide, |
| 235 | 2-[8-(3-fluoro-benzyl)-1,4,5,6,7,8-hexahydro-cycloheptapyrazol-3-yl]-ethenesulfonic acid [(1R)-1-phenyl-ethyl]-amide, |

-continued

| Cpd | Name |
|---|---|
| 236 | (2E,8E)-2-[8-(4-chloro-benzylidene)-1,4,5,6,7,8-hexahydro-cycloheptapyrazol-3-yl]-ethenesulfonic acid [(1R)-1-phenyl-ethyl]-amide, |
| 237 | (2E,8E)-2-[8-(4-chloro-benzylidene)-1,4,5,6,7,8-hexahydro-cycloheptapyrazol-3-yl]-ethenesulfonic acid [(1S)-1-phenyl-ethyl]-amide, |
| 238 | (8E)-(2S)-2-{[8-(4-chloro-benzylidene)-1,4,5,6,7,8-hexahydro-cycloheptapyrazole-3-carbonyl]-amino}-3-(4-fluoro-phenyl)-propionic acid methyl ester, |
| 239 | (8E)-8-(3-chloro-benzylidene)-1,4,5,6,7,8-hexahydro-cycloheptapyrazole-3-carboxylic acid [(1R)-2-hydroxy-1-phenyl-ethyl]-amide, |
| 240 | (8E)-(2S)-2-{[8-(3-chloro-benzylidene)-1,4,5,6,7,8-hexahydro-cycloheptapyrazole-3-carbonyl]-amino}-3-(4-fluoro-phenyl)-propionic acid methyl ester, |
| 241 | (8E)-(2S)-2-{[8-(3-fluoro-benzylidene)-1-methyl-1,4,5,6,7,8-hexahydro-cycloheptapyrazole-3-carbonyl]-amino}-3-(4-fluoro-phenyl)-propionic acid methyl ester, |
| 242 | (8E)-8-(3-fluoro-benzylidene)-1-methyl-1,4,5,6,7,8-hexahydro-cycloheptapyrazole-3-carboxylic acid [(1R)-2-hydroxy-1-phenyl-ethyl]-amide, |
| 243 | (8E)-[8-(3-fluoro-benzylidene)-1-methyl-1,4,5,6,7,8-hexahydro-cycloheptapyrazol-3-yl]-imidazol-1-yl-methanone, |
| 244 | (8E)-(2S)-8-(3-fluoro-benzylidene)-1-methyl-1,4,5,6,7,8-hexahydro-cycloheptapyrazole-3-carboxylic acid [1-hydroxymethyl-2-(4-hydroxy-phenyl)-ethyl]-amide, |
| 245 | (8E)-(2R)-2-{[8-(3-chloro-benzylidene)-1,4,5,6,7,8-hexahydro-cycloheptapyrazole-3-carbonyl]-amino}-3-(4-fluoro-phenyl)-propionic acid methyl ester, |
| 246 | (8E)-(2S)-8-(3-chloro-benzylidene)-1,4,5,6,7,8-hexahydro-cycloheptapyrazole-3-carboxylic acid [1-hydroxymethyl-2-(4-hydroxy-phenyl)-ethyl]-amide, |
| 247 | (8E)-(2R)-2-{[8-(4-chloro-benzylidene)-1,4,5,6,7,8-hexahydro-cycloheptapyrazole-3-carbonyl]-amino}-3-(4-fluoro-phenyl)-propionic acid methyl ester, |
| 248 | (8E)-(2R)-2-{[8-(3-fluoro-benzylidene)-1-methyl-1,4,5,6,7,8-hexahydro-cycloheptapyrazole-3-carbonyl]-amino}-3-(4-fluoro-phenyl)-propionic acid methyl ester, |
| 249 | (8E)-8-(3-fluoro-benzylidene)-1-methyl-1,4,5,6,7,8-hexahydro-cycloheptapyrazole-3-carboxylic acid [(1R)-3-hydroxy-1-phenyl-propyl]-amide, |
| 250 | (8E)-8-(3-chloro-benzylidene)-1,4,5,6,7,8-hexahydro-cycloheptapyrazole-3-carboxylic acid [(1R)-3-hydroxy-1-phenyl-propyl]-amide, |
| 251 | (8R*)-(3-chloro-benzyl)-1,4,5,6,7,8-hexahydro-cycloheptapyrazole-3-carboxylic acid [(1S)-2-methoxy-1-phenyl-ethyl]-amide, |
| 252 | (8S*)-(3-chloro-benzyl)-1,4,5,6,7,8-hexahydro-cycloheptapyrazole-3-carboxylic acid [(1S)-2-methoxy-1-phenyl-ethyl]-amide, |
| 253 | (8S*)-(3-chloro-benzyl)-1,4,5,6,7,8-hexahydro-cycloheptapyrazole-3-carboxylic acid [(1R)-2-methoxy-1-phenyl-ethyl]-amide, |
| 254 | (8R*)-(3-chloro-benzyl)-1,4,5,6,7,8-hexahydro-cycloheptapyrazole-3-carboxylic acid [(1R)-2-methoxy-1-phenyl-ethyl]-amide, |
| 255 | (2E)-[8-(3-chloro-benzyl)-1,4,5,6,7,8-hexahydro-cycloheptapyrazol-3-yl]-ethenesulfonic acid piperidin-1-ylamide, |
| 256 | 8-(3-chloro-benzyl)-1,4,5,6,7,8-hexahydro-cycloheptapyrazole-3-carboxylic acid [(1S)-1-phenyl-ethyl]-amide, or |
| 257 | 8-(3-chloro-benzyl)-1,4,5,6,7,8-hexahydro-cycloheptapyrazole-3-carboxylic acid [(1R)-1-phenyl-ethyl]-amide. |

Representative compounds described herein further include compounds selected from:

| Cpd | Name |
|---|---|
| 2 | 8-(4-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide, |
| 3 | (2E)-2-[8-(3-chloro-benzyl)-1-(2,4-dichloro-phenyl)-1,4,5,6,7,8-hexahydro-cycloheptapyrazol-3-yl]-ethenesulfonic acid [(1S)-1-phenyl-ethyl]-amide, |
| 4 | 8-(3-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide, |
| 7 | 8-(3-chloro-benzyl)-1-cyclohexyl-1,4,5,6,7,8-hexahydro-cycloheptapyrazole-3-carboxylic acid [(1S)-1-phenyl-ethyl]-amide, |
| 15 | 8-(3-chloro-benzyl)-1-(2,4-dichloro-phenyl)-1,4,5,6,7,8-hexahydro-cycloheptapyrazole-3-carboxylic acid [(2S)-1,3,3-trimethyl-bicyclo[2.2.1]hept-2-yl]-amide, |
| 16 | 8-(4-chloro-benzyl)-1-cyclohexyl-1,4,5,6,7,8-hexahydro-cycloheptapyrazole-3-carboxylic acid adamantan-2-ylamide, |
| 19 | 8-(3-chloro-benzyl)-1-cyclohexyl-1,4,5,6,7,8-hexahydro-cycloheptapyrazole-3-carboxylic acid adamantan-1-ylamide, |

-continued

| Cpd | Name |
|---|---|
| 22 | 8-(3-chloro-benzyl)-1-(2,4-dichloro-phenyl)-1,4,5,6,7,8-hexahydro-cycloheptapyrazole-3-carboxylic acid adamantan-1-ylamide, |
| 25 | 8-(4-chloro-benzyl)-1-(2,4-dichloro-phenyl)-1,4,5,6,7,8-hexahydro-cycloheptapyrazole-3-carboxylic acid cyclobutylamide, |
| 26 | 8-(4-chloro-benzyl)-1-(2,4-dichloro-phenyl)-1,4,5,6,7,8-hexahydro-cycloheptapyrazole-3-carboxylic acid 4-trifluoromethyl-benzylamide, |
| 28 | 8-(3-chloro-benzyl)-1-(2,4-dichloro-phenyl)-1,4,5,6,7,8-hexahydro-cycloheptapyrazole-3-carboxylic acid piperidin-1-ylamide, |
| 30 | 1,8-bis-(4-chloro-benzyl)-1,4,5,6,7,8-hexahydro-cycloheptapyrazole-3-carboxylic acid cyclobutylamide, |
| 40 | 8-(2-chloro-benzyl)-1-methyl-1,4,5,6,7,8-hexahydro-cycloheptapyrazole-3-carboxylic acid [(2S)-1,3,3-trimethyl-bicyclo[2.2.1]hept-2-yl]-amide, |
| 41 | 1-(2,4-dichloro-phenyl)-8-(3-fluoro-benzyl)-1,4,5,6,7,8-hexahydro-cycloheptapyrazole-3-carboxylic acid cyclobutylamide, |
| 42 | 1-(2,4-dichloro-phenyl)-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 44 | 1-cyclohexyl-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 45 | 1-cyclohexyl-8-(3-fluoro-benzyl)-1,4,5,6,7,8-hexahydro-cycloheptapyrazole-3-carboxylic acid [(1S)-1-phenyl-ethyl]-amide, |
| 47 | 1-benzyl-8-phenyl-1,4,5,6,7,8-hexahydro-cycloheptapyrazole-3-carboxylic acid [(2S)-1,3,3-trimethyl-bicyclo[2.2.1]hept-2-yl]-amide, |
| 48 | 1-benzyl-8-phenyl-1,4,5,6,7,8-hexahydro-cycloheptapyrazole-3-carboxylic acid [(1S)-1-phenyl-ethyl]-amide, |
| 53 | 1-cyclohexyl-8-(3-fluoro-benzyl)-1,4,5,6,7,8-hexahydro-cycloheptapyrazole-3-carboxylic acid benzylamide, |
| 58 | 1-cyclohexyl-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 59 | 1-cyclohexyl-8-(4-fluoro-benzyl)-1,4,5,6,7,8-hexahydro-cycloheptapyrazole-3-carboxylic acid cyclopentylamide, |
| 61 | 1-cyclohexyl-8-(4-fluoro-benzyl)-1,4,5,6,7,8-hexahydro-cycloheptapyrazole-3-carboxylic acid benzylamide, |
| 63 | (2S)-2-{[1-cyclohexyl-8-(4-fluoro-benzyl)-1,4,5,6,7,8-hexahydro-cycloheptapyrazole-3-carbonyl]-amino}-3-(4-fluoro-phenyl)-propionic acid methyl ester, |
| 64 | 1-cyclohexyl-8-(4-fluoro-benzyl)-1,4,5,6,7,8-hexahydro-cycloheptapyrazole-3-carboxylic acid [(1S)-1-phenyl-ethyl]-amide, |
| 65 | 1-cyclohexyl-8-(4-fluoro-benzyl)-1,4,5,6,7,8-hexahydro-cycloheptapyrazole-3-carboxylic acid 4-trifluoromethyl-benzylamide, |
| 67 | (8S*)-1-cyclohexyl-8-(4-fluoro-benzyl)-1,4,5,6,7,8-hexahydro-cycloheptapyrazole-3-carboxylic acid [(1R)-2-hydroxy-1-phenyl-ethyl]-amide, |
| 75 | (2E)-2-[1-cyclohexyl-8-(3-fluoro-benzyl)-1,4,5,6,7,8-hexahydro-cycloheptapyrazol-3-yl]-ethenesulfonic acid [(1S)-1-phenyl-ethyl]-amide, |
| 77 | (2R)-2-{[(8R)-1-(2,4-dichloro-phenyl)-8-(3-fluoro-benzyl)-1,4,5,6,7,8-hexahydro-cycloheptapyrazole-3-carbonyl]-amino}-3-(4-fluoro-phenyl)-propionic acid methyl ester, |
| 78 | (2R)-2-{[(8S)-1-(2,4-dichloro-phenyl)-8-(3-fluoro-benzyl)-1,4,5,6,7,8-hexahydro-cycloheptapyrazole-3-carbonyl]-amino}-3-(4-fluoro-phenyl)-propionic acid methyl ester, |
| 80 | (2R)-2-{[1-(2,4-dichloro-phenyl)-8-(3-fluoro-benzyl)-1,4,5,6,7,8-hexahydro-cycloheptapyrazole-3-carbonyl]-amino}-3-(4-hydroxy-phenyl)-propionic acid methyl ester, |
| 82 | (2R)-2-{[1-cyclohexyl-8-(3-fluoro-benzyl)-1,4,5,6,7,8-hexahydro-cycloheptapyrazole-3-carbonyl]-amino}-3-(4-hydroxy-phenyl)-propionic acid methyl ester, |
| 83 | (2R)-2-{[1-cyclohexyl-8-(4-fluoro-benzyl)-1,4,5,6,7,8-hexahydro-cycloheptapyrazole-3-carbonyl]-amino}-3-(4-hydroxy-phenyl)-propionic acid methyl ester, |
| 84 | 1-(2,4-dichloro-phenyl)-8-(3-fluoro-benzyl)-1,4,5,6,7,8-hexahydro-cycloheptapyrazole-3-carboxylic acid piperidin-1-ylamide, |
| 91 | 1-(2,4-dichloro-phenyl)-8-(3-fluoro-benzyl)-1,4,5,6,7,8-hexahydro-cycloheptapyrazole-3-carboxylic acid morpholin-4-ylamide, |
| 92 | 1-(2,4-difluoro-phenyl)-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 93 | (2E)-2-[1-(2,4-difluoro-phenyl)-8-(3-fluoro-benzyl)-1,4,5,6,7,8-hexahydro-cycloheptapyrazol-3-yl]-ethenesulfonic acid [(1S)-1-phenyl-ethyl]-amide, |
| 96 | (2E)-2-[8-(3-fluoro-benzyl)-1,4,5,6,7,8-hexahydro-cycloheptapyrazol-3-yl]-ethenesulfonic acid [(1S)-1-phenyl-ethyl]-amide, |
| 97 | 1-(2,4-difluoro-phenyl)-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide, |
| 98 | (2R)-2-{[1-(2,4-difluoro-phenyl)-8-(4-fluoro-benzyl)-1,4,5,6,7,8-hexahydro-cycloheptapyrazole-3-carbonyl]-amino}-3-(4-hydroxy-phenyl)-propionic acid methyl ester, |
| 101 | (2E)-2-[8-(4-fluoro-benzyl)-1-methyl-1,4,5,6,7,8-hexahydro-cycloheptapyrazol-3-yl]-ethenesulfonic acid [(1S)-1-phenyl-ethyl]-amide, |

| Cpd | Name |
|---|---|
| 102 | (2R)-2-{[8-(3-chloro-benzyl)-1-(2,4-dichloro-phenyl)-1,4,5,6,7,8-hexahydro-cycloheptapyrazole-3-carbonyl]-amino}-3-(4-hydroxy-phenyl)-propionic acid methyl ester, |
| 103 | (2R)-2-{[8-(3-chloro-benzyl)-1-(2,4-dichloro-phenyl)-1,4,5,6,7,8-hexahydro-cycloheptapyrazole-3-carbonyl]-amino}-3-(4-fluoro-phenyl)-propionic acid methyl ester, |
| 104 | (2E)-2-[8-(3-fluoro-benzyl)-1-methyl-1,4,5,6,7,8-hexahydro-cycloheptapyrazol-3-yl]-ethenesulfonic acid [(1S)-1-phenyl-ethyl]-amide, |
| 105 | (2R,3S)-3-{[1-cyclohexyl-8-(3-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 106 | (2R,3S)-3-{[1-cyclohexyl-8-(4-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 107 | (2E)-2-[1-(2,4-difluoro-phenyl)-8-(4-fluoro-benzyl)-1,4,5,6,7,8-hexahydro-cycloheptapyrazol-3-yl]-ethenesulfonic acid [(1S)-1-phenyl-ethyl]-amide, |
| 108 | (2E)-2-[8-(4-fluoro-benzyl)-1,4,5,6,7,8-hexahydro-cycloheptapyrazol-3-yl]-ethenesulfonic acid [(1S)-1-phenyl-ethyl]-amide, |
| 109 | (2R,3S)-3-{[8-(3-chloro-benzyl)-1-(2,4-dichloro-phenyl)-1,4,5,6,7,8-hexahydro-cycloheptapyrazole-3-carbonyl]-amino}-bicyclo[2.2.1]heptane-2-carboxylic acid ethyl ester, |
| 110 | (2R,3S)-3-{[1-(2,4-difluoro-phenyl)-8-(4-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 111 | (2R,3S)-3-{[1-(2,4-difluoro-phenyl)-8-(3-fluoro-benzyl)-1,4,5,6,7,8-hexahydro-cycloheptapyrazole-3-carbonyl]-amino}-bicyclo[2.2.1]heptane-2-carboxylic acid ethyl ester, |
| 112 | (8R*)-8-(3-chloro-benzyl)-1-(2,4-dichloro-phenyl)-1,4,5,6,7,8-hexahydro-cycloheptapyrazole-3-carboxylic acid [(1R,2S)-2-hydroxy-indan-1-yl]-amide, |
| 113 | (8S*)-8-(3-chloro-benzyl)-1-(2,4-dichloro-phenyl)-1,4,5,6,7,8-hexahydro-cycloheptapyrazole-3-carboxylic acid [(1R,2S)-2-hydroxy-indan-1-yl]-amide, |
| 114 | (8R*)-1-cyclohexyl-8-(3-fluoro-benzyl)-1,4,5,6,7,8-hexahydro-cycloheptapyrazole-3-carboxylic acid [(1R,2S)-2-hydroxy-indan-1-yl]-amide, |
| 115 | (8S*)-1-cyclohexyl-8-(3-fluoro-benzyl)-1,4,5,6,7,8-hexahydro-cycloheptapyrazole-3-carboxylic acid [(1R,2S)-2-hydroxy-indan-1-yl]-amide, |
| 121 | (8S*)-1-cyclohexyl-8-(4-fluoro-benzyl)-1,4,5,6,7,8-hexahydro-cycloheptapyrazole-3-carboxylic acid [(1R,2S)-2-hydroxy-indan-1-yl]-amide, |
| 122 | (2E)-2-[1-(2,4-difluoro-phenyl)-8-(4-fluoro-benzyl)-1,4,5,6,7,8-hexahydro-cycloheptapyrazol-3-yl]-ethenesulfonic acid piperidin-1-ylamide, |
| 126 | (2E)-2-[8-(4-fluoro-benzyl)-1-methyl-1,4,5,6,7,8-hexahydro-cycloheptapyrazol-3-yl]-ethenesulfonic acid morpholin-4-ylamide, |
| 129 | 8-(4-fluoro-benzyl)-1,4,5,6,7,8-hexahydro-cycloheptapyrazole-3-carboxylic acid benzylamide, |
| 130 | 8-(4-fluoro-benzyl)-1-methanesulfonyl-1,4,5,6,7,8-hexahydro-cycloheptapyrazole-3-carboxylic acid benzylamide, |
| 131 | (8E)-8-(4-chloro-benzylidene)-1-(2,4-dichloro-phenyl)-1,4,5,6,7,8-hexahydro-cycloheptapyrazole-3-carboxylic acid [(1R)-1-phenyl-ethyl]-amide, |
| 132 | (8E)-8-(4-chloro-benzylidene)-1-(2,4-dichloro-phenyl)-1,4,5,6,7,8-hexahydro-cycloheptapyrazole-3-carboxylic acid [(1R)-1-cyclohexyl-ethyl]-amide, |
| 133 | (8E)-8-(4-chloro-benzylidene)-1-(2,4-dichloro-phenyl)-1,4,5,6,7,8-hexahydro-cycloheptapyrazole-3-carboxylic acid piperidin-1-ylamide, |
| 134 | (8E)-8-(4-chloro-benzylidene)-1-(2,4-dichloro-phenyl)-1,4,5,6,7,8-hexahydro-cycloheptapyrazole-3-carboxylic acid morpholin-4-ylamide, |
| 135 | (8E)-8-(4-chloro-benzylidene)-1-(2,4-dichloro-phenyl)-1,4,5,6,7,8-hexahydro-cycloheptapyrazole-3-carboxylic acid 4-sulfamoyl-benzylamide, |
| 136 | (8E)-N-[8-(4-chloro-benzylidene)-1-(2,4-dichloro-phenyl)-1,4,5,6,7,8-hexahydro-cycloheptapyrazole-3-carbonyl]-benzenesulfonamide, |
| 137 | (8E)-8-(4-chloro-benzylidene)-1-(2,4-dichloro-phenyl)-1,4,5,6,7,8-hexahydro-cycloheptapyrazole-3-carboxylic acid [1-(4-chloro-phenyl)-ethyl]-amide, |
| 138 | (8E)-8-(4-chloro-benzylidene)-1-(2,4-dichloro-phenyl)-1,4,5,6,7,8-hexahydro-cycloheptapyrazole-3-carboxylic acid [(1S)-1-cyclohexyl-ethyl]-amide, |
| 139 | (8E)-8-(4-chloro-benzylidene)-1-(2,4-dichloro-phenyl)-1,4,5,6,7,8-hexahydro-cycloheptapyrazole-3-carboxylic acid [(1S)-1-phenyl-ethyl]-amide, |
| 140 | (8E)-8-(4-chloro-benzylidene)-1,4,5,6,7,8-hexahydro-cycloheptapyrazole-3-carboxylic acid [(1R)-1-cyclohexyl-ethyl]-amide, |
| 141 | (8E)-8-(4-chloro-benzylidene)-1,4,5,6,7,8-hexahydro-cycloheptapyrazole-3-carboxylic acid [(1S)-1-phenyl-ethyl]-amide, |
| 142 | (8E)-8-(4-chloro-benzylidene)-1,4,5,6,7,8-hexahydro-cycloheptapyrazole-3-carboxylic acid [(1R)-1-phenyl-ethyl]-amide, |
| 143 | (8E)-8-(4-chloro-benzylidene)-1,4,5,6,7,8-hexahydro-cycloheptapyrazole-3-carboxylic acid [(1S)-1-cyclohexyl-ethyl]-amide, |
| 144 | (8E)-8-(4-chloro-benzylidene)-1,4,5,6,7,8-hexahydro-cycloheptapyrazole-3-carboxylic acid piperidin-1-ylamide, |
| 145 | (8E)-8-(4-chloro-benzylidene)-1,4,5,6,7,8-hexahydro-cycloheptapyrazole-3-carboxylic acid morpholin-4-ylamide, |
| 146 | (8E)-1-(2,4-dichloro-phenyl)-8-(4-fluoro-benzylidene)-1,4,5,6,7,8-hexahydro-cycloheptapyrazole-3-carboxylic acid [(1R)-1-phenyl-ethyl]-amide, |

-continued

| Cpd | Name |
|---|---|
| 147 | (8E)-1-(2,4-dichloro-phenyl)-8-(4-fluoro-benzylidene)-1,4,5,6,7,8-hexahydro-cycloheptapyrazole-3-carboxylic acid [(1R)-1-cyclohexyl-ethyl]-amide, |
| 148 | (8E)-1-(2,4-dichloro-phenyl)-8-(4-fluoro-benzylidene)-1,4,5,6,7,8-hexahydro-cycloheptapyrazole-3-carboxylic acid [(1S)-1-cyclohexyl-ethyl]-amide, |
| 149 | (8E)-1-(2,4-dichloro-phenyl)-8-(4-fluoro-benzylidene)-1,4,5,6,7,8-hexahydro-cycloheptapyrazole-3-carboxylic acid [(1S)-1-phenyl-ethyl]-amide, |
| 150 | (8E)-1-(2,4-dichloro-phenyl)-8-(4-fluoro-benzylidene)-1,4,5,6,7,8-hexahydro-cycloheptapyrazole-3-carboxylic acid piperidin-1-ylamide, |
| 151 | (8E)-1-(2,4-dichloro-phenyl)-8-(4-fluoro-benzylidene)-1,4,5,6,7,8-hexahydro-cycloheptapyrazole-3-carboxylic acid morpholin-4-ylamide, |
| 152 | (8E)-8-(4-chloro-benzylidene)-1-(2,4-dichloro-phenyl)-1,4,5,6,7,8-hexahydro-cycloheptapyrazole-3-carboxylic acid pyridin-2-ylamide, |
| 155 | (8E)-8-(4-chloro-benzylidene)-1-(2,4-dichloro-phenyl)-1,4,5,6,7,8-hexahydro-cycloheptapyrazole-3-carboxylic acid (pyridin-2-ylmethyl)-amide, |
| 156 | (8E)-8-(4-chloro-benzylidene)-1-(2,4-dichloro-phenyl)-1,4,5,6,7,8-hexahydro-cycloheptapyrazole-3-carboxylic acid (pyridin-4-ylmethyl)-amide, |
| 157 | (8E)-8-(4-chloro-benzylidene)-1-(2,4-dichloro-phenyl)-1,4,5,6,7,8-hexahydro-cycloheptapyrazole-3-carboxylic acid (2-pyridin-2-yl-ethyl)-amide, |
| 160 | (2E)-2-[8-(3-chloro-benzyl)-1,4,5,6,7,8-hexahydro-cycloheptapyrazol-3-yl]-ethenesulfonic acid [(1S)-1-phenyl-ethyl]-amide, |
| 164 | 8-(3-chloro-benzyl)-1,4,5,6,7,8-hexahydro-cycloheptapyrazole-3-carboxylic acid [(1S)-2-hydroxy-1-phenyl-ethyl]-amide, |
| 165 | 8-(3-chloro-benzyl)-1,4,5,6,7,8-hexahydro-cycloheptapyrazole-3-carboxylic acid [(1R)-2-hydroxy-1-phenyl-ethyl]-amide, |
| 166 | 8-(3-chloro-benzyl)-1,4,5,6,7,8-hexahydro-cycloheptapyrazole-3-carboxylic acid [(1S)-1-benzyl-2-hydroxy-ethyl]-amide, |
| 167 | 8-(3-chloro-benzyl)-1,4,5,6,7,8-hexahydro-cycloheptapyrazole-3-carboxylic acid [(1R)-1-benzyl-2-hydroxy-ethyl]-amide, |
| 172 | 1-(2,4-difluoro-phenyl)-8-(4-fluoro-benzyl)-1,4,5,6,7,8-hexahydro-cycloheptapyrazole-3-carboxylic acid [(1S)-2-chloro-1-phenyl-ethyl]-amide, |
| 180 | (8E)-8-(4-chloro-benzylidene)-1-pyridin-4-yl-1,4,5,6,7,8-hexahydro-cycloheptapyrazole-3-carboxylic acid [(1R)-1-cyclohexyl-ethyl]-amide, |
| 181 | (8E)-8-(4-chloro-benzylidene)-1-pyridin-4-yl-1,4,5,6,7,8-hexahydro-cycloheptapyrazole-3-carboxylic acid [(1S)-1-cyclohexyl-ethyl]-amide, |
| 184 | (8E)-8-(4-chloro-benzylidene)-1-(4-sulfamoyl-phenyl)-1,4,5,6,7,8-hexahydro-cycloheptapyrazole-3-carboxylic acid [(1R)-1-phenyl-ethyl]-amide, |
| 185 | (8E)-8-(4-chloro-benzylidene)-1-(4-sulfamoyl-phenyl)-1,4,5,6,7,8-hexahydro-cycloheptapyrazole-3-carboxylic acid [(1R)-1-cyclohexyl-ethyl]-amide, |
| 186 | 8-(3-chloro-benzyl)-1-(4-trifluoromethyl-pyrimidin-2-yl)-1,4,5,6,7,8-hexahydro-cycloheptapyrazole-3-carboxylic acid [(1R)-1-benzyl-2-hydroxy-ethyl]-amide, |
| 188 | (8E)-[1-(2,4-dichloro-phenyl)-8-(4-fluoro-benzylidene)-1,4,5,6,7,8-hexahydro-cycloheptapyrazol-3-yl]-(2-pyridin-2-yl-pyrrolidin-1-yl)-methanone, |
| 189 | (8E)-8-(4-chloro-benzylidene)-1-(2-chloro-phenyl)-1,4,5,6,7,8-hexahydro-cycloheptapyrazole-3-carboxylic acid [(1R)-1-cyclohexyl-ethyl]-amide, |
| 190 | (8E)-8-(4-chloro-benzylidene)-1-(2-chloro-phenyl)-1,4,5,6,7,8-hexahydro-cycloheptapyrazole-3-carboxylic acid [(1R)-1-phenyl-ethyl]-amide, |
| 195 | (8E)-8-(4-chloro-benzylidene)-1-(2,5-dichloro-phenyl)-1,4,5,6,7,8-hexahydro-cycloheptapyrazole-3-carboxylic acid [(1R)-1-phenyl-ethyl]-amide, |
| 196 | (8E)-8-(4-chloro-benzylidene)-1-(2,5-dichloro-phenyl)-1,4,5,6,7,8-hexahydro-cycloheptapyrazole-3-carboxylic acid [(1R)-1-cyclohexyl-ethyl]-amide, |
| 197 | (8E)-8-(4-chloro-benzylidene)-1-(2,5-dichloro-phenyl)-1,4,5,6,7,8-hexahydro-cycloheptapyrazole-3-carboxylic acid [(1S)-1-cyclohexyl-ethyl]-amide, |
| 198 | (8E)-8-(4-chloro-benzylidene)-1-(2,5-dichloro-phenyl)-1,4,5,6,7,8-hexahydro-cycloheptapyrazole-3-carboxylic acid [(1S)-1-phenyl-ethyl]-amide, |
| 202 | (8E)-1-(2,4-dichloro-phenyl)-8-(4-fluoro-benzylidene)-1,4,5,6,7,8-hexahydro-cycloheptapyrazole-3-carboxylic acid [(1R)-1-phenyl-propyl]-amide, |
| 204 | (8E)-1-(2,4-dichloro-phenyl)-8-(4-fluoro-benzylidene)-1,4,5,6,7,8-hexahydro-cycloheptapyrazole-3-carboxylic acid [(1S)-2-hydroxy-1-phenyl-ethyl]-amide, |
| 205 | (8E)-1-(2,4-dichloro-phenyl)-8-(4-fluoro-benzylidene)-1,4,5,6,7,8-hexahydro-cycloheptapyrazole-3-carboxylic acid (1-methyl-1-phenyl-ethyl)-amide, |
| 206 | (8E)-[1-(2,4-dichloro-phenyl)-8-(4-fluoro-benzylidene)-1,4,5,6,7,8-hexahydro-cycloheptapyrazol-3-yl]-(3,4,5,6-tetrahydro-2H-[2,2']bipyridinyl-1-yl)-methanone, |
| 207 | (8E)-1-(2,4-dichloro-phenyl)-8-(4-fluoro-benzylidene)-1,4,5,6,7,8-hexahydro-cycloheptapyrazole-3-carboxylic acid (1R)-indan-1-ylamide, |
| 208 | (8E)-1-(2,4-dichloro-phenyl)-8-(4-fluoro-benzylidene)-1,4,5,6,7,8-hexahydro-cycloheptapyrazole-3-carboxylic acid [(1S,2R)-2-hydroxy-indan-1-yl]-amide, |
| 209 | (8E)-1-(2,4-dichloro-phenyl)-8-(4-fluoro-benzylidene)-1,4,5,6,7,8-hexahydro-cycloheptapyrazole-3-carboxylic acid (1,2,3,4-tetrahydro-naphthalen-1-yl)-amide, |
| 210 | (8E)-1-(2,4-dichloro-phenyl)-8-(4-methoxy-benzylidene)-1,4,5,6,7,8-hexahydro-cycloheptapyrazole-3-carboxylic acid (pyridin-2-ylmethyl)-amide, |
| 211 | (8E)-1-(2,4-dichloro-phenyl)-8-(4-methoxy-benzylidene)-1,4,5,6,7,8-hexahydro-cycloheptapyrazole-3-carboxylic acid (1-methyl-1-phenyl-ethyl)-amide, |
| 212 | (8E)-1-(2,4-dichloro-phenyl)-8-(4-methoxy-benzylidene)-1,4,5,6,7,8-hexahydro-cycloheptapyrazole-3-carboxylic acid [(1R)-1-phenyl-ethyl]-amide, |

-continued

| Cpd | Name |
|---|---|
| 213 | (8E)-1-(2,4-dichloro-phenyl)-8-(4-methoxy-benzylidene)-1,4,5,6,7,8-hexahydro-cycloheptapyrazole-3-carboxylic acid [(1S)-1-phenyl-ethyl]-amide, |
| 214 | (8E)-1-(2,4-dichloro-phenyl)-8-(4-methoxy-benzylidene)-1,4,5,6,7,8-hexahydro-cycloheptapyrazole-3-carboxylic acid [(1R)-1-cyclohexyl-ethyl]-amide, |
| 215 | (8E)-1-(2,4-dichloro-phenyl)-8-(4-methoxy-benzylidene)-1,4,5,6,7,8-hexahydro-cycloheptapyrazole-3-carboxylic acid [(1S)-2-hydroxy-1-phenyl-ethyl]-amide, |
| 216 | (8E)-1-(2,4-dichloro-phenyl)-8-(4-methoxy-benzylidene)-1,4,5,6,7,8-hexahydro-cycloheptapyrazole-3-carboxylic acid (1R)-indan-1-ylamide, |
| 217 | (8E)-1-(2,4-dichloro-phenyl)-8-(4-methoxy-benzylidene)-1,4,5,6,7,8-hexahydro-cycloheptapyrazole-3-carboxylic acid piperidin-1-ylamide, |
| 222 | (8E)-1-(2,4-dichloro-phenyl)-8-(4-methoxy-benzylidene)-1,4,5,6,7,8-hexahydro-cycloheptapyrazole-3-carboxylic acid (1-pyridin-2-yl-ethyl)-amide, |
| 223 | (8E)-[8-(4-chloro-benzylidene)-1,4,5,6,7,8-hexahydro-cycloheptapyrazol-3-yl]-piperidin-1-yl-methanone, |
| 224 | (8E)-1-(2,4-dichloro-phenyl)-8-(4-fluoro-benzylidene)-1,4,5,6,7,8-hexahydro-cycloheptapyrazole-3-carboxylic acid (1-pyridin-2-yl-ethyl)-amide, |
| 225 | (8E)-1-(2,4-dichloro-phenyl)-8-(4-fluoro-benzylidene)-1,4,5,6,7,8-hexahydro-cycloheptapyrazole-3-carboxylic acid [(1R)-1-pyridin-2-yl-ethyl]-amide, |
| 226 | (8E)-1-(2,4-dichloro-phenyl)-8-(4-methoxy-benzylidene)-1,4,5,6,7,8-hexahydro-cycloheptapyrazole-3-carboxylic acid (hexahydro-cyclopenta[c]pyrrol-2-yl)-amide, |
| 227 | (8E)-1-(2,4-dichloro-phenyl)-8-(4-methoxy-benzylidene)-1,4,5,6,7,8-hexahydro-cycloheptapyrazole-3-carboxylic acid [(1R)-1-pyridin-2-yl-ethyl]-amide, |
| 228 | (8S*)-8-(3-chloro-benzyl)-1,4,5,6,7,8-hexahydro-cycloheptapyrazole-3-carboxylic acid [(1R)-2-hydroxy-1-phenyl-ethyl]-amide, |
| 229 | (8R*)-8-(3-chloro-benzyl)-1,4,5,6,7,8-hexahydro-cycloheptapyrazole-3-carboxylic acid [(1R)-2-hydroxy-1-phenyl-ethyl]-amide, |
| 230 | (8R*)-8-(3-chloro-benzyl)-1,4,5,6,7,8-hexahydro-cycloheptapyrazole-3-carboxylic acid [(1S)-2-hydroxy-1-phenyl-ethyl]-amide, |
| 231 | (8S*)-8-(3-chloro-benzyl)-1,4,5,6,7,8-hexahydro-cycloheptapyrazole-3-carboxylic acid [(1S)-2-hydroxy-1-phenyl-ethyl]-amide, |
| 232 | (2E)-2-[(8R*)-8-(3-fluoro-benzyl)-1,4,5,6,7,8-hexahydro-cycloheptapyrazol-3-yl]-ethenesulfonic acid [(1S)-1-phenyl-ethyl]-amide, |
| 234 | (8E)-8-(4-chloro-benzylidene)-1,4,5,6,7,8-hexahydro-cycloheptapyrazole-3-carboxylic acid [(1R)-2-hydroxy-1-phenyl-ethyl]-amide, |
| 237 | (2E,8E)-2-[8-(4-chloro-benzylidene)-1,4,5,6,7,8-hexahydro-cycloheptapyrazol-3-yl]-ethenesulfonic acid [(1S)-1-phenyl-ethyl]-amide, |
| 238 | (8E)-(2S)-2-{[8-(4-chloro-benzylidene)-1,4,5,6,7,8-hexahydro-cycloheptapyrazole-3-carbonyl]-amino}-3-(4-fluoro-phenyl)-propionic acid methyl ester, |
| 239 | (8E)-8-(3-chloro-benzylidene)-1,4,5,6,7,8-hexahydro-cycloheptapyrazole-3-carboxylic acid [(1R)-2-hydroxy-1-phenyl-ethyl]-amide, |
| 240 | (8E)-(2S)-2-{[8-(3-chloro-benzylidene)-1,4,5,6,7,8-hexahydro-cycloheptapyrazole-3-carbonyl]-amino}-3-(4-fluoro-phenyl)-propionic acid methyl ester, |
| 241 | (8E)-(2S)-2-{[8-(3-fluoro-benzylidene)-1-methyl-1,4,5,6,7,8-hexahydro-cycloheptapyrazole-3-carbonyl]-amino}-3-(4-fluoro-phenyl)-propionic acid methyl ester, |
| 242 | (8E)-8-(3-fluoro-benzylidene)-1-methyl-1,4,5,6,7,8-hexahydro-cycloheptapyrazole-3-carboxylic acid [(1R)-2-hydroxy-1-phenyl-ethyl]-amide, |
| 244 | (8E)-(2S)-8-(3-fluoro-benzylidene)-1-methyl-1,4,5,6,7,8-hexahydro-cycloheptapyrazole-3-carboxylic acid [1-hydroxymethyl-2-(4-hydroxy-phenyl)-ethyl]-amide, |
| 245 | (8E)-(2R)-2-{[8-(3-chloro-benzylidene)-1,4,5,6,7,8-hexahydro-cycloheptapyrazole-3-carbonyl]-amino}-3-(4-fluoro-phenyl)-propionic acid methyl ester, |
| 247 | (8E)-(2R)-2-{[8-(4-chloro-benzylidene)-1,4,5,6,7,8-hexahydro-cycloheptapyrazole-3-carbonyl]-amino}-3-(4-fluoro-phenyl)-propionic acid methyl ester, |
| 248 | (8E)-(2R)-2-{[8-(3-fluoro-benzylidene)-1-methyl-1,4,5,6,7,8-hexahydro-cycloheptapyrazole-3-carbonyl]-amino}-3-(4-fluoro-phenyl)-propionic acid methyl ester, |
| 249 | (8E)-8-(3-fluoro-benzylidene)-1-methyl-1,4,5,6,7,8-hexahydro-cycloheptapyrazole-3-carboxylic acid [(1R)-3-hydroxy-1-phenyl-propyl]-amide, |
| 250 | (8E)-8-(3-chloro-benzylidene)-1,4,5,6,7,8-hexahydro-cycloheptapyrazole-3-carboxylic acid [(1R)-3-hydroxy-1-phenyl-propyl]-amide, |
| 251 | (8R*)-(3-chloro-benzyl)-1,4,5,6,7,8-hexahydro-cycloheptapyrazole-3-carboxylic acid [(1S)-2-methoxy-1-phenyl-ethyl]-amide, |
| 252 | (8S*)-(3-chloro-benzyl)-1,4,5,6,7,8-hexahydro-cycloheptapyrazole-3-carboxylic acid [(1S)-2-methoxy-1-phenyl-ethyl]-amide, |
| 253 | (8S*)-(3-chloro-benzyl)-1,4,5,6,7,8-hexahydro-cycloheptapyrazole-3-carboxylic acid [(1R)-2-methoxy-1-phenyl-ethyl]-amide, |
| 254 | (8R*)-(3-chloro-benzyl)-1,4,5,6,7,8-hexahydro-cycloheptapyrazole-3-carboxylic acid [(1R)-2-methoxy-1-phenyl-ethyl]-amide, |

-continued

| Cpd | Name |
|---|---|
| 255 | (2E)-[8-(3-chloro-benzyl)-1,4,5,6,7,8-hexahydro-cycloheptapyrazol-3-yl]-ethenesulfonic acid piperidin-1-ylamide, |
| 256 | 8-(3-chloro-benzyl)-1,4,5,6,7,8-hexahydro-cycloheptapyrazole-3-carboxylic acid [(1S)-1-phenyl-ethyl]-amide, or |
| 257 | 8-(3-chloro-benzyl)-1,4,5,6,7,8-hexahydro-cycloheptapyrazole-3-carboxylic acid [(1R)-1-phenyl-ethyl]-amide. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations and formulae have the indicated meanings:

| Abbreviation | Meaning |
|---|---|
| Cpd | compound |
| EDCI | 1-(3-dimethylaminopropyl)-3-ethylcarbodiimide |
| DCM | dichloromethane |
| DMAP | 4-dimethylaminopyridine |
| EtOAc | ethyl acetate |
| $Et_2O$ | anhydrous ether |
| $K_2CO_3$ | potassium carbonate |
| LDA | lithium diisopropylamine |
| LiHMDS or LHMDS | lithium bis(trimethylsilyl)amide |
| min(s)/hr(s) | minute(s)/hour(s) |
| $N_2$ | nitrogen |
| RT/rt/r.t. | room temperature |
| $SOCl_2$ | thionyl chloride |
| TEA or $Et_3N$ | triethylamine |
| THF | tetrahydrofuran |

Scheme A

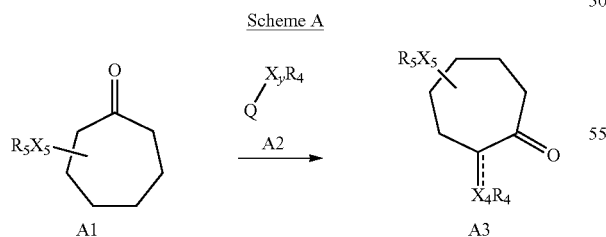

A solution of cycloheptanone Compound A1 (in a solvent such as THF and the like) is added dropwise to a reagent solution (such as LDA in a solvent such as anhydrous THF and the like) at −78° C. under an inert atmosphere (using a gas such as nitrogen and the like) and reacted, with stirring, at −78° C. for about 1 hr. A solution of Compound A2 (in a solvent such as anhydrous THF and the like, wherein Q-$X_y$ represents a suitable reaction group and wherein certain portions of Q-$X_y$ are incorporated into $X_4R_4$ as a product of the reaction) is added dropwise and the mixture is stirred for about 5 hrs, while warming to r.t., to provide Compound A3 after workup.

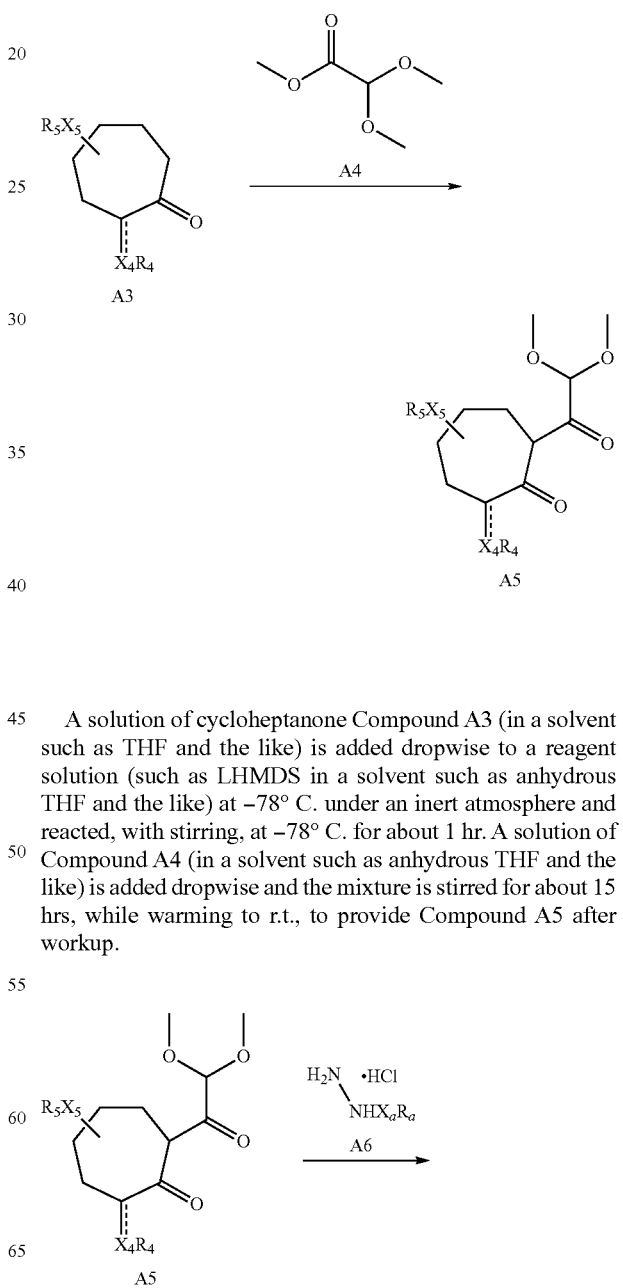

A solution of cycloheptanone Compound A3 (in a solvent such as THF and the like) is added dropwise to a reagent solution (such as LHMDS in a solvent such as anhydrous THF and the like) at −78° C. under an inert atmosphere and reacted, with stirring, at −78° C. for about 1 hr. A solution of Compound A4 (in a solvent such as anhydrous THF and the like) is added dropwise and the mixture is stirred for about 15 hrs, while warming to r.t., to provide Compound A5 after workup.

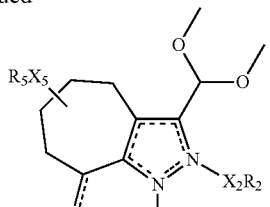

A7

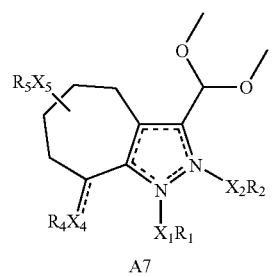

A7

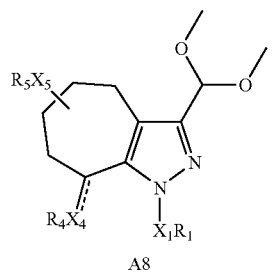

A8

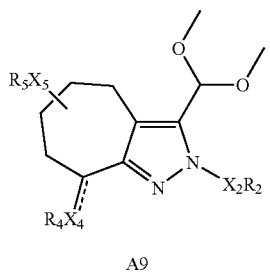

A9

A reagent (such as K₂CO₃ and the like) and a substituted hydrazine mono or dihydrochloride Compound A6 are added to a solution of Compound A5 (in a solvent such as one or more of MeOH, EtOH, CH₂Cl₂ and the like) at a temperature of about 0° C. under an inert atmosphere. The mixture is stirred overnight, while warming to r.t., to provide Compound A7 after workup.

The $X_aR_a$ substituent moiety on Compound A6 represents the possibility that, after isomer separation, the substituted amine group may be found either on the $N^1$ position as $X_1R_1$ or on the $N^2$ position as $X_2R_2$. Compound A7 represents a mixture of isomers, wherein a mixture of $X_1R_1$ and $X_2R_2$ isomers are present.

The hydrazine hydrochloride or dihydrochloride Compound A6 may be converted to the free base by methods known to those skilled in the art. In the examples of the present invention, the free base is prepared either in situ (as shown for illustrative purposes in this Scheme) or separately (then added to the reaction mixture) by reaction with K₂CO₃.

As illustrated in this Scheme, Compound A6 may also be further substituted with a variety of $X_aR_a$ substituents (as previously defined herein). In many instances, the substituted hydrazine Compound A6 is commercially available. When not commercially available, a particularly substituted Compound A6 may be prepared by methods known to those skilled in the art.

More specifically, a halogenated $X_aR_a$ substituent moiety is reacted with a hydrazine hydrate solution at reflux and used without further purification in place of Compound A6.

The Compound A7 isomeric mixture is separated via flash chromatography (eluted with a suitable solvent mixture such as about 10% to about 30% EtOAc and the like in hexane and the like) to provide a purified major isomer Compound A8 and a minor isomer Compound A9. The major isomer Compound A8 is substituted on the $N^1$ position with $X_1R_1$ ($X_2R_2$ is necessarily absent). The minor isomer Compound A9 is substituted on the $N^2$ position with $X_2R_2$ (wherein $X_1R_1$ is absent).

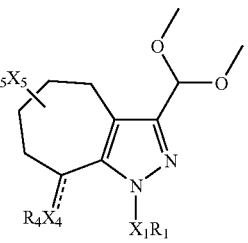

A8

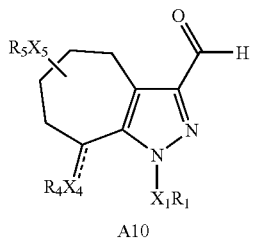

A10

An acid (such as 3N HCl and the like) is added to a solution of Compound A8 (in a solvent such as acetone and the like) at about 0° C. under an inert atmosphere. The mixture is stirred for about 4 hrs, while warming to r.t., to provide Compound A10 after workup.

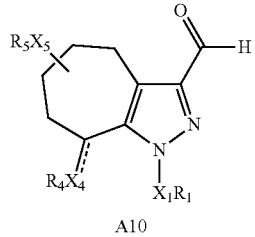

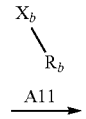

A11

A10

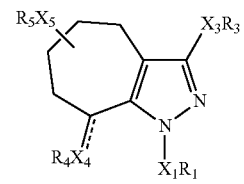

A12

A reagent solution (such as 1M potassium tert-butoxide in a solvent such as THF and the like) is added dropwise to a solution of Compound A11 (in a solvent such as anhydrous THF and the like; wherein $X_b$ represents a suitable reaction group and wherein certain portions of $X_bR_b$ are incorporated into $X_3R_3$ as a product of the reaction). After about 45 mins, a solution of Compound A10 (in a solvent such as THF and the like) is added dropwise. The mixture is reacted for about 15 hrs, while warming to r.t., to provide Compound A12 after workup.

For purposes of this Scheme, $X_bR_b$ is an alkylsulfonylamino moiety or an alkylcarbamoyl moiety each further substituted on the amino portion. In general, Compound A11 is commercially available. When not commercially available, a particularly substituted Compound A11 may be prepared by methods known to those skilled in the art.

Scheme B

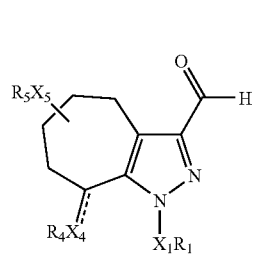

A10

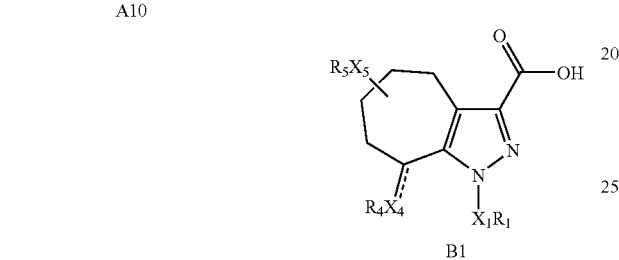

B1

A solution of Compound A10 (in a solvent such as acetone and the like) is added dropwise to a reagent solution (such as Jone's Reagent and the like) at about 0° C. under an inert atmosphere. The resulting suspension is stirred overnight, while warming to r.t., to provide Compound B1 after workup.

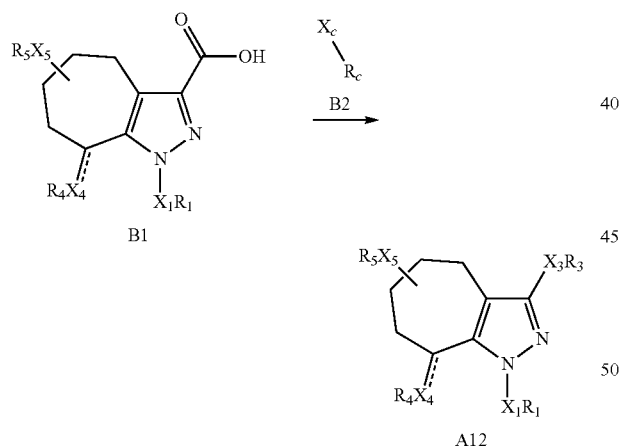

A reagent solution (such as one or more of EDCI, DMAP and the like) and Compound B2 (wherein $X_c$ represents a suitable reaction group and wherein certain portions of $X_cR_c$ are incorporated into $X_3R_3$ as a product of the reaction) are added to a solution of Compound B1 (in a solvent such as $CH_2CL_2$ and the like) at about 0° C. under an inert atmosphere. The mixture is stirred for about 6 hrs, while warming to r.t., to provide Compound A12 after workup.

For purposes of this Scheme, $X_c$ is an optionally substituted amino moiety, whereby the Compound A12 $X_3R_3$ substituent moiety incorporates the C(O) portion of the $C^3$ substituent from Compound B1 and the amine portion from $X_cR_c$.

Scheme C

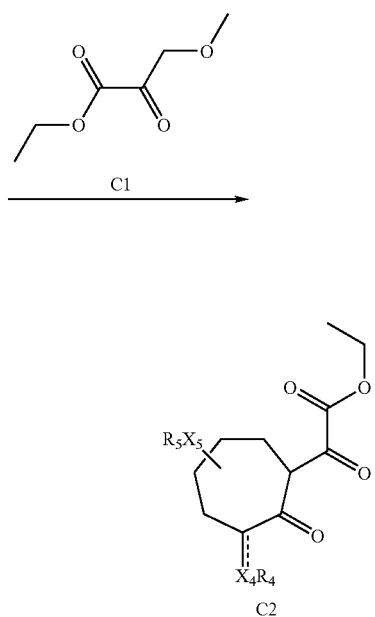

A solution of Compound A3 (in a solvent such as $Et_2O$, THF and the like or a mixture thereof) is added dropwise to a reagent solution (such as LHMDS and the like in a solvent such as $Et_2O$ or THF and the like or a mixture thereof) at −78° C. under an inert atmosphere and stirred at about −78° C. for about 40 mins. A solution of Compound C1 (in a solvent such as $Et_2O$ and the like) is added dropwise and the mixture is stirred at about −78° C. for about 1 hr, then allowed to warm to r.t. over a period of about 2 hrs to yield Compound C2 after workup, as a crude product used without further purification in the next step.

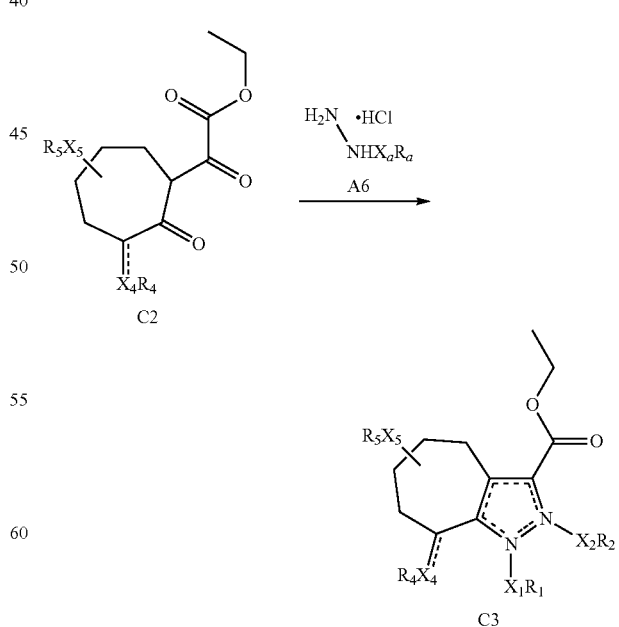

Using the procedure of Scheme A and Compound C2 in place of Compound A5 provides Compound C3 after workup.

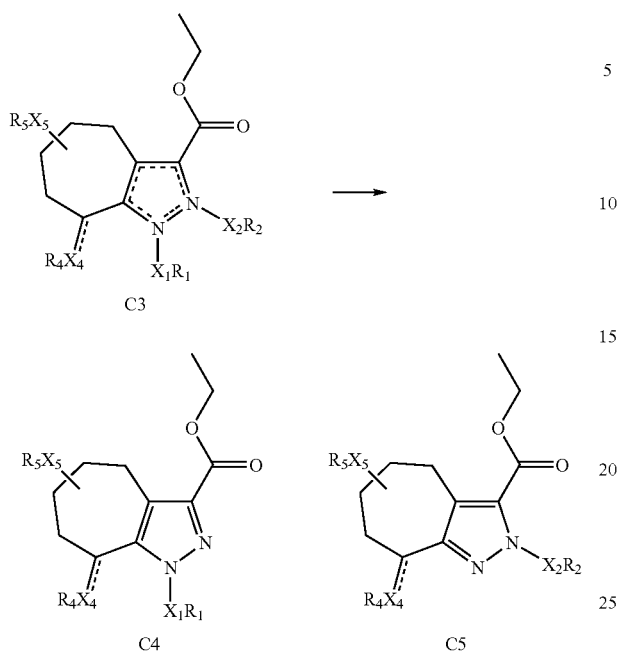

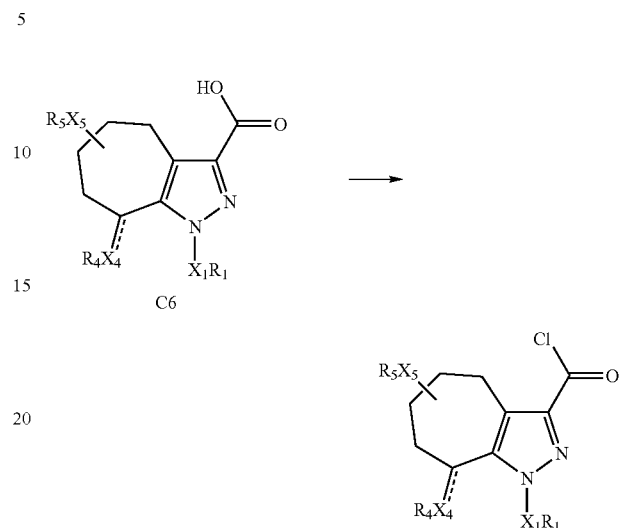

Using the procedure of Scheme A and Compound C3 in place of Compound A7, the Compound C3 isomeric mixture is separated via flash chromatography (eluted with a suitable solvent mixture such as 20% or 30% EtOAc:hexane and the like) to provide a major isomer Compound C4 and a minor isomer Compound C5.

solvent such as water, MeOH, THF and the like or a mixture thereof) and stirred overnight to provide Compound C6 after workup.

A reagent solution (such as $SOCl_2$ and the like in a solvent such as $CH_2Cl_2$ and the like) is added to Compound C6 at ambient temperature under an inert nitrogen atmosphere. The reaction mixture is stirred at reflux temperature for about 15 mins to provide Compound C7 after workup.

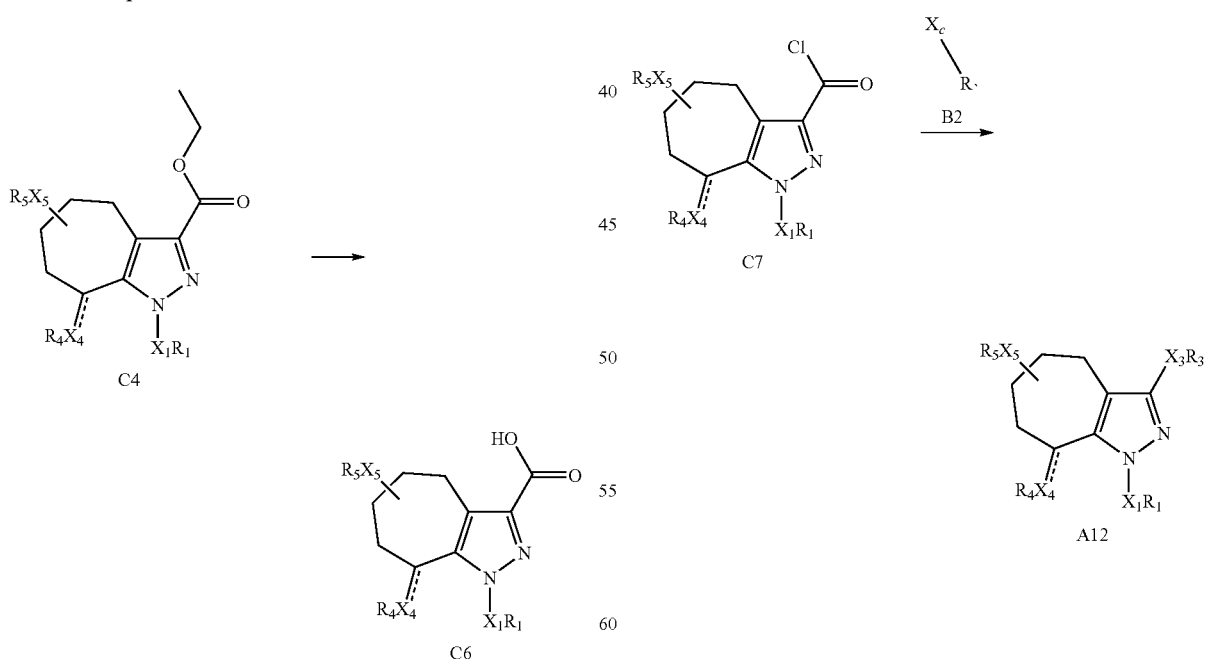

The separated major isomer Compound C4 is treated with a reagent solution (such as a mixture of NaOH or LiOH in a A solution of Compound C7 (optionally mixed with TEA and the like) is added to a solution of Compound B2 (in a solvent such as $CH_2Cl_2$ and the like) at ambient temperature under an inert nitrogen atmosphere. The mixture is stirred at r.t. for a period of time to provide Compound A12 after workup.

The synthetic examples that follow herein describe more completely the preparation of particular compounds included within the scope of the present invention.

Example 1

(2E)-2-[1-(2,4-difluoro-phenyl)-8-(3-fluoro-benzyl)-1,4,5,6,7,8-hexahydro-cycloheptapyrazol-3-yl]-ethenesulfonic acid piperidin-1-ylamide (Cpd123)

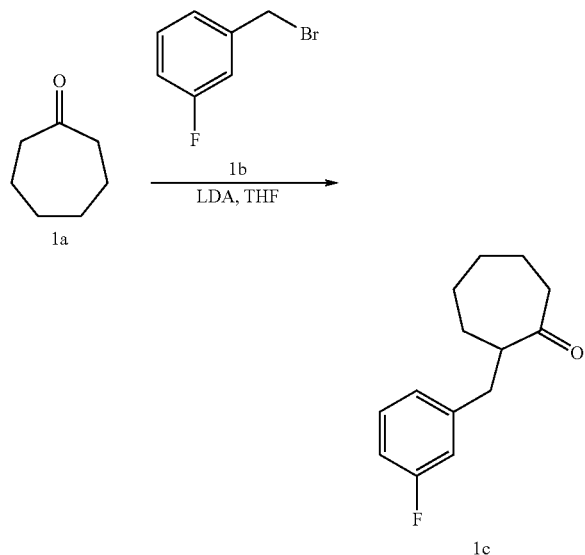

Cycloheptanone Compound 1a (3.0 g, 26.8 mmol) in THF (5 mL) was added dropwise to a solution of LDA (17.6 mL, 31.7 mmol) in anhydrous THF (50 mL) at −78° C. under a N₂ atmosphere. The mixture was stirred at −78° C. for 60 mins, then 1-bromomethyl-3-fluoro-benzene Compound 1b (5.0 g, 26.5 mmol) in anhydrous THF (10 mL) was added dropwise. The mixture was stirred for 5 hrs, while warming to r.t. The reaction was quenched with water (5 mL) and the organic layer was diluted with EtOAc (100 mL), then washed with water and brine. The organic layer was separated and dried with anhydrous sodium sulfate, then filtered and concentrated in vacuo to yield a crude oil which was purified by flash chromatography using 3% EtOAc in hexane to afford 2-(3-fluoro-benzyl)-cycloheptanone Compound 1c (4.72 g, 80%).

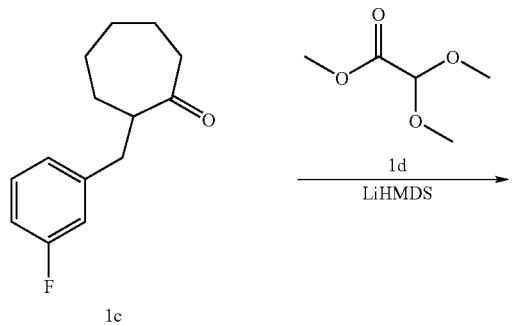

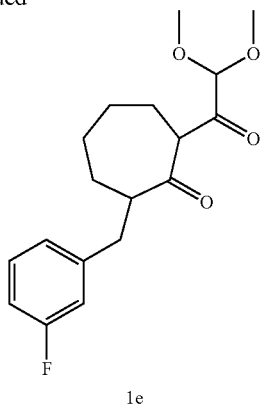

A solution of Compound 1c (2.94 g, 13.9 mmol) in THF (5 mL) was added dropwise to a 1M solution of LiHMDS (22.2 mL, 22.2 mmol) in anhydrous THF (25 mL) at −78° C. under a N₂ atmosphere. The mixture was stirred at −78° C. for 60 mins, then a solution of dimethoxy-acetic acid methyl ester Compound 1d (1.8 g, 13.4 mmol) in anhydrous THF (5 mL) was added dropwise. The mixture was stirred for 15 hrs, while warming to r.t. The reaction was quenched with water (5 mL) and diluted with EtOAc (100 mL). The organic layer was separated, washed with water and brine and dried with anhydrous sodium sulfate, then filtered and concentrated in vacuo to yield a crude oil which was purified by flash chromatography using 10% EtOAc in hexane to afford 2-(2,2-dimethoxy-acetyl)-7-(3-fluoro-benzyl)-cycloheptanone Compound 1e (2.80 g, 65%).

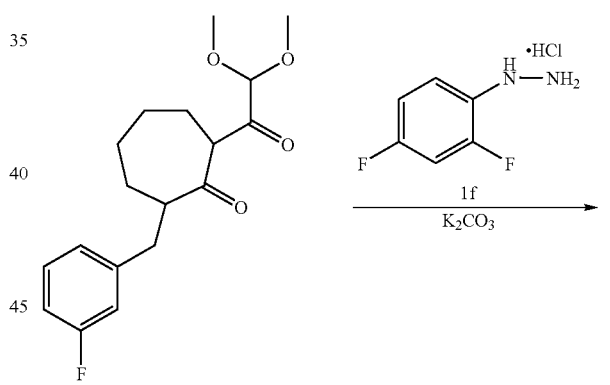

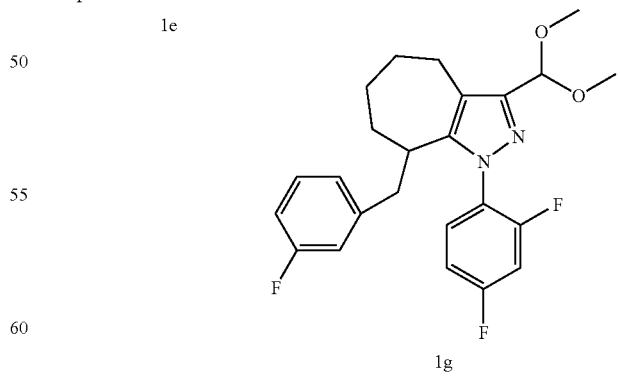

K₂CO₃ (1.65 g, 12.0 mmol) and (2,4-difluoro-phenyl)-hydrazine hydrochloride Compound 1f (1.80 g, 10 mmol) were added to a solution of Compound 1e (3.2 g, 10.0 mmol) in MeOH (50 mL) at 0° C. under a N₂ atmosphere. The mixture was stirred overnight, while warming to r.t. The reaction was quenched with water (20 mL) and the organic layer was diluted with EtOAc (200 mL), then washed with water and brine. The organic layer was separated and dried with anhydrous sodium sulfate, then filtered and concentrated in vacuo to yield a crude oil which was purified by flash chromatography using 20% EtOAc in hexane to afford 1-(2,4-difluoro-phenyl)-3-dimethoxymethyl-8-(3-fluoro-benzyl)-1,4,5,6,7,8-hexahydro-cycloheptapyrazole Compound 1g (3.01 g, 70%) as a colorless oil.

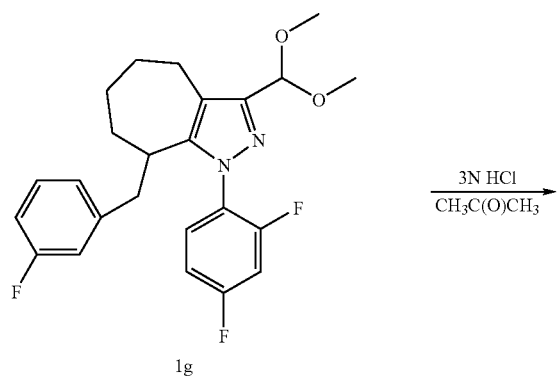

3N HCl (8 mL) was added to a solution of Compound 1g (1.66 g, 4.9 mmol) in acetone (50 mL) at 0° C. under a $N_2$ atmosphere. The mixture was stirred for 4 hrs, while warming to r.t. The reaction was quenched with water (20 mL), neutralized to pH 7 with $K_2CO_3$ and diluted with DCM (100 mL). The organic layer was washed with water and brine, separated and dried with anhydrous sodium sulfate, then filtered and concentrated in vacuo to yield 1-(2,4-difluoro-phenyl)-8-(3-fluoro-benzyl)-1,4,5,6,7,8-hexahydro-cycloheptapyrazole-3-carbaldehyde Compound 1h (1.79 g, 95%) as a colorless oil.

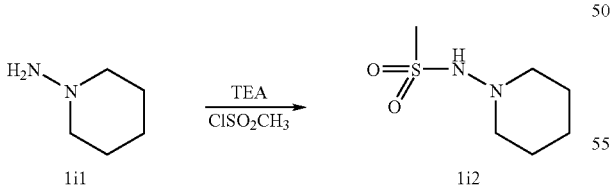

TEA (2.43 mL, 17.46 mmol) and methanesulfonylchloride (2.0 g, 17.46 mmol). were added to a solution of piperidin-1-ylamine Compound 1i1 (1.75 g, 17.46 mmol) at 0° C., under a $N_2$ atmosphere. The mixture was stirred for 3 hrs, while warming to r.t. The reaction was quenched with water (20 mL) and the organic layer was diluted with $CH_2Cl_2$ (100 mL), washed with water and brine, separated and dried with anhydrous sodium sulfate, then filtered and concentrated in vacuo to yield N-piperidin-1-yl-methanesulfonamide Compound 1i2 as an oil.

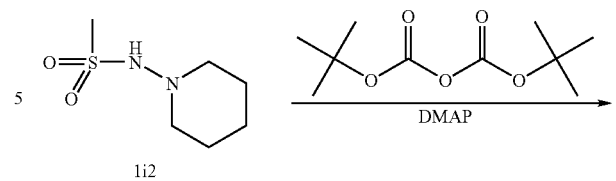

Carbonic acid di-tert-butyl ester (4.57 g, 20.95 mmol) and DMAP (8 mg) were added to a solution of Compound 1i2 in $CH_2Cl_2$ (10 mL) at 0° C. under a $N_2$ atmosphere. The mixture was stirred overnight, while warming to r.t. The reaction was quenched with a saturated solution of $NaHCO_3$ (10 mL). The organic layer was separated and dried with anhydrous sodium sulfate, filtered and concentrated in vacuo to yield a crude product which was purified by flash chromatography using 10% EtOAc in Hexane to afford (methylsulfonyl) 1-piperidinyl-carbamic acid t-butyl ester Compound 1i (3.89 g, 80%) as a colorless oil.

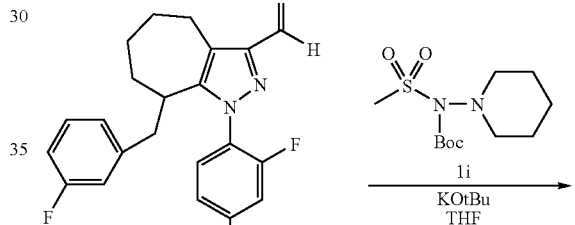

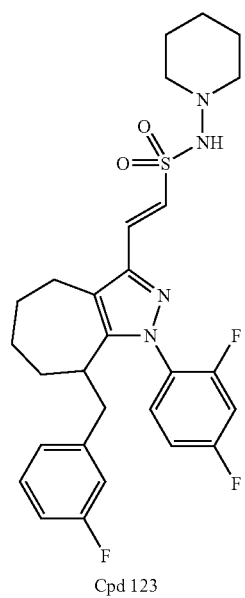

A 1M solution of potassium tert-butoxide in THF (0.75 mL, 0.75 mmol) was added dropwise to a solution of Compound 1i (0.070 g, 0.250 mmol) in anhydrous THF (5 mL) at −78° C. under a N₂ atmosphere. After 45 mins, a solution of Compound 1h (0.096 g, 0.250 mmol) in THF (3 mL) was added dropwise. The mixture was reacted for 15 hrs, while warming to r.t. The reaction was quenched with water (5 mL) and diluted with EtOAc (100 mL). The organic layer was separated, washed with water and brine and dried with anhydrous sodium sulfate, then filtered and concentrated in vacuo to yield a crude oil which was purified by flash chromatography using 20% EtOAc in hexane to afford Compound 123 (0.10 g, 75%) as a white solid. $^1$H NMR (CDCl$_3$, 300 MHz) δ 7.53 (d, J=15.3 Hz, 1H), 7.00 (d, J=15.3 Hz, 1H), 6.92-6.62 (m, 7H), 5.26 (s, 1H), 3.01-2.59 (m, 9H), 2.10-1.25 (m, 12H).

By following the relevant steps in the procedure of Example 1 and other procedures provided herein, and substituting the appropriate starting materials, reagents and solvents, the following compounds were prepared:

| Cpd | Name | MS |
|---|---|---|
| 3 | (2E)-2-[8-(3-chloro-benzyl)-1-(2,4-dichloro-phenyl)-1,4,5,6,7,8-hexahydro-cycloheptapyrazol-3-yl]-ethenesulfonic acid [(1S)-1-phenyl-ethyl]-amide | 616.2 |
| 75 | (2E)-2-[1-cyclohexyl-8-(3-fluoro-benzyl)-1,4,5,6,7,8-hexahydro-cycloheptapyrazol-3-yl]-ethenesulfonic acid [(1S)-1-phenyl-ethyl]-amide | 534.2 |
| 93 | (2E)-2-[1-(2,4-difluoro-phenyl)-8-(3-fluoro-benzyl)-1,4,5,6,7,8-hexahydro-cycloheptapyrazol-3-yl]-ethenesulfonic acid [(1S)-1-phenyl-ethyl]-amide | 566.2 |
| 94 | (2E)-2-[1-(2,4-difluoro-phenyl)-8-(3-fluoro-benzyl)-1,4,5,6,7,8-hexahydro-cycloheptapyrazol-3-yl]-ethenesulfonic acid [(1S)-1-cyclohexyl-ethyl]-amide | 572.3 |
| 96 | (2E)-2-[8-(3-fluoro-benzyl)-1,4,5,6,7,8-hexahydro-cycloheptapyrazol-3-yl]-ethenesulfonic acid [(1S)-1-phenyl-ethyl]-amide | 454.2 |
| 101 | (2E)-2-[8-(4-fluoro-benzyl)-1-methyl-1,4,5,6,7,8-hexahydro-cycloheptapyrazol-3-yl]-ethenesulfonic acid [(1S)-1-phenyl-ethyl]-amide | 468.1 |
| 104 | (2E)-2-[8-(3-fluoro-benzyl)-1-methyl-1,4,5,6,7,8-hexahydro-cycloheptapyrazol-3-yl]-ethenesulfonic acid [(1S)-1-phenyl-ethyl]-amide | 468 |
| 107 | (2E)-2-[1-(2,4-difluoro-phenyl)-8-(4-fluoro-benzyl)-1,4,5,6,7,8-hexahydro-cycloheptapyrazol-3-yl]-ethenesulfonic acid [(1S)-1-phenyl-ethyl]-amide | 566 |
| 108 | (2E)-2-[8-(4-fluoro-benzyl)-1,4,5,6,7,8-hexahydro-cycloheptapyrazol-3-yl]-ethenesulfonic acid [(1S)-1-phenyl-ethyl]-amide | 454 |
| 122 | (2E)-2-[1-(2,4-difluoro-phenyl)-8-(4-fluoro-benzyl)-1,4,5,6,7,8-hexahydro-cycloheptapyrazol-3-yl]-ethenesulfonic acid piperidin-1-ylamide | 545 |
| 124 | (2E)-2-[8-(3-fluoro-benzyl)-1-methyl-1,4,5,6,7,8-hexahydro-cycloheptapyrazol-3-yl]-ethenesulfonic acid piperidin-1-ylamide | 447 |
| 125 | (2E)-2-[8-(3-fluoro-benzyl)-1-methyl-1,4,5,6,7,8-hexahydro-cycloheptapyrazol-3-yl]-ethenesulfonic acid morpholin-4-ylamide | 449 |
| 126 | (2E)-2-[8-(4-fluoro-benzyl)-1-methyl-1,4,5,6,7,8-hexahydro-cycloheptapyrazol-3-yl]-ethenesulfonic acid morpholin-4-ylamide | 449 |
| 127 | (2E)-2-[1-(2,4-difluoro-phenyl)-8-(4-fluoro-benzyl)-1,4,5,6,7,8-hexahydro-cycloheptapyrazol-3-yl]-ethenesulfonic acid morpholin-4-ylamide | 547 |
| 128 | (2E)-2-[8-(4-fluoro-benzyl)-1-methyl-1,4,5,6,7,8-hexahydro-cycloheptapyrazol-3-yl]-ethenesulfonic acid piperidin-1-ylamide | 447 |
| 160 | (2E)-2-[8-(3-chloro-benzyl)-1,4,5,6,7,8-hexahydro-cycloheptapyrazol-3-yl]-ethenesulfonic acid [(1S)-1-phenyl-ethyl]-amide | 470.1 |
| 232 | (2E)-2-[(8R*)-8-(3-fluoro-benzyl)-1,4,5,6,7,8-hexahydro-cycloheptapyrazol-3-yl]-ethenesulfonic acid [(1S)-1-phenyl-ethyl]-amide $^1$H NMR(CD$_2$Cl$_2$, 400 MHz) δ 7.12-7.29 (m, 7H), 6.79-6.91 (m, 3H), 6.49 (m, 1H), 4.89 (m, 1H), 4.51 (m, 1H), 3.09 (m, 2H), 2.82 (m, 1H), 2.53 (m, 2H), 1.92 (m, 1H), 1.73 (m, 4H), 1.51 (d, 3H). | 454 |
| 233 | (2E)-2-[(8S*)-8-(3-fluoro-benzyl)-1,4,5,6,7,8-hexahydro-cycloheptapyrazol-3-yl]-ethenesulfonic acid [(1S)-1-phenyl-ethyl]-amide | 454 |
| 235 | (2E)-2-[8-(3-fluoro-benzyl)-1,4,5,6,7,8-hexahydro-cycloheptapyrazol-3-yl]-ethenesulfonic acid [(1R)-1-phenyl-ethyl]-amide | 454 |
| 236 | (2E,8E)-2-[8-(4-chloro-benzylidene)-1,4,5,6,7,8-hexahydro-cycloheptapyrazol-3-yl]-ethenesulfonic acid [(1R)-1-phenyl-ethyl]-amide | 468 |
| 237 | (2E,8E)-2-[8-(4-chloro-benzylidene)-1,4,5,6,7,8-hexahydro-cycloheptapyrazol-3-yl]-ethenesulfonic acid [(1S)-1-phenyl-ethyl]-amide $^1$H NMR(CDCl$_3$, 400 MHz) δ 7.20-7.35 (m, 10H), 6.72 (s, 1H), 6.55 (d, 1H), 4.85 (d, 1H), 4.60 (m, 1H), 2.66 (m, 2H), 2.54 (m, 2H), 1.85 (m, 4H), 1.60 (d, 3H). | 468 |
| 255 | (2E)-[8-(3-chloro-benzyl)-1,4,5,6,7,8-hexahydro-cycloheptapyrazol-3-yl]-ethenesulfonic acid piperidin-1-ylamide | 449 |

Example 2

1-(2,4-difluoro-phenyl)-8-(3-fluoro-benzyl)-1,4,5,6,7,8-hexahydro-cycloheptapyrazole-3-carboxylic acid morpholin-4-ylamide (Cpd 116)

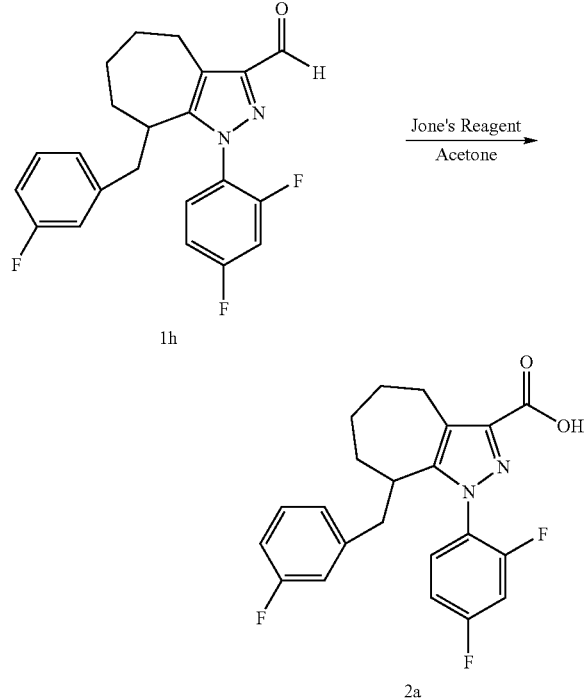

Jone's Reagent (5.75 mL, 8.6 mmol) was added to a solution of 1-(2,4-difluoro-phenyl)-8-(3-fluoro-benzyl)-1,4,5,6,7,8-hexahydro-cycloheptapyrazole-3-carbaldehyde Compound 1h (1.65 g, 4.31 mmol) in acetone (20 mL) at 0° C. under a $N_2$ atmosphere. The resulting suspension was stirred overnight, while warming to r.t., then filtered through a pad of celite to afford 1-(2,4-difluoro-phenyl)-8-(3-fluoro-benzyl)-1,4,5,6,7,8-hexahydro-cycloheptapyrazole-3-carboxylic acid Compound 2a as a solid.

EDCI (0.19 g, 0.99 mmol), DMAP (8 mg), and morpholin-4-ylamine (0.035 g, 0.33 mmol) were added to a solution of Compound 2a (0.13 g, 0.33 mmol) in $CH_2CL_2$ (5 mL) at 0° C. under a $N_2$ atmosphere. The mixture was stirred for 6 hrs, while warming to r.t. The organic layer was concentrated in vacuo and purified by flash chromatography using 15% EtOAc in hexane to afford Compound 116 (0.10 g, 65%) as a white solid. $^1$H NMR (CDCl$_3$, 400 Mhz) δ 7.6 (s, 1H), 7.09-7.04 (m, 1H), 6.93-6.38 (m, 5H), 3.94-3.90 (m, 1H), 3.85-3.81 (m, 4H), 2.96-2.90 (m, 6H), 2.70-2.58 (m, 2H), 2.09-1.91 (m, 4H), 1.80-1.62 (m, 1H), 1.49-1.36 (m, 1H).

By following the relevant steps in the procedure of Example 2 and substituting the appropriate starting materials, reagents and solvents, the following compounds were prepared:

| Cpd | Name | MS |
|---|---|---|
| 1 | 1-(4-fluoro-phenyl)-8-(4-methyl-benzyl)-1,4,5,6,7,8-hexahydro-cycloheptapyrazole-3-carboxylic acid (1,3,3-trimethyl-bicyclo[2.2.1]hept-2-yl)-amide | 514 |
| 2 | 8-(4-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide | 522.3 |
| 4 | 8-(3-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide | 522.3 |
| 5 | 8-(4-chloro-benzyl)-1-cyclohexyl-1,4,5,6,7,8-hexahydro-cycloheptapyrazole-3-carboxylic acid [(1S)-1-phenyl-ethyl]-amide | 490 |
| 6 | 8-(4-chloro-benzyl)-1-cyclohexyl-1,4,5,6,7,8-hexahydro-cycloheptapyrazole-3-carboxylic acid [(1R)-1-phenyl-ethyl]-amide | 492.3 |
| 7 | 8-(3-chloro-benzyl)-1-cyclohexyl-1,4,5,6,7,8-hexahydro-cycloheptapyrazole-3-carboxylic acid [(1S)-1-phenyl-ethyl]-amide | 490.2 |
| 8 | 8-(3-chloro-benzyl)-1-cyclohexyl-1,4,5,6,7,8-hexahydro-cycloheptapyrazole-3-carboxylic acid [(1R)-1-phenyl-ethyl]-amide | 490.2 |
| 9 | 8-(3-chloro-benzyl)-1-cyclohexyl-1,4,5,6,7,8-hexahydro-cycloheptapyrazole-3-carboxylic acid (hexahydro-2,5-methano-pentalen-3a-yl)-amide | 506.2 |
| 10 | 8-(3-chloro-benzyl)-1-cyclohexyl-1,4,5,6,7,8-hexahydro-cycloheptapyrazole-3-carboxylic acid (1-adamantan-1-yl-ethyl)-amide | 548.3 |

-continued

| Cpd | Name | MS |
|---|---|---|
| 11 | 8-(2-chloro-benzyl)-1-cyclohexyl-1,4,5,6,7,8-hexahydro-cycloheptapyrazole-3-carboxylic acid [(2S)-1,3,3-trimethyl-bicyclo[2.2.1]hept-2-yl]-amide | 522.3 |
| 12 | 8-(3-chloro-benzyl)-1-cyclohexyl-1,4,5,6,7,8-hexahydro-cycloheptapyrazole-3-carboxylic acid adamantan-2-ylamide | 520.4 |
| 13 | 8-(2-chloro-benzyl)-1-cyclohexyl-1,4,5,6,7,8-hexahydro-cycloheptapyrazole-3-carboxylic acid adamantan-2-ylamide | 520.3 |
| 14 | 8-(4-chloro-benzyl)-1-(2,4-dichloro-phenyl)-1,4,5,6,7,8-hexahydro-cycloheptapyrazole-3-carboxylic acid [(2S)-1,3,3-trimethyl-bicyclo[2.2.1]hept-2-yl]-amide | 586.2 |
| 15 | 8-(3-chloro-benzyl)-1-(2,4-dichloro-phenyl)-1,4,5,6,7,8-hexahydro-cycloheptapyrazole-3-carboxylic acid [(2S)-1,3,3-trimethyl-bicyclo[2.2.1]hept-2-yl]-amide | 586.2 |
| 16 | 8-(4-chloro-benzyl)-1-cyclohexyl-1,4,5,6,7,8-hexahydro-cycloheptapyrazole-3-carboxylic acid adamantan-2-ylamide | 522.3 |
| 17 | 8-(3-chloro-benzyl)-1-(2,4-dichloro-phenyl)-1,4,5,6,7,8-hexahydro-cycloheptapyrazole-3-carboxylic acid adamantan-2-ylamide | 582.2 |
| 18 | 8-(4-chloro-benzyl)-1-(2,4-dichloro-phenyl)-1,4,5,6,7,8-hexahydro-cycloheptapyrazole-3-carboxylic acid adamantan-2-ylamide | 582 |
| 19 | 8-(3-chloro-benzyl)-1-cyclohexyl-1,4,5,6,7,8-hexahydro-cycloheptapyrazole-3-carboxylic acid adamantan-1-ylamide | 520.3 |
| 20 | 8-(4-chloro-benzyl)-1-cyclohexyl-1,4,5,6,7,8-hexahydro-cycloheptapyrazole-3-carboxylic acid adamantan-1-ylamide | 520.2 |
| 21 | 8-(2-chloro-benzyl)-1-cyclohexyl-1,4,5,6,7,8-hexahydro-cycloheptapyrazole-3-carboxylic acid adamantan-1-ylamide | 520.2 |
| 22 | 8-(3-chloro-benzyl)-1-(2,4-dichloro-phenyl)-1,4,5,6,7,8-hexahydro-cycloheptapyrazole-3-carboxylic acid adamantan-1-ylamide | 584.1 |
| 23 | 8-(2-chloro-benzyl)-1-cyclohexyl-1,4,5,6,7,8-hexahydro-cycloheptapyrazole-3-carboxylic acid cyclobutylamide | 440.2 |
| 24 | 8-(3-chloro-benzyl)-1-(2,4-dichloro-phenyl)-1,4,5,6,7,8-hexahydro-cycloheptapyrazole-3-carboxylic acid cyclobutylamide | 502 |
| 25 | 8-(4-chloro-benzyl)-1-(2,4-dichloro-phenyl)-1,4,5,6,7,8-hexahydro-cycloheptapyrazole-3-carboxylic acid cyclobutylamide | 502 |
| 26 | 8-(4-chloro-benzyl)-1-(2,4-dichloro-phenyl)-1,4,5,6,7,8-hexahydro-cycloheptapyrazole-3-carboxylic acid 4-trifluoromethyl-benzylamide | 609 |
| 27 | 8-(4-chloro-benzyl)-1-(2,4-dichloro-phenyl)-1,4,5,6,7,8-hexahydro-cycloheptapyrazole-3-carboxylic acid piperidin-1-ylamide | 556.2(M + Na) |
| 28 | 8-(3-chloro-benzyl)-1-(2,4-dichloro-phenyl)-1,4,5,6,7,8-hexahydro-cycloheptapyrazole-3-carboxylic acid piperidin-1-ylamide | 533 |
| 29 | 1-(4-chloro-benzyl)-8-(3-chloro-benzyl)-1,4,5,6,7,8-hexahydro-cycloheptapyrazole-3-carboxylic acid cyclobutylamide | 484.2 |
| 30 | 1,8-bis-(4-chloro-benzyl)-1,4,5,6,7,8-hexahydro-cycloheptapyrazole-3-carboxylic acid cyclobutylamide | 483.1 |
| 31 | 8-(2-chloro-benzyl)-1-cyclohexyl-1,4,5,6,7,8-hexahydro-cycloheptapyrazole-3-carboxylic acid cyclopropylamide | 426.1 |
| 32 | 8-(3-chloro-benzyl)-1-cyclohexyl-1,4,5,6,7,8-hexahydro-cycloheptapyrazole-3-carboxylic acid cyclopropylamide | 426.1 |
| 33 | 8-(4-chloro-benzyl)-1-cyclohexyl-1,4,5,6,7,8-hexahydro-cycloheptapyrazole-3-carboxylic acid cyclopropylamide | 426.1 |
| 34 | 1,8-bis-(4-chloro-benzyl)-1,4,5,6,7,8-hexahydro-cycloheptapyrazole-3-carboxylic acid cyclopropylamide | 492.1(M + Na) |
| 35 | 1-(4-chloro-benzyl)-8-(3-chloro-benzyl)-1,4,5,6,7,8-hexahydro-cycloheptapyrazole-3-carboxylic acid cyclopropylamide | 470.1 |
| 36 | 8-(3-chloro-benzyl)-1-cyclohexyl-1,4,5,6,7,8-hexahydro-cycloheptapyrazole-3-carboxylic acid cyclobutylamide | 440.2 |
| 37 | 8-(4-chloro-benzyl)-1-cyclohexyl-1,4,5,6,7,8-hexahydro-cycloheptapyrazole-3-carboxylic acid cyclobutylamide | 440.2 |
| 38 | 8-(4-chloro-benzyl)-1-(2,4-dichloro-phenyl)-1,4,5,6,7,8-hexahydro-cycloheptapyrazole-3-carboxylic acid cyclopropylamide | 488.1 |
| 39 | 8-(2-chloro-benzyl)-1-methyl-1,4,5,6,7,8-hexahydro-cycloheptapyrazole-3-carboxylic acid cyclobutylamide | 372.1 |
| 40 | 8-(2-chloro-benzyl)-1-methyl-1,4,5,6,7,8-hexahydro-cycloheptapyrazole-3-carboxylic acid [(2S)-1,3,3-trimethyl-bicyclo[2.2.1]hept-2-yl]-amide | 454.2 |
| 41 | 1-(2,4-dichloro-phenyl)-8-(3-fluoro-benzyl)-1,4,5,6,7,8-hexahydro-cycloheptapyrazole-3-carboxylic acid cyclobutylamide | 486.1 |
| 42 | 1-(2,4-dichloro-phenyl)-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide | 568.2 |
| 43 | 1-cyclohexyl-8-(3-fluoro-benzyl)-1,4,5,6,7,8-hexahydro-cycloheptapyrazole-3-carboxylic acid cyclobutylamide | 424.2 |
| 44 | 1-cyclohexyl-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide | 506.2 |
| 45 | 1-cyclohexyl-8-(3-fluoro-benzyl)-1,4,5,6,7,8-hexahydro-cycloheptapyrazole-3-carboxylic acid [(1S)-1-phenyl-ethyl]-amide | 474.3 |

-continued

| Cpd | Name | MS |
|---|---|---|
| 46 | 4-{[1-cyclohexyl-8-(3-fluoro-benzyl)-1,4,5,6,7,8-hexahydro-cycloheptapyrazole-3-carbonyl]-amino}-piperidine-1-carboxylic acid tert-butyl ester | 553.3 |
| 47 | 1-benzyl-8-phenyl-1,4,5,6,7,8-hexahydro-cycloheptapyrazole-3-carboxylic acid [(2S)-1,3,3-trimethyl-bicyclo[2.2.1]hept-2-yl]-amide | 482 |
| 48 | 1-benzyl-8-phenyl-1,4,5,6,7,8-hexahydro-cycloheptapyrazole-3-carboxylic acid [(1S)-1-phenyl-ethyl]-amide | 450 |
| 49 | 1-cyclohexyl-8-(3-fluoro-benzyl)-1,4,5,6,7,8-hexahydro-cycloheptapyrazole-3-carboxylic acid cyclopropylamide | 410.2 |
| 50 | 1-cyclohexyl-8-(3-fluoro-benzyl)-1,4,5,6,7,8-hexahydro-cycloheptapyrazole-3-carboxylic acid piperidin-1-ylamide | 453.3 |
| 51 | 1-cyclohexyl-8-(3-fluoro-benzyl)-1,4,5,6,7,8-hexahydro-cycloheptapyrazole-3-carboxylic acid cyclohexylamide | 452.2 |
| 52 | 1-cyclohexyl-8-(3-fluoro-benzyl)-1,4,5,6,7,8-hexahydro-cycloheptapyrazole-3-carboxylic acid cyclopentylamide | 438.3 |
| 53 | 1-cyclohexyl-8-(3-fluoro-benzyl)-1,4,5,6,7,8-hexahydro-cycloheptapyrazole-3-carboxylic acid benzylamide | 460.2 |
| 54 | [1-cyclohexyl-8-(3-fluoro-benzyl)-1,4,5,6,7,8-hexahydro-cycloheptapyrazol-3-yl]-(4-phenyl-piperazin-1-yl)-methanone | 515.2 |
| 55 | 1-cyclohexyl-8-(3-fluoro-benzyl)-1,4,5,6,7,8-hexahydro-cycloheptapyrazole-3-carboxylic acid [(1R)-2-hydroxy-1-phenyl-ethyl]-amide | 490.2 |
| 56 | 1-cyclohexyl-8-(4-fluoro-benzyl)-1,4,5,6,7,8-hexahydro-cycloheptapyrazole-3-carboxylic acid cyclopropylamide | 410.2 |
| 57 | 1-cyclohexyl-8-(4-fluoro-benzyl)-1,4,5,6,7,8-hexahydro-cycloheptapyrazole-3-carboxylic acid cyclobutylamide | 424.2 |
| 58 | 1-cyclohexyl-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide | 506.2 |
| 59 | 1-cyclohexyl-8-(4-fluoro-benzyl)-1,4,5,6,7,8-hexahydro-cycloheptapyrazole-3-carboxylic acid cyclopentylamide | 438.3 |
| 60 | [1-cyclohexyl-8-(4-fluoro-benzyl)-1,4,5,6,7,8-hexahydro-cycloheptapyrazol-3-yl]-(4-phenyl-piperazin-1-yl)-methanone | 515.2 |
| 61 | 1-cyclohexyl-8-(4-fluoro-benzyl)-1,4,5,6,7,8-hexahydro-cycloheptapyrazole-3-carboxylic acid benzylamide | 460.2 |
| 62 | 1-cyclohexyl-8-(4-fluoro-benzyl)-1,4,5,6,7,8-hexahydro-cycloheptapyrazole-3-carboxylic acid piperidin-1-ylamide | 453.1 |
| 63 | (2S)-2-{[1-cyclohexyl-8-(4-fluoro-benzyl)-1,4,5,6,7,8-hexahydro-cycloheptapyrazole-3-carbonyl]-amino}-3-(4-fluoro-phenyl)-propionic acid methyl ester | 550.3 |
| 64 | 1-cyclohexyl-8-(4-fluoro-benzyl)-1,4,5,6,7,8-hexahydro-cycloheptapyrazole-3-carboxylic acid [(1S)-1-phenyl-ethyl]-amide | 474.2 |
| 65 | 1-cyclohexyl-8-(4-fluoro-benzyl)-1,4,5,6,7,8-hexahydro-cycloheptapyrazole-3-carboxylic acid 4-trifluoromethyl-benzylamide | 528.2 |
| 66 | (8R)-1-cyclohexyl-8-(4-fluoro-benzyl)-1,4,5,6,7,8-hexahydro-cycloheptapyrazole-3-carboxylic acid [(1R)-2-hydroxy-1-phenyl-ethyl]-amide | 490.4 |
| 67 | (8S)-1-cyclohexyl-8-(4-fluoro-benzyl)-1,4,5,6,7,8-hexahydro-cycloheptapyrazole-3-carboxylic acid [(1R)-2-hydroxy-1-phenyl-ethyl]-amide | 490.2 |
| 68 | 1-benzyl-8-phenyl-1,4,5,6,7,8-hexahydro-cycloheptapyrazole-3-carboxylic acid piperidin-1-ylamide | 429 |
| 69 | 1-benzyl-8-phenyl-1,4,5,6,7,8-hexahydro-cycloheptapyrazole-3-carboxylic acid 3-trifluoromethyl-benzylamide | 504 |
| 70 | 1-(2,4-dichloro-phenyl)-8-(4-fluoro-benzyl)-1,4,5,6,7,8-hexahydro-cycloheptapyrazole-3-carboxylic acid cyclobutylamide | 486.1 |
| 71 | 1-(2,4-dichloro-phenyl)-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide | 568.2 |
| 72 | (2S)-2-{[1-(2,4-dichloro-phenyl)-8-(4-fluoro-benzyl)-1,4,5,6,7,8-hexahydro-cycloheptapyrazole-3-carbonyl]-amino}-3-(4-fluoro-phenyl)-propionic acid methyl ester | 612.2 |
| 73 | (2S)-2-{[1-cyclohexyl-8-(3-fluoro-benzyl)-1,4,5,6,7,8-hexahydro-cycloheptapyrazole-3-carbonyl]-amino}-3-(4-fluoro-phenyl)-propionic acid methyl ester | 550.2 |
| 74 | (2S,3R)-3-{[1-cyclohexyl-8-(3-fluoro-benzyl)-1,4,5,6,7,8-hexahydro-cycloheptapyrazole-3-carbonyl]-amino}-bicyclo[2.2.1]hept-5-ene-2-carboxylic acid ethyl ester | 534.3 |
| 76 | 8-(4-chloro-benzyl)-1-(2,4-dichloro-phenyl)-1,4,5,6,7,8-hexahydro-cycloheptapyrazole-3-carboxylic acid [(1S)-1-phenyl-ethyl]-amide | 554 |
| 77 | (2R)-2-{[(8R)-1-(2,4-dichloro-phenyl)-8-(3-fluoro-benzyl)-1,4,5,6,7,8-hexahydro-cycloheptapyrazole-3-carbonyl]-amino}-3-(4-fluoro-phenyl)-propionic acid methyl ester | 613.2 |
| 78 | (2R)-2-{[(8S)-1-(2,4-dichloro-phenyl)-8-(3-fluoro-benzyl)-1,4,5,6,7,8-hexahydro-cycloheptapyrazole-3-carbonyl]-amino}-3-(4-fluoro-phenyl)-propionic acid methyl ester | 613.2 |

-continued

| Cpd | Name | MS |
|---|---|---|
| 79 | (2S,3R)-3-{[1-(2,4-dichloro-phenyl)-8-(3-fluoro-benzyl)-1,4,5,6,7,8-hexahydro-cycloheptapyrazole-3-carbonyl]-amino}-bicyclo[2.2.1]hept-5-ene-2-carboxylic acid ethyl ester | 596.2 |
| 80 | (2R)-2-{[1-(2,4-dichloro-phenyl)-8-(3-fluoro-benzyl)-1,4,5,6,7,8-hexahydro-cycloheptapyrazole-3-carbonyl]-amino}-3-(4-hydroxy-phenyl)-propionic acid methyl ester | 611.2 |
| 81 | (2R)-2-{[1-(2,4-dichloro-phenyl)-8-(4-fluoro-benzyl)-1,4,5,6,7,8-hexahydro-cycloheptapyrazole-3-carbonyl]-amino}-3-(4-hydroxy-phenyl)-propionic acid methyl ester | 632.1(M + Na) |
| 82 | (2R)-2-{[1-cyclohexyl-8-(3-fluoro-benzyl)-1,4,5,6,7,8-hexahydro-cycloheptapyrazole-3-carbonyl]-amino}-3-(4-hydroxy-phenyl)-propionic acid methyl ester | 548.3 |
| 83 | (2R)-2-{[1-cyclohexyl-8-(4-fluoro-benzyl)-1,4,5,6,7,8-hexahydro-cycloheptapyrazole-3-carbonyl]-amino}-3-(4-hydroxy-phenyl)-propionic acid methyl ester | 548.3 |
| 84 | 1-(2,4-dichloro-phenyl)-8-(3-fluoro-benzyl)-1,4,5,6,7,8-hexahydro-cycloheptapyrazole-3-carboxylic acid piperidin-1-ylamide | 516.3 |
| 85 | 1-(2,4-dichloro-phenyl)-8-(4-fluoro-benzyl)-1,4,5,6,7,8-hexahydro-cycloheptapyrazole-3-carboxylic acid piperidin-1-ylamide | 516.2 |
| 86 | 1-benzyl-8-phenyl-1,4,5,6,7,8-hexahydro-cycloheptapyrazole-3-carboxylic acid (2,2,2-trifluoro-ethyl)-amide | 428 |
| 87 | (2R)-2-[(1-benzyl-8-phenyl-1,4,5,6,7,8-hexahydro-cycloheptapyrazole-3-carbonyl)-amino]-3-(4-fluoro-phenyl)-propionic acid methyl ester | 526 |
| 88 | (2S,3R)-3-{[1-cyclohexyl-8-(4-fluoro-benzyl)-1,4,5,6,7,8-hexahydro-cycloheptapyrazole-3-carbonyl]-amino}-bicyclo[2.2.1]hept-5-ene-2-carboxylic acid ethyl ester | 534.1 |
| 89 | 1-cyclohexyl-8-(4-fluoro-benzyl)-1,4,5,6,7,8-hexahydro-cycloheptapyrazole-3-carboxylic acid morpholin-4-ylamide | 455 |
| 90 | 1-cyclohexyl-8-(3-fluoro-benzyl)-1,4,5,6,7,8-hexahydro-cycloheptapyrazole-3-carboxylic acid morpholin-4-ylamide | 455.1 |
| 91 | 1-(2,4-dichloro-phenyl)-8-(3-fluoro-benzyl)-1,4,5,6,7,8-hexahydro-cycloheptapyrazole-3-carboxylic acid morpholin-4-ylamide | 517.9 |
| 92 | 1-(2,4-difluoro-phenyl)-8-(3-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide | 536.2 |
| 95 | (2R)-2-{[1-(2,4-difluoro-phenyl)-8-(3-fluoro-benzyl)-1,4,5,6,7,8-hexahydro-cycloheptapyrazole-3-carbonyl]-amino}-3-(4-hydroxy-phenyl)-propionic acid methyl ester | 578.3 |
| 97 | 1-(2,4-difluoro-phenyl)-8-(4-fluoro-benzyl)-1,4,5,6,7,8-hexahydro-cycloheptapyrazole-3-carboxylic acid [(2S)-1,3,3-trimethyl-bicyclo[2.2.1]hept-2-yl]-amide | 536.2 |
| 98 | (2R)-2-{[1-(2,4-difluoro-phenyl)-8-(4-fluoro-benzyl)-1,4,5,6,7,8-hexahydro-cycloheptapyrazole-3-carbonyl]-amino}-3-(4-hydroxy-phenyl)-propionic acid methyl ester | 578.2 |
| 99 | (2S,3R)-3-{[1-(2,4-difluoro-phenyl)-8-(3-fluoro-benzyl)-1,4,5,6,7,8-hexahydro-cycloheptapyrazole-3-carbonyl]-amino}-bicyclo[2.2.1]hept-5-ene-2-carboxylic acid ethyl ester | 564 |
| 100 | 1-(2,4-difluoro-phenyl)-8-(3-fluoro-benzyl)-1,4,5,6,7,8-hexahydro-cycloheptapyrazole-3-carboxylic acid [(1R,2S)-2-hydroxy-indan-1-yl]-amide | 532.5 |
| 102 | (2R)-2-{[8-(3-chloro-benzyl)-1-(2,4-dichloro-phenyl)-1,4,5,6,7,8-hexahydro-cycloheptapyrazole-3-carbonyl]-amino}-3-(4-hydroxy-phenyl)-propionic acid methyl ester | 626 |
| 103 | (2R)-2-{[8-(3-chloro-benzyl)-1-(2,4-dichloro-phenyl)-1,4,5,6,7,8-hexahydro-cycloheptapyrazole-3-carbonyl]-amino}-3-(4-fluoro-phenyl)-propionic acid methyl ester | 628 |
| 105 | (2R,3S)-3-{[1-cyclohexyl-8-(3-fluoro-benzyl)-1,4,5,6,7,8-hexahydro-cycloheptapyrazole-3-carbonyl]-amino}-bicyclo[2.2.1]heptane-2-carboxylic acid ethyl ester | 536 |
| 106 | (2R,3S)-3-{[1-cyclohexyl-8-(4-fluoro-benzyl)-1,4,5,6,7,8-hexahydro-cycloheptapyrazole-3-carbonyl]-amino}-bicyclo[2.2.1]heptane-2-carboxylic acid ethyl ester | 536 |
| 109 | (2R,3S)-3-{[8-(3-chloro-benzyl)-1-(2,4-dichloro-phenyl)-1,4,5,6,7,8-hexahydro-cycloheptapyrazole-3-carbonyl]-amino}-bicyclo[2.2.1]heptane-2-carboxylic acid ethyl ester | 614 |
| 110 | (2R,3S)-3-{[1-(2,4-difluoro-phenyl)-8-(4-fluoro-benzyl)-1,4,5,6,7,8-hexahydro-cycloheptapyrazole-3-carbonyl]-amino}-bicyclo[2.2.1]heptane-2-carboxylic acid ethyl ester | 566 |
| 111 | (2R,3S)-3-{[1-(2,4-difluoro-phenyl)-8-(3-fluoro-benzyl)-1,4,5,6,7,8-hexahydro-cycloheptapyrazole-3-carbonyl]-amino}-bicyclo[2.2.1]heptane-2-carboxylic acid ethyl ester | 566 |
| 112 | (8R)-8-(3-chloro-benzyl)-1-(2,4-dichloro-phenyl)-1,4,5,6,7,8-hexahydro-cycloheptapyrazole-3-carboxylic acid [(1R,2S)-2-hydroxy-indan-1-yl]-amide | 580 |
| 113 | (8S)-8-(3-chloro-benzyl)-1-(2,4-dichloro-phenyl)-1,4,5,6,7,8-hexahydro-cycloheptapyrazole-3-carboxylic acid [(1R,2S)-2-hydroxy-indan-1-yl]-amide | 580 |

-continued

| Cpd | Name | MS |
|---|---|---|
| 114 | (8R)-1-cyclohexyl-8-(3-fluoro-benzyl)-1,4,5,6,7,8-hexahydro-cycloheptapyrazole-3-carboxylic acid [(1R,2S)-2-hydroxy-indan-1-yl]-amide | 502 |
| 115 | (8S)-1-cyclohexyl-8-(3-fluoro-benzyl)-1,4,5,6,7,8-hexahydro-cycloheptapyrazole-3-carboxylic acid [(1R,2S)-2-hydroxy-indan-1-yl]-amide | 502 |
| 117 | 8-(3-chloro-benzyl)-1-(2,4-dichloro-phenyl)-1,4,5,6,7,8-hexahydro-cycloheptapyrazole-3-carboxylic acid morpholin-4-ylamide | 533 |
| 118 | [1-(2,4-difluoro-phenyl)-8-(3-fluoro-benzyl)-1,4,5,6,7,8-hexahydro-cycloheptapyrazol-3-yl]-morpholin-4-yl-methanone | 470 |
| 119 | 1-(2,4-difluoro-phenyl)-8-(4-fluoro-benzyl)-1,4,5,6,7,8-hexahydro-cycloheptapyrazole-3-carboxylic acid [(1R,2S)-2-hydroxy-indan-1-yl]-amide | 532 |
| 120 | (8R)-1-cyclohexyl-8-(4-fluoro-benzyl)-1,4,5,6,7,8-hexahydro-cycloheptapyrazole-3-carboxylic acid [(1R,2S)-2-hydroxy-indan-1-yl]-amide | 502 |
| 121 | (8S)-1-cyclohexyl-8-(4-fluoro-benzyl)-1,4,5,6,7,8-hexahydro-cycloheptapyrazole-3-carboxylic acid [(1R,2S)-2-hydroxy-indan-1-yl]-amide | 502 |
| 129 | 8-(4-fluoro-benzyl)-1,4,5,6,7,8-hexahydro-cycloheptapyrazole-3-carboxylic acid benzylamide | 378 |
| 130 | 8-(4-fluoro-benzyl)-1-methanesulfonyl-1,4,5,6,7,8-hexahydro-cycloheptapyrazole-3-carboxylic acid benzylamide | 456 |
| 158 | (8R)-8-(3-chloro-benzyl)-1-(2,4-dichloro-phenyl)-1,4,5,6,7,8-hexahydro-cycloheptapyrazole-3-carboxylic acid [(1S)-1-hydroxymethyl-2-methyl-propyl]-amide | 556(M + Na) |
| 159 | (8S)-8-(3-chloro-benzyl)-1-(2,4-dichloro-phenyl)-1,4,5,6,7,8-hexahydro-cycloheptapyrazole-3-carboxylic acid [(1S)-1-hydroxymethyl-2-methyl-propyl]-amide | 556(M + Na) |
| 161 | (8R)-8-(3-chloro-benzyl)-1-(2,4-dichloro-phenyl)-1,4,5,6,7,8-hexahydro-cycloheptapyrazole-3-carboxylic acid [(1S)-2-hydroxy-1-phenyl-ethyl]-amide | 570 |
| 162 | (8S)-8-(3-chloro-benzyl)-1-(2,4-dichloro-phenyl)-1,4,5,6,7,8-hexahydro-cycloheptapyrazole-3-carboxylic acid [(1S)-2-hydroxy-1-phenyl-ethyl]-amide | 570 |
| 163 | 8-(3-chloro-benzyl)-1-(2,4-dichloro-phenyl)-1,4,5,6,7,8-hexahydro-cycloheptapyrazole-3-carboxylic acid [(1R)-1-benzyl-2-hydroxy-ethyl]-amide | 582 |
| 164 | 8-(3-chloro-benzyl)-1,4,5,6,7,8-hexahydro-cycloheptapyrazole-3-carboxylic acid [(1S)-2-hydroxy-1-phenyl-ethyl]-amide | 424 |
| 165 | 8-(3-chloro-benzyl)-1,4,5,6,7,8-hexahydro-cycloheptapyrazole-3-carboxylic acid [(1R)-2-hydroxy-1-phenyl-ethyl]-amide | 424 |
| 166 | 8-(3-chloro-benzyl)-1,4,5,6,7,8-hexahydro-cycloheptapyrazole-3-carboxylic acid [(1S)-1-benzyl-2-hydroxy-ethyl]-amide | 438.1 |
| 167 | 8-(3-chloro-benzyl)-1,4,5,6,7,8-hexahydro-cycloheptapyrazole-3-carboxylic acid [(1R)-1-benzyl-2-hydroxy-ethyl]-amide | 438.1 |
| 168 | 1-(2,4-difluoro-phenyl)-8-(3-fluoro-benzyl)-1,4,5,6,7,8-hexahydro-cycloheptapyrazole-3-carboxylic acid [(1S)-2-hydroxy-1-phenyl-ethyl]-amide | 520.2 |
| 169 | 1-(2,4-difluoro-phenyl)-8-(3-fluoro-benzyl)-1,4,5,6,7,8-hexahydro-cycloheptapyrazole-3-carboxylic acid [(1S)-2-chloro-1-phenyl-ethyl]-amide | 538 |
| 172 | 1-(2,4-difluoro-phenyl)-8-(4-fluoro-benzyl)-1,4,5,6,7,8-hexahydro-cycloheptapyrazole-3-carboxylic acid [(1S)-2-chloro-1-phenyl-ethyl]-amide | 538 |
| 173 | 1-(2,4-difluoro-phenyl)-8-(3-fluoro-benzyl)-1,4,5,6,7,8-hexahydro-cycloheptapyrazole-3-carboxylic acid [(1R)-1-phenyl-ethyl]-amide | 504.1 |
| 174 | 1-cyclohexyl-8-(3-fluoro-benzyl)-1,4,5,6,7,8-hexahydro-cycloheptapyrazole-3-carboxylic acid [(1R)-1-phenyl-ethyl]-amide | 474.1 |
| 175 | 8-(3-chloro-benzyl)-1-(4-trifluoromethyl-pyrimidin-2-yl)-1,4,5,6,7,8-hexahydro-cycloheptapyrazole-3-carboxylic acid [(1R)-1-phenyl-ethyl]-amide | 554.1 |
| 176 | 8-(3-chloro-benzyl)-1-(4-trifluoromethyl-pyrimidin-2-yl)-1,4,5,6,7,8-hexahydro-cycloheptapyrazole-3-carboxylic acid [(1R)-2-hydroxy-1-phenyl-ethyl]-amide | 570 |
| 177 | 8-(3-chloro-benzyl)-1-(7-chloro-quinolin-4-yl)-1,4,5,6,7,8-hexahydro-cycloheptapyrazole-3-carboxylic acid [(1R)-1-phenyl-ethyl]-amide | 569 |
| 178 | 8-(3-chloro-benzyl)-1-(4-trifluoromethyl-pyrimidin-2-yl)-1,4,5,6,7,8-hexahydro-cycloheptapyrazole-3-carboxylic acid [(1R)-2-chloro-1-phenyl-ethyl]-amide | 588.2 |
| 179 | 8-(3-chloro-benzyl)-1-(4-trifluoromethyl-pyrimidin-2-yl)-1,4,5,6,7,8-hexahydro-cycloheptapyrazole-3-carboxylic acid [(1S)-2-chloro-1-phenyl-ethyl]-amide | 590.1 |
| 186 | 8-(3-chloro-benzyl)-1-(4-trifluoromethyl-pyrimidin-2-yl)-1,4,5,6,7,8-hexahydro-cycloheptapyrazole-3-carboxylic acid [(1R)-1-benzyl-2-hydroxy-ethyl]-amide | 584.1 |

-continued

| Cpd | Name | MS |
|---|---|---|
| 187 | 8-(3-chloro-benzyl)-1-(4-trifluoromethyl-pyrimidin-2-yl)-1,4,5,6,7,8-hexahydro-cycloheptapyrazole-3-carboxylic acid [(1R)-1-benzyl-2-chloro-ethyl]-amide | 602 |
| 218 | (2S,3R)-3-{[1-(4-fluoro-phenyl)-8-(4-methyl-benzyl)-1,4,5,6,7,8-hexahydro-cycloheptapyrazole-3-carbonyl]-amino}-bicyclo[2.2.1]heptane-2-carboxylic acid ethyl ester | 544 |
| 228 | (8S)-8-(3-chloro-benzyl)-1,4,5,6,7,8-hexahydro-cycloheptapyrazole-3-carboxylic acid [(1R)-2-hydroxy-1-phenyl-ethyl]-amide | 424 |
| 229 | (8R)-8-(3-chloro-benzyl)-1,4,5,6,7,8-hexahydro-cycloheptapyrazole-3-carboxylic acid [(1R)-2-hydroxy-1-phenyl-ethyl]-amide | 424 |
| 230 | (8R)-8-(3-chloro-benzyl)-1,4,5,6,7,8-hexahydro-cycloheptapyrazole-3-carboxylic acid [(1S)-2-hydroxy-1-phenyl-ethyl]-amide<br>$^1$H NMR(CD$_3$OD, 400 MHz) δ 7.12-7.38 (m, 8H), 6.93 (m, 1H), 5.09 (m, 1H), 3.81 (m, 2H), 3.41 (m, 1H), 3.21 (m, 1H), 3.05 (m, 1H), 2.81 (m, 1H), 2.67 (m, 1H), 1.96 (m, 1H), 1.81 (m, 3H), 1.65 (m, 1H), 1.39 (m, 1H). | 424 |
| 231 | (8S)-8-(3-chloro-benzyl)-1,4,5,6,7,8-hexahydro-cycloheptapyrazole-3-carboxylic acid [(1S)-2-hydroxy-1-phenyl-ethyl]-amide | 424 |
| 251 | (8R*)-(3-chloro-benzyl)-1,4,5,6,7,8-hexahydro-cycloheptapyrazole-3-carboxylic acid [(1S)-2-methoxy-1-phenyl-ethyl]-amide<br>$^1$H NMR(CD$_2$Cl$_2$, 400 MHz) δ 7.65 (m, 1H), 7.19-7.39 (m, 7H), 7.12 (m, 1H), 6.93 (m, 1H), 5.21 (m, 1H), 3.69 (m, 2H), 3.43 (m, 1H), 3.33 (s, 3H), 3.19 (m, 1H), 3.01 (m, 1H), 2.69-2.86 (m, 2H), 1.72 (m, 5H), 1.49 (m, 1H). | 438 |
| 252 | (8S*)-(3-chloro-benzyl)-1,4,5,6,7,8-hexahydro-cycloheptapyrazole-3-carboxylic acid [(1S)-2-methoxy-1-phenyl-ethyl]-amide | 438 |
| 253 | (8S*)-(3-chloro-benzyl)-1,4,5,6,7,8-hexahydro-cycloheptapyrazole-3-carboxylic acid [(1R)-2-methoxy-1-phenyl-ethyl]-amide | 438 |
| 254 | (8R*)-(3-chloro-benzyl)-1,4,5,6,7,8-hexahydro-cycloheptapyrazole-3-carboxylic acid [(1R)-2-methoxy-1-phenyl-ethyl]-amide<br>$^1$H NMR(CD$_2$Cl$_2$, 400 MHz) δ 7.63 (m, 1H), 7.30 (m, 5H), 7.17 (m, 1H), 7.08 (m, 1H), 6.89 (m, 1H), 5.22 (m, 1H), 3.64 (m, 2H), 3.41 (m, 1H), 3.32 (s, 3H), 3.12 (m, 1H), 2.98 (m, 1H), 2.77 (m, 2H), 1.80 (m, 5H), 1.48 (m, 1H). | 438 |
| 256 | 8-(3-chloro-benzyl)-1,4,5,6,7,8-hexahydro-cycloheptapyrazole-3-carboxylic acid [(1S)-1-phenyl-ethyl]-amide<br>$^1$H NMR(CDCl$_3$, 400 MHz) δ 7.32 (m, 4H), 7.19 (m, 2H), 7.10 (m, 2H), 6.85 (m, 1H), 5.23 (m, 1H), 3.49 (m, 1H), 3.12 (m, 1H), 2.95 (m, 1H), 2.78 (m, 2H), 1.85 (m, 5H), 1.55 (m, 4H). | 408 |
| 257 | 8-(3-chloro-benzyl)-1,4,5,6,7,8-hexahydro-cycloheptapyrazole-3-carboxylic acid [(1R)-1-phenyl-ethyl]-amide<br>$^1$H NMR(CDCl$_3$, 400 MHz) δ 7.32 (m, 4H), 7.17 (m, 2H), 7.09 (m, 2H), 6.82 (m, 1H), 5.22 (m, 1H), 3.48 (m, 1H), 3.09 (m, 1H), 2.95 (m, 1H), 2.79 (m, 2H), 1.84 (m, 5H), 1.56 (m, 4H). | 408 |

Example 3

(8E)-1-(2,4-dichloro-phenyl)-8-(4-fluoro-benzylidene)-1,4,5,6,7,8-hexahydro-cycloheptapyrazole-3-carboxylic acid [(1R)-1-phenyl-ethyl]-amide (Cpd 146)

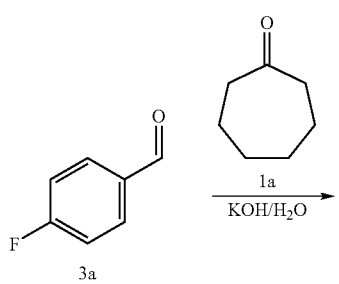

-continued

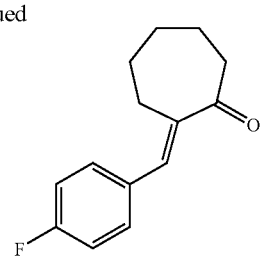

A solution of KOH (0.25 g, 4.46 mmol) in water (4.4 mL) was added to 4-fluoro-benzaldehyde Compound 3a (1.07 mL, 10 mmol) and the suspension was heated to 65° C. Cycloheptanone Compound 1a (1.18 mL, 10 mmol) was added dropwise over a period of 15 mins. The mixture was refluxed for 5 hrs, then stirred overnight at room temperature. The reaction mixture was acidified with 1N HCl (26 mL) and extracted with EtOAc (100 mL). The organic layer was washed with brine and dried over Na$_2$SO4, then filtered and concentrated. The resulting yellow residue was purified on a silica gel column (using with 6% EtOAc/Hexane) to give 2-(4-fluoro-benzylidene)-cycloheptanone Compound 3b (1.1 g, 50.4%).

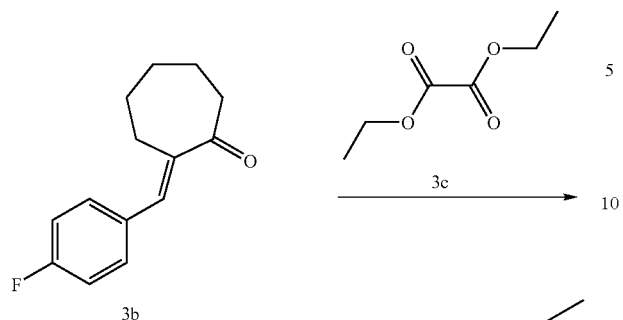

A solution of Compound 3b (1.1 g, 5.04 mmol) in THF (5 mL) was added dropwise to a solution of LHMDS (5.04 mL, 1M solution in THF) at −78° C. and the mixture was stirred at −78° C. for 1 hr. Oxalic acid diethyl ester Compound 3c (0.68 mL, 5.04 mmol) was added dropwise and the mixture was stirred at −78° C. for 1 hr. The mixture was allowed to gradually warm to r.t. and was stirred at rt overnight. The reaction mixture was acidified with 1N HCl and extracted with EtOAc (150 mL). The organic layer was washed with 1N HCl (1×) and water (2×), dried over sodium sulfate, then filtered and concentrated to give [3-(4-fluoro-benzylidene)-2-oxo-cycloheptyl]-oxo-acetic acid ethyl ester Compound 3d as a yellow oil which was used in the next step without further purification.

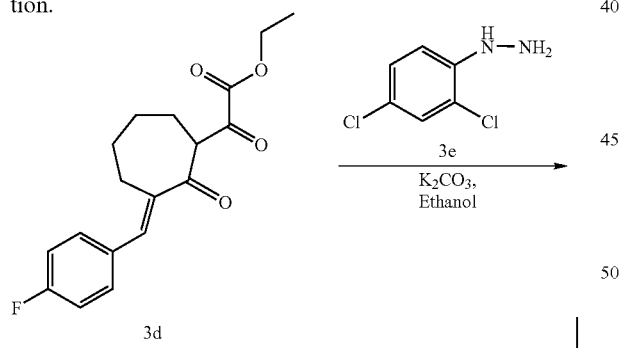

K$_2$CO3 (1.39 g, 10.08 mmol) and (2,4-dichloro-phenyl)-hydrazine Compound 3e (0.89 g, 5.04 mmol) were added to a suspension of Compound 3d (5.04 mmol) in ethanol (30 mL). The mixture was stirred at r.t. overnight, then filtered and washed with ethanol (20 mL). The filtrate was concentrated and purified on silica gel column (using 20% EtOAc/Hexane) to give 1-(2,4-dichloro-phenyl)-8-(4-fluoro-benzylidene)-1,4,5,6,7,8-hexahydro-cycloheptapyrazole-3-carboxylic acid ethyl ester (0.8 g, 34.5%, for last 2 steps).

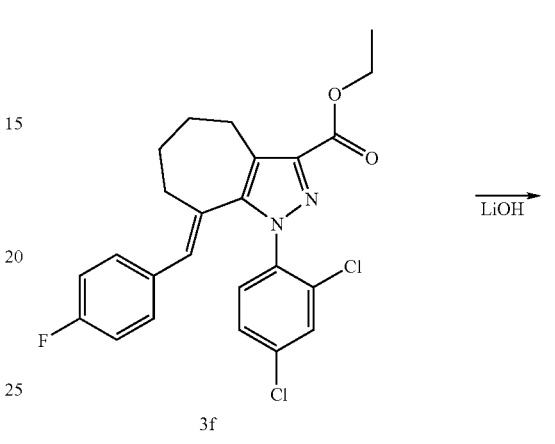

Compound 3f (0.8 g, 1.74 mmol) was dissolved in a mixture of THF (18 mL) and ethanol (2 mL), then aqueous LiOH (0.25 g, 10.4 mmol in 6 mL water) was added. The mixture was stirred at r.t. overnight, then concentrated and acidified with 1N HCl (50 mL). The aqueous solution was extracted with EtOAc (100 mL) and the organic layer was washed with brine and dried over magnesium sulfate, then filtered and concentrated to give 1-(2,4-dichloro-phenyl)-8-(4-fluoro-benzylidene)-1,4,5,6,7,8-hexahydro-cycloheptapyrazole-3-carboxylic acid Compound 3g (0.73 g, 98%) as a yellow solid.

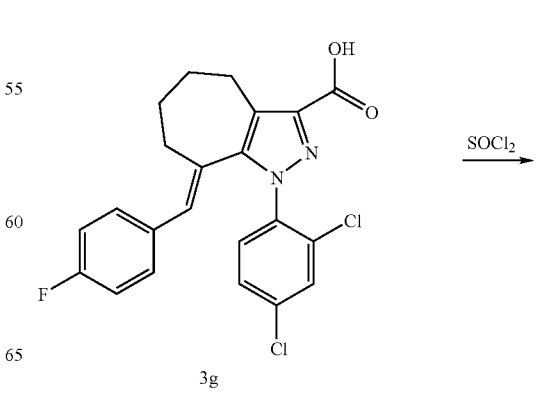

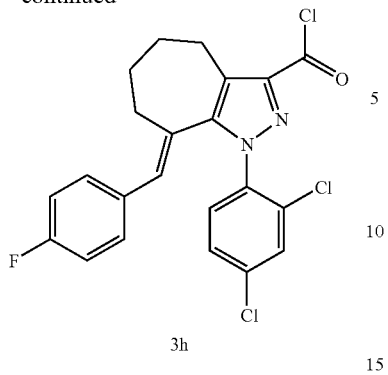

3h

SOCl$_2$ (0.99 mL, 13.5 mmol) was added to a solution of Compound 3g (0.73 g, 1.69 mmol) in DCM (5 mL). The mixture was refluxed for 3 hrs, then concentrated under high vacuum to give 1-(2,4-dichloro-phenyl)-8-(4-fluoro-benzylidene)-1,4,5,6,7,8-hexahydro-cycloheptapyrazole-3-carbonyl chloride Compound 3h (0.70 g, 92%) as a yellow solid.

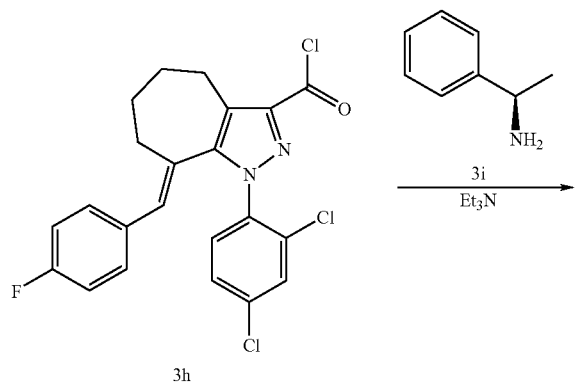

3h     3i    Et$_3$N

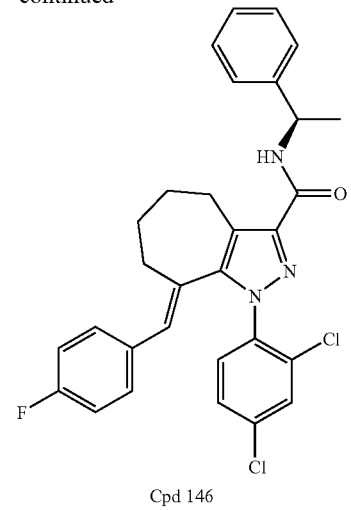

Cpd 146

A mixture of (R)-(+)-α-methyl benzylamine Compound 3i (0.065 g, 0.54 mmol) and Et$_3$N (0.15 mL, 1.08 mmol) were added to a solution of Compound 3h (0.12 g, 0.27 mmol) was taken up in DCM (5 mL). The mixture was stirred at r.t. for 1 hr, then diluted with DCM and washed with 1N HCl. The organic layer was washed with water and dried over sodium sulfate, then filtered and concentrated. The resulting yellow residue was purified on silica gel column (using 20% EtOAc/Hexane) to give Compound 146 (0.12 g, 84%) as a pale yellow powder. MS m/z 534 (M+H$^+$).

By following the relevant steps in the procedure of Example 3 and substituting the appropriate starting materials, reagents and solvents, the following compounds were prepared:

| Cpd | Name | MS |
|---|---|---|
| 131 | (8E)-8-(4-chloro-benzylidene)-1-(2,4-dichloro-phenyl)-1,4,5,6,7,8-hexahydro-cycloheptapyrazole-3-carboxylic acid [(1R)-1-phenyl-ethyl]-amide | 550 |
| 132 | (8E)-8-(4-chloro-benzylidene)-1-(2,4-dichloro-phenyl)-1,4,5,6,7,8-hexahydro-cycloheptapyrazole-3-carboxylic acid [(1R)-1-cyclohexyl-ethyl]-amide | 556 |
| 133 | (8E)-8-(4-chloro-benzylidene)-1-(2,4-dichloro-phenyl)-1,4,5,6,7,8-hexahydro-cycloheptapyrazole-3-carboxylic acid piperidin-1-ylamide | 529 |
| 134 | (8E)-8-(4-chloro-benzylidene)-1-(2,4-dichloro-phenyl)-1,4,5,6,7,8-hexahydro-cycloheptapyrazole-3-carboxylic acid morpholin-4-ylamide | 531 |
| 135 | (8E)-8-(4-chloro-benzylidene)-1-(2,4-dichloro-phenyl)-1,4,5,6,7,8-hexahydro-cycloheptapyrazole-3-carboxylic acid 4-sulfamoyl-benzylamide | 615 |
| 136 | (8E)-N-[8-(4-chloro-benzylidene)-1-(2,4-dichloro-phenyl)-1,4,5,6,7,8-hexahydro-cycloheptapyrazole-3-carbonyl]-benzenesulfonamide | 586 |
| 137 | (8E)-8-(4-chloro-benzylidene)-1-(2,4-dichloro-phenyl)-1,4,5,6,7,8-hexahydro-cycloheptapyrazole-3-carboxylic acid [1-(4-chloro-phenyl)-ethyl]-amide | 584 |
| 138 | (8E)-8-(4-chloro-benzylidene)-1-(2,4-dichloro-phenyl)-1,4,5,6,7,8-hexahydro-cycloheptapyrazole-3-carboxylic acid [(1S)-1-cyclohexyl-ethyl]-amide | 556 |
| 139 | (8E)-8-(4-chloro-benzylidene)-1-(2,4-dichloro-phenyl)-1,4,5,6,7,8-hexahydro-cycloheptapyrazole-3-carboxylic acid [(1S)-1-phenyl-ethyl]-amide | 550 |
| 140 | (8E)-8-(4-chloro-benzylidene)-1,4,5,6,7,8-hexahydro-cycloheptapyrazole-3-carboxylic acid [(1R)-1-cyclohexyl-ethyl]-amide | 412 |
| 141 | (8E)-8-(4-chloro-benzylidene)-1,4,5,6,7,8-hexahydro-cycloheptapyrazole-3-carboxylic acid [(1S)-1-phenyl-ethyl]-amide | 406 |

-continued

| Cpd | Name | MS |
|---|---|---|
| 142 | (8E)-8-(4-chloro-benzylidene)-1,4,5,6,7,8-hexahydro-cycloheptapyrazole-3-carboxylic acid [(1R)-1-phenyl-ethyl]-amide | 406 |
| 143 | (8E)-8-(4-chloro-benzylidene)-1,4,5,6,7,8-hexahydro-cycloheptapyrazole-3-carboxylic acid [(1S)-1-cyclohexyl-ethyl]-amide | 412 |
| 144 | (8E)-8-(4-chloro-benzylidene)-1,4,5,6,7,8-hexahydro-cycloheptapyrazole-3-carboxylic acid piperidin-1-ylamide | 385 |
| 145 | (8E)-8-(4-chloro-benzylidene)-1,4,5,6,7,8-hexahydro-cycloheptapyrazole-3-carboxylic acid morpholin-4-ylamide | 387 |
| 147 | (8E)-1-(2,4-dichloro-phenyl)-8-(4-fluoro-benzylidene)-1,4,5,6,7,8-hexahydro-cycloheptapyrazole-3-carboxylic acid [(1R)-1-cyclohexyl-ethyl]-amide | 540 |
| 148 | (8E)-1-(2,4-dichloro-phenyl)-8-(4-fluoro-benzylidene)-1,4,5,6,7,8-hexahydro-cycloheptapyrazole-3-carboxylic acid [(1S)-1-cyclohexyl-ethyl]-amide | 540 |
| 149 | (8E)-1-(2,4-dichloro-phenyl)-8-(4-fluoro-benzylidene)-1,4,5,6,7,8-hexahydro-cycloheptapyrazole-3-carboxylic acid [(1S)-1-phenyl-ethyl]-amide | 534 |
| 150 | (8E)-1-(2,4-dichloro-phenyl)-8-(4-fluoro-benzylidene)-1,4,5,6,7,8-hexahydro-cycloheptapyrazole-3-carboxylic acid piperidin-1-ylamide | 513 |
| 151 | (8E)-1-(2,4-dichloro-phenyl)-8-(4-fluoro-benzylidene)-1,4,5,6,7,8-hexahydro-cycloheptapyrazole-3-carboxylic acid morpholin-4-ylamide | 515 |
| 152 | (8E)-8-(4-chloro-benzylidene)-1-(2,4-dichloro-phenyl)-1,4,5,6,7,8-hexahydro-cycloheptapyrazole-3-carboxylic acid pyridin-2-ylamide | 523 |
| 153 | (8E)-8-(4-chloro-benzylidene)-1-(2,4-dichloro-phenyl)-1,4,5,6,7,8-hexahydro-cycloheptapyrazole-3-carboxylic acid pyridin-4-ylamide | 523 |
| 154 | (8E)-8-(4-chloro-benzylidene)-1-(2,4-dichloro-phenyl)-1,4,5,6,7,8-hexahydro-cycloheptapyrazole-3-carboxylic acid (4-sulfamoyl-phenyl)-amide | 601 |
| 155 | (8E)-8-(4-chloro-benzylidene)-1-(2,4-dichloro-phenyl)-1,4,5,6,7,8-hexahydro-cycloheptapyrazole-3-carboxylic acid (pyridin-2-ylmethyl)-amide | 537 |
| 156 | (8E)-8-(4-chloro-benzylidene)-1-(2,4-dichloro-phenyl)-1,4,5,6,7,8-hexahydro-cycloheptapyrazole-3-carboxylic acid (pyridin-4-ylmethyl)-amide | 537 |
| 157 | (8E)-8-(4-chloro-benzylidene)-1-(2,4-dichloro-phenyl)-1,4,5,6,7,8-hexahydro-cycloheptapyrazole-3-carboxylic acid (2-pyridin-2-yl-ethyl)-amide | 551 |
| 170 | (8E)-8-(4-chloro-benzylidene)-1-pyridin-4-yl-1,4,5,6,7,8-hexahydro-cycloheptapyrazole-3-carboxylic acid [(1R)-1-phenyl-ethyl]-amide | 483 |
| 171 | (8E)-8-(4-chloro-benzylidene)-1-pyridin-4-yl-1,4,5,6,7,8-hexahydro-cycloheptapyrazole-3-carboxylic acid [(1S)-1-phenyl-ethyl]-amide | 483 |
| 180 | (8E)-8-(4-chloro-benzylidene)-1-pyridin-4-yl-1,4,5,6,7,8-hexahydro-cycloheptapyrazole-3-carboxylic acid [(1R)-1-cyclohexyl-ethyl]-amide | 489 |
| 181 | (8E)-8-(4-chloro-benzylidene)-1-pyridin-4-yl-1,4,5,6,7,8-hexahydro-cycloheptapyrazole-3-carboxylic acid [(1S)-1-cyclohexyl-ethyl]-amide | 489 |
| 182 | (8E)-8-(4-chloro-benzylidene)-1-pyridin-4-yl-1,4,5,6,7,8-hexahydro-cycloheptapyrazole-3-carboxylic acid piperidin-1-ylamide | 462 |
| 183 | (8E)-8-(4-chloro-benzylidene)-1-pyridin-4-yl-1,4,5,6,7,8-hexahydro-cycloheptapyrazole-3-carboxylic acid morpholin-4-ylamide | 462 |
| 184 | (8E)-8-(4-chloro-benzylidene)-1-(4-sulfamoyl-phenyl)-1,4,5,6,7,8-hexahydro-cycloheptapyrazole-3-carboxylic acid [(1R)-1-phenyl-ethyl]-amide | 561 |
| 185 | (8E)-8-(4-chloro-benzylidene)-1-(4-sulfamoyl-phenyl)-1,4,5,6,7,8-hexahydro-cycloheptapyrazole-3-carboxylic acid [(1R)-1-cyclohexyl-ethyl]-amide | 567 |
| 188 | (8E)-[1-(2,4-dichloro-phenyl)-8-(4-fluoro-benzylidene)-1,4,5,6,7,8-hexahydro-cycloheptapyrazol-3-yl]-(2-pyridin-2-yl-pyrrolidin-1-yl)-methanone | 561 |
| 189 | (8E)-8-(4-chloro-benzylidene)-1-(2-chloro-phenyl)-1,4,5,6,7,8-hexahydro-cycloheptapyrazole-3-carboxylic acid [(1R)-1-cyclohexyl-ethyl]-amide | 522 |
| 190 | (8E)-8-(4-chloro-benzylidene)-1-(2-chloro-phenyl)-1,4,5,6,7,8-hexahydro-cycloheptapyrazole-3-carboxylic acid [(1R)-1-phenyl-ethyl]-amide | 516 |
| 191 | (8E)-8-(4-chloro-benzylidene)-1-(2-chloro-phenyl)-1,4,5,6,7,8-hexahydro-cycloheptapyrazole-3-carboxylic acid [(1S)-1-phenyl-ethyl]-amide | 516 |
| 192 | (8E)-8-(4-chloro-benzylidene)-1-(2-chloro-phenyl)-1,4,5,6,7,8-hexahydro-cycloheptapyrazole-3-carboxylic acid [(1S)-1-cyclohexyl-ethyl]-amide | 522 |
| 193 | (8E)-8-(4-chloro-benzylidene)-1-(2-chloro-phenyl)-1,4,5,6,7,8-hexahydro-cycloheptapyrazole-3-carboxylic acid piperidin-1-ylamide | 495 |
| 194 | (8E)-8-(4-chloro-benzylidene)-1-(2-chloro-phenyl)-1,4,5,6,7,8-hexahydro-cycloheptapyrazole-3-carboxylic acid morpholin-4-ylamide | 497 |
| 195 | (8E)-8-(4-chloro-benzylidene)-1-(2,5-dichloro-phenyl)-1,4,5,6,7,8-hexahydro-cycloheptapyrazole-3-carboxylic acid [(1R)-1-phenyl-ethyl]-amide | 550 |

-continued

| Cpd | Name | MS |
|---|---|---|
| 196 | (8E)-8-(4-chloro-benzylidene)-1-(2,5-dichloro-phenyl)-1,4,5,6,7,8-hexahydro-cycloheptapyrazole-3-carboxylic acid [(1R)-1-cyclohexyl-ethyl]-amide | 556 |
| 197 | (8E)-8-(4-chloro-benzylidene)-1-(2,5-dichloro-phenyl)-1,4,5,6,7,8-hexahydro-cycloheptapyrazole-3-carboxylic acid [(1S)-1-cyclohexyl-ethyl]-amide | 556 |
| 198 | (8E)-8-(4-chloro-benzylidene)-1-(2,5-dichloro-phenyl)-1,4,5,6,7,8-hexahydro-cycloheptapyrazole-3-carboxylic acid [(1S)-1-phenyl-ethyl]-amide | 550 |
| 199 | (8E)-8-(4-chloro-benzylidene)-1-(2,5-dichloro-phenyl)-1,4,5,6,7,8-hexahydro-cycloheptapyrazole-3-carboxylic acid piperidin-1-ylamide | 529 |
| 200 | (8E)-8-(4-chloro-benzylidene)-1-(2,5-dichloro-phenyl)-1,4,5,6,7,8-hexahydro-cycloheptapyrazole-3-carboxylic acid morpholin-4-ylamide | 531 |
| 201 | (8E)-[8-(4-chloro-benzylidene)-1-(2,5-dichloro-phenyl)-1,4,5,6,7,8-hexahydro-cycloheptapyrazol-3-yl]-morpholin-4-yl-methanone | 516 |
| 202 | (8E)-1-(2,4-dichloro-phenyl)-8-(4-fluoro-benzylidene)-1,4,5,6,7,8-hexahydro-cycloheptapyrazole-3-carboxylic acid [(1R)-1-phenyl-propyl]-amide | 548 |
| 203 | (8E)-1-(2,4-dichloro-phenyl)-8-(4-fluoro-benzylidene)-1,4,5,6,7,8-hexahydro-cycloheptapyrazole-3-carboxylic acid [(1R)-2-hydroxy-1-phenyl-ethyl]-amide | 550 |
| 204 | (8E)-1-(2,4-dichloro-phenyl)-8-(4-fluoro-benzylidene)-1,4,5,6,7,8-hexahydro-cycloheptapyrazole-3-carboxylic acid [(1S)-2-hydroxy-1-phenyl-ethyl]-amide | 550 |
| 205 | (8E)-1-(2,4-dichloro-phenyl)-8-(4-fluoro-benzylidene)-1,4,5,6,7,8-hexahydro-cycloheptapyrazole-3-carboxylic acid (1-methyl-1-phenyl-ethyl)-amide | 548 |
| 206 | (8E)-[1-(2,4-dichloro-phenyl)-8-(4-fluoro-benzylidene)-1,4,5,6,7,8-hexahydro-cycloheptapyrazol-3-yl]-(3,4,5,6-tetrahydro-2H-[2,2']bipyridinyl-1-yl)-methanone | 575 |
| 207 | (8E)-1-(2,4-dichloro-phenyl)-8-(4-fluoro-benzylidene)-1,4,5,6,7,8-hexahydro-cycloheptapyrazole-3-carboxylic acid (1R)-indan-1-ylamide | 546 |
| 208 | (8E)-1-(2,4-dichloro-phenyl)-8-(4-fluoro-benzylidene)-1,4,5,6,7,8-hexahydro-cycloheptapyrazole-3-carboxylic acid [(1S,2R)-2-hydroxy-indan-1-yl]-amide | 562 |
| 209 | (8E)-1-(2,4-dichloro-phenyl)-8-(4-fluoro-benzylidene)-1,4,5,6,7,8-hexahydro-cycloheptapyrazole-3-carboxylic acid (1,2,3,4-tetrahydro-naphthalen-1-yl)-amide | 560 |
| 210 | (8E)-1-(2,4-dichloro-phenyl)-8-(4-methoxy-benzylidene)-1,4,5,6,7,8-hexahydro-cycloheptapyrazole-3-carboxylic acid (pyridin-2-ylmethyl)-amide | 533 |
| 211 | (8E)-1-(2,4-dichloro-phenyl)-8-(4-methoxy-benzylidene)-1,4,5,6,7,8-hexahydro-cycloheptapyrazole-3-carboxylic acid (1-methyl-1-phenyl-ethyl)-amide | 560 |
| 212 | (8E)-1-(2,4-dichloro-phenyl)-8-(4-methoxy-benzylidene)-1,4,5,6,7,8-hexahydro-cycloheptapyrazole-3-carboxylic acid [(1R)-1-phenyl-ethyl]-amide | 546 |
| 213 | (8E)-1-(2,4-dichloro-phenyl)-8-(4-methoxy-benzylidene)-1,4,5,6,7,8-hexahydro-cycloheptapyrazole-3-carboxylic acid [(1S)-1-phenyl-ethyl]-amide | 546 |
| 214 | (8E)-1-(2,4-dichloro-phenyl)-8-(4-methoxy-benzylidene)-1,4,5,6,7,8-hexahydro-cycloheptapyrazole-3-carboxylic acid [(1R)-1-cyclohexyl-ethyl]-amide | 552 |
| 215 | (8E)-1-(2,4-dichloro-phenyl)-8-(4-methoxy-benzylidene)-1,4,5,6,7,8-hexahydro-cycloheptapyrazole-3-carboxylic acid [(1S)-2-hydroxy-1-phenyl-ethyl]-amide | 562 |
| 216 | (8E)-1-(2,4-dichloro-phenyl)-8-(4-methoxy-benzylidene)-1,4,5,6,7,8-hexahydro-cycloheptapyrazole-3-carboxylic acid (1R)-indan-1-ylamide | 558 |
| 217 | (8E)-1-(2,4-dichloro-phenyl)-8-(4-methoxy-benzylidene)-1,4,5,6,7,8-hexahydro-cycloheptapyrazole-3-carboxylic acid piperidin-1-ylamide | 525 |
| 219 | (8E)-1-cyclohexyl-8-(4-fluoro-benzylidene)-1,4,5,6,7,8-hexahydro-cycloheptapyrazole-3-carboxylic acid [(1R)-2-hydroxy-1-phenyl-ethyl]-amide | 488 |
| 220 | (8E)-8-(4-fluoro-benzylidene)-1-(4-trifluoromethyl-pyrimidin-2-yl)-1,4,5,6,7,8-hexahydro-cycloheptapyrazole-3-carboxylic acid [(1S)-2-hydroxy-1-phenyl-ethyl]-amide | 552 |
| 221 | (8E)-1-(2,4-dichloro-phenyl)-8-(4-methoxy-benzylidene)-1,4,5,6,7,8-hexahydro-cycloheptapyrazole-3-carboxylic acid [(1R,2R)-2-hydroxy-cyclopentyl]-amide | 526 |
| 222 | (8E)-1-(2,4-dichloro-phenyl)-8-(4-methoxy-benzylidene)-1,4,5,6,7,8-hexahydro-cycloheptapyrazole-3-carboxylic acid (1-pyridin-2-yl-ethyl)-amide | 547 |
| 223 | (8E)-[8-(4-chloro-benzylidene)-1,4,5,6,7,8-hexahydro-cycloheptapyrazol-3-yl]-piperidin-1-yl-methanone | 370 |
| 224 | (8E)-1-(2,4-dichloro-phenyl)-8-(4-fluoro-benzylidene)-1,4,5,6,7,8-hexahydro-cycloheptapyrazole-3-carboxylic acid (1-pyridin-2-yl-ethyl)-amide | 535 |

-continued

| Cpd | Name | MS |
|---|---|---|
| 225 | (8E)-1-(2,4-dichloro-phenyl)-8-(4-fluoro-benzylidene)-1,4,5,6,7,8-hexahydro-cycloheptapyrazole-3-carboxylic acid [(1R)-1-pyridin-2-yl-ethyl]-amide | 535 |
| 226 | (8E)-1-(2,4-dichloro-phenyl)-8-(4-methoxy-benzylidene)-1,4,5,6,7,8-hexahydro-cycloheptapyrazole-3-carboxylic acid (hexahydro-cyclopenta[c]pyrrol-2-yl)-amide | 551 |
| 227 | (8E)-1-(2,4-dichloro-phenyl)-8-(4-methoxy-benzylidene)-1,4,5,6,7,8-hexahydro-cycloheptapyrazole-3-carboxylic acid [(1R)-1-pyridin-2-yl-ethyl]-amide | 547 |
| 234 | (8E)-8-(4-chloro-benzylidene)-1,4,5,6,7,8-hexahydro-cycloheptapyrazole-3-carboxylic acid [(1R)-2-hydroxy-1-phenyl-ethyl]-amide | 422 |
| 238 | (8E)-(2S)-2-{[8-(4-chloro-benzylidene)-1,4,5,6,7,8-hexahydro-cycloheptapyrazole-3-carbonyl]-amino}-3-(4-fluoro-phenyl)-propionic acid methyl ester | 482 |
| 239 | (8E)-8-(3-chloro-benzylidene)-1,4,5,6,7,8-hexahydro-cycloheptapyrazole-3-carboxylic acid [(1R)-2-hydroxy-1-phenyl-ethyl]-amide | 422 |
| 240 | (8E)-(2S)-2-{[8-(3-chloro-benzylidene)-1,4,5,6,7,8-hexahydro-cycloheptapyrazole-3-carbonyl]-amino}-3-(4-fluoro-phenyl)-propionic acid methyl ester | 482 |
| 241 | (8E)-(2S)-2-{[8-(3-fluoro-benzylidene)-1-methyl-1,4,5,6,7,8-hexahydro-cycloheptapyrazole-3-carbonyl]-amino}-3-(4-fluoro-phenyl)-propionic acid methyl ester | 480 |
| 242 | (8E)-8-(3-fluoro-benzylidene)-1-methyl-1,4,5,6,7,8-hexahydro-cycloheptapyrazole-3-carboxylic acid [(1R)-2-hydroxy-1-phenyl-ethyl]-amide | 420 |
| 243 | (8E)-[8-(3-fluoro-benzylidene)-1-methyl-1,4,5,6,7,8-hexahydro-cycloheptapyrazol-3-yl]-imidazol-1-yl-methanone | 351 |
| 244 | (8E)-(2S)-8-(3-fluoro-benzylidene)-1-methyl-1,4,5,6,7,8-hexahydro-cycloheptapyrazole-3-carboxylic acid [1-hydroxymethyl-2-(4-hydroxy-phenyl)-ethyl]-amide | 450 |
| 245 | (8E)-(2R)-2-{[8-(3-chloro-benzylidene)-1,4,5,6,7,8-hexahydro-cycloheptapyrazole-3-carbonyl]-amino}-3-(4-fluoro-phenyl)-propionic acid methyl ester | 482 |
| 246 | (8E)-(2S)-8-(3-chloro-benzylidene)-1,4,5,6,7,8-hexahydro-cycloheptapyrazole-3-carboxylic acid [1-hydroxymethyl-2-(4-hydroxy-phenyl)-ethyl]-amide | 452 |
| 247 | (8E)-(2R)-2-{[8-(4-chloro-benzylidene)-1,4,5,6,7,8-hexahydro-cycloheptapyrazole-3-carbonyl]-amino}-3-(4-fluoro-phenyl)-propionic acid methyl ester | 482 |
| 248 | (8E)-(2R)-2-{[8-(3-fluoro-benzylidene)-1-methyl-1,4,5,6,7,8-hexahydro-cycloheptapyrazole-3-carbonyl]-amino}-3-(4-fluoro-phenyl)-propionic acid methyl ester | 480 |
| 249 | (8E)-8-(3-fluoro-benzylidene)-1-methyl-1,4,5,6,7,8-hexahydro-cycloheptapyrazole-3-carboxylic acid [(1R)-3-hydroxy-1-phenyl-propyl]-amide | 434 |
| 250 | (8E)-8-(3-chloro-benzylidene)-1,4,5,6,7,8-hexahydro-cycloheptapyrazole-3-carboxylic acid [(1R)-3-hydroxy-1-phenyl-propyl]-amide | 436 |

Additional compounds may be made according to the synthetic methods of the present invention by one skilled in the art, differing only in possible starting materials, reagents and conditions used in the instant methods.

BIOLOGICAL EXAMPLES

The following examples illustrate that the compounds of the present invention are CB receptor modulators useful for treating, ameliorating or preventing a cannabinoid receptor mediated syndrome, disorder or disease in a subject in need thereof.

Example 1

Binding Assay for CB1 or CB2 Agonists or Inverse Agonists

The human CB1 and CB2 receptors were stably expressed in SK-N-MC cells transfected with pcDNA3 CB-1 (human) or pcDNA3 CB-2 (human). The cells were grown in T-180 cell culture flasks under standard cell culture conditions at 37° C. in a 5% $CO_2$ atmosphere. The cells were harvested by trysinization and homogenized in a homogenization buffer (10 mM Tris, 0.2 mM $MgCl_2$, 5 mM KCl, with protease inhibitors aprotinin, leupeptin, pepstatin A and bacitracin) and centrifuged (2000 g). The supernatant was then centrifuged in 2M sucrose (31,300 g) to produce a semi-purified membrane pellet. The pellet was resuspended in homogenization and stored at −80° C.

On the day of the assay, the pellet was thawed on ice and diluted in assay buffer (50 mM Tris-HCl, 5 mM $MgCl_2$, 2.5 mM EDTA, 0.5 mg/mL fatty acid free bovine serum aldumin, pH 7.5). The diluted membrane pellet was added with buffer, either a test compound or vehicle standard and the radioligand $[H]^{3+}$-CP-55,940 (0.2 mM) to the wells of a 96-well polypropylene plate. Non-specific binding was measured in wells containing WIN 55,212 (10 uM). The plate was covered and incubated for 90 minutes at 30° C. The contents were then aspirated onto a Packard Unifilter GF/C filter bottom plate prewet with 0.5% polyethyleneimine. The wells of the polypropylene plate were rinsed and aspirated seven times with a 0.9% saline-0.5% Tween 20 solution. The Unifilter plate was dried, a scintillation cocktail was added to each well and the counts representing binding were quantitated in a TopCount scintillation counter.

CB1 and CB2 Receptor Binding Results

For compounds tested, an $IC_{50}$ binding value was obtained from percent inhibition studies in which various test concentrations were used. The binding value was calculated by linear regression.

For compounds without an $IC_{50}$ binding value, the percent inhibition (%) was obtained at a test concentration of [1] 1 μM, [2] 0.2 μM, [3] 0.0001 μM, [4] 0.0003 μM, [5] value shown is an average percent inhibition, [6] 2 μM, [7] 0.015 μM, [8] 0.25 μM, [9] 0.003 μM, [10] 0.5 μM, [11] 0.002 μM, [12] 0.008 μM or [13] 0.0125 μM.

TABLE 1

Cannabinoid CB1 Receptor Binding $IC_{50}$ (μM)

| Cpd | $IC_{50}$ |
|---|---|
| 1 | 0.2 |
| 2 | [1]21% |
| 3 | 1.3, [1]60% |
| 4 | [1]51% |
| 5 | [1]22% |
| 6 | [1]26% |
| 7 | 1.1, [1]68% |
| 8 | [1]30% |
| 9 | [1]18% |
| 10 | [1]0% |
| 11 | [1]17% |
| 12 | [1]36% |
| 13 | [1]0% |
| 14 | [1]29% |
| 15 | [1]58% |
| 16 | [1]21% |
| 17 | [1]37% |
| 18 | [1]3% |
| 19 | [1]18% |
| 20 | [1]4% |
| 21 | [1]32% |
| 22 | [1]58% |
| 23 | [1]0% |
| 24 | [1]28% |
| 25 | 51%, [1]71%, [10]30% |
| 26 | 63%, [1]70%, [6]55% |
| 27 | [1]0% |
| 28 | 0.1, [1]65% |
| 29 | [1]13% |
| 30 | [1]28% |
| 31 | [1]0% |
| 32 | [1]0% |
| 33 | [1]0% |
| 34 | [1]0% |
| 35 | [1]22% |
| 36 | [1]25% |
| 37 | [1]15% |
| 38 | [1]39% |
| 39 | [1]0% |
| 40 | 0.07, [1]84% |
| 41 | 0.5, [1]68% |
| 42 | 0.3, [1]65% |
| 43 | [1]14% |
| 44 | 0.2, [1]82% |
| 45 | 0.7, [1]54% |
| 46 | [1]45% |
| 47 | 0.1, [1]91% |
| 48 | 0.3, [1]63% |
| 49 | [1]33% |
| 50 | [1]32% |
| 51 | [1]36% |
| 52 | [1]26% |
| 53 | [1]33% |
| 54 | [1]18% |

TABLE 1-continued

Cannabinoid CB1 Receptor Binding $IC_{50}$ (μM)

| Cpd | $IC_{50}$ |
|---|---|
| 55 | [1]50% |
| 56 | [1]0% |
| 57 | [1]35% |
| 58 | 0.2, [1]75% |
| 59 | [1]27% |
| 60 | [1]38% |
| 61 | [1]36% |
| 62 | [1]5% |
| 63 | [1]29% |
| 64 | [1]51% |
| 65 | [1]29% |
| 66 | [1]16% |
| 67 | [1]44% |
| 68 | [8]0% |
| 69 | [8]23% |
| 70 | [5]37% |
| 71 | [5]43% |
| 72 | [5]38% |
| 73 | [5]24% |
| 74 | [5]1% |
| 75 | 0.2, [5]77% |
| 76 | [5]44% |
| 77 | 51%, [5]57%, [1]44% |
| 78 | 0.4, [5]59% |
| 79 | [5]37% |
| 80 | 0.7, [5]51% |
| 81 | [5]42% |
| 82 | 1, [5]46% |
| 83 | 0.1, [5]90% |
| 84 | 0.7, [5]67% |
| 85 | [5]39% |
| 86 | [8]0% |
| 87 | [8]4% |
| 88 | [1]2% |
| 89 | [1]11% |
| 90 | [1]1% |
| 91 | 0.3, [1]68% |
| 92 | 0.1, [1]86% |
| 93 | 0.4, [1]70% |
| 94 | [1]38% |
| 95 | [1]36% |
| 96 | [1]0% |
| 97 | [1]38% |
| 98 | [1]51% |
| 99 | [1]17% |
| 100 | [1]31% |
| 101 | [1]28% |
| 102 | 0.6, [1]77%, [10]55% |
| 103 | 0.3, [1]76%, [10]56% |
| 104 | [1]19% |
| 105 | [1]2% |
| 106 | [1]45% |
| 107 | 0.3, [1]72%, [10]59% |
| 108 | 44%, [1]55%, [10]33% |
| 109 | 0.3, [1]72%, [10]60% |
| 110 | 56%, [1]63%, [10]48% |
| 111 | 54%, [1]62%, [10]45% |
| 112 | [1]49% |
| 113 | 53%, [1]62%, [10]44% |
| 114 | [1]17% |
| 115 | 0.5, [1]79%, [10]67% |
| 116 | [1]14% |
| 117 | [1]44% |
| 118 | [1]4% |
| 119 | [1]39% |
| 120 | [1]9% |
| 121 | 0.4, [1]80%, [10]70% |
| 122 | [1]0% |
| 123 | [1]47% |
| 124 | [1]14% |
| 125 | [1]0% |
| 126 | [1]0% |
| 127 | [1]36% |
| 128 | [1]0% |
| 129 | 94%, [8]100%, |

TABLE 1-continued

Cannabinoid CB1 Receptor Binding IC$_{50}$ (μM)

| Cpd | IC$_{50}$ |
|---|---|
|  | [12]90%, [11]92% |
| 130 | 0.06, [8]84% |
| 131 | 0.006, [8]93%, [7]53% |
| 132 | 0.005, [8]94%, [7]64% |
| 133 | 0.1, [8]66% |
| 134 | [8]58% |
| 135 | 0.05, [8]65% |
| 136 | [8]39% |
| 137 | 0.01, [8]77%, [7]57% |
| 138 | 0.03, [2]71% |
| 139 | 0.05, [2]72% |
| 140 | 0.006, [2]97% |
| 141 | 0.006, [2]95% |
| 142 | 0.01, [2]83% |
| 143 | 0.002, 77%, [2]99%, [11]55% |
| 144 | 0.03, [2]69% |
| 145 | [2]54% |
| 146 | 0.008, 0.01, [2]93%, [2]94% |
| 147 | 0.007, [2]94% |
| 148 | 0.08, [2]69% |
| 149 | 0.1, [2]66% |
| 150 | 0.1, [2]65% |
| 151 | [2]51% |
| 152 | 47%, [2]66%, [13]28% |
| 153 | [2]44% |
| 154 | [2]33% |
| 155 | 0.07, [2]72% |
| 156 | [2]50% |
| 157 | 0.1, [2]68% |
| 158 | [2]14% |
| 159 | [2]40% |
| 160 | [2]2% |
| 161 | [2]35% |
| 162 | [2]16% |
| 163 | [2]44% |
| 164 | [2]26% |
| 165 | [2]79% |
| 166 | [2]24% |
| 167 | [2]57% |
| 168 | [2]18% |
| 169 | [2]24% |
| 170 | [2]29% |
| 171 | [2]2% |
| 172 | [2]64% |
| 173 | [2]32% |
| 174 | [2]0% |
| 175 | [2]30% |
| 176 | [2]4% |
| 177 | [2]4% |
| 178 | [2]29% |
| 179 | [2]0% |
| 180 | [2]40% |
| 181 | [2]32% |
| 182 | [2]21% |
| 183 | [2]0% |
| 184 | 0.05, [2]78% |
| 185 | 0.03, [2]75% |
| 186 | [2]12% |
| 187 | [2]12% |
| 188 | 0.1, [2]64% |
| 189 | 0.05, [2]78% |
| 190 | 0.08, [2]76% |
| 191 | [2]47% |
| 192 | [2]45% |
| 193 | [2]43% |
| 194 | [2]19% |
| 195 | [2]63% |
| 196 | [2]67% |
| 197 | 0.03, [2]83% |
| 198 | 0.02, [2]87% |
| 199 | [2]30% |
| 200 | [2]15% |
| 201 | [2]11% |
| 202 | 0.01, [2]91% |
| 203 | [2]37% |
| 204 | 0.03, [2]88% |
| 205 | 0.02, [2]93% |
| 206 | 0.08, [2]73% |
| 207 | 0.02, [2]90% |
| 208 | 0.07, [2]76% |
| 209 | 0.03, [2]88% |
| 210 | 0.04, [2]76% |
| 211 | 0.007, [2]92% |
| 212 | 0.006, [2]94% |
| 213 | 0.06, [2]71% |
| 214 | 0.007, [2]95% |
| 215 | 0.01, [2]88% |
| 216 | 0.009, [2]91% |
| 217 | 0.06, [2]75% |
| 222 | 0.03, [2]48% |
| 223 | [2]40% |
| 224 | 0.008, [2]87% |
| 225 | 0.005, 0.006, 0.007, [2]90%, [2]89%, [5]96% |
| 226 | 0.04, [2]72% |
| 227 | 0.009, [2]90% |
| 228 | [2]0% |
| 229 | 0.06, [2]73% |
| 230 | 0.3 |
| 231 | 0.3 |
| 232 | 0.3, [2]0% |
| 233 | [2]0% |
| 234 | 0.02, [2]87% |
| 235 | [2]0% |
| 236 | [2]0% |
| 237 | 0.3, [2]0% |
| 238 | 0.03, [2]85% |
| 239 | 0.03, [2]80% |
| 240 | 0.2, [2]35% |
| 241 | 0.2, [2]33% |
| 242 | 0.02, [2]80% |
| 243 | [2]0% |
| 244 | 0.1, [2]68% |
| 245 | 0.006, [2]68% |
| 246 | [2]0% |
| 247 | 0.002, [2]91% |
| 248 | 0.007, [2]89% |

TABLE 2

Cannabinoid CB2 Receptor Binding IC$_{50}$ (μM)

| Cpd | IC$_{50}$ |
|---|---|
| 1 | 0.3 |
| 2 | 53% |
| 3 | 26% |
| 4 | 36% |
| 5 | 34% |
| 6 | 4% |
| 7 | 12% |
| 8 | 5% |
| 9 | 4% |
| 10 | 8% |
| 11 | 21% |
| 12 | 31% |
| 13 | 14% |
| 14 | 7% |
| 15 | 54% |
| 16 | 68% |
| 17 | 11% |
| 18 | 23% |
| 19 | 51% |
| 20 | 28% |
| 21 | 26% |
| 22 | 25% |

TABLE 2-continued

Cannabinoid CB2 Receptor Binding IC$_{50}$ (μM)

| Cpd | IC$_{50}$ |
|---|---|
| 23 | 24% |
| 24 | 0% |
| 25 | 19% |
| 26 | 29%, [1]35%, [6]22% |
| 27 | 0% |
| 28 | 11% |
| 29 | 18% |
| 30 | 0.6, [1]65% |
| 31 | 35% |
| 32 | 0% |
| 33 | 0% |
| 34 | 0% |
| 35 | 36% |
| 36 | 0% |
| 37 | 10% |
| 38 | 0% |
| 39 | 30% |
| 40 | 75%, [1]84%, [7]65% |
| 41 | 46% |
| 42 | 0.3, [1]52% |
| 43 | 42% |
| 44 | 0.6, [1]75% |
| 45 | 42% |
| 46 | 0% |
| 47 | 0.03, [1]94% |
| 48 | 42% |
| 49 | 9% |
| 50 | 31% |
| 51 | 30% |
| 52 | 21% |
| 53 | 52% |
| 54 | 41% |
| 55 | 18% |
| 56 | 42% |
| 57 | 29% |
| 58 | 74%, [1]98%, [7]65% |
| 59 | 60% |
| 60 | 38% |
| 61 | 71% |
| 62 | 5% |
| 63 | 69% |
| 64 | 0.6, [1]70% |
| 65 | 52% |
| 66 | 33% |
| 67 | 55% |
| 68 | [8]27% |
| 69 | [8]12% |
| 70 | 3% |
| 71 | 32% |
| 72 | 10% |
| 73 | 8% |
| 74 | 10% |
| 75 | 27% |
| 76 | 38% |
| 77 | 28% |
| 78 | 23% |
| 79 | 29% |
| 80 | 23% |
| 81 | 28% |
| 82 | 0.06, [5]88% |
| 83 | 0.01, [5]98% |
| 84 | 11% |
| 85 | 5% |
| 86 | [8]22% |
| 87 | [8]0% |
| 88 | 32% |
| 89 | 0% |
| 90 | 2% |
| 91 | 0% |
| 92 | 0.2, [1]82% |
| 93 | 58% |
| 94 | 1% |
| 95 | 35% |
| 96 | 72%, [1]94%, [7]50% |
| 97 | 0.3, [1]71% |
| 98 | 43% |
| 99 | 24% |
| 100 | 9% |
| 101 | 0.04, [1]97% |
| 102 | 59% |
| 103 | 57% |
| 104 | 93% |
| 105 | 82% |
| 106 | 95% |
| 107 | 64% |
| 108 | 100% |
| 109 | 48% |
| 110 | 59% |
| 111 | 65% |
| 112 | 16% |
| 113 | 28% |
| 114 | 47% |
| 115 | 99% |
| 116 | 24% |
| 117 | 22% |
| 118 | 31% |
| 119 | 38% |
| 120 | 16% |
| 121 | 95% |
| 122 | 0% |
| 123 | 14% |
| 124 | 47% |
| 125 | 30% |
| 126 | 65% |
| 127 | 0% |
| 128 | 0% |
| 129 | [8]86% |
| 130 | [8]98% |
| 131 | [8]34% |
| 132 | [8]42% |
| 133 | [8]29% |
| 134 | [8]28% |
| 135 | [8]25% |
| 136 | [8]18% |
| 137 | [8]0% |
| 138 | [2]22% |
| 139 | [2]30% |
| 140 | [2]100% |
| 141 | [2]97% |
| 142 | [2]98% |
| 143 | [2]100% |
| 144 | [2]90% |
| 145 | [2]68% |
| 146 | 2.3, 3%, [2]10% |
| 147 | [2]23% |
| 148 | [2]39% |
| 149 | [2]4% |
| 150 | [2]3% |
| 151 | [2]15% |
| 152 | [2]21% |
| 153 | [2]0% |
| 154 | [2]7% |
| 155 | [2]8% |
| 156 | [2]36% |
| 157 | [2]5% |
| 158 | [2]0% |
| 159 | [2]3% |
| 160 | [2]75% |
| 161 | [2]3% |
| 162 | [2]5% |
| 163 | [2]7% |
| 164 | [2]94% |
| 165 | [2]98% |
| 166 | [2]75% |
| 167 | [2]97% |
| 168 | [2]11% |
| 169 | [2]14% |
| 170 | [2]27% |
| 171 | [2]38% |
| 172 | [2]41% |

TABLE 2-continued

Cannabinoid CB2 Receptor Binding IC$_{50}$ (μM)

| Cpd | IC$_{50}$ |
|---|---|
| 173 | $^{(2)}$19% |
| 174 | $^{(2)}$33% |
| 175 | $^{(2)}$36% |
| 176 | $^{(2)}$43% |
| 177 | $^{(2)}$27% |
| 178 | $^{(2)}$29% |
| 179 | $^{(2)}$29% |
| 180 | $^{(2)}$86% |
| 181 | $^{(2)}$57% |
| 182 | $^{(2)}$31% |
| 183 | $^{(2)}$14% |
| 184 | $^{(2)}$27% |
| 185 | $^{(2)}$56% |
| 186 | $^{(2)}$58% |
| 187 | $^{(2)}$23% |
| 188 | $^{(2)}$36% |
| 189 | $^{(2)}$17% |
| 190 | $^{(2)}$12% |
| 191 | $^{(2)}$7% |
| 192 | $^{(2)}$7% |
| 193 | $^{(2)}$16% |
| 194 | $^{(2)}$10% |
| 195 | $^{(2)}$37% |
| 196 | $^{(2)}$49% |
| 197 | $^{(2)}$67% |
| 198 | $^{(2)}$68% |
| 199 | $^{(2)}$30% |
| 200 | $^{(2)}$6% |
| 201 | $^{(2)}$0% |
| 202 | $^{(2)}$9% |
| 203 | $^{(2)}$30% |
| 204 | $^{(2)}$34% |
| 205 | $^{(2)}$27% |
| 206 | $^{(2)}$22% |
| 207 | $^{(2)}$1% |
| 208 | $^{(2)}$31% |
| 209 | $^{(2)}$8% |
| 210 | $^{(2)}$49% |
| 211 | $^{(2)}$37% |
| 212 | $^{(2)}$42% |
| 213 | $^{(2)}$19% |
| 214 | $^{(2)}$43% |
| 215 | $^{(2)}$24% |
| 216 | $^{(2)}$33% |
| 217 | $^{(2)}$52% |
| 221 | $^{(2)}$24% |
| 222 | $^{(2)}$41% |
| 223 | $^{(2)}$58% |
| 224 | $^{(2)}$4% |
| 225 | $^{(1)}$16%, $^{(2)}$6%, $^{(2)}$9% |
| 226 | $^{(2)}$48% |
| 227 | $^{(2)}$19% |
| 228 | $^{(2)}$45% |
| 229 | 0.02, $^{(2)}$95% |
| 230 | 0.04 |
| 231 | 0.2 |
| 232 | 0.06 $^{(2)}$81% |
| 233 | $^{(2)}$20% |
| 234 | 0.06, $^{(2)}$93% |
| 235 | $^{(2)}$41% |
| 236 | $^{(2)}$41% |
| 237 | 0.1, $^{(2)}$64% |
| 238 | 0.01, $^{(2)}$93% |
| 239 | 0.02, $^{(2)}$91% |
| 240 | 0.04, $^{(2)}$78% |
| 241 | 0.1, $^{(2)}$62% |
| 242 | 0.1, $^{(2)}$50% |
| 243 | $^{(2)}$0% |
| 244 | 0.02, $^{(2)}$78% |
| 245 | 0.002, $^{(2)}$93% |
| 246 | $^{(2)}$15% |
| 247 | 0.001, $^{(2)}$96% |
| 248 | 0.003, $^{(2)}$96% |

Modified Binding Assay for CB1 or CB2 Agonists or Inverse Agonists

Additional receptor binding studies were performed with minor modifications as detailed below.

The human CB1 and CB2 receptors were stably expressed in CHO cells as described in Rinaldi-Carmona, M., Calandra, B., Shire, D., Bouaboula, M., Oustric, D., Barth, F., Casellas, P., Ferrara, P. and Le Fur, G. (1996) *J. PharmacoL Exp. Ther.*, 278: 871-878 and Munro, S., Thomas, K. L. and Abu-Shaar, M. (1993) *Nature*, 365: 61-65, respectively. [$^3$H]CP 55940 (0.5 nM) was used as the radioligand for the CB1 receptor binding assay. [$^3$H]WIN 55212 (0.8 nM) was used as the radioligand for the CB2 receptor binding assay. Incubation was carried out for 120 minutes at 37° C.

The specific ligand binding to the receptors is defined as the difference between the total binding and the nonspecific binding determined in the presence of an excess of unlabelled ligand. The results are expressed as a percent of control specific binding ((measured specific binding/control specific binding)×100) obtained in the presence of the test compounds.

The IC$_{50}$ values (concentration causing a half-maximal inhibition of control specific binding) were determined by non-linear regression analysis of the competition curves generated with mean replicate values using Hill equation curve fitting (where Y=specific binding, D=minimum specific binding, A=maximum specific binding, C=compound concentration, C$_{50}$=IC$_{50}$ and nH=slope factor):

$$Y = D + [(A-D)/(1+(C/C_{50})^{nH})]$$

CB1 and CB2 Receptor Binding Results

For compounds tested, an IC$_{50}$ binding value was obtained from percent inhibition studies in which various test concentrations were used. Results are shown in Table 3.

TABLE 3

CB1/CB2 Receptor Binding IC$_{50}$ (μM)

| Cpd | CB1 IC$_{50}$ | CB2 IC$_{50}$ |
|---|---|---|
| 164 | 0.87 | 0.23 |
| 230 | 0.37 | 0.092 |
| 231 | >3 | 1.8 |
| 237 | >3 | 0.69 |

Example 2

Functional Cell-Based Assay for CB1 or CB2 Agonist and Inverse Agonist Effects on Intra-Cellular Adenylate Cyclase Activity The CB1 and CB2 receptors are G-protein coupled receptors (GPCR), which influence cell function via the Gi-protein. These receptors modulate the activity of intracellular adenylate cyclase, which in turn produces the intracellular signal messenger cyclic-AMP (cAMP).

At baseline, or during non-ligand bound conditions, these receptors are constitutively active and tonically suppress adenylate cyclase activity. The binding of an agonist causes further receptor activation and produces additional suppression of adenylate cyclase activity. The binding of an inverse agonist inhibits the constitutive activity of the receptors and results in an increase in adenylate cyclase activity.

By monitoring intracellular adenylate cyclase activity, the ability of compounds to act as agonists or inverse agonists can be determined.

Assay

Test compounds were evaluated in SK-N-MC cells which, using standard transfection procedures, were stably transfected with human cDNA for pcDNA3-CRE β-gal and pcDNA3 CB1 receptor (human) or pcDNA3 CB2 receptor (human). By expressing CRE β-gal, the cells produced β-galactosidase in response to CRE promoter activation by cAMP. Cells expressing CRE β-gal and either the human CB1 or CB2 receptor will produce less β-galactosidase when treated with a CB1/CB2 agonist and will produce more β-galactosidase when treated with a CB1/CB2 inverse agonist.

Cell Growth

The cells were grown in 96-well plates under standard cell culture conditions at 37° C. in a 5% $CO_2$ atmosphere and culture media (wherein the media was supplemented with 2 mM L-glutamine, 1M sodium pyruvate, 10% FBS (fetal bovine serum) and antibiotics). After 3 days, the culture media was removed and a test compound in assay media (MEM with 0.1% low fatty acid BSA (bovine serum albumin) was added to the cell. The plates were incubated for 30 minutes at 37° C. and the plate cells were then treated with forskolin over a 4-6 hour period, then washed and lysed. The β-galactosidase activity was quantitated using commercially available kit reagents (Promega Corp. Madison, Wis.) and a Vmax Plate Reader (Molecular Devices, Inc).

CB1 Receptor Mediated Change in CRE β-Gal Expression

For cells expressing CRE β-gal and the CB1 receptor, CB1 agonists reduced β-galactosidase activity in a dose-dependent manner and CB1 inverse agonists increased β-galactosidase activity in a dose-dependent manner.

The change in forskolin induced β-galactosidase activity was determined by setting a vehicle treated cell's activity value at 100% and expressing the β-galactosidase activity measured in a corresponding compound treated cell as a percent of the vehicle treated cell activity.

CB1 Receptor Results

The $EC_{50}$ value for functional activity for compounds tested was calculated by linear regression and was obtained from studies in which varying compound concentrations were used.

Where an $EC_{50}$ value was not obtained for a test compound, the value shown (in %) represents change in functional activity and was obtained from a study in which one compound concentration was used.

TABLE 4

CB1 Receptor Functional Inverse Agonist $EC_{50}$ (μM)

| Cpd | $EC_{50}$ |
|---|---|
| 3 | 0.07 |
| 8 | 0.4 |
| 25 | 1.2 |
| 26 | 0.6 |
| 28 | 0.05 |
| 41 | 0.1 |
| 42 | 0.3 |
| 45 | 1.1 |
| 48 | 0.3 |
| 55 | 0.4 |
| 75 | 0.07 |
| 77 | 0.1 |
| 78 | 0.2 |
| 79 | 0.5 |
| 80 | 0.06 |
| 81 | 0.3 |
| 84 | 0.1 |
| 85 | 0.3 |
| 91 | 0.07 |
| 92 | 0.09 |
| 93 | 0.05 |
| 94 | 0.2 |
| 99 | 0.2 |
| 102 | 0.07 |
| 104 | 0.1 |
| 110 | 0.1 |
| 111 | 0.09 |
| 112 | 0.06 |
| 113 | 0.1 |
| 114 | 0.04 |
| 117 | 0.3 |
| 118 | 0.1 |
| 120 | 0.1 |
| 122 | 0.06 |
| 123 | 2.9 |
| 124 | 3.4 |
| 128 | 2.7 |
| 131 | <0.03 |
| 132 | 0.01 |
| 133 | 0.03 |
| 134 | 0.01 |
| 135 | <0.03 |
| 136 | 0.03 |
| 137 | 0.03 |
| 138 | 0.1 |
| 146 | 0.02 |
| 147 | 0.03 |
| 148 | 0.2 |
| 149 | 0.06 |
| 150 | 0.02 |
| 151 | 0.06 |
| 152 | 0.2 |
| 155 | 0.03 |
| 156 | 0.09 |
| 157 | 0.04 |
| 172 | 0.1 |
| 184 | 0.003 |
| 185 | <0.003 |
| 188 | 0.01 |
| 189 | 0.01 |
| 190 | 0.009 |
| 197 | 0.003 |
| 202 | 0.009 |
| 204 | 0.003 |
| 205 | 0.009 |
| 206 | 0.01 |
| 207 | 0.007 |
| 208 | 0.01 |
| 209 | 0.01 |
| 210 | 0.02 |
| 211 | 0.02 |
| 212 | 0.02 |
| 213 | 0.01 |
| 214 | 0.03 |
| 215 | 0.01 |
| 216 | 0.05 |
| 217 | 0.02 |
| 222 | 0.03 |
| 224 | 0.004 |
| 225 | 0.001 |
| 226 | 0.003 |
| 227 | 0.002 |

TABLE 5

CB1 Receptor Functional Agonist $EC_{50}$ (μM)

| Cpd | $EC_{50}$ |
|---|---|
| 40 | 0.1 |
| 58 | 1.4 |
| 83 | 1.7 |
| 107 | 19.8 |

TABLE 5-continued

CB1 Receptor Functional Agonist $EC_{50}$ (µM)

| Cpd | $EC_{50}$ |
|---|---|
| 116 | 0.3 |
| 130 | <0.03 |
| 165 | 0.03 |
| 167 | 0.05 |
| 198 | 0.02 |
| 229 | 0.06 |
| 230 | 1.0 |
| 231 | >5 |
| 232 | >5 |
| 234 | 0.008 |
| 237 | 1.7 |
| 238 | 0.15 |
| 239 | 0.02 |
| 240 | 1.6 |
| 241 | 2.8 |
| 242 | 0.03 |
| 244 | 0.6 |
| 245 | 0.08 |
| 247 | 0.008 |
| 249 | >5 |
| 250 | >5 |
| 251 | 0.41 |
| 252 | >5 |
| 253 | >5 |
| 254 | 0.08 |

TABLE 6

CB1 Receptor Functional Activity

| Cpd | Activity |
|---|---|
| 4 | 22% |
| 7 | 32% |
| 12 | 11% |
| 14 | 8% |
| 15 | 18% |
| 17 | 22% |
| 21 | 7% |
| 22 | 24% |
| 27 | 11% |
| 44 | 26% |
| 47 | 11% |
| 64 | 24% |
| 68 | 35% |
| 69 | 30% |
| 82 | 20% |
| 86 | 30% |
| 87 | 40% |
| 105 | 25% |
| 109 | 10% |
| 115 | 25% |
| 121 | 35% |
| 126 | 2% |
| 127 | 3% |

CB2 Receptor Mediated Change in CRE β-gal Expression

For cells expressing CRE β-gal and the CB2 receptor, CB2 agonists reduced β-galactosidase activity in a dose-dependent manner and CB2 inverse agonists increase β-galactosidase activity in a dose-dependent manner.

The change in forskolin induced β-galactosidase activity was determined by setting a vehicle treated cell's activity value at 100% and expressing the β-galactosidase activity measured in a corresponding compound treated cell as a percent of the vehicle treated cell activity.

CB2 Receptor Functional Activity Results

The $EC_{50}$ value for functional activity for compounds tested was calculated by linear regression and was obtained from studies in which varying compound concentrations were used.

The value of 1% for Compound 142 represents change in functional activity and was obtained from a study in which one compound concentration was used.

TABLE 7

CB2 Receptor Functional Agonist $EC_{50}$ (µM)

| Cpd | $EC_{50}$ |
|---|---|
| 229 | 0.002 |
| 230 | 0.002 |
| 231 | 0.012 |
| 232 | 0.009 |
| 234 | 0.005 |
| 237 | 0.009 |
| 238 | 0.001 |
| 239 | 0.0006 |
| 240 | 0.013 |
| 241 | 0.018 |
| 242 | 0.011 |
| 244 | 0.005 |
| 245 | 0.001 |
| 247 | 0.004 |
| 249 | 0.047 |
| 250 | 0.13 |
| 251 | 0.003 |
| 252 | 0.019 |
| 253 | 0.20 |
| 254 | 0.002 |

Modified Functional Cell-Based Assay for CB1 or CB2 Agonist Effects on Intra-Cellular Adenylate Cyclase Activity Additional functional activity studies were performed with minor modifications. Beta galactosidase activity was quantified using the luminescent Beta-Glo Assay System (Promega Corp. Madison, Wis.) and an Orion Microplate Luminometer (Berthold Detection Systems, Oak Ridge, Tenn.). The $EC_{50}$ values were calculated using GraphPad Prism and a four parameter logistic equation.

CB1/CB2 Receptor Results

The functional activity $EC_{50}$ value for compounds tested (shown in Table 8) were obtained from studies in which varying compound concentrations were used. With the exception of Cpd 237 (n=3), one sample for each compound was tested.

TABLE 8

CB1/CB2 Receptor Functional Activity $EC_{50}$ (µM)

| Cpd | CB1 $EC_{50}$ | CB2 $EC_{50}$ |
|---|---|---|
| 164 | >1.0 | 0.025 |
| 230 | >1.0 | 0.011 |
| 231 | >1.0 | 0.082 |
| 232 | ~3.2 | 0.15 |
| 233 | ~4.4 | ~1.3 |
| 237 | 3.6 | 3.2 |

Example 3

Acute Treatment (Ob/Ob Mice)

The effect of acute, single-dose administration of a compound of the invention is tested in hyperphagic obese ob/ob mice. Animals are orally administered (gavage) either test compound or vehicle. Body weight, plasma triglycerides and plasma glucose are monitored.

Animals administered a test compound are expected to have a relatively dose-dependent decrease in body weight, plasma triglycerides and plasma glucose compared to animals administered vehicle.

Example 4

Oil of Mustard Induced Colitis Model

In the distal colon, the oil of mustard colitis model is characterized by a discontinuous pattern of mucosal epithelial damage, submucosal edema, infiltration of inflammatory cells (including macrophages, neutrophils and lymphocytes) into the mucosa and submucosa, increased wet weight of the colon, shrinkage of the colon length, diarrhea and apparent inflammation (see, Kimball E. S., Palmer J. M., D'Andrea M. R., Homby P. J. and Wade P. R., Acute colitis induction by oil of mustard results in later development of an IBS-like accelerated upper GI transit in mice, *Am. J Physiol. Gastrointest. Liver Physiol.*, 2005, 288: G 1266-1273).

Colitis Induction

Male CD-1 mice (Charles River Laboratories, Kingston, N.C.) (9-11 weeks old) and fresh oil of mustard (OM) (allyl isothiocyanate, 98% purity, Sigma-Aldrich St. Louis, Mo.) were used.

The mice (9 per treatment group) were briefly anesthetized with ketamine/xylasine (Sigma, St. Louis, Mo.) and a solution of 0.5% OM in 30% ethanol (50 μL) was administered intracolonically (to a depth of 4 cm) via syringe (equipped with a ball-tipped 22 G needle).

A test compound was orally administered one day prior to colitis induction for assessing a prophylactic regimen or one day post-induction for assessing a therapeutic regimen. A test compound was orally administered daily thereafter. Two days after OM administration, the last test compound dose was administered.

Three days after OM administration, the animals were sacrificed. The colons were resected, examined for signs of inflammation, weighed after removing fecal contents and the length from the aboral end of the cecum to the anus was measured. The fecal contents were examined for signs of diarrhea. The distal colon between the $1^{st}$ and the $4^{th}$ centimeter was removed and placed in 10% neutral buffered formalin for histological analysis.

Macroscopic Observations and Criteria

The macroscopic observations of colon inflammation (a measure of colon damage), colon weight and length and stool consistency and appearance were assigned a score and used to evaluate colitis severity.

The four observation scores for each colon were combined, whereby a combined score of 0 represents a normal colon and a combined score of 15 represents a maximally affected colon. Statistical analyses were performed in Graphpad Prism 4.0 using ANOVA.

|  | 0 | 1 | 2 | 3 | 4 |
|---|---|---|---|---|---|
|  | Weight Score | | | | |
| Weight Gain | <5% | 5-14% | 15-24% | 25-35% | >35% |
|  | Length Score | | | | |
| Shortening | <5% | 5-14% | 15-24% | 25-35% | >35% |
|  | Stool Score | | | | |
| Fecal Pellet Formation | normal (well-formed) | loosely-shaped, moist | amorphous, moist, sticky | diarrhea | |
|  | Damage Score | | | | |
| Inflammation | none observed | mild, localized erythema | moderate, more widely distributed erythema | severe, extensively distributed erythema | penetrating ulcers, bloody lesions |

Microscopic (Histological) Examination

Histological analyses of tissues consisted of staining paraffin-embedded tissue sections with hematoxylin-eosin dye. The tissues were examined using light microscopy by an investigator who was blinded to the sample groups.

Histological Observations and Criteria

The microscopic observations of epithelial damage, cellular infiltration and damage or alteration of smooth muscle architecture (a measure of muscle damage) were assigned a score and used to evaluate colitis severity.

The scores for each colon were combined, whereby a combined score of 0 represents a normal colon and a combined score of 9 represents a maximally affected colon. Statistical analyses were performed in Graphpad Prism 4.0 using ANOVA.

Criteria and Observations

|  | 0 | 1 | 2 | 3 |
|---|---|---|---|---|
|  | Epithelial Damage Score | | | |
| Epithelium Loss | intact | $\leq 1/3$ loss | $>1/3$ to $2/3$ loss | $>2/3$ loss |
|  | Cellular Infiltration Score | | | |
| Focal Areas of Infiltration | none | 1-2 focal areas | >2 focal areas | N/A |

-continued

|  | 0 | 1 | 2 | 3 |
|---|---|---|---|---|
| Infiltrated Cell Presence | none | ≦⅓ of entire colon length | >⅓ to ⅔ of entire colon length | ≧⅔ of entire colon length |

| | Architecture Score | | |
|---|---|---|---|
| Muscle Damage (any evidence of edema, hyperplasia or loss of architecture) | no damage observed | ≦⅓ of entire colon length | ≦⅔ of entire colon length | ≧⅔ of entire colon length |

Prophylactic and Therapeutic Colitis Treatment Regimen Results

The Macroscopic Score and Microscopic Score results for each treatment group in the prophylactic and therapeutic regimens were each combined into a mean score and expressed as % inhibition of colitis (% Inh). Test (#) represents the number of experiments at each dose level.

TABLE 9

Prophylactic Regimen

| Cpd | Dose (mg/kg) | Test (#) | % Inh (Macro) | % Inh (Micro) |
|---|---|---|---|---|
| 96 | 2.5 | 1 | 8.0 ± 16.7 | ND |
| 96 | 5 | 2 | 10.8 ± 13.4 | ND |
| 108 | 2.5 | 1 | 51.2 ± 19.1 | ND |
| 108 | 5 | 2 | 13.4 ± 13.3 | ND |

TABLE 10

Therapeutic Regimen

| Cpd | Dose (mg/kg) | Test (#) | % Inh (Macro) | % Inh (Micro) |
|---|---|---|---|---|
| 96 | 5 | 1 | 7.6 ± 11.5 | ND |
| 198 | 5 | 1 | 41.0 ± 17 | ND |
| 228 | 5 | 1 | 51.7 ± 13.2 | ND |
| 229 | 5 | 1 | 56.9 ± 11.6 | ND |
| 230 | 5 | 1 | 25.9 ± 24.7 | ND |
| 231 | 5 | 1 | −19 ± 20.7 | ND |

Example 5

Dextran Sulfate Sodium (DSS) Induced Colitis Model

In the distal colon, the DSS colitis model is characterized by a discontinuous pattern of mucosal epithelial damage, infiltration of inflammatory cells (including macrophages, neutrophils and lymphocytes) into the mucosa and submucosa, decreased wet weight of the colon, shrinkage of the colon length and diarrhea (see, Blumberg R. S., Saubermann L. J. and Strober W., Animal models of mucosal inflammation and their relation to human inflammatory bowel disease, *Current Opinion in Immunology*, 1999, Vol. 11: 648-656; Egger B., Bajaj-Elliott M., MacDonald T. T., Inglin R., Eysselein, V. E. and Buchler M. W., Characterization of acute murine dextran sodium sulphate colitis: Cytokine profile and dose dependency, *Digestion*, 2000, Vol. 62: 240-248; Stevceva L., Pavli P., Husband A. J. and Doe, W. F., The inflammatory infiltrate in the acute stage of the dextran sulphate sodium induced colitis: B cell response differs depending on the percentage of DSS used to induce it, *BMC Clinical Pathology*, 2001, Vol 1: 3-13; and Diaz-Granados, Howe K., Lu J. and McKay D. M., Dextran sulfate sodium-induced colonic histopathology, but not altered epithelial ion transport, is reduced by inhibition of phosphodiesterase activity, *Amer. J. Patholog*, 2000, Vol. 156: 2169-2177).

Colitis Induction

Female Balb/c mice are provided with a solution of 5% DSS (45 kD molecular weight) in tap water ad libitum over a 7-day period. The DSS solution is replenished daily and the amount consumed is measured.

The mice are orally administered a test compound on the day of colitis induction and then daily thereafter. Six days after the initial DSS administration, the last test compound dose is administered.

Seven days after the initial DSS administration, the animals are sacrificed. The colons are resected, examined for signs of inflammation, weighed after removing fecal contents and the length from the aboral end of the cecum to the anus is measured. The fecal contents are examined for signs of diarrhea. The distal colon between the $1^{st}$ and the $4^{th}$ centimeter is removed and placed in 10% neutral buffered formalin for histological analysis.

Macroscopic Observations and Criteria

The macroscopic observations of colon inflammation (a measure of colon damage), colon length and stool consistency and appearance are assigned a score and used to evaluate colitis severity.

The three observation scores for each colon are combined, whereby a combined score of 0 represents a normal colon and a combined score of 11 represents a maximally affected colon. Statistical analyses are performed in Graphpad Prism 4.0 using ANOVA.

|  | 0 | 1 | 2 | 3 | 4 |
|---|---|---|---|---|---|
|  | Weight Score | | | | |
| Weight Gain | <5% | 5-14% | 15-24% | 25-35% | >35% |
|  | Length Score | | | | |
| Shortening | <5% | 5-14% | 15-24% | 25-35% | >35% |

-continued

|  | 0 | 1 | 2 | 3 | 4 |
|---|---|---|---|---|---|
| | | | Stool Score | | |
| Fecal Pellet Formation | normal (well-formed) | loosely-shaped, moist | amorphous, moist, sticky | severe diarrhea | |
| | | | Damage Score | | |
| Inflammation | none observed | mild, reddening observed | moderate, more widely distributed reddening | severe, extensively distributed reddening | penetrating ulcers, bloody lesions |

Microscopic (Histological) Examination

Histological analyses of tissues consists of staining paraffin-embedded tissue sections with hematoxylin-eosin dye. The tissues are examined using light microscopy by an investigator who is blinded to the sample groups.

Histological Observations and Criteria

The microscopic observations of epithelial damage, cellular infiltration and damage or alteration of smooth muscle architecture (a measure of muscle damage) are assigned a score and used to evaluate colitis severity.

The scores for each colon are combined, whereby a combined score of 0 represents a normal colon and a combined score of 9 represents a maximally affected colon. Statistical analyses are performed in Graphpad Prism 4.0 using ANOVA.

Criteria and Observations

|  | 0 | 1 | 2 | 3 |
|---|---|---|---|---|
| | | Epithelial Damage Score | | |
| Epithelium Loss | intact | $\leq 1/3$ loss | $>1/3$ to $2/3$ loss | $>2/3$ loss |
| | | Cellular Infiltration Score | | |
| Focal Areas of Infiltration | none | 1-2 focal areas | >2 focal areas | N/A |
| Infiltrated Cell Presence | none | $\leq 1/3$ of entire colon length | $>1/3$ to $2/3$ of entire colon length | $\geq 2/3$ of entire colon length |
| | | Architecture Score | | |
| Muscle Damage (any evidence of edema, hyperplasia or loss of architecture) | no damage observed | $\leq 1/3$ of entire colon length | $\leq 2/3$ of entire colon length | $\geq 2/3$ of entire colon length |

Colitis Treatment Regimen Results

The Macroscopic Score and Microscopic Score results for each treatment group are each combined into a mean score and expressed as % inhibition of colitis (% Inh).

Example 6

Postoperative Inflammatory Ileus

Acute gastrointestinal inflammation can arise from direct disturbance to the bowel during surgery, or from severe bodily trauma. Inflammation typically leads to the development of bowel stasis, or ileus, defined as the temporary impairment of coordinated gastrointestinal motility. Ileus can occur in any portion of the gastrointestinal tract, e.g., the stomach, small intestine and/or the colon. The ileus can result from any factor that causes ileus, e.g., surgery: abdominal surgery such as transplantation surgery or abdominal surgery other than transplantation surgery, orthopedic surgery; traumatic injury e.g. falls, car accident, personal assault, or any sequelae resulting from traumatic injury e.g. limb fractures, rib fractures, fractures of the spine, thoracic lesions, ischemia, retroperitoneal hecatomb; intraperitoneal inflammation e.g. intraabdominal sepsis, acute appendicitis, cholecystitis, pancreatitis, ureteric colic, basal pneumonia; myocardial infarction; metabolic disturbances; or any combination thereof.

One of the most common causes of acute gastrointestinal inflammation, and therefore ileus, is disturbance to the bowel during abdominal surgery. Touching and manipulating the bowel initiates an inflammatory event within the bowel wall that leads to suppression of the neuromuscular apparatus and loss of coordinated gastrointestinal motility. The resulting "postoperative ileus" is characterized by delayed gastric emptying, dilatation of the small bowel and colon, abdominal distension, loss of normal propulsive contractile patterns, and inability to evacuate gas or stool. Holte, K. and H. Kehlet (2000). "Postoperative ileus: a preventable event." *Br J Surg* 87(11): 1480-93. In the clinical setting postoperative ileus leads to increased patient discomfort (abdominal distension, nausea, emesis), and is a major contributing factor to prolonged hospital stay.

The mechanisms contributing to the development of ileus are complex and include the activation of sympathetic reflexes, the release of central inhibitory humoral agents from the hypothalamic-pituitary axis, norepinephrine release from the bowel wall, as well as anesthetic and analgesic agents (Livingston, E. H. and E. P. Passaro (1990) "Postoperative ileus." *Digestive Diseases and Sciences* 35(1): 121-132; and Bauer, A. J., N. T. Schwarz, et al. (2002) "Ileus in critical illness: mechanisms and management." *Curr Opin Crit Care* 8(2): 152-7).

The central event underlying this process, is the initiation of an acute inflammatory response within the wall of the GI tract. Studies employing rodent models of post-operative ileus demonstrated that the muscularis externa is a highly immunologically active compartment. Normally resident within the muscularis externa is an impressive array of resident macrophages, which form an extensive network of cells from the esophagus to the colon (Mikkelsen, H. B. (1995) "Macrophages in the external muscle layers of mammalian intestines." *Histology and Histopathology* 10: 719-736; and, Kalff, J. C., W. H. Schraut et al. (1998) "Surgical manipulation of the gut elicits an intestinal muscularis inflammatory response resulting in paralytic ileus." *Annals of Surgery* 228: 652-663) and which are poised to defend the gastrointestinal tract from insult. Disturbances to the bowel during abdominal surgery activate this macrophage network, initiating a local molecular inflammatory response. Activated macrophages release pro-inflammatory cytokines and chemokines that suppress the neuromuscular apparatus and induce the expression of adhesion molecules on the vascular endothelium (Kalff, Schraut, et al. (1998); Kalff, J. C., N. T. Schwarz, et al. (1998) "Leukocytes of the intestinal muscularis: their phenotype and isolation." *J Leukoc Biol* 63(6): 683-91; Josephs, M. D., G. Cheng, et al. (1999) "Products of cyclooxygenase-2 catalysis regulate postoperative bowel motility." *J Surg Res* 86(1): 50-4; Kalff, J. C., T. M. Carlos, et al. (1999) "Surgically induced leukocytic infiltrates within the rat intestinal muscularis mediate postoperative ileus." *Gastroenterology* 117: 378-387; Kalff, J. C., W. H. Schraut, et al. (2000) "Role of inducible nitric oxide synthase in postoperative intestinal smooth muscle dysfunction in rodents." *Gastroenterology* 118(2): 316-27; and, Wehner, S., N. T. Schwarz, et al. (2005) "Induction of IL-6 within the rodent intestinal muscularis after intestinal surgical stress." *Surgery* 137(4): 436-46).

This in turn leads to a cellular inflammatory response characterized by recruitment of leucocytes (monocytes, neutrophils, t-cells, mast cells) from the systemic circulation (Kalff, J. C., N. T. Schwarz, et al. (1997) "Phagocyte activation and infiltration of the intestinal muscularis with impairment of small bowel motility after surgical manipulation." *Langenbecks Archiv für Chirurgie Suppl.*: 425-428; and, Kalff, J. C., B. M. Buchholz, et al. (1999) "Biphasic response to gut manipulation and temporal correlation of cellular infiltrates and muscle dysfunction in rat." *Surgery* 126(3): 498-509). Infiltrating leukocytes release additional cytokines as well as prostaglandins, nitric oxide, proteases and reactive oxygen species that further contribute to neuromuscular dysfunction (von Ritter, C., R. Be, et al. (1989) "Neutrophilic proteases: mediators of formyl-methionyl-leucyl-phenylalanine-induced ileitis in rats." *Gastroenterology* 97(3): 605-9; and, Bielefeldt, K. and J. L. Conklin (1997) "Intestinal motility during hypoxia and reoxygenation in vitro." *Dig Dis Sci* 42(5): 878-84).

The compounds of the present invention prevent or treat ileus by inhibiting the influx of immunologically activated circulating leukocytes into the muscle wall of the gastrointestinal tract, or by inhibiting their activity. The compounds of the present invention also prevent or treat ileus by preventing the inflammatory sequelae that lead to impaired gastrointestinal contractile function.

Induction of Postoperative Ileus

Male CD-1 mice were anesthetized by inhaled isoflurane and prepared for surgery. The abdomen was shaved of hair and treated with antiseptic solution. The animal was then covered with a surgical drape, leaving the abdomen exposed. A mid-line laparotomy was performed, and the entire small intestine was exteriorized onto the sterile drape. Using two moistened, sterile, cotton-tipped applicators, the small intestine was then gently compressed along its length from the ligament of Treitz to the ileo-cecal junction. The small intestine was then returned to the abdominal cavity and the incision closed by two layers of sutures.

Administration of Compounds

Age-matched mice were randomly assigned to groups (6 animals per group) and injected intraperitoneally (i.p.) with "vehicle" (a mixture of 5% ethanol/5% Tween80/90% of 5% dextran in water w/v) containing various doses of a test compound 1 hr prior to laparotomy. The second group was injected intraperitoneally with vehicle. The third group was administered intragastrically (1 mg/kg) a mixture (1 mg/mL) of dexamethasone in 20% hydroxypropyl methyl dextran in water, once per day for two days prior to surgery and 5 hrs post-laparotomy. The fourth group received no intervention and served as naïve controls.

Method of Measuring Gastrointestinal Motility—Upper Gastrointestinal Transit—Fluorescein-isothiocyanate (FITC)-Dextran Technique:

Upper gastrointestinal transit was measured 24 hr post-laparotomy. Mice were fed a test meal consisting of 150 µL of FITC-dextran solution (5 mg/mL of 70,000 molecular weight dextran conjugated to fluorescein-isothiocyanate in 0.5% hydroxypropyl methylcellulose/deionized water) administered intragastrically by an 18 gauge feeding tube. Following oral administration of the FITC-dextran test meal, animals were returned to their home cages. Following a 45 min test period, mice were euthanized by isoflurane overdose and exsanguination. The entire gastrointestinal tract from the lower esophageal sphincter to the terminal colon was removed. The bowel segments were opened along the mesenteric border. The tissue and luminal contents of the stomach, 10 equal segments of small intestine, the cecum, and 3 equal segments of colon were placed in individual Eppendorf tubes containing 1 ml of PBS. The tissue was vigorously mixed on a tabletop vortex, and solid materials were pelletized by centrifugation. Aliquots of the cleared supernatant were read in duplicate on a 96-well fluorescence plate reader to quantify the magnitude of the fluorescent signal in each segment of bowel.

These values were used to calculate the Geometric Center (REF), which is defined as the weighted average distribution of the fluorescent signal along the gastrointestinal tract:

$$GC=\Sigma(\% \text{ of total fluorescent signal per segment} \times \text{segment number})/100,$$

Higher GC values represent faster rates of transit on scale of 1 to 15. Normal mice exhibit a GC=8 following a 45 minute test duration.

Microscopic Myeloperoxidase Histological Examination

Microscopic histological examination was performed on harvested tissues 24 hr post-laparotomy. Activated immune cells such as neutrophils and monocytes exhibit myeloperoxidase activity. Hanker-Yates reagent (Polysciences Inc.) forms an insoluble, blue-black polymer in the presence of hydrogen peroxide and peroxidase enzyme activity. Segments of mid small bowel were collected from the centrifuge tubes described in the previous section. Whole mounts of the muscle layer were prepared by opening the tube of bowel along the mesenteric border and pinning the tissue flat in a Sylgard™ lined Petri dish with the mucosal surface facing upward. The tissue was stretched to 1.5 times its length and 2.5 times its width, and the mucosa removed by fine dissection. The remaining muscularis whole mounts were then fixed with 100% ethanol for 45 min, washed 3 times with PBS, and incubated for 20 min in PBS containing 0.1% hydrogen peroxide and 1 mg/ml Hanker-Yates reagent (Polysciences, Inc). The reagent is polymerized in the presence of hydrogen peroxide and peroxidase activity to form a blue-black deposit. Following a second wash with PBS, the whole mounts were mounted on glass slides, cover-slipped, and viewed on an optical microscope. Myeloperoxidase containing leukocytes were counted in 6 to 8 adjacent 200× optical fields, and the mean cell counts were calculated and recorded.

Postoperative Ileus Results

The presence of myeloperoxidase (MPO) positive immune cells in the intestinal muscularis is rare in normal animals. The number of infiltrating leukocytes is markedly increased following surgical manipulation of the small bowel. The magnitude of this infiltrate is significantly reduced following treatment with dexamethasone or with a test compound of the present invention as shown in Table 11.

TABLE 11

| Treatment | Compound | Dose (mg/kg) | MPO-Positive Cells (Per 200× Optical Field |
|---|---|---|---|
| Baseline | None | — | 0.23 ± 0.08 |
| Surgical | Vehicle | 0 | 254.3 ± 8.9 |
| Manipulation | Dexamethasone | 1 | 29.8 ± 3.9* |
| | Cpd 237 | 1 | 57.8 ± 17.0* |
| | Cpd 237 | 3 | 41.3 ± 9.4* |
| | Cpd 237 | 10 | 77.7 ± 25.7* |
| | Cpd 237 | 30 | 60.3 ± 20.9* |
| | Cpd 232 | 10 | 127.6 ± 25.7* |
| | Cpd 232 | 30 | 60.2 ± 20.8* |

Data are mean ± SE.
Statistical significance determined by ANOVA, followed by Bonferroni post-hoc test.
*Compares drug-treated with vehicle-treated animals, $p < 0.001$.

Gastrointestinal Motility Associated with Post-Operative Inflammatory Ileus

Surgical manipulation of the small bowel leads to a significant delay in gastrointestinal transit, going from a Geometric Center of 8.4 in normal mice to 3.3 in vehicle treated animals. Treatment with dexamethasone leads to partial recovery. The results shown in Table 12 for test compounds of the present invention show a dose-dependent increase in transit, to a level comparable to that achieved by dexamethasone.

Accordingly, the compounds of the present invention attenuated the impairment of gastrointestinal motility associated with post-operative inflammatory ileus.

TABLE 12

| Treatment | Compound | Dose (mg/kg) | Geometric Center |
|---|---|---|---|
| Baseline | None | — | 8.4 ± 0.25 |
| Surgical | Vehicle | 0 | 3.3 ± 0.15 |
| Manipulation | Dexamethasone | 1 | 6.0 ± 0.14* |
| | Cpd 237 | 1 | 3.8 ± 0.40 |
| | Cpd 237 | 3 | 3.6 ± 0.53 |
| | Cpd 237 | 10 | 4.7 ± 0.40 |
| | Cpd 237 | 30 | 5.6 ± 0.76* |
| | Cpd 232 | 10 | 4.0 ± 0.59 |
| | Cpd 232 | 30 | 5.6 ± 0.16* |

Data are mean ± SE.
Statistical significance determined by ANOVA followed by Bonferroni post-hoc test.
*Compares drug-treated with vehicle-treated animals, $p < 0.001$.

It is to be understood that the preceding description of the invention and various examples thereof have emphasized certain aspects. Numerous other equivalents not specifically elaborated on or discussed may nevertheless fall within the spirit and scope of the present invention or the following claims and are intended to be included.

What is claimed is:

1. A compound or a salt thereof selected from the group consisting of:
   (8E)-8-(3-fluoro-benzylidene)-1-methyl-1,4,5,6,7,8-hexahydro-cycloheptapyrazole-3-carboxylic acid [(1R)-3-hydroxy-1-phenyl-propyl]-amide,
   (8E)-8-(3-chloro-benzylidene)-1,4,5,6,7,8-hexahydro-cycloheptapyrazole-3-carboxylic acid [(1R)-3-hydroxy-1-phenyl-propyl]-amide,
   (8R*)-(3-chloro-benzyl)-1,4,5,6,7,8-hexahydro-cycloheptapyrazole-3-carboxylic acid [(1S)-2-methoxy-1-phenyl-ethyl]-amide,
   (8S*)-(3-chloro-benzyl)-1,4,5,6,7,8-hexahydro-cycloheptapyrazole-3-carboxylic acid [(1S)-2-methoxy-1-phenyl-ethyl]-amide,
   (8S*)-(3-chloro-benzyl)-1,4,5,6,7,8-hexahydro-cycloheptapyrazole-3-carboxylic acid [(1R)-2-methoxy-1-phenyl-ethyl]-amide,
   (8R*)-(3-chloro-benzyl)-1,4,5,6,7,8-hexahydro-cycloheptapyrazole-3-carboxylic acid [(1R)-2-methoxy-1-phenyl-ethyl]-amide,
   (2E)-[8-(3-chloro-benzyl)-1,4,5,6,7,8-hexahydro-cycloheptapyrazol-3-yl]-ethenesulfonic acid piperidin-1-ylamide,
   8-(3-chloro-benzyl)-1,4,5,6,7,8-hexahydro-cycloheptapyrazole-3-carboxylic acid [(1S)-1-phenyl-ethyl]-amide, or
   8-(3-chloro-benzyl)-1,4,5,6,7,8-hexahydro-cycloheptapyrazole-3-carboxylic acid [(1R)-1-phenyl-ethyl]-amide.

* * * * *